United States Patent
Xu et al.

(10) Patent No.: US 11,534,443 B2
(45) Date of Patent: Dec. 27, 2022

(54) QUINAZOLINE COMPOUNDS, PREPARATION METHOD, USE, AND PHARMACEUTICAL COMPOSITION THEREOF

(71) Applicant: INSTITUTE OF MATERIA MEDICA, CHINESE ACADEMY OF MEDICAL SCIENCES, Beijing (CN)

(72) Inventors: Heng Xu, Beijing (CN); Xiaoguang Chen, Beijing (CN); Songwen Lin, Beijing (CN); Ming Ji, Beijing (CN); Jing Jin, Beijing (CN); Deyu Wu, Beijing (CN); Chunyang Wang, Beijing (CN); Yuanhao Lv, Beijing (CN)

(73) Assignee: INSTITUTE OF MATERIA MEDICA, CHINESE ACADEMY OF MEDICAL SCIENCES, Beijing (CN)

( * ) Notice: Subject to any disclaimer, the term of this patent is extended or adjusted under 35 U.S.C. 154(b) by 58 days.

(21) Appl. No.: 16/473,901

(22) PCT Filed: Dec. 26, 2017

(86) PCT No.: PCT/CN2017/118771
§ 371 (c)(1),
(2) Date: Jun. 26, 2019

(87) PCT Pub. No.: WO2018/121550
PCT Pub. Date: Jul. 5, 2018

(65) Prior Publication Data
US 2021/0128559 A1    May 6, 2021

(30) Foreign Application Priority Data

Dec. 26, 2016 (CN) .......................... 201611204309.8
Dec. 26, 2016 (CN) .......................... 201611211589.5
Dec. 26, 2016 (CN) .......................... 201611214102.9

(51) Int. Cl.
| | |
|---|---|
| *C07D 405/12* | (2006.01) |
| *C07D 405/14* | (2006.01) |
| *C07D 401/04* | (2006.01) |
| *C07D 401/14* | (2006.01) |
| *A61P 35/00* | (2006.01) |
| *A61K 31/517* | (2006.01) |
| *A61K 31/5377* | (2006.01) |

(52) U.S. Cl.
CPC ........ *A61K 31/517* (2013.01); *A61K 31/5377* (2013.01); *A61P 35/00* (2018.01); *C07D 401/04* (2013.01); *C07D 401/14* (2013.01); *C07D 405/12* (2013.01); *C07D 405/14* (2013.01)

(58) Field of Classification Search
CPC .. C07D 401/04; C07D 401/10; C07D 401/14; C07D 405/14; C07D 409/14
See application file for complete search history.

(56) References Cited

FOREIGN PATENT DOCUMENTS

| | | |
|---|---|---|
| CN | 1440408 | 9/2003 |
| CN | 108239074 | 7/2018 |
| CN | 108239075 | 7/2018 |
| CN | 108239076 | 7/2018 |
| JP | 2010526823 | 8/2010 |
| JP | 2010528027 | 8/2010 |
| JP | 2010532320 | 10/2010 |
| JP | 2011500823 | 1/2011 |
| NO | 1181346 | 11/2001 |
| NO | 2014169167 | 10/2014 |
| WO | 2008157191 A2 | 12/2008 |

OTHER PUBLICATIONS

Fu, Wei; International Search Report; ISA/CN; 7 pages; PCT/CN2017/118771; dated Mar. 23, 2018.
Jn, Songwen et al. 2014. "Identification of novel 7-amino-5-methyl-1,6-naphthyridin-2(1H)-one derivatives as potent 13K/mTOR dual inhibitors". Bioorganic & Medicinal Chemistry Letters, vol. 24. pp. 790-793.

*Primary Examiner* — Erich A Leeser
(74) *Attorney, Agent, or Firm* — Nexsen Pruet, PLLC

(57) ABSTRACT

The invention relates to quinazoline compounds, the preparation method, use, and the pharmaceutical composition thereof. The said quinazoline compounds, which are represented by Formula (I), are phosphatidylinositol 3-kinase (PI3K) inhibitors, and can be applied to prevent and/or treat PI3K activity-related diseases, such as cancer, immune diseases, cardiovascular diseases, viral infections, inflammation, metabolism/endocrine function disorders or neurological diseases.

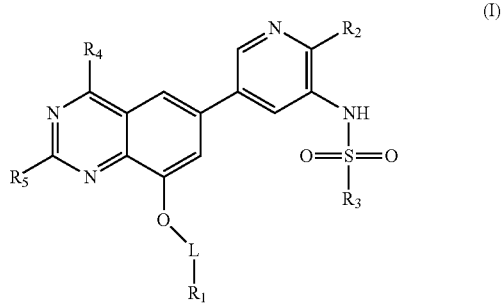

13 Claims, 2 Drawing Sheets

QUINAZOLINE COMPOUNDS, PREPARATION METHOD, USE, AND PHARMACEUTICAL COMPOSITION THEREOF

CROSS-REFERENCE TO RELATED APPLICATIONS

This application claims priority under 35 U.S.C. § 371 to International Patent Appln. No. PCT/CN2017/118771, filed Dec. 26, 2017; which claims priority to: Chinese Patent Appln. No. CN201611211589.5, filed Dec. 26, 2016; Chinese Patent Appln. No. CN201611204309.8, filed Dec. 26, 2016; and to Chinese Patent Appln. No. CN201611214102.9, filed Dec. 26, 2016, the entireties of which are incorporated by reference herein.

FIELD

This invention belongs to the technical field of pharmacy, and relates to a series of quinazoline compounds, their preparation method, use, and pharmaceutical composition.

BACKGROUND

Phosphatidylinositol 3-kinases (PI3K) belong to lipid kinases family and can be divided into three classes (I, II and III) according to differences of their structure, regulating effect and lipid substrate specificities. At present, the most intensively studied are class I PI3Ks, which are heterodimers consisting of a regulatory subunit (p85) and a catalytic subunit (p110). Class I PI3Ks include 4 subtypes. Among them, two subtypes, PI3Kα and PI3Kβ, are widely existed in various cells, while the other two subtypes PI3Kδ and PI3Kγ are mainly distributed in leukocytes (Vanhaesebroeck, et al., Trends Biochem Sci., 2005, 30(4):194-204). As a main downstream effector of receptor tyrosine kinase (RTK) and G protein coupled receptor (GPCR), PI3K generates phosphatidylinositol 3,4,5-triphosphate (PIP3) by catalyzing phosphatidylinositol 4,5-diphosphate (PIP2), thereby transducting signals of various growth factors and cytokines into cells. Then PIP3, as intracellular second messenger, can activate serine/threonine protein kinase B (AKT) and downstream effectors including mammalian target of rapamycin (mTOR), thereby regulating multiple cell functions.

PI3K signaling pathway is one of the most common abnormal signaling pathways in tumor cells, and has key influence on the occurrence and development of tumors. In particular, amplification and mutation of the PIK3CA gene, which encoding the p110α, have frequently occurred in most tumors such as breast cancer, lung cancer, intestinal cancer, ovarian cancer, head and neck cancer, stomach cancer, prostate cancer, brain cancer, liver cancer, gastrointestinal tumor and leukemia (Zhao, et al. Nat. Drug Discov. 2009, 8:627-644). In recent years, PI3K and other related nodes in its pathway such as AKT and mTOR have become popular targets for targeting anti-tumor drugs. PI3K inhibitors with various structural skeleton types have been reported and all exhibited excellent antitumor effect in cellular and animal models, and many compounds have entered clinical trials as monotherapy or combination therapy for solid tumor and hematologic tumor, such as BKM120 (Novartis, phase III clinical trial), BEZ235 (Novartis, phase II clinical trial), PF-05212384 (Pfizer, phase II clinical trial), BAY 80-6946 (Bayer, phase III clinical trial), XL147 (Exelixis, phase I/II clinical trial), etc. In 2014, the first PI3K inhibitor, Idelalisib (Gilead, PI3Kδ selective inhibitor), was approved by FDA for the treatment of chronic lymphocytic leukemia (CLL), recurrent follicular B cell non-hodgkin's lymphoma (FL) and recurrent small lymphocytic lymphoma (SLL). In addition to tumor, PI3K also plays an important role in regulating inflammation, immune diseases, cardiovascular diseases, viral infections, metabolism/endocrine function disorders or neurological diseases. Some compounds such as GSK2269557 (chronic obstructive pulmonary disease, phase II clinical trial), GSK2126458 (idiopathic pulmonary fibrosis, phase I clinical trial), UCB-5857 (primary sjogren's syndrome, phase II clinical trial), and RV-1729 (chronic obstructive pulmonary disease, phase I clinical trial), have entered clinical trials against these diseases.

PI3K has become a very attractive drug target. However, there is still a need to develop safer and more effective PI3K inhibitors for prevention and/or treatment of cancers, immune diseases, cardiovascular diseases, viral infections, inflammation, metabolism/endocrine function disorders or neurological diseases.

SUMMARY

The technical problem to be solved by the present invention is to provide a novel PI3K inhibitor, and a preparation method, a pharmaceutical composition and use thereof. The PI3K inhibitor has a strong inhibitory activity against Class I PI3K, including PI3Kα, PI3Kβ, PI3Kγ and/or PI3Kδ, especially PI3Kα, resulting a better prevention and/or treatment effect on PI3K-mediated diseases such as cancer, autoimmune diseases, cardiovascular diseases, viral infections, inflammation, metabolism/endocrine function disorders or neurological diseases.

In order to solve the above technical problems, the present invention provides the following technical solutions.

The first aspect of the present invention is to provide a compound represented by Formula (I), or a stereoisomer, a geometric isomer, a tautomer or a pharmaceutically acceptable salt thereof:

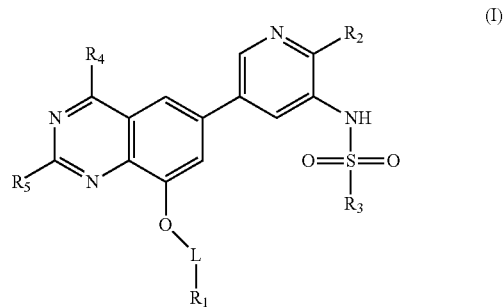

wherein, $R_4$ is $C_{1-3}$ alkyl;

L is selected from a single bond or $C_{1-3}$ alkylene, wherein the $C_{1-3}$ alkylene is optionally substituted with one or more Ra;

Ra is selected from hydrogen, halogen or $C_{1-3}$ alkyl;

$R_1$ is selected from hydrogen, $C_{1-3}$ alkyl, $C_{1-3}$ alkoxy, 3- to 7-membered cycloalkyl, 3- to 7-membered heterocycloalkyl or 5- to 6-membered heteroaryl; when said $R_1$ is not hydrogen, it is optionally substituted with m $R_6$;

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino;

$R_2$ is selected from $C_{1-3}$ alkoxy, halogen or $C_{1-3}$ alkyl;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with one or more groups that are independently selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy;

$R_5$ is selected from hydrogen, amino, $C_{1-3}$ alkylamino, $C_{1-3}$ alkylcarbonylamino or cyclopropylmethylamino.

In a preferred embodiment, the present invention provides a compound represented by Formula (II), or a stereoisomer, a geometric isomer, a tautomer or a pharmaceutically acceptable salt thereof:

(II)

wherein,

L is selected from a single bond or $C_{1-3}$ alkylene, wherein the $C_{1-3}$ alkylene is optionally substituted with one or more Ra;

Ra is selected from hydrogen, halogen or $C_{1-3}$ alkyl, preferably $C_{1-3}$ alkyl;

$R_1$ is selected from hydrogen, $C_{1-3}$ alkyl, $C_{1-3}$ alkoxy, 3- to 7-membered cycloalkyl or 3- to 7-membered heterocycloalkyl; when $R_1$ is not hydrogen, it is optionally substituted with m $R_6$;

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino; $R_2$ is selected from $C_{1-3}$ alkoxy, halogen or $C_{1-3}$ alkyl;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with one or more groups that are independently selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy.

In a further preferred embodiment, the present invention provides a compound represented by Formula (II), or a stereoisomer, a geometric isomer, a tautomer or a pharmaceutically acceptable salt thereof, wherein, L is selected from a single bond or $C_{1-3}$ alkylene, wherein $C_{1-3}$ alkylene is optionally substituted with one or more Ra;

Ra is selected from hydrogen, halogen or $C_{1-3}$ alkyl, preferably $C_{1-3}$ alkyl;

$R_1$ is selected from cyclopropyl, cyclobutyl, cyclopentyl and cyclohexyl; optionally, $R_1$ is substituted with m $R_6$;

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino;

$R_2$ is selected from $C_{1-3}$ alkoxy, halogen or $C_{1-3}$ alkyl;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with one or more groups that are independently selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy.

In a still further preferred embodiment, the present invention provides a compound represented by formula (II), or a stereoisomer, a geometric isomer, a tautomer or a pharmaceutically acceptable salt thereof, wherein, L is selected from a single bond or $C_{1-3}$ alkylene, wherein $C_{1-3}$ alkylene is optionally substituted with one or more Ra;

Ra is selected from hydrogen, halogen or $C_{1-3}$ alkyl, preferably $C_{1-3}$ alkyl;

$R_1$ is 3- to 7-membered heterocycloalkyl containing oxygen, and $R_1$ is optionally substituted with m $R_6$.

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino;

$R_2$ is selected from $C_{1-3}$ alkoxy, halogen or $C_{1-3}$ alkyl;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with one or more groups that are independently selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy.

In a further preferred embodiment, $R_1$ is selected from:

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino.

In a further preferred embodiment, $R_1$ is selected from:

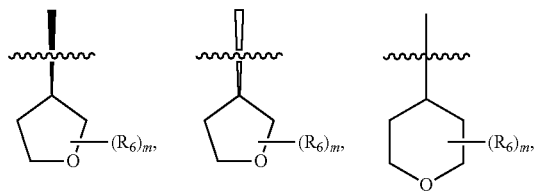

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino.

In a further preferred embodiment, each $R_6$ is independently selected from F, methyl or methoxy.

In a still further preferred embodiment, the present invention provides a compound represented by formula (II), or a stereoisomer, a geometric isomer, a tautomer or a pharmaceutically acceptable salt thereof,
wherein,
L is selected from a single bond or —CH$_2$—,
$R_1$ is selected from hydrogen, $C_{1-3}$ alkyl, $C_{1-3}$ alkoxy, 3- to 7-membered cycloalkyl or 3- to 7-membered heterocycloalkyl; preferably, $R_1$ is selected from 3- to 7-membered cycloalkyl, including but not limited to cyclopropyl, cyclobutyl, cyclopentyl and cyclohexyl; or preferably, $R_1$ is selected from 3- to 7-membered heterocycloalkyl and further preferably, 3- to 7-membered oxygen-containing heterocycloalkyl, including but not limited to

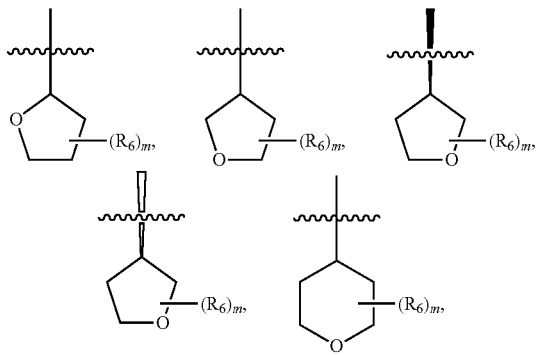

when $R_1$ is not hydrogen, it is optionally substituted with m $R_6$;

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino; preferably, each $R_6$ is independently selected from F, methyl or methoxy;

$R_2$ is selected from $C_{1-3}$ alkoxy, halogen or $C_{1-3}$ alkyl;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with one or more groups that are independently selected from hydrogen, halogen, $C_{1-3}$ alkyl, amino, $C_{1-3}$ alkylamino, di($C_{1-3}$ alkyl) amino, trifluoromethyl, difluoromethyl, cyano or $C_{1-3}$ alkoxy.

In a still further preferred embodiment, the present invention provides a compound represented by formula (II), or a stereoisomer, a geometric isomer, a tautomer or a pharmaceutically acceptable salt thereof,
wherein,
L is selected from a single bond or $C_{1-3}$ alkylene, wherein $C_{1-3}$ alkylene is optionally substituted with one or more Ra; preferably, L is selected from a single bond or —CH$_2$—;

Ra is selected from hydrogen, halogen or $C_{1-3}$ alkyl, preferably, $C_{1-3}$ alkyl;

$R_1$ is selected from hydrogen, $C_{1-3}$ alkyl, $C_{1-3}$ alkoxy, 3- to 7-membered cycloalkyl or 3- to 7-membered heterocycloalkyl; preferably, $R_1$ is selected from 3- to 7-membered cycloalkyl, including but not limited to cyclopropyl, cyclobutyl, cyclopentyl and cyclohexyl; or preferably, $R_1$ is selected from 3- to 7-membered heterocycloalkyl and further preferably 3- to 7-membered heterocycloalkyl containing oxygen, including but not limited to

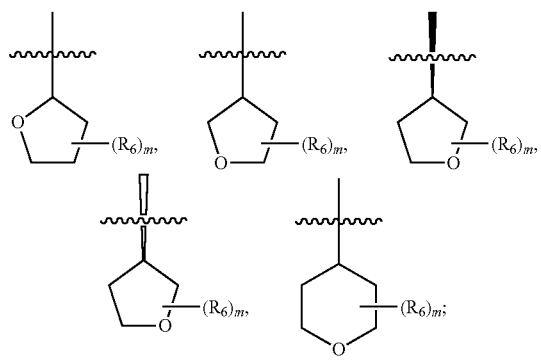

when $R_1$ is not hydrogen, it is optionally substituted with m $R_6$;

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino; preferably, each $R_6$ is independently selected from from F, methyl or methoxy;

$R_2$ is selected from methoxy, chloro or methyl.

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with one or more groups that are independently selected from hydrogen, halogen, $C_{1-3}$ alkyl, amino, $C_{1-3}$ alkylamino, di($C_{1-3}$ alkyl) amino, trifluoromethyl, difluoromethyl, cyano or $C_{1-3}$ alkoxy.

In a still further preferred embodiment, the present invention provides a compound represented by formula (II), a stereoisomer, a geometric isomer, a tautomer or a pharmaceutically acceptable salt thereof,
wherein,
L is selected from a single bond or $C_{1-3}$ alkylene, wherein $C_{1-3}$ alkylene is optionally substituted with one or more Ra; preferably, L is selected from a single bond or —CH$_2$—;

Ra is selected from hydrogen, halogen or $C_{1-3}$ alkyl, preferably, $C_{1-3}$ alkyl;

$R_1$ is selected from hydrogen, $C_{1-3}$ alkyl, $C_{1-3}$ alkoxy, 3- to 7-membered cycloalkyl or 3- to 7-membered heterocycloalkyl; preferably, $R_1$ is selected from 3- to 7-membered cycloalkyl, including but not limited to cyclopropyl, cyclobutyl, cyclopentyl and cyclohexyl; or preferably, $R_1$ is selected from 3- to 7-membered heterocycloalkyl and further preferably 3- to 7-membered heterocycloalkyl containing oxygen, including but not limited to

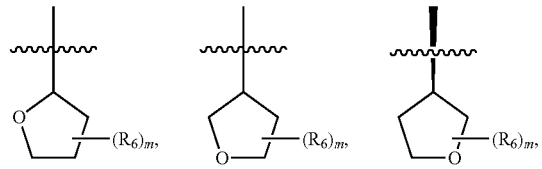

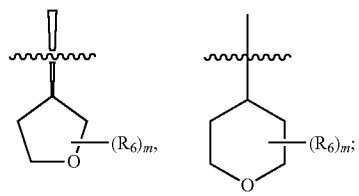

when R₁ is not hydrogen, it is optionally substituted with m R₆;

m is 0, 1, 2, 3 or 4;

each R₆ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino; preferably, each R₆ is independently selected from F, methyl or methoxy;

R₂ is selected from $C_{1-3}$ alkoxy, halogen or $C_{1-3}$ alkyl; preferably, R₂ is selected from methoxy, chloro or methyl;

R₃ is selected from $C_{1-3}$ alkyl, 3- to 7-membered cycloalkyl, phenyl or thienyl, wherein phenyl or thienyl are optionally substituted with one or more groups that are independently selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy.

In a further preferred embodiment, R₃ is selected from phenyl or thienyl, wherein phenyl or thienyl is optionally substituted with one or more substitutents that are independently selected from fluoro or chloro.

Specifically, the compounds preferred according to the present invention are as follows:

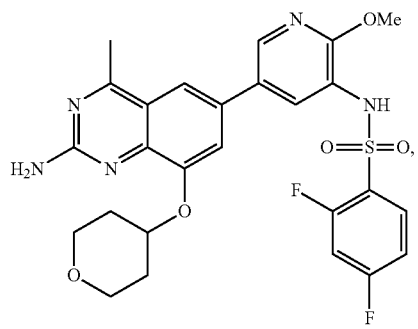

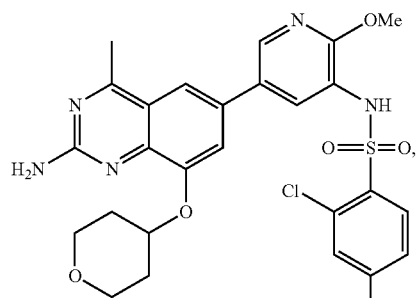

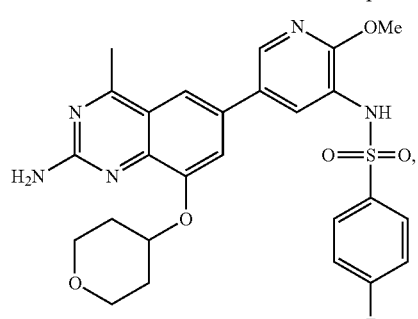

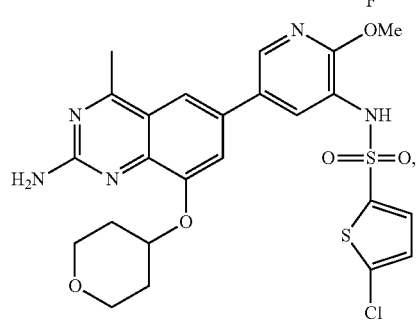

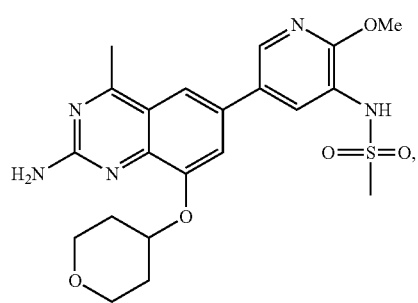

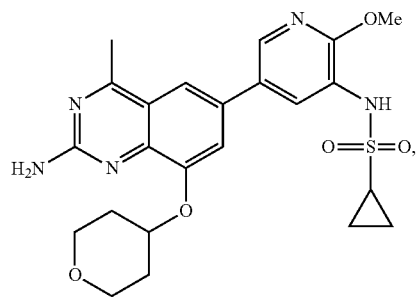

-continued
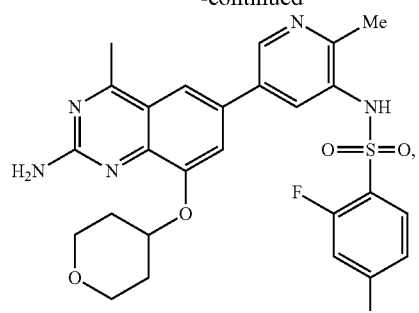
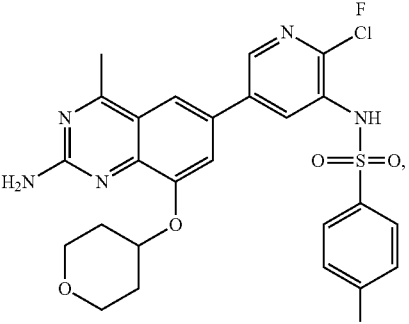
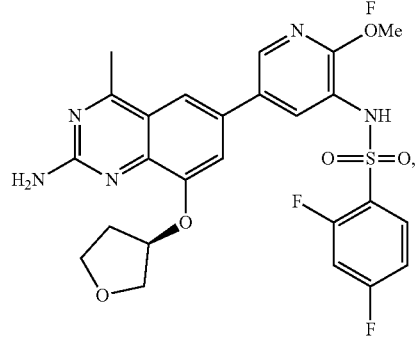
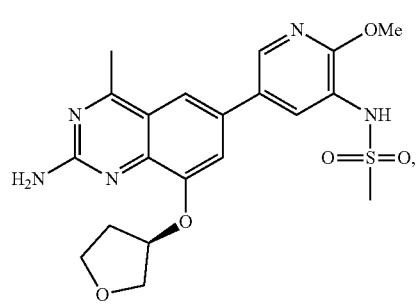
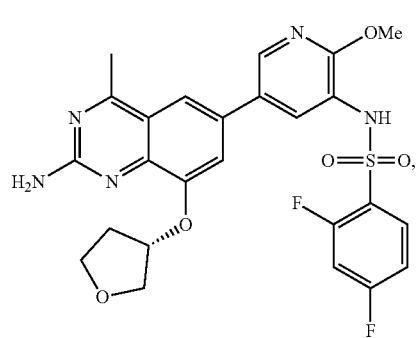
-continued
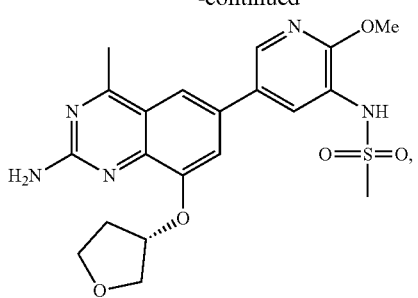
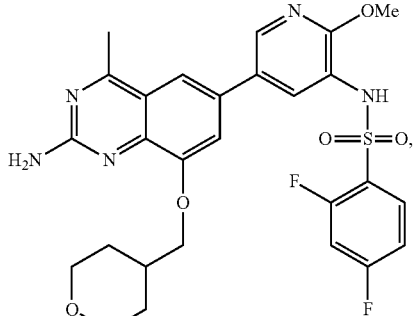
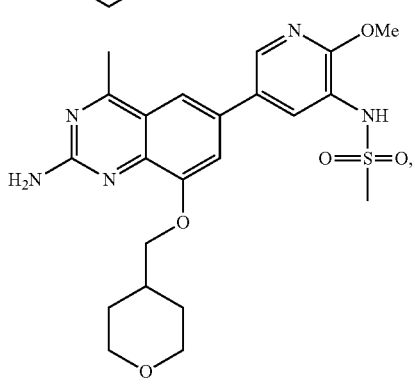
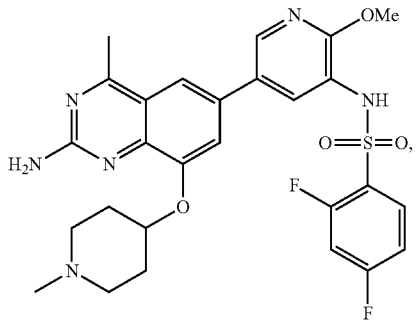
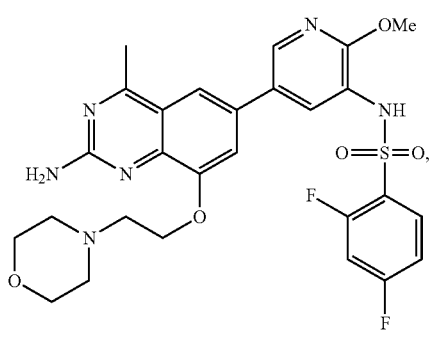

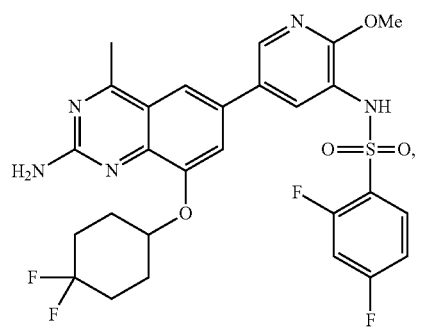
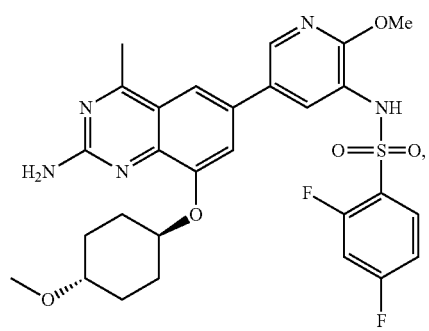
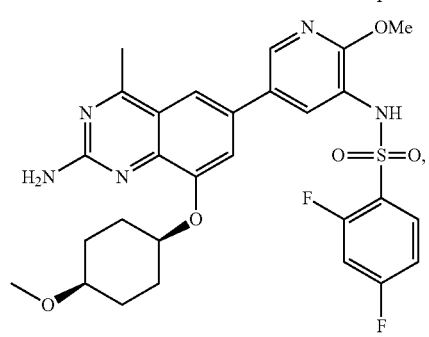
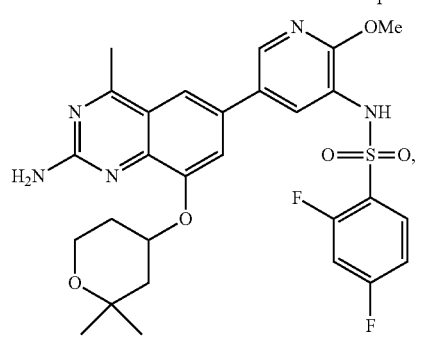
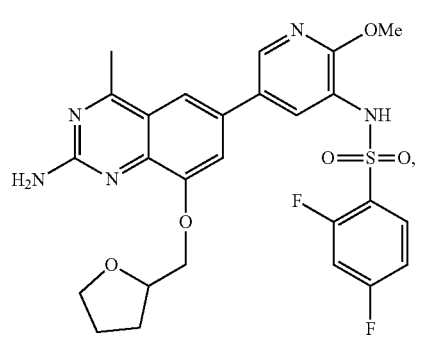
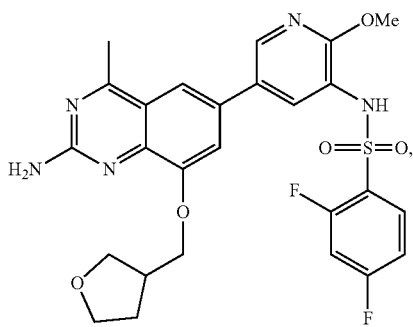
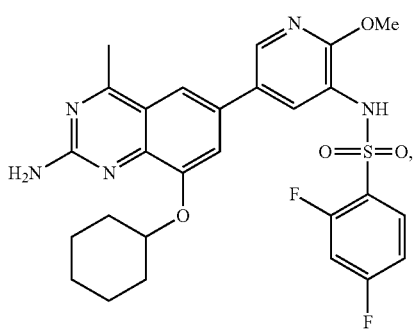
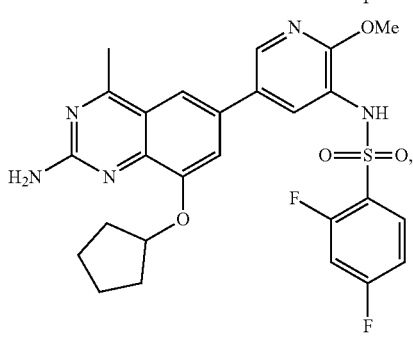
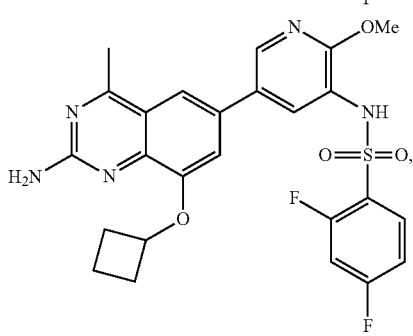
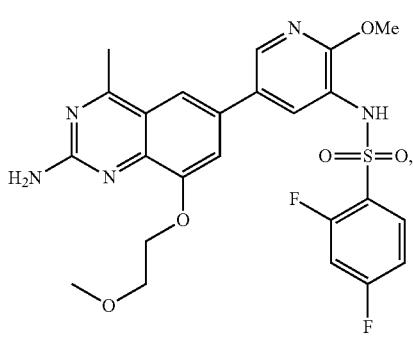

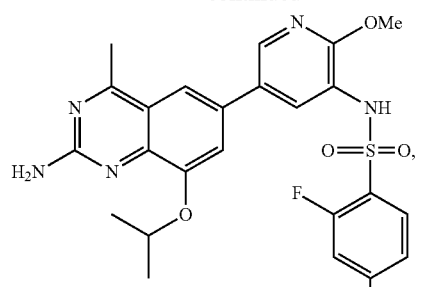
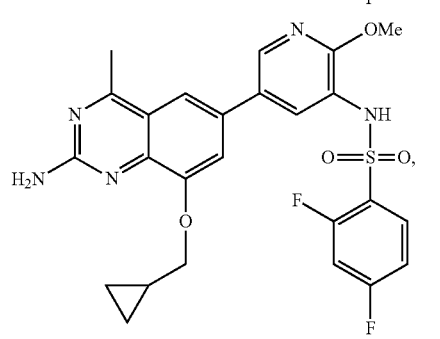
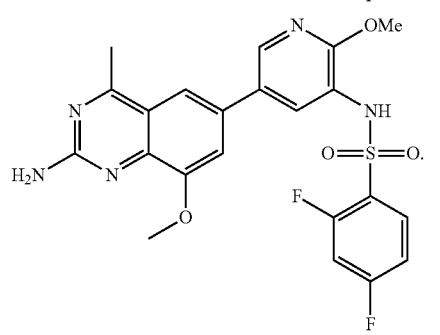
and
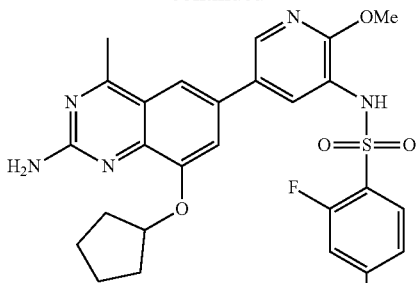
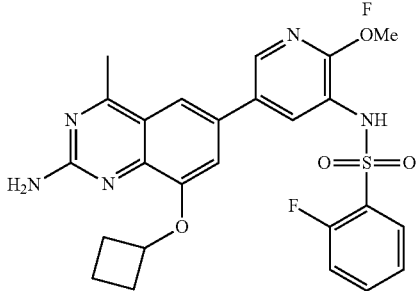
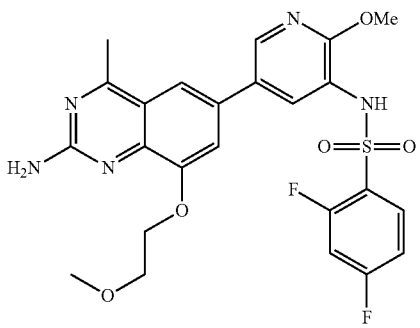
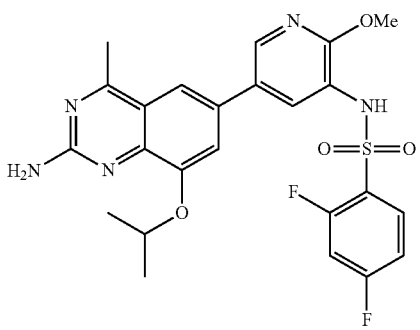
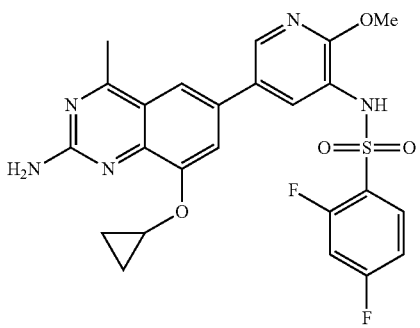

-continued

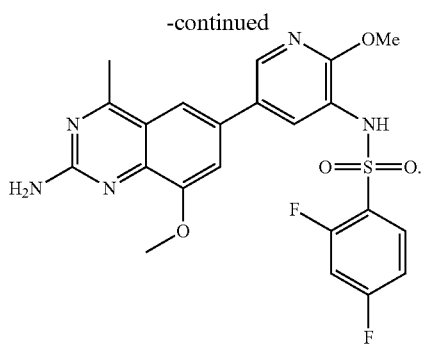

In another preferred embodiment, the present invention provides a compound represented by formula (III), or a stereoisomer, a geometric isomer, a tautomer or a pharmaceutically acceptable salt thereof,

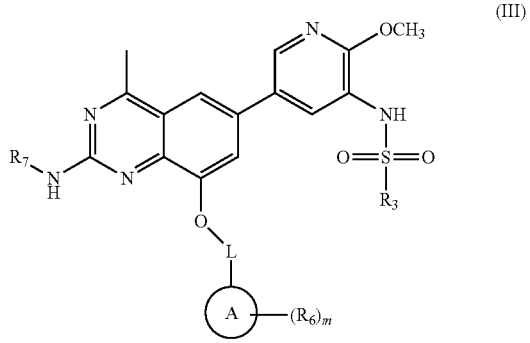

(III)

wherein, $R_7$ is selected from $C_{1-3}$ alkyl, $C_{1-3}$ alkylcarbonyl or cyclopropylmethyl;

L is selected from a single bond or $C_{1-3}$ alkylene, wherein $C_{1-3}$ alkylene is optionally substituted with one or more Ra;

Ra is selected from hydrogen, halogen or $C_{1-3}$ alkyl;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with at least one group that is selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy;

ring A is selected from 3- to 7-membered cycloalkyl or 3-7 heterocycloalkyl;

each $R_6$ is independently selected from hydrogen, $C_{1-3}$ alkyl, halogen, cyano, trifluoromethyl, $C_{1-3}$ alkoxy, $C_{1-3}$ alkyl substituted with hydroxyl, $C_{1-3}$ alkylamino, or di($C_{1-3}$ alkyl)amino;

m is 0, 1, 2, 3 or 4.

In a further preferred embodiment, the present invention provides a compound represented by formula (III), or a stereoisomer, a geometric isomer, a tautomer or a pharmaceutically acceptable salt thereof, wherein, $R_7$ is selected from $C_{1-3}$ alkyl, $C_{1-3}$ alkylcarbonyl or cyclopropylmethyl;

L is selected from a single bond or $C_{1-3}$ alkylene, wherein $C_{1-3}$ alkylene is optionally substituted with one or more Ra;

Ra is selected from hydrogen, halogen or $C_{1-3}$ alkyl;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with at least one group that is selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy;

ring A is selected from cyclopropyl, cyclobutyl, cyclopentyl and cyclohexyl;

each $R_6$ is independently selected from hydrogen, $C_{1-3}$ alkyl, halogen, cyano, trifluoromethyl, $C_{1-3}$ alkoxy, $C_{1-3}$ alkyl substituted with hydroxyl, $C_{1-3}$ alkylamino or di($C_{1-3}$ alkyl)amino;

m is 0, 1, 2, 3 or 4.

In a still further preferred embodiment, the present invention provides a compound represented by formula (III), or a stereoisomer, a geometric isomer, a tautomer or a pharmaceutically acceptable salt thereof, wherein, $R_7$ is selected from $C_{1-3}$ alkyl, $C_{1-3}$ alkylcarbonyl or cyclopropylmethyl;

L is selected from a single bond or $C_{1-3}$ alkylene, wherein $C_{1-3}$ alkylene is optionally substituted with one or more Ra;

Ra is selected from hydrogen, halogen or $C_{1-3}$ alkyl;

$R_3$ is selected from hydrogen, $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with at least one group that is selected from halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy;

ring A is 3- to 7-membered heterocycloalkyl containing oxygen;

each $R_6$ is independently selected from hydrogen, $C_{1-3}$ alkyl, halogen, cyano, trifluoromethyl, $C_{1-3}$ alkoxy, hydroxyl-substituted $C_{1-3}$ alkyl, $C_{1-3}$ alkylamino, or di($C_{1-3}$ alkyl)amino;

m is 0, 1, 2, 3 or 4.

In a further preferred embodiment, ring A is selected from:

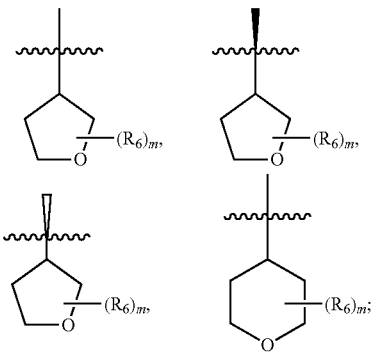

each $R_6$ is independently selected from hydrogen, $C_{1-3}$ alkyl, halogen, cyano, trifluoromethyl, $C_{1-3}$ alkoxy, $C_{1-3}$ alkyl substituted with hydroxyl, $C_{1-3}$ alkylamino or di($C_{1-3}$ alkyl)amino;

m is 0, 1, 2, 3 or 4.

In a further preferred embodiment, each $R_6$ is independently selected from methyl.

In a still further preferred embodiment, the present invention provides a compound represented by formula (III), or a stereoisomer, a geometric isomer, a tautomer or pharmaceutically acceptable salt, wherein, $R_7$ is selected from $C_{1-3}$ alkyl, $C_{1-3}$ alkylcarbonyl or cyclopropylmethyl; L is selected from a single bond or —$CH_2$—;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with at least one group that is selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy;

ring A is selected from 3- to 7-membered cycloalkyl or 3- to 7-membered heterocycloalkyl; preferably, ring A is selected from 3- to 7-membered cycloalkyl, including but not limited to cyclopropyl, cyclobutyl, cyclopentyl and cyclohexyl; or preferably, ring A is selected from 3- to 7-membered heterocycloalkyl and further preferably 3- to 7-membered heterocycloalkyl containing oxygen, including but not limited to

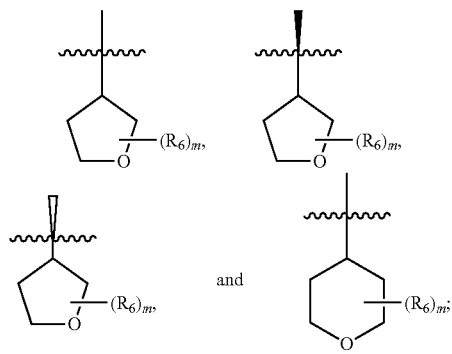

each $R_6$ is independently selected from hydrogen, $C_{1-3}$ alkyl, halogen, cyano, trifluoromethyl, $C_{1-3}$ alkoxy, hydroxyl-substituted $C_{1-3}$ alkyl, $C_{1-3}$ alkylamino or di($C_{1-3}$ alkyl)amino;

m is 0, 1, 2, 3 or 4.

In a still further preferred embodiment, the present invention provides a compound represented by formula (III), or a stereoisomer, a geometric isomer, a tautomer or a pharmaceutically acceptable salt thereof.

wherein, $R_7$ is selected from methyl, ethyl, cyclopropylmethyl or acetyl;

L is selected from a single bond or $C_{1-3}$ alkylene, wherein the $C_{1-3}$ alkylene is optionally substituted with one or more Ra; preferably, L is selected from a single bond or —$CH_2$—.

Ra is selected from hydrogen, halogen or $C_{1-3}$ alkyl; preferably, $C_{1-3}$ alkyl;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with at least one group that is selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy;

ring A is selected from 3- to 7-membered cycloalkyl or 3- to 7-membered heterocycloalkyl; preferably, ring A is selected from 3- to 7-membered cycloalkyl, including but not limited to cyclopropyl, cyclobutyl, cyclopentyl and cyclohexyl; or preferably, ring A is selected from 3- to 7-membered heterocycloalkyl and further preferably 3- to 7-membered heterocycloalkyl containing oxygen, including but not limited to

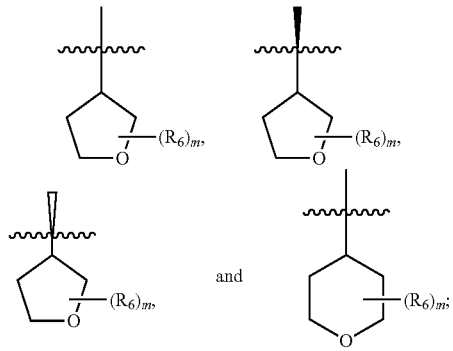

each $R_6$ is independently selected from hydrogen, $C_{1-3}$ alkyl, halogen, cyano, trifluoromethyl, $C_{1-3}$ alkoxy, $C_{1-3}$ alkyl substituted with hydroxyl, $C_{1-3}$ alkylamino or di($C_{1-3}$ alkyl)amino;

m is 0, 1, 2, 3 or 4.

In a still further preferred embodiment, the present invention provides a compound represented by formula (III), or a stereoisomer, a geometric isomer, a tautomer or a pharmaceutically acceptable salt thereof, wherein, $R_7$ is selected from $C_{1-3}$ alkyl, $C_{1-3}$ alkylcarbonyl or cyclopropylmethyl; preferably, $R_1$ is selected from methyl, ethyl, cyclopropylmethyl or acetyl;

L is selected from a single bond or $C_{1-3}$ alkylene, wherein the $C_{1-3}$ alkylene is optionally substituted with one or more Ra; preferably, L is selected from a single bond or —$CH_2$—;

Ra is selected from hydrogen, halogen or $C_{1-3}$ alkyl; preferably $C_{1-3}$ alkyl;

$R_3$ is selected from $C_{1-3}$ alkyl, 3- to 7-membered cycloalkyl, phenyl or thienyl, wherein the phenyl and thienyl are optionally substituted with one or more groups that are independently selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy; ring A is selected from 3- to 7-membered cycloalkyl or 3- to 7-membered heterocycloalkyl; preferably, ring A is selected from 3- to 7-membered cycloalkyl, including but not limited to cyclopropyl, cyclobutyl, cyclopentyl and cyclohexyl; or preferably, ring A is selected from 3- to 7-membered heterocycloalkyl and further preferably 3- to 7-membered heterocycloalkyl containing oxygen, including but not limited to

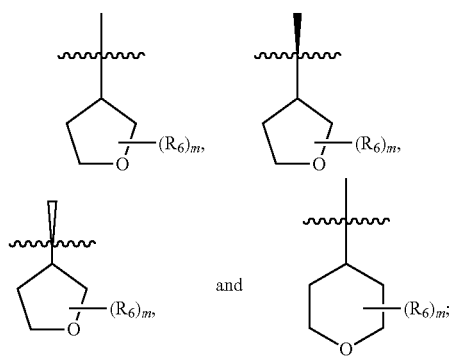

each $R_6$ is independently selected from hydrogen, $C_{1-3}$ alkyl, halogen, cyano, trifluoromethyl, $C_{1-3}$ alkoxy, hydroxyl-substituted $C_{1-3}$ alkyl, $C_{1-3}$ alkylamino or di($C_{1-3}$ alkyl)amino;

m is 0, 1, 2, 3 or 4.

In a further preferred embodiment, $R_3$ is selected from phenyl or thienyl, wherein phenyl and thienyl are optionally substituted with one or more substitutents that are independently selected from fluoro or chloro.

Specifically, the compounds preferred according to the invention are as follows:

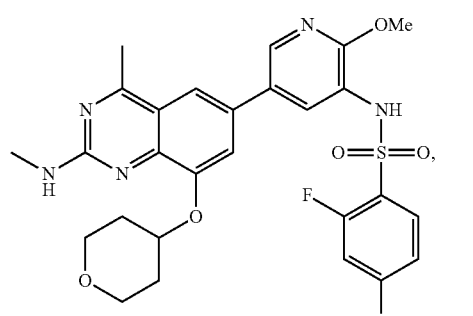

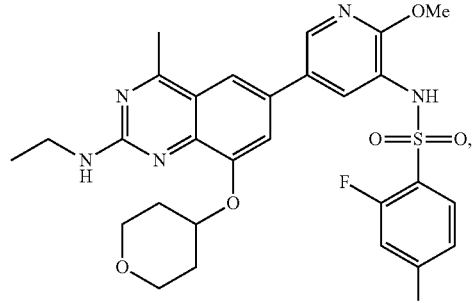

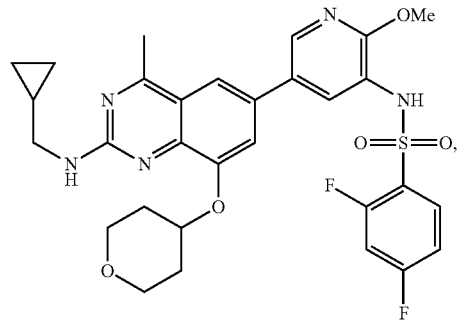

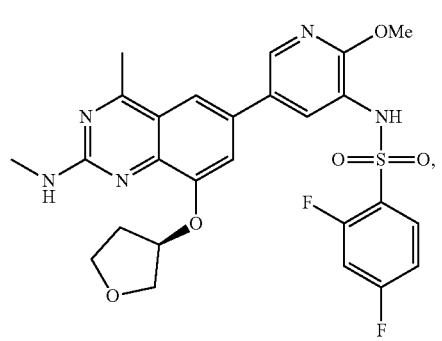

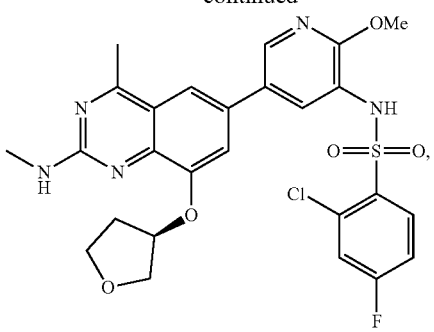

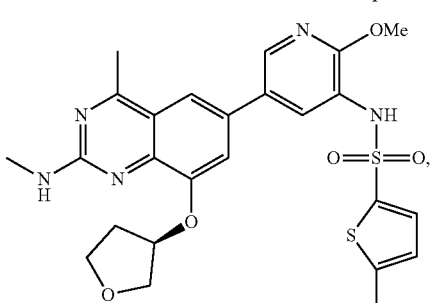

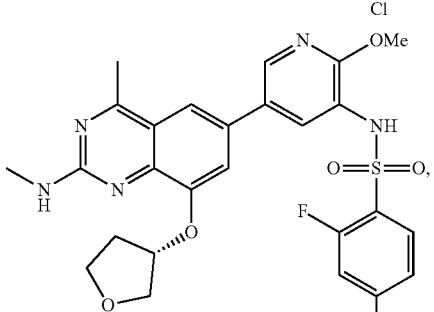

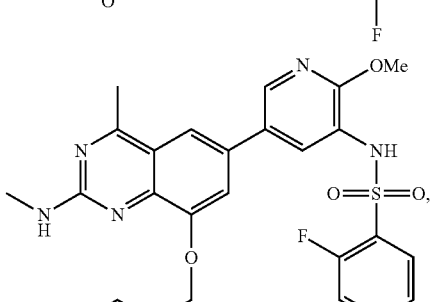

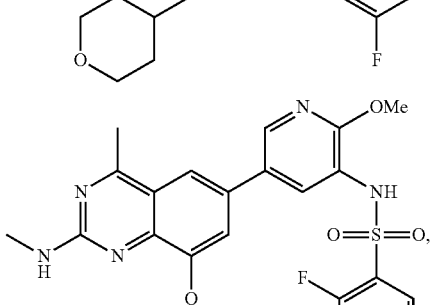

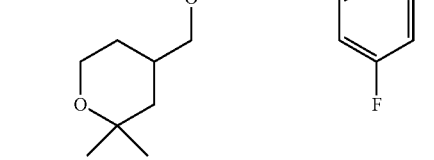

-continued

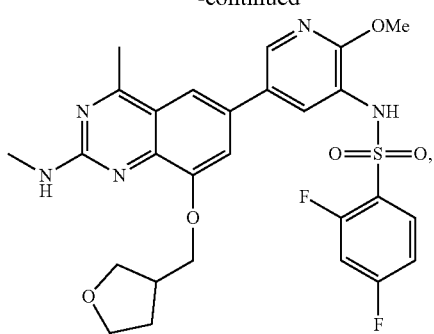

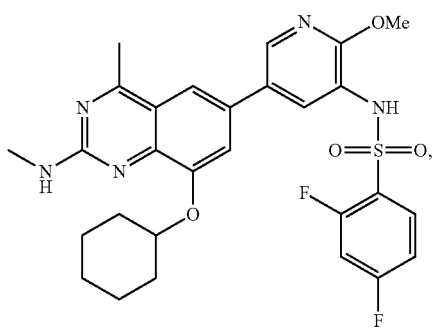

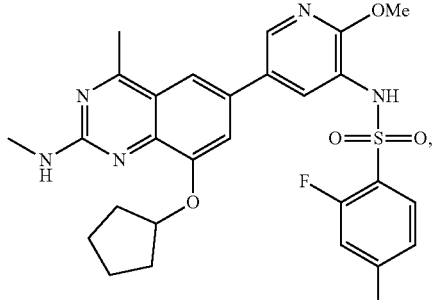

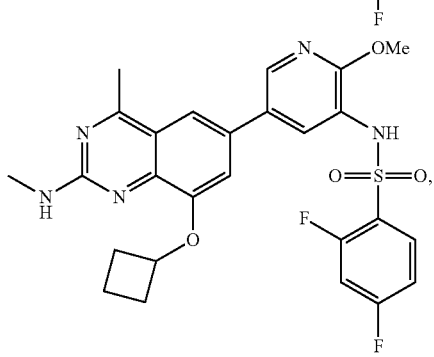

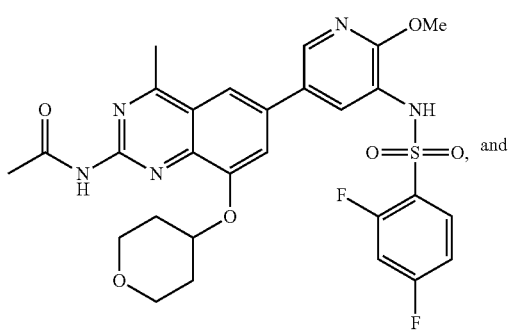

and

-continued

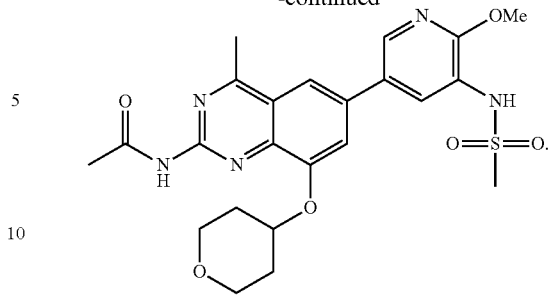

In a still preferred embodiment, the present invention provides a compound represented by formula (IV), or a stereoisomer, a geometric isomer, a tautomer or a pharmaceutically acceptable salt thereof,

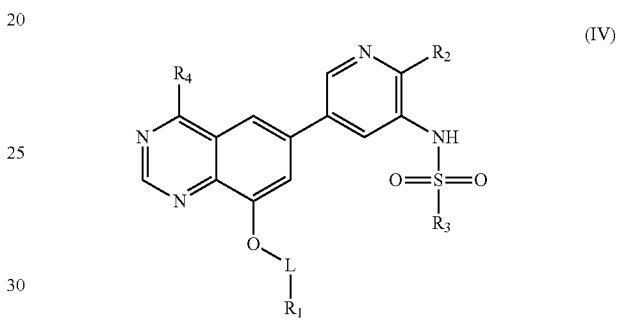

(IV)

wherein, $R_4$ is $C_{1-3}$ alkyl, preferably methyl;

L is selected from a single bond or $C_{1-3}$ alkylene, wherein the $C_{1-3}$ alkylene is optionally substituted with one or more Ra;

Ra is selected from hydrogen, halogen or $C_{1-3}$ alkyl;

$R_1$ is selected from hydrogen, $C_{1-3}$ alkyl, $C_{1-3}$ alkoxy, 3- to 7-membered cycloalkyl, 3- to 7-membered heterocycloalkyl or 5- to 6-membered heteroaryl. When $R_1$ is not hydrogen, it is optionally substituted with m $R_6$;

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino;

$R_2$ is selected from $C_{1-3}$ alkoxy, halogen or $C_{1-3}$ alkyl;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with one or more groups that are independently selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy.

In a further preferred embodiment, the present invention provides a compound represented by formula (IV), or a stereoisomer, a geometric isomer, a tautomer or a pharmaceutically acceptable salt thereof, wherein, $R_4$ is $C_{1-3}$ alkyl, preferably methyl;

L is selected from a single bond or $C_{1-3}$ alkylene, wherein the $C_{1-3}$ alkylene is optionally substituted with one or more Ra;

Ra is selected from hydrogen, halogen or $C_{1-3}$ alkyl;

$R_1$ is selected from cyclopropyl, cyclobutyl, cyclopentyl and cyclohexyl; $R_1$ is optionally substituted with m $R_6$;

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino;

$R_2$ is selected from $C_{1-3}$ alkoxy, halogen or $C_{1-3}$ alkyl;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with one or more groups that are independently selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy.

In a still further preferred embodiment, the present invention provides a compound represented by formula (IV), or a stereoisomer, a geometric isomer, a tautomer or a pharmaceutically acceptable salt, wherein, $R_4$ is $C_{1-3}$ alkyl, preferably methyl;

L is selected from a single bond or $C_{1-3}$ alkylene, wherein the $C_{1-3}$ alkylene is optionally substituted with one or more Ra;

Ra is selected from hydrogen, halogen or $C_{1-3}$ alkyl;

$R_1$ is 3- to 7-membered heterocycloalkyl containing oxygen, and $R_2$ is optionally substituted with m $R_6$;

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino;

$R_2$ is selected from $C_{1-3}$ alkoxy, halogen or $C_{1-3}$ alkyl;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with one or more groups that are independently selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy.

In a further preferred embodiment, $R_1$ is selected from:

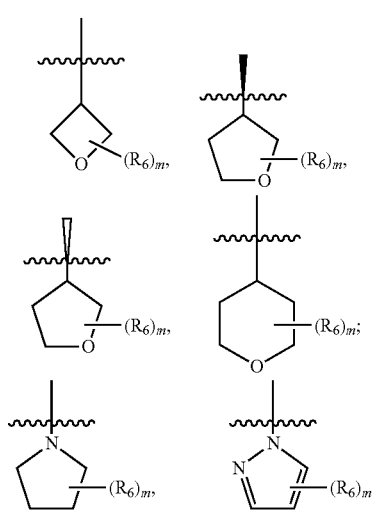

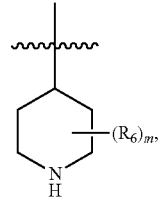 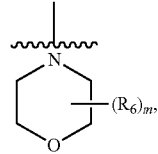

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino.

In a further preferred embodiment, $R_2$ is selected from:

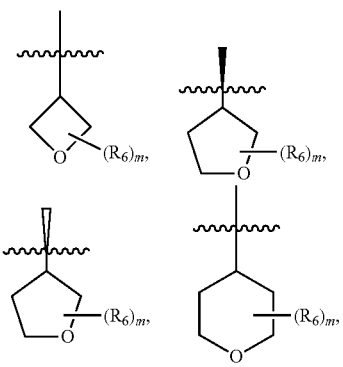

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino.

In a further preferred embodiment, $R_6$ is independently selected from F or methyl.

In a still further preferred embodiment, the present invention provides a compound represented by formula (IV), or a stereoisomer, a geometric isomer, a tautomer or a pharmaceutically acceptable salt thereof, wherein, $R_4$ is $C_{1-3}$ alkyl, preferably methyl;

L is selected from a single bond or —$CH_2$—, $R_1$ is selected from hydrogen, $C_{1-3}$ alkyl, $C_{1-3}$ alkoxy, 3- to 7-membered cycloalkyl, 3- to 7-membered heterocycloalkyl or 5- to 6-membered heteroaryl; preferably, $R_1$ is selected from 3- to 7-membered cycloalkyl, including but not limited to cyclopropyl, cyclobutyl, cyclopentyl and cyclohexyl; or preferably, $R_1$ is 3- to 7-membered heterocycloalkyl and further preferably 3- to 7-membered heterocycloalkyl containing oxygen, including but not limited to

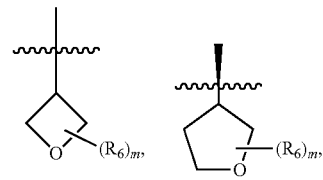

-continued

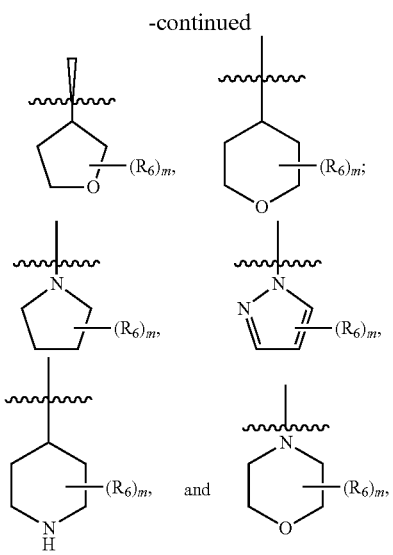

preferably including but not limited to

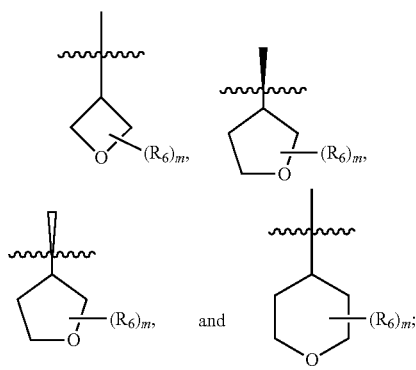

when R₁ is not hydrogen, it is optionally substituted with m R₆.

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino; preferably, Rb is independently selected from F or methyl;

$R_2$ is selected from $C_{1-3}$ alkoxy, halogen or $C_{1-3}$ alkyl;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with one or more groups that are independently selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy.

In a still further preferred embodiment, the present invention provides a compound represented by formula (IV), or a stereoisomer, a geometric isomer, a tautomer or a pharmaceutically acceptable salt thereof, wherein, $R_4$ is $C_{1-3}$ alkyl, preferably methyl;

L is selected from a single bond or $C_{1-3}$ alkylene, wherein the $C_{1-3}$ alkylene is optionally substituted with one or more Ra; preferably, L is selected from a single bond or —CH₂—;

$R_1$ is selected from hydrogen, $C_{1-3}$ alkyl, $C_{1-3}$ alkoxy, 3- to 7-membered cycloalkyl, 3- to 7-membered heterocycloalkyl or 5- to 6-membered heteroaryl; preferably, $R_1$ is selected from 3- to 7-membered cycloalkyl, including but not limited to cyclopropyl, cyclobutyl, cyclopentyl and cyclohexyl; or preferably, $R_1$ is 3- to 7-membered heterocycloalkyl and further preferably 3- to 7-membered heterocycloalkyl containing oxygen, including but not limited to

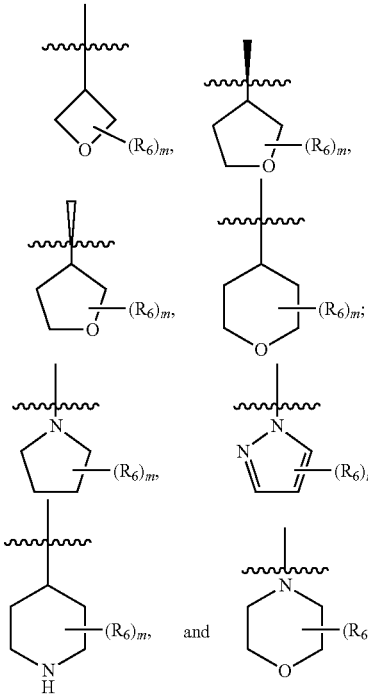

preferably including but not limited to

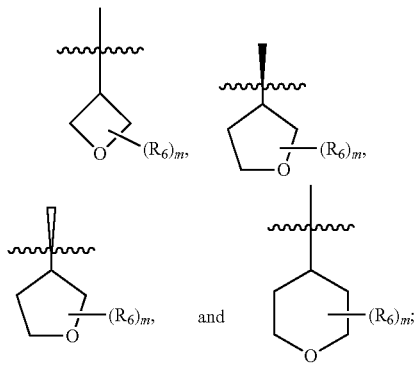

when R₁ is not hydrogen, it is optionally substituted with m R₆;

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino; preferably, Rb is independently selected from F or methyl;

$R_2$ is selected from methoxy, chloro or methyl;

$R_3$ is selected from $C_{1-3}$ alkyl, 3- to 7-membered cycloalkyl, 6- to 10-membered aryl or 5- to 6-membered heteroaryl, wherein 6- to 10-membered aryl and 5- to 6-membered heteroaryl are optionally substituted with one or more groups that are independently selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy.

In a still further preferred embodiment, the present invention provides a compound represented by formula (IV), or a stereoisomer, a geometric isomer, a tautomer or a pharmaceutically acceptable salt thereof, wherein, $R_4$ is $C_{1-3}$ alkyl, preferably methyl;

L is selected from a single bond or $C_{1-3}$ alkylene, wherein the $C_{1-3}$ alkylene is optionally substituted with one or more Ra; preferably, L is selected from a single bond or —$CH_2$—;

$R_1$ is selected from hydrogen, $C_{1-3}$ alkyl, $C_{1-3}$ alkoxy, 3- to 7-membered cycloalkyl, 3- to 7-membered heterocycloalkyl or 5- to 6-membered heteroaryl; preferably, $R_1$ is selected from 3- to 7-membered cycloalkyl, including but not limited to cyclopropyl, cyclobutyl, cyclopentyl and cyclohexyl; or preferably, $R_1$ is 3- to 7-membered heterocycloalkyl and further preferably 3- to 7-membered heterocycloalkyl containing oxygen, including but not limited to

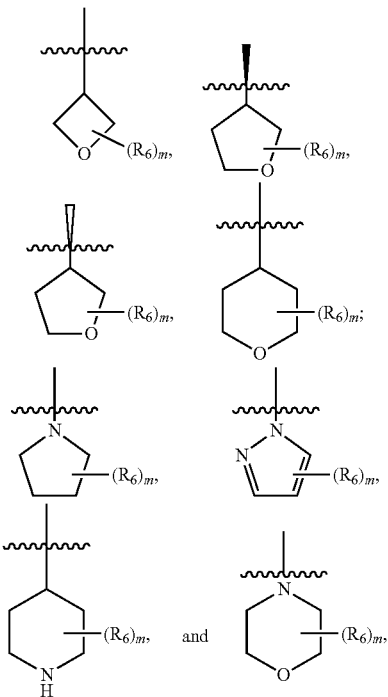

preferably including but not limited to

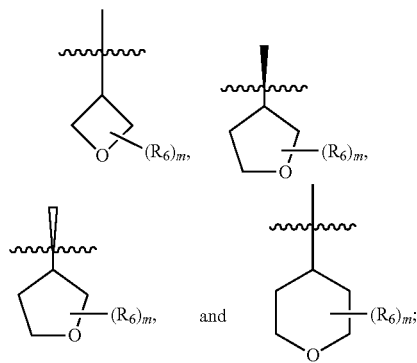

when $R_1$ is not hydrogen, it is optionally substituted with m $R_6$.

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino; preferably, Rb is independently selected from F or methyl;

$R_2$ is selected from $C_{1-3}$ alkoxy, halogen or $C_{1-3}$ alkyl; preferably, $R_2$ is selected from methoxy, chloro or methyl;

$R_3$ is selected from hydrogen, $C_{1-3}$ alkyl, 3- to 7-membered cycloalkyl, phenyl or thienyl, wherein the phenyl or thienyl are optionally substituted with one or more groups that are independently selected from halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy.

In a further preferred embodiment, $R_3$ is selected from phenyl or thienyl, wherein phenyl and thienyl are optionally substituted with one or more substitutents independently selected from fluoro or chloro.

Specifically, the compounds preferred according to the invention are as follows:

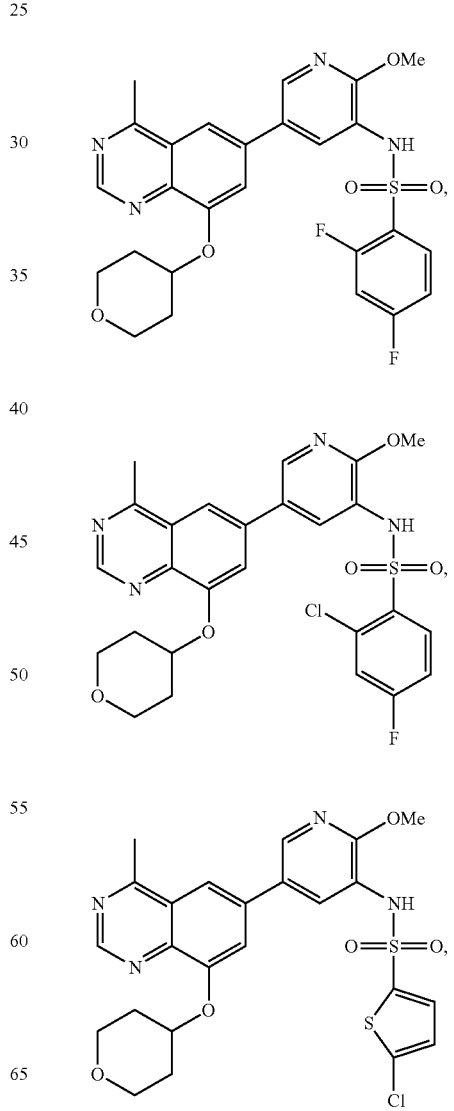

-continued
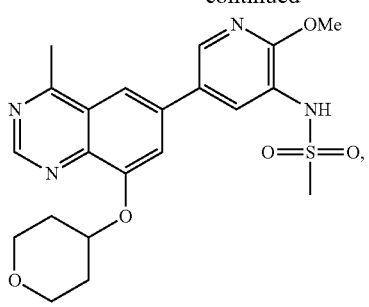
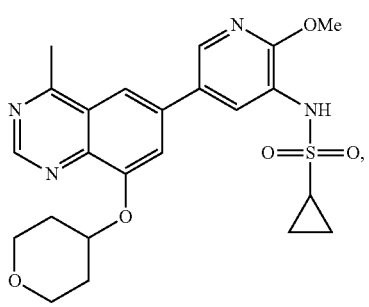
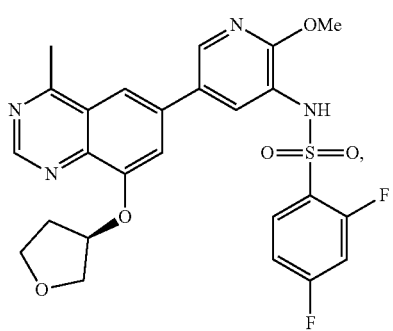
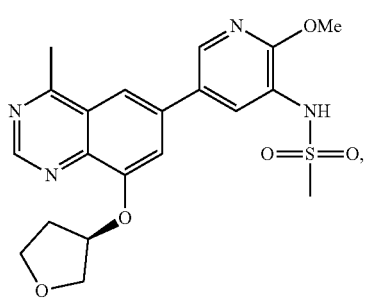
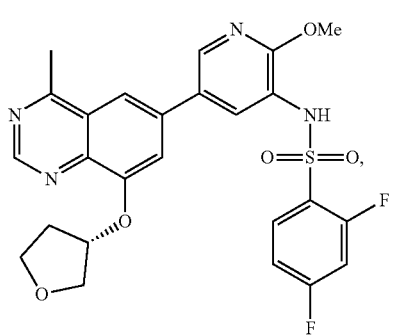
-continued
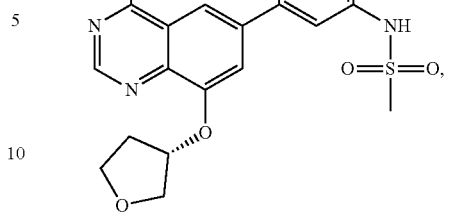
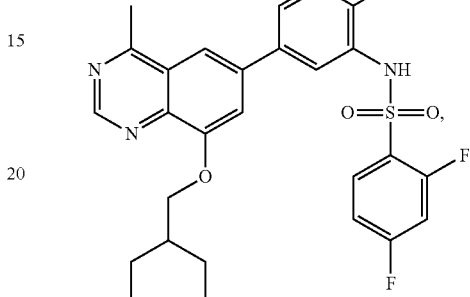
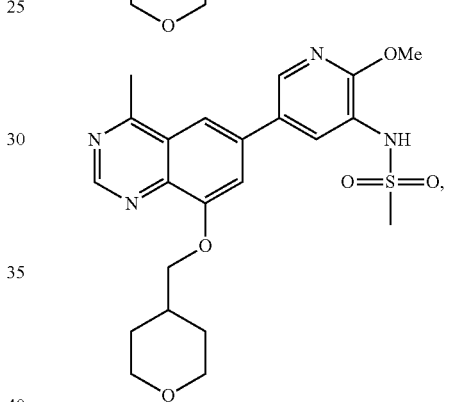
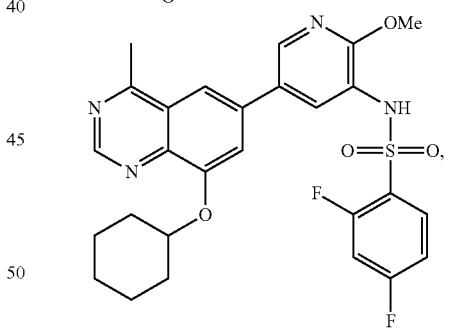
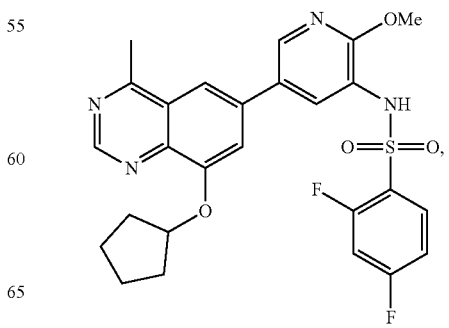

31
-continued
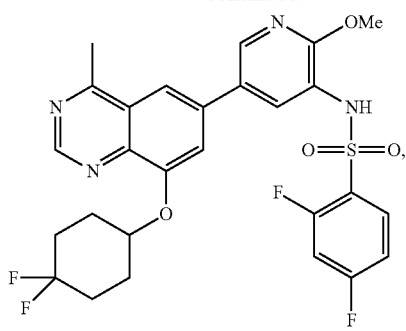
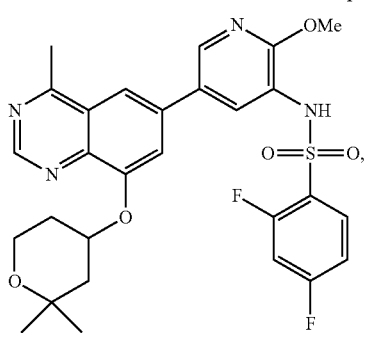
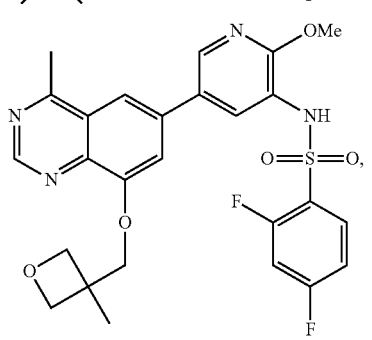
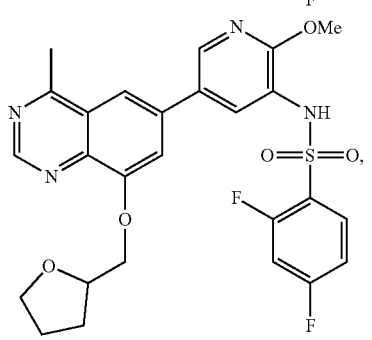
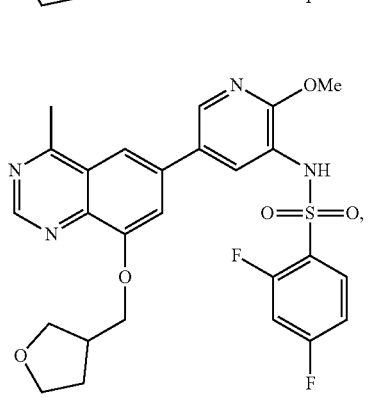
32
-continued
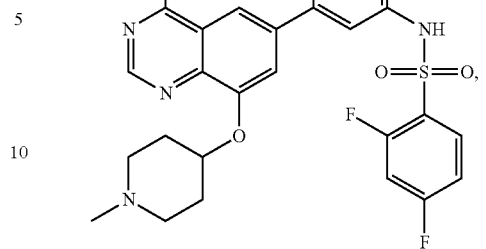
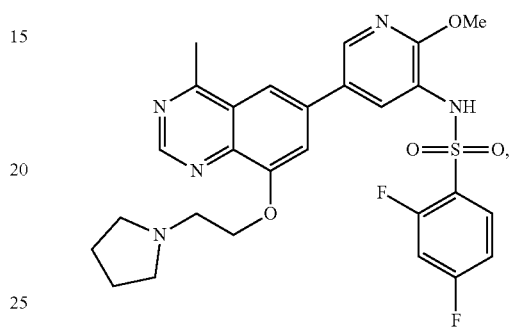
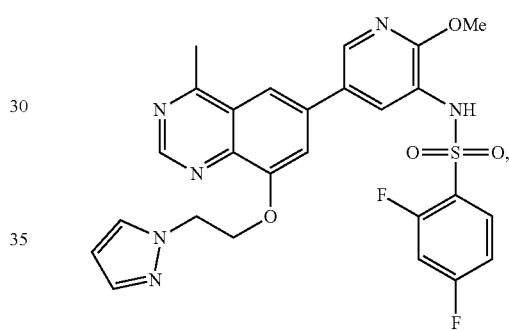
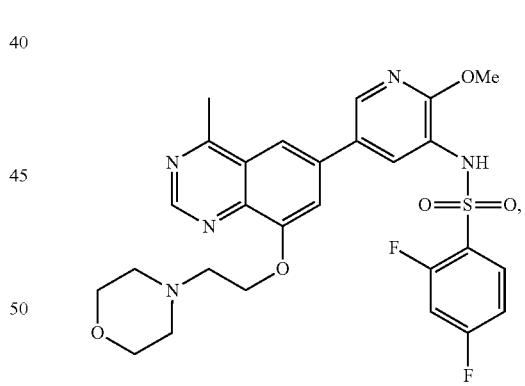
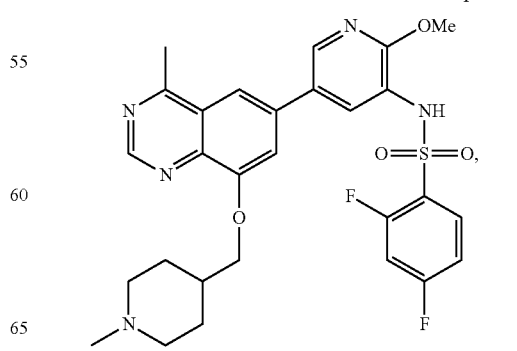

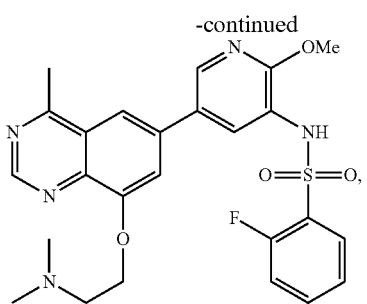
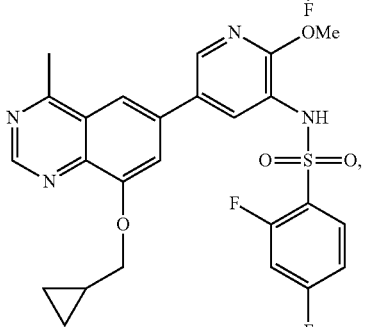
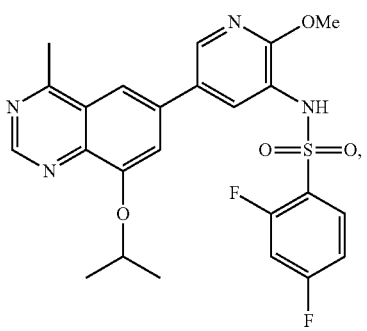
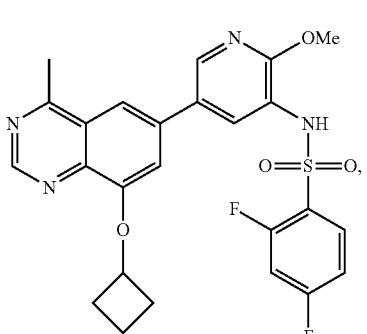
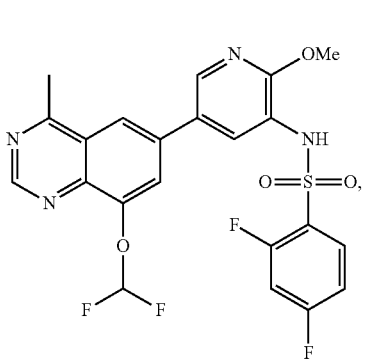
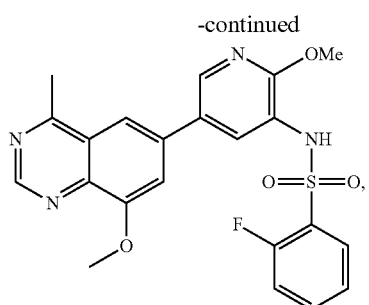
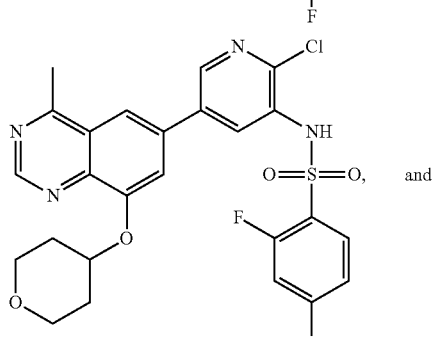
and
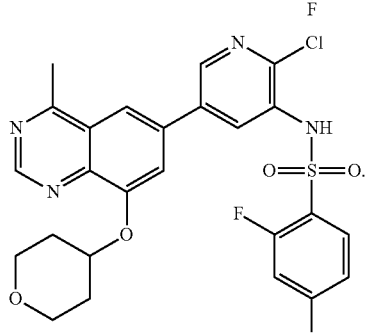
The second aspect of the present invention provides a method for preparing the said compound, or a stereoisomer, a geometric isomer, a tautomer or a pharmaceutically acceptable salt thereof, which includes the following steps of:
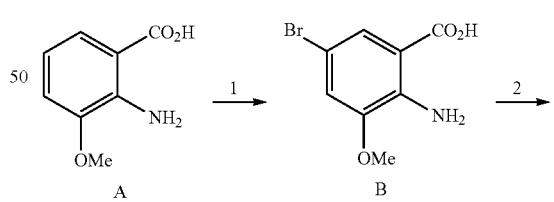
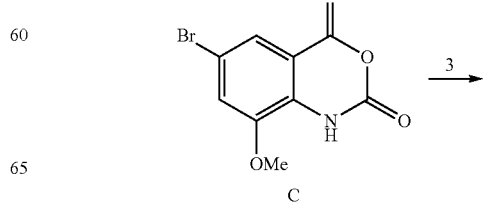

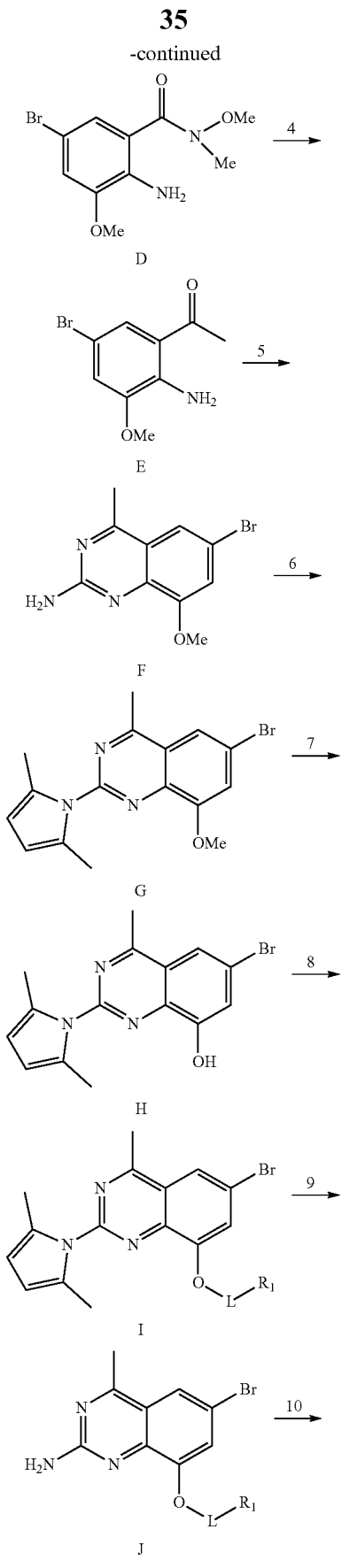

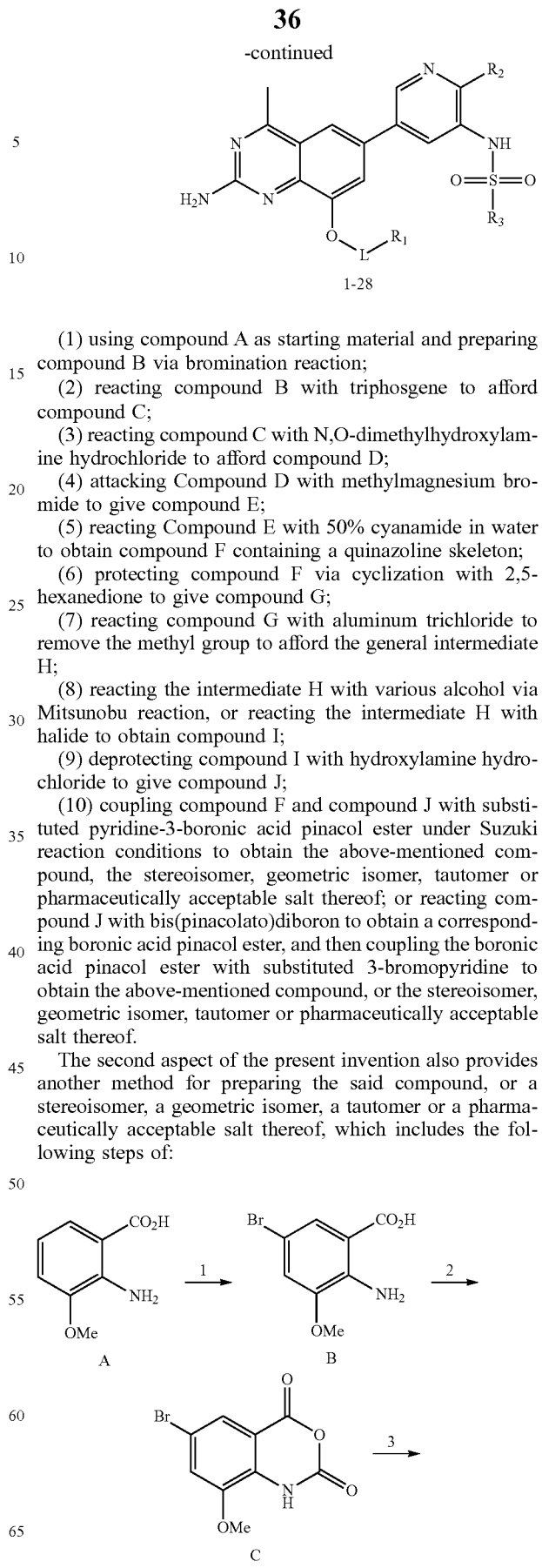

(1) using compound A as starting material and preparing compound B via bromination reaction;

(2) reacting compound B with triphosgene to afford compound C;

(3) reacting compound C with N,O-dimethylhydroxylamine hydrochloride to afford compound D;

(4) attacking Compound D with methylmagnesium bromide to give compound E;

(5) reacting Compound E with 50% cyanamide in water to obtain compound F containing a quinazoline skeleton;

(6) protecting compound F via cyclization with 2,5-hexanedione to give compound G;

(7) reacting compound G with aluminum trichloride to remove the methyl group to afford the general intermediate H;

(8) reacting the intermediate H with various alcohol via Mitsunobu reaction, or reacting the intermediate H with halide to obtain compound I;

(9) deprotecting compound I with hydroxylamine hydrochloride to give compound J;

(10) coupling compound F and compound J with substituted pyridine-3-boronic acid pinacol ester under Suzuki reaction conditions to obtain the above-mentioned compound, the stereoisomer, geometric isomer, tautomer or pharmaceutically acceptable salt thereof; or reacting compound J with bis(pinacolato)diboron to obtain a corresponding boronic acid pinacol ester, and then coupling the boronic acid pinacol ester with substituted 3-bromopyridine to obtain the above-mentioned compound, or the stereoisomer, geometric isomer, tautomer or pharmaceutically acceptable salt thereof.

The second aspect of the present invention also provides another method for preparing the said compound, or a stereoisomer, a geometric isomer, a tautomer or a pharmaceutically acceptable salt thereof, which includes the following steps of:

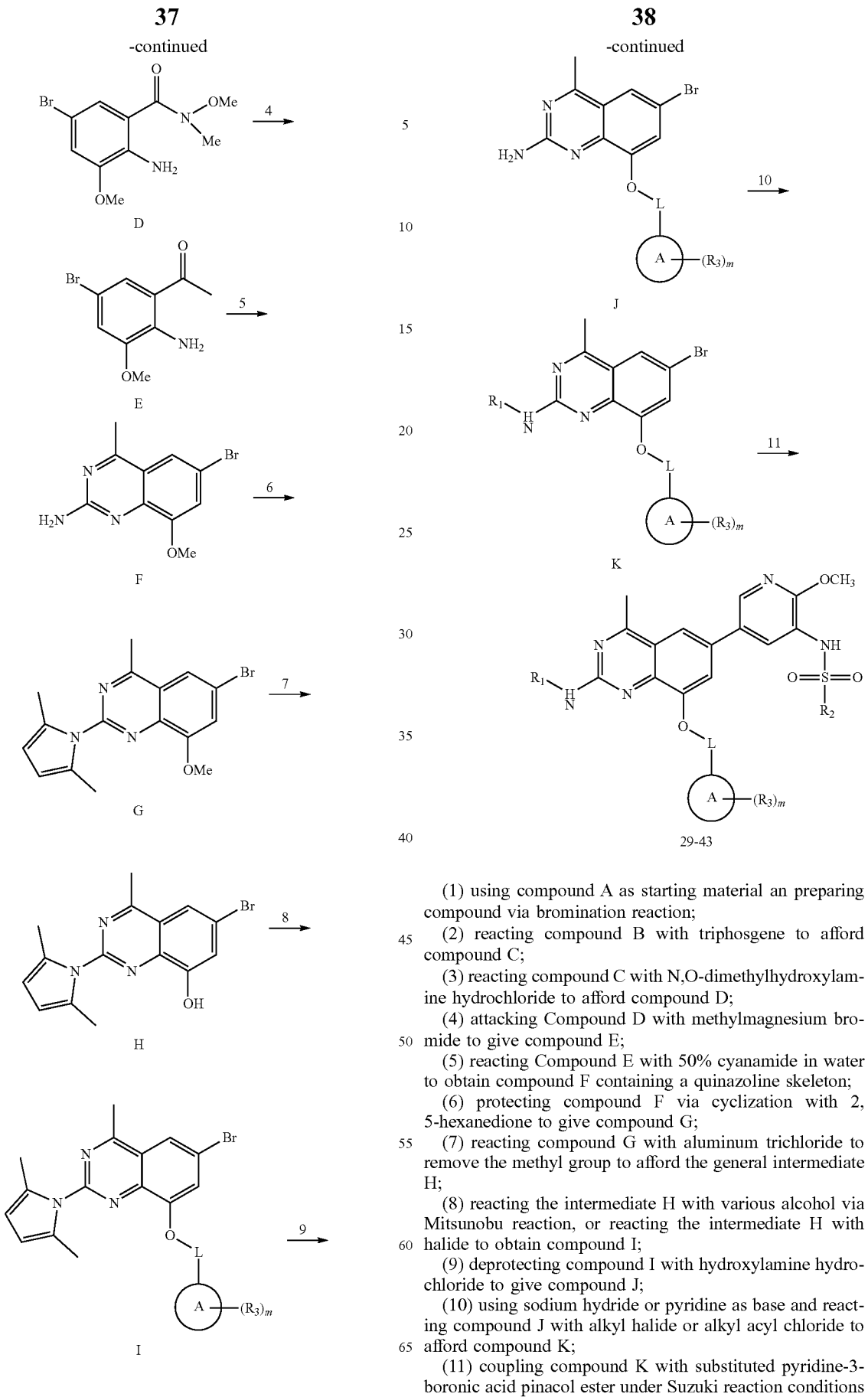

(1) using compound A as starting material an preparing compound via bromination reaction;

(2) reacting compound B with triphosgene to afford compound C;

(3) reacting compound C with N,O-dimethylhydroxylamine hydrochloride to afford compound D;

(4) attacking Compound D with methylmagnesium bromide to give compound E;

(5) reacting Compound E with 50% cyanamide in water to obtain compound F containing a quinazoline skeleton;

(6) protecting compound F via cyclization with 2,5-hexanedione to give compound G;

(7) reacting compound G with aluminum trichloride to remove the methyl group to afford the general intermediate H;

(8) reacting the intermediate H with various alcohol via Mitsunobu reaction, or reacting the intermediate H with halide to obtain compound I;

(9) deprotecting compound I with hydroxylamine hydrochloride to give compound J;

(10) using sodium hydride or pyridine as base and reacting compound J with alkyl halide or alkyl acyl chloride to afford compound K;

(11) coupling compound K with substituted pyridine-3-boronic acid pinacol ester under Suzuki reaction conditions to obtain the above-mentioned compound, the stereoisomer, geometric isomer, tautomer or pharmaceutically acceptable salt thereof.

The second aspect of the present invention also provides another method for preparing the said compound, or a stereoisomer, a geometric isomer, a tautomer or a pharmaceutically acceptable salt thereof, which includes the following steps of:

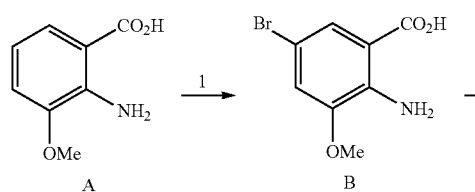

(1) using compound A as starting material and preparing compound B via bromination reaction;

(2) reacting compound B with triphosgene to afford compound C;

(3) reacting compound C with N,O-dimethylhydroxylamine hydrochloride to afford compound D;

(4) attacking compound D with methylmagnesium bromide to give compound E;

(5) reacting compound E with ammonium formate and formamide to obtain compound L containing a quinazoline skeleton.

(6) reacting compound L with aluminum trichloride to remove the methyl group to afford the general intermediate M.

(7) reacting the intermediate M with various alcohol via Mitsunobu reaction, or reacting the intermediate M with halide to obtain compound N;

(8) coupling compound N with substituted pyridine-3-boronic acid pinacol ester under Suzuki reaction conditions to obtain the above-mentioned compound, the stereoisomer, geometric isomer, tautomer or pharmaceutically acceptable salt thereof; or reacting compound N with bis(pinacolato)diboron to obtain a corresponding boronic acid pinacol ester, and then coupling the boronic acid pinacol ester with substituted 3-bromopyridine to obtain the above-mentioned compound, or the stereoisomer, geometric isomer, tautomer or pharmaceutically acceptable salt thereof.

The third aspect of the present invention provides a pharmaceutical composition, which comprise an above-mentioned compound, or a stereoisomer, a geometric isomer, a tautomer or a pharmaceutically acceptable salt thereof, as well as an optional pharmaceutically acceptable carrier and/or excipient. Preferably, the pharmaceutical composition further comprises one or more active pharmaceutical ingredients for prevention and/or treatment of cancer, immune diseases, cardiovascular diseases, viral infections, inflammation, metabolism/endocrine function disorders or neurological diseases in addition to the above-mentioned compound, or the stereoisomer, the geometric isomer, the tautomer or the pharmaceutically acceptable salt thereof. Preferably, the pharmaceutical composition is a pharmaceutically acceptable pharmaceutical preparation for prevention and/or treatment of cancer, immune diseases, cardiovascular diseases, viral infections, inflammation, metabolism/endocrine function disorders or neurological diseases.

In another aspect, the present invention also provides a pharmaceutical preparation, which comprises at least one compound mentioned above, or a stereoisomer, a geometric isomer, a tautomer or a pharmaceutically acceptable salt thereof, and optionally a pharmaceutically acceptable carrier and/or excipient. Preferably, the pharmaceutical preparation is selected from the following preparations: parenteral preparation, such as solution for injection or suspension; enteral preparation, such as oral preparation, e.g. tablet or capsule; topical preparation such as lotion, gel, ointment, emulsion, nasal preparation, suppository, transdermal preparation or ophthalmic preparation.

In another aspect, the present invention also provides use of the compound, or a stereoisomer, a geometric isomer, a tautomer or a pharmaceutically acceptable salt thereof, or the pharmaceutical composition in the preparation of a medicament for preventing and/or treating cancer, immune diseases, cardiovascular diseases, viral infections, inflammation, metabolism/endocrine function disorders or neurological diseases. In other words, the present invention provides a method for prevention and/or treatment of cancer, immune diseases, cardiovascular diseases, viral infections, inflammation, metabolism/endocrine function disorders or neurological diseases. The method includes administering a prophylactically and/or therapeutically effective amount of the compound, the stereoisomer, the geometric isomer, the tautomer or the pharmaceutically acceptable salt thereof, or the pharmaceutical composition to a subject in need thereof.

Some of the terms used in the present invention are defined as follows, and other undefined terms have the meaning known to those skilled in the art.

Halogen refers to fluorine, chlorine, bromine or iodine.

$C_{1-3}$ alkylene refers to a straight or branched bivalent saturated hydrocarbon radical having 1 to 3 carbon atoms. Examples of such groups include, but are not limited to: methylene (—CH$_2$—), ethylene (—CH$_2$CH$_2$—), and propylene (—CH$_2$CH$_2$CH$_2$—).

$C_{1-3}$ alkyl refers to a straight or branched saturated aliphatic hydrocarbon radical having 1 to 3 carbon atoms. Examples of such groups include, but are not limited to: methyl, ethyl, propyl, isopropyl.

3- To 7-membered cycloalkyl refers to a saturated monocyclic, fused, spirolcyclic or polycyclic structure having 3 to 7 carbon ring atoms. Examples of such groups include, but are not limited to: cyclopropyl, cyclobutyl, cyclopentyl, cyclopentenyl, cyclohexyl and cycloheptyl.

3- To 7-membered heterocycloalkyl refers to a saturated or partially unsaturated (i.e. having one or more double bonds and/or triple bonds in ring) carbon ring group having 3 to 7 ring atoms, wherein one or more ring atoms are heteroatoms selected from nitrogen, oxygen or S(O)m (m is an integer of 0-2), but not including —O—O—, —O—S— or —S—S— as part of the ring, and the rest of ring atoms are carbon. Specific examples of 3- to 7-membered saturated heterocycloalkyl include but are not limited to: oxiranyl, aziridinyl, azetidinyl, oxetanyl, thiacyclobutyl, dihydrofuranyl, tetrahydrofuranyl, tetrahydrothienyl, pyrrolidinyl, imidazolidinyl, pyrazolidinyl, oxazolidinyl, isoxazolidinyl, thiazolidinyl, isothiazolidinyl, 1,4-dioxanyl, 1,3-dioxanyl, 1,3-dithiacyclohexyl, piperidyl, morpholinyl, piperazinyl, dihydropyranyl, tetrahydropyranyl, tetrahydrothiopyranyl, etc.; preferably, oxacyclobutyl, tetrahydrofuranyl, tetrahydropyranyl, piperidinyl, morpholinyl, piperazinyl.

$C_{1-3}$ alkoxy refers to —O-alkyl, wherein the alkyl contains 1 to 3 carbon atoms and is straight, branched or cyclic. Examples of such groups include, but are not limited to: methoxy, ethoxy, n-propoxy, iso-propoxy, or cyclopropoxy.

Aryl refers to a monocyclic or bicyclic aromatic carbon ring group, which usually has 6 to 10 carbon atoms, such as phenyl or naphthyl, preferably phenyl.

Heteroaryl refers to 5- or 6-membered aromatic heterocyclic group of a single ring, including but not limited to: 5-membered heteroaryl: furyl, thienyl, pyrrolyl, oxazolyl, isoxazolyl, thiazolyl, isothiazolyl, imidazolyl, pyrazolyl, triazolyl (1,2,4-triazolyl, 1,3,4-triazolyl or 1,2,3-triazolyl), thiadiazolyl (1,3,4-thiadiazolyl, 1,2,5-thiadiazolyl, 1,2,3-thiadiazolyl or 1,2,4-thiadiazolyl) and oxadiazolyl (1,3,4-oxadiazolyl, 1,2,5-oxadiazolyl, 1,2,3-oxadiazolyl or 1,2,4-oxadiazolyl), and 6-membered heteroaryl: pyridinyl, pyrimidinyl, pyrazinyl and pyridazinyl, and bicyclic group such as benzofuranyl, benzothienyl, indazolyl, purinyl, quinolyl, isoquinolyl, phthalazinyl, naphthyridinyl, chinocalinyl, quinazolinyl, cinnolyl, pteridyl, indolizinyl, indolyl, isoindolyl. The preferred heteroaryl groups are thienyl, thiazolyl, pyridyl and pyrimidyl.

A single bond refers to direct connection of two groups, for example, in O-L-R, when L is a single bond, actually the structure is O—R.

"Optionally" means that the event or environment described subsequently can but does not have to occur, and the description includes the situation where the event or circumstance occurs or does not occur. For example, "alkyl optionally substituted with halogen" means that halogen can but does not have to exist. The description includes situation of alkyl substituted with halogen and situation of alkyl unsubstituted with halogen.

If a group, for example, "$R_6$", is depicted as "floating" on ring A in the formula:

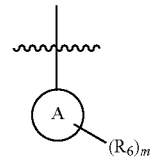

it means that "$R_6$" may reside on any atom of the ring system, and is considered as replacement of a depicted, implied or clearly defined hydrogen on one of the ring atoms, as long as a stable structure is formed.

The compound of the present invention may contain one or more chiral centers, which exist in different stereoisomeric forms. All stereoisomeric forms of the compound of the present invention, including but not limited to diastereomer, enantiomer and atropisomer and their mixture (such as racemic mixture) are included in the scope of the present invention.

The compound of the present invention includes its geometrical isomer. For example, if the compound of the present invention contains double bond or fused ring, these compounds can have geometrical isomers, and their cis-form and trans-form and mixture of cis-forms and trans-forms are included in the scope of the present invention.

The compound of the present invention includes its tautomer. Tautomer refers to structural isomers of different energies that are mutually converted via low energy barriers, such as ketone-enol and imine-enamine tautomerizations.

The compound of the present invention also includes its isotopically-labelled compound, wherein one or more atoms are replaced by an atom having the same atomic number but different atomic mass or mass number usually found in nature. Examples include but are not limited to: hydrogen isotopes $^2$H and $^3$H; carbon isotopes $^{11}$C, $^{13}$C and $^{14}$C; chlorine isotope $^{36}$Cl; fluorine isotope $^{18}$F; iodine isotopes $^{123}$I and $^{121}$I; nitrogen isotopes $^3$N and $^{15}$N; oxygen isotopes $^{15}$O, $^{17}$O and $^{18}$O; phosphorus isotope $^{32}$P and sulfur isotope $^{35}$S.

Various hydrates, solvates and polymorphs of the compound of the present invention or its salt are also included in the scope of the present invention.

The prodrug of the compound of the present invention is also included in the scope of the present invention. Some derivatives of the compound of the present invention have weak or no pharmacological activity themselves, but when these derivatives are administered in vivo or to body, they can be converted into the compound of the present invention having pharmacological activity by means of such as hydrolytic cleavage, and these derivatives are referred to as prodrugs. Further information on prodrug use can be found in Pro-drugs as Novel Delivery Systems, Vol. 14, ACS Symposium Series (T. Higuchi and W. Stella) and Bioreversible Carriers in Drug Design, Pergamon Press, 1987 (ed. E. b. Roche, American Pharmaceutical Association).

The compound of the present invention includes pharmaceutically acceptable salt.

Pharmaceutically acceptable salt refers to a salt that is pharmaceutically acceptable and has pharmacological activity required by the parent compound. The pharmaceutically acceptable salt was described in detail by Berge et al. in J. Pharma. Sci., 1977, 66, 1-19, and the literature is hereby incorporated by reference. The compound of the present invention can include sufficient acidic groups, sufficient alkaline groups or functional groups with both acidic and alkaline properties, and react with corresponding inorganic or organic bases, or inorganic and organic acids to form pharmaceutically acceptable salt. Examples of pharmaceutically acceptable salt include sulfate salt, pyrosulfate salt, bisulfate salt, sulfite salt, bisulfite salt, phosphate salt, monohydrogen phosphate salt, dihydrogen phosphate salt, metaphosphate salt, pyrophosphate salt, hydrochloride, hydrobromide, hydriodate salt, acetate salt, propionate salt, decanoate salt, caprylate salt, acrylate salt, formate salt, isobutyrate salt, caproate salt, enanthate salt, propiolate salt, oxalate salt, malonate salt, succinate salt, suberate salt, sebacate salt, fumarate salt, maleate salt, acetylene-1,4-dicarboxylate salt, butyne-1,6-dicarboxylate salt, benzoate salt, chlorinated benzoate salt, methylbenzoate salt, dinitrobenzoate salt, hydroxybenzoate salt, methoxybenzoate salt, phthalate salt, sulfonate salt, xylenesulfonate salt, phenylacetate salt, phenylpropionate salt, phenylbutyrate salt, citrate salt, lactate salt, gamma-hydroxybutyrate salt, hydroxyacetate salt, tartrate salt, methane sulfonate salt, propanesulfonate salt, naphthalene-1-sulfonate salt, naphthalene-2-sulfonate salt and mandelate salt.

When the compound of the present invention is used as drug, it is usually administered in the form of pharmaceutical composition. Therefore, pharmaceutical composition comprising the compound of the present invention and pharmaceutically acceptable carriers, diluents or excipients is also included in the scope of the invention. The carriers, auxiliaries and excipients used herein include any and all solvents, diluents or other liquid excipients, dispersants or suspending agents, surfactants, isotonic agents, thickeners or emulsifiers, preservatives, solid binders, lubricants, etc. suitable for the desired specific preparation. Various carriers for preparing pharmaceutically acceptable compositions and known technique for their preparation are disclosed in Remington: The Science and Practice of Pharmacy, 21' edition, 2005, ed. D. B. Troy, Lippincott Williams&Wilkins, Philadelphia, Encyclopedia of Pharmaceutical Technology, eds. and J. Swarbrick, J. C. Boylan, 1988-1999, Marcel Dekker, New York, the contents of which are hereby incorporated by reference.

The composition of the present invention can be administered in any route suitable for diseases to be treated, in particular administration routes as follows: parenterally, such as in injection solution or suspension form; transenterally, such as orally, for example in tablet or capsule form; topically, such as in lotion, gel, ointment or emulsion form or in nasal or suppository form. Topical administration is for example applied to the skin. Another form of topical administration is administration to eye.

Pharmaceutical composition can be administered in solid, semi-solid, liquid or gaseous form, or can be as dried powder, such as in freeze-drying form. Pharmaceutical composition can be packaged in transportable form, including, for example, solid preparation such as capsule, medicine capsule, cachet, gelatin, paper, tablet, suppository, pellet, pill, lozenge and pastille. The packaging type generally depends on administration route. Implantable sustained release preparations as well as transdermal preparations are also included.

Examples of materials as pharmaceutically acceptable carrier include, but are not limited to: ion exchanger, alumina, aluminum stearate, lecithin, serum protein (e.g. human serum albumin), buffering substance (e.g., phosphate salt), glycine, sorbic acid and potassium sorbate, partial glyceride mixture of saturated fatty acids, water, salt or electrolyte (for example, protamine sulfate, disodium hydrogen phosphate, potassium hydrogen phosphate, sodium chloride, zinc salt), colloidal silicon dioxide, magnesium trisilicate, polyvinylpyrrolidone, polyacrylate, wax, polyethylene-polyoxypropylene block copolymer, lanolin, sugar (e.g. lactose, glucose and sucrose), starch (such as corn starch and potato starch), cellulose and its derivatives such as sodium carboxymethyl cellulose, ethyl cellulose and cellulose acetate; Tragacanth powder; malt; gelatin; talc powder; excipient such as cocoa butter and wax for suppository; oil such as peanut oil, cottonseed oil, safflower oil, sesame oil, olive oil, corn oil and soybean oil; glycol such as propylene glycol or polyethylene glycol; ester such as ethyl oleate and ethyl laurate; agar; buffer agent such as magnesium hydroxide and aluminum hydroxide; alginic acid; pyrogen-free water; isotonic brine; Ringer's liquid; ethanol; and phosphate buffer, and other non-toxic and compatible lubricants such as sodium lauryl sulfate and magnesium stearate. According to the judge of preparation preparing personnel, colorant, releaser, coating agent, sweetener, flavoring agent, fragrant agent, preservative and antioxidant can also be present in the composition.

The compound of the present invention can be used alone or in combination with other therapeutic agents for treating the diseases or symptoms (such as cancer) described in the invention. In some embodiments, the compound of the present invention is combined in pharmaceutical combination preparation or combined in administration scheme as combination therapy with a second compound having high-proliferation resistance or for treating highly proliferative diseases (such as cancer). The second compound in the pharmaceutical combination preparation or quantitative administration scheme preferably has activity complementary to the compound of the present invention, so that they do not adversely affect each other. Such compounds appropriately exist in combination with quantity that is effective for planning purpose. In one embodiment, the compound of the present invention is combined with other anti-tumor drugs. The antitumor drugs include: alkylating agents including but not limited to cyclophosphamide, nitrogen mustard, melphalan, chlorambucil, carmostine; platinum metals including but not limited to carboplatin, cisplatin, oxaliplatin; topoisomerase inhibitors including but not limited to topotecan, camptothecin, topotecan, irinotecan; antibiotics including but not limited to anisomycin, actinomycin D, daunorubicin, doxorubicin, mitoxantrone, bleomycin and mithramycin; anti-microtubule or anti-mitotic agents including but not limited to paclitaxel, vinorelbine, docetaxel, doxorubicin; antimetabolites including but not limited to fluorouracil, methotrexate, cytarabine, mecaptopurine, thioguanine and gemcitabine; antibodies including but not limited to herceptin and bevacizumab; hormones including but not limited to letrazole, vorazole, tamoxifen, toremifene, fulvestrant, flutamide, nilutamide and triptorelin; kinase inhibitors such as EGFR kinase inhibitors including but not limited to gefitinib, erlotinib, lapatinib and afatinib; VEGFR inhibitors including but not limited to sorafenib, regorafenib, sunitinib, cabozantinib, pazopanib, vandetanib, axitinib; ALK inhibitors including but not limited to crizotinib, ceritinib and alectinib; Bcr-Abl inhibitors including but are not limited to imatinib, ponatinib, nilotinib and dasatinib; BTK inhibitors including but not limited to ibrutinib; B-RAF inhibitors including but not limited to vemurafenib; Cyclin-dependent kinase CDK4/6 inhibitor palbociclib; mTOR inhibitors including but not limited to rapamycin and everolimus; deacetylase inhibitors including but not limited to vorinostat; and PD1/PDL1 antibodies such as Keytruda (Pembrolizumab) and Opdivo (Nivolumab).

In the fourth aspect of the present invention, there is provided use of the compound, its stereoisomer, geometric isomer, tautomer or pharmaceutically acceptable salt in the first aspect, or the pharmaceutical composition in the third aspect in the preparation of medicaments for preventing and/or treating PI3K-mediated diseases. Wherein, PI3K-mediated diseases include cancer, immune diseases, cardiovascular diseases, viral infections, inflammation, metabolism/endocrine function disorders or neurological diseases.

The compound of the present invention has high inhibitory activity against PI3KC, and has strong anti-proliferative activity against human lung cancer cell NCI-H460 with high expression of PI3Kα in vitro. Efficacy study in vivo shows that the compound of the present invention has significant inhibitory effect on growth of human lung cancer cell line NCI-H460 and human gastric cancer cell line HGC-27 in subcutaneous xenograft tumor in nude mice, both in tumor volume and tumor weight.

DETAILED DESCRIPTION

Figure 1:
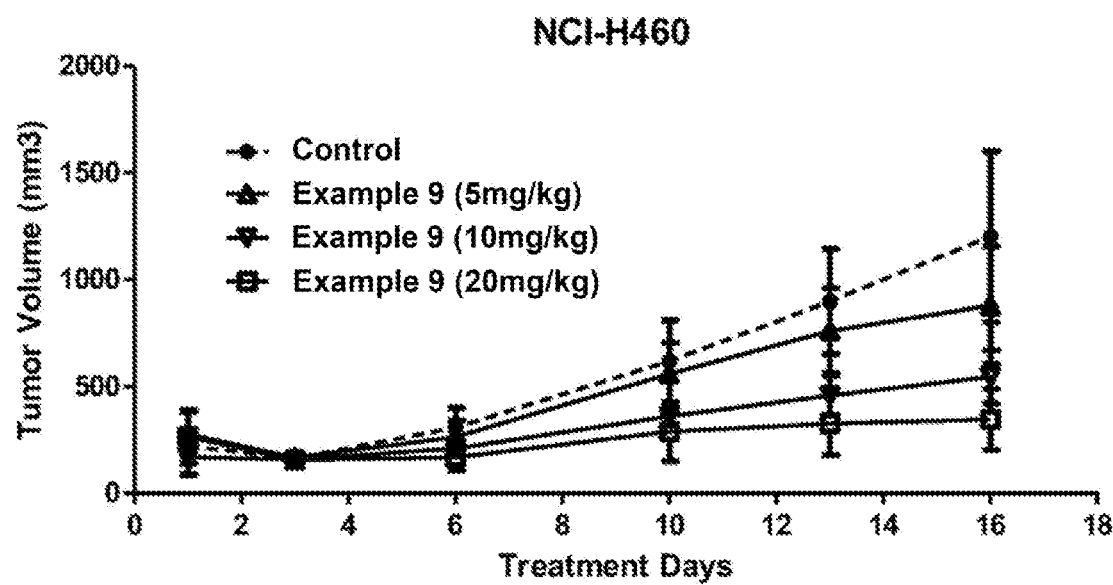
FIG. 1 is a tumor growth curve, which shows growth inhibitory effect of Example 9 on human lung cancer NCI-H460 subcutaneous xenograft tumor in nude mice.

The followings are the specific examples of the present invention, which further describe the technical solution of the present invention, but the protection scope of the present invention is not limited to these examples. Any change or equivalent substitution that does not depart from the present invention is included in the protection scope of the present invention.

In the following examples, molecule with single chiral center exists in the form of racemic mixture unless structural formula or chemical name is specified otherwise. Molecules with two or more chiral centers exist in form of diastereomer racemic mixture unless structural formula or chemical name is specified otherwise. Single enantiomer/diastereomer can be obtained by methods known to those skilled in the art.

Methods of Preparation

The compounds of the present invention can be synthesized according to the synthetic scheme in the present invention and/or techniques well known in the art. For example, the compounds provided by the invention can be prepared according to the following general synthetic method.

General Synthetic Method

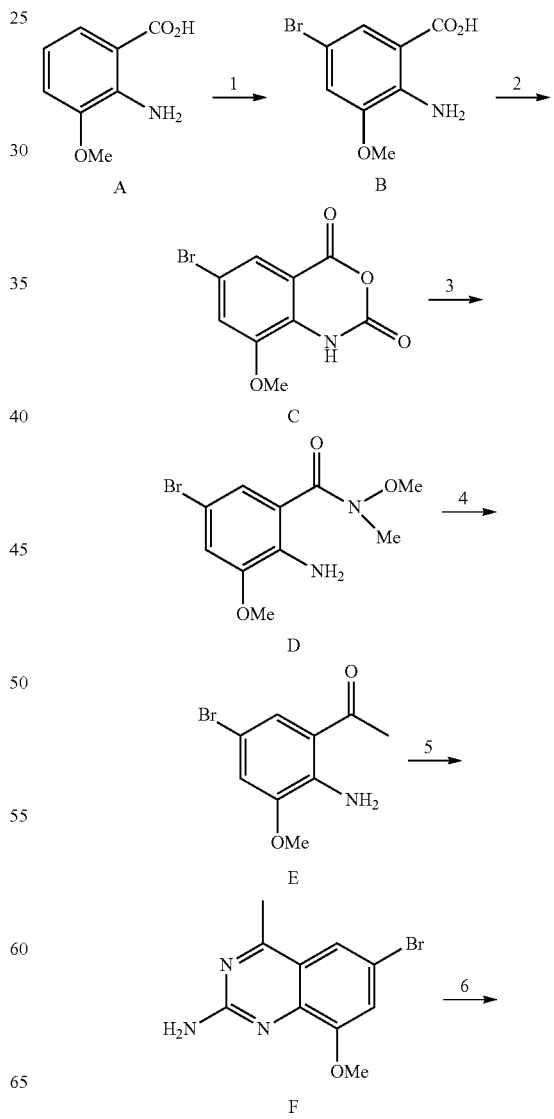

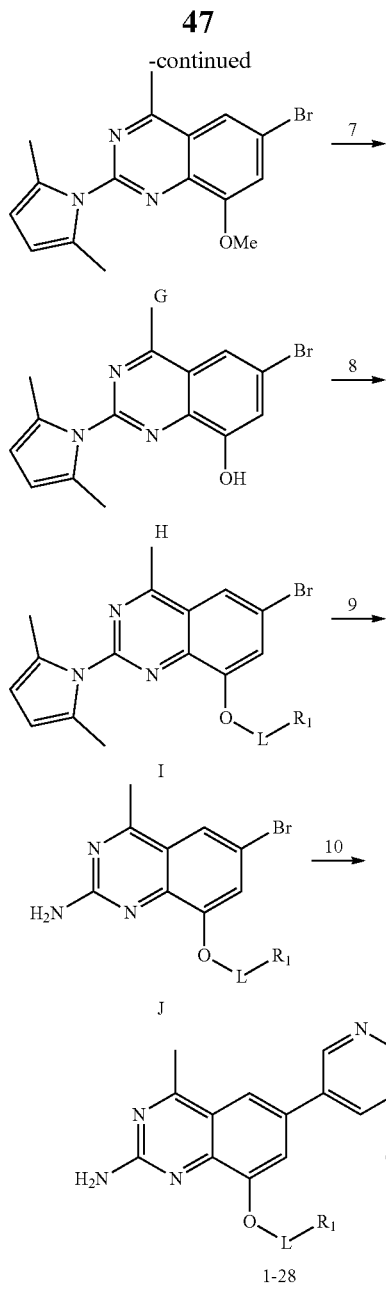

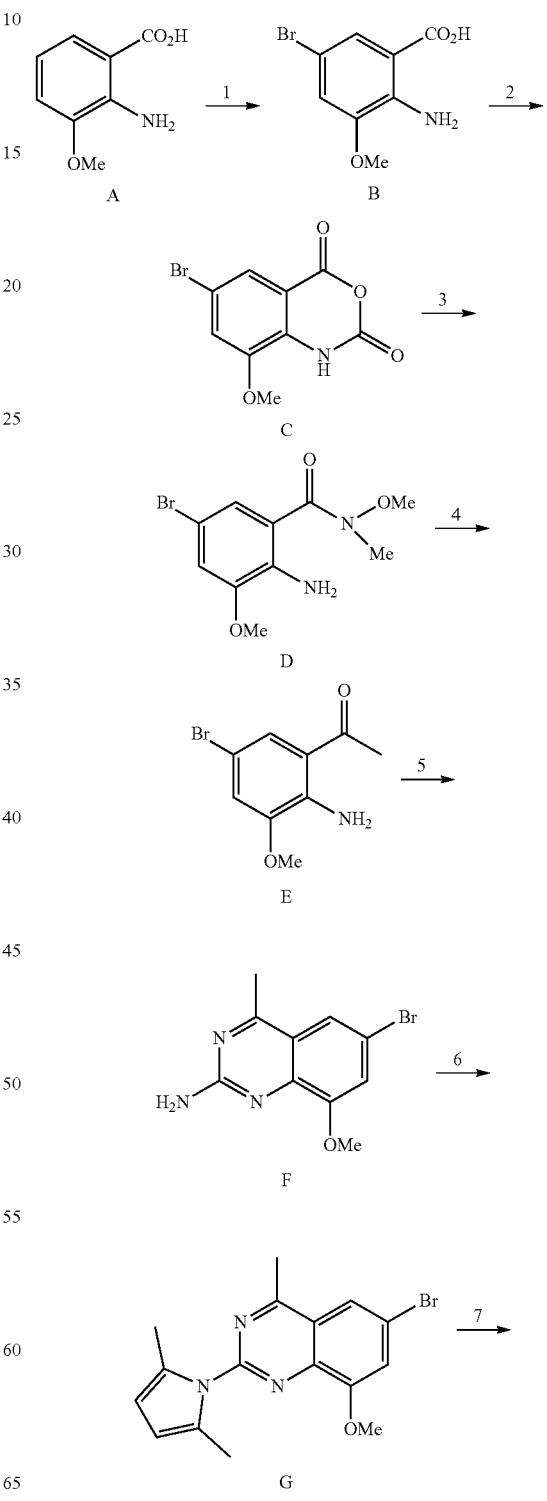

tions known by those skilled in the art, compound F and J were coupled with substituted pyridine-3-boronic acid pinacol ester to obtain compounds 1-28. Alternatively, compound J was reacted with bis(pinacolato)diboron to give the corresponding boronic acid pinacol ester, which was then coupled with substituted 3-bromopyridine to obtain the final product compounds 1-28.

Particularly, in the general synthetic method, the quinazoline compounds of the present invention can be prepared by 10-step reactions. For example, the starting material A was converted to compound B by bromination reaction, which was reacted with triphosgene to afford compound C. Compound C was reacted with N,O-dimethylhydroxylamine hydrochloride to afford compound D, which was attacked with methylmagnesium bromide to give compound E. Compound E was reacted with 50% cyanamide in water to obtain compound F containing a quinazoline skeleton, whose amino group was protected by cyclization with 2,5-hexanedione. The obtained compound G was reacted with aluminum trichloride to remove the methyl group to afford the general intermediate H.

The intermediate H was reacted with various alcohol via Mitsunobu reaction, or reacted with halide to obtain compound I, which was deprotected by hydroxylamine hydrochloride to give compound J. Under Suzuki reaction condi-

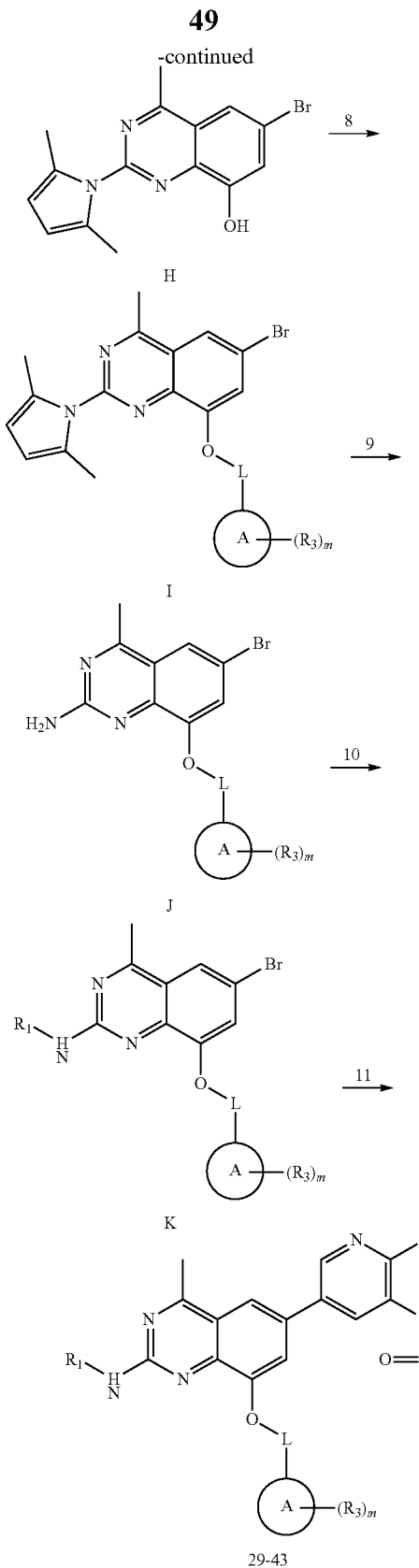

was reacted with triphosgene to afford compound C. Compound C was reacted with N,O-dimethylhydroxylamine hydrochloride to afford compound D, which was attacked by methylmagnesium bromide to give compound E. Compound E was reacted with 50% cyanamide in water to obtain compound F containing a quinazoline skeleton, whose amino group was protected by cyclization with 2,5-hexanedione. The obtained compound G was reacted with aluminum trichloride to remove the methyl group to afford the general intermediate H. The intermediate H was reacted with various alcohol via Mitsunobu reaction, or reacted with various halide to obtain compound I, which was deprotected by hydroxylamine hydrochloride to give compound J. Using sodium hydride or pyridine as base, compound J was reacted with alkyl halide or alkyl acyl chloride to afford compound K. Under Suzuki reaction conditions known by those skilled in the art, compound K was coupled with substituted pyridine-3-boronic acid pinacol ester to obtain compounds 29-43.

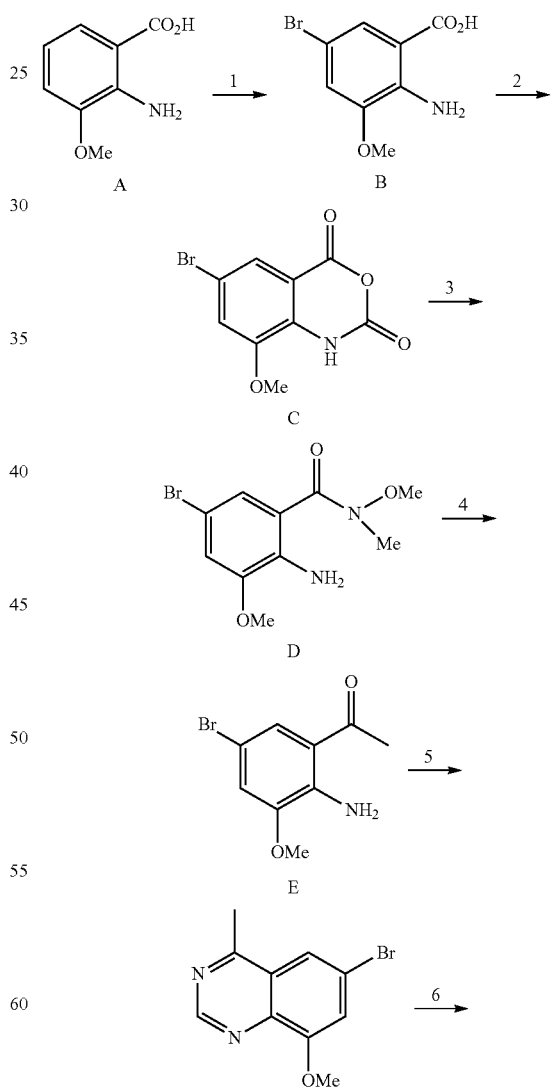

In another general synthetic method, the quinazoline compounds of the present invention can be prepared by 11-step reactions. For example, the starting material A was converted to compound B by bromination reaction, which

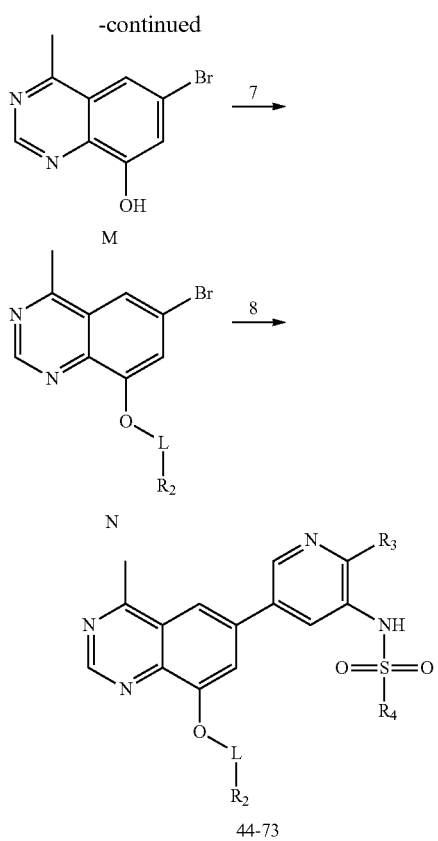

In another general synthetic method, the quinazoline compounds of the present invention can be prepared by 8-step reactions. For example, the starting material A was converted to compound B by bromination reaction, which was reacted with triphosgene to afford compound C. Compound C was reacted with N,O-dimethylhydroxylamine hydrochloride to afford compound D, which was attacked with methylmagnesium bromide to give compound E. Compound E was reacted with ammonium formate and formamide obtain compound L containing a quinazoline skeleton, which was reacted with aluminum trichloride to remove the methyl group to afford the general intermediate M. The intermediate M was reacted with various alcohol via Mitsunobu reaction, or reacted with halide to obtain compound N. Under Suzuki reaction conditions known by those skilled in the art, compounds L and N was coupled with substituted pyridine-3-boronic acid pinacol ester to obtain compounds 44-73. Alternatively, compound N was reacted with bis(pinacolato)diboron to give the corresponding boronic acid pinacol ester, which was then coupled with substituted 3-bromopyridine to obtain the final product compounds 44-73.

The compounds of the present invention can be synthesized according to one or more synthetic schemes and/or techniques well known in the art. Those skilled in the art should realize that the synthetic method of some embodiments described in detail in the present invention can be easily applied to other embodiments. In some embodiments, the compound described herein can be prepared by appropriate combinations of synthetic methods known in the art. Many starting materials and other reagents can be purchased from commercial suppliers, such as Alfa aesar (China) chemical co., LTD., or easily prepared by synthetic methods commonly used in the art.

$^1$H NMR spectra were recorded on instruments operated at 400 MHz or 500 MHz. $^1$H NMR spectra were obtained in solution form (reported as ppm), using CDCl$_3$ (7.26 ppm) or DMSO-d$_6$ (2.50 ppm) or internal standard tetramethylsilane (0.00 ppm) as reference standard. When reporting peak multiplicity, the following abbreviations are used: s (singlet), d (doublet), t (triplet), q (quartet), m (multiplet), br (broad peak), dd (double-doublet), dt (double-triplet). The given coupling constant is measured in Hertz (Hz).

(R)- and (S)-isomers of non-restrictive exemplary compounds, if present, can be separated by methods known by those skilled in the art if needed, such as can be separated by, for example, crystallization through forming diastereomeric salts or complexes; can be separated by, for example, crystallization or chromatography through forming diastereomeric derivatives; by allowing one enantiomer to selectively react with an enantiomer specific reagent, then separating the modified and unmodified enantiomers; or through chromatographic separation in chiral environment such as chiral chromatographic column. Selectively, specific enantiomers can be prepared by asymmetric synthesis using optically-active reagents, substrates, catalysts or solvents, or prepared by converting one enantiomer into another one through asymmetric conversion.

In the following preparative methods and examples, "Me" means methyl, "Et" means ethyl, "Ph" means phenyl, "PE" means petroleum ether, "EtOAc" means ethyl acetate, "MeOH" means methanol, "DMF" means N,N-dimethyl formamide, "CDCl$_3$" means chloroform-d, "DMSO-d$_6$" means dimethyl sulfoxide-d$_6$, "NMP" means 1-methyl-2-pyrrolidinone, "DCM" means dichloromethane, "DCE" means 1,2-dichloroethane, "THF" means tetrahydrofuran, "HCl" means hydrochloric acid, "TsOH" means 4-methyl-benzenesulfonic acid, "AlCl$_3$" means aluminium chloride, "TEA" means trimethylamine, "NBS" means N-bromosuccinimide, "Na$_2$SO$_4$" means sodium sulphate, "K$_2$CO$_3$" means potassium carbonate, "MeMgBr" means methylmagnesium bromide, "DEAD" means diethyl azodicarboxylate, "PPh$_3$" means triphenylphosphine, "PdCl$_2$(dppf)" means [1,1'-bis(diphenylphosphino)ferrocene]dichloropalladium (II), "Ar" means argon, "M" means molarity, "r.t." means room temperature, "min" means minute, "h" means hour, "mL" means milliliter, "mmol" means millimole, "M" means micromole, "nM" means nanomole, "° C." means degree Celsius.

Preparation of general intermediate (H)

Step 1: Preparation of
2-amino-5-bromo-3-methoxybenzoic Acid (B)

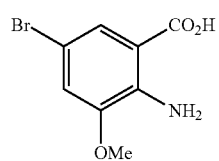

NBS (28.04 g, 157.5 mmol) was added to a solution of 2-amino-3-methoxybenzoic acid (25.08 g, 150 mmol) in DMF (200 mL) in five portions over 20 minutes. The mixture was stirred at r.t. for 2 h. The reaction mixture was diluted with water (2 L) and extracted with EtOAc (500 mL×4). The combined organic layers were washed with water (500 mL×3) and brine (500 mL), dried over anhydrous Na$_2$SO$_4$, filtered and concentrated to afford the crude product (B) as a black brown solid (35 g, 95% yield), which was used in the next step without purification.

$^1$H NMR (400 MHz, DMSO-d$_6$) δ 7.42 (d, J=2.2 Hz, 1H), 7.07 (d, J=2.2 Hz, 1H), 3.84 (s, 3H).

Step 2: Preparation of 6-bromo-8-methoxy-2H-benzo[d][1,3]oxazine-2,4(1H)-dione (C)

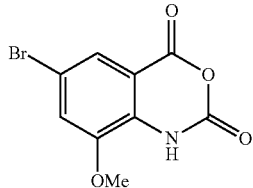

C

A mixture of compound (B) (35 g, 142.2 mmol) and triphosgene (32 g, 107.8 mmol) in anhydrous THF (350 mL) was refluxed for 3 h. After cooling to r.t., the resulting solid was collected by filtration, washed with PE/EtOAc solution (1:1, v/v, 200 mL), and dried to afford the product (C) as a pale yellow solid (30.78 g, 80% yield).

$^1$H NMR (400 MHz, DMSO-d$_6$) δ 11.43 (s, 1H), 7.56 (d, J=2.0 Hz, 1H), 7.55 (d, J=2.0 Hz, 1H), 3.92 (s, 3H).

Step 3: Preparation of 2-amino-5-bromo-N,3-dimethoxy-N-methylbenzamide (D)

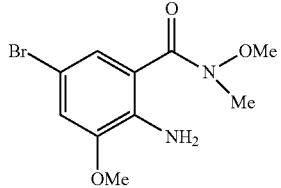

D

A mixture of compound (C) (30.78 g, 113.12 mmol), N,O-dimethylhydroxylamine hydrochloride (16.55 g, 169.68 mmol) and TEA (26.7 mL, 192.3 mmol) in 1,4-dioxane (300 mL) was refluxed overnight. The volatiles were removed under reduced pressure. The residue was diluted with water (500 mL), and extracted with EtOAc (200 mL×3). The combined organic layers were washed with water (200 mL×2) and brine (200 mL), dried with anhydrous Na$_2$SO$_4$, filtered and concentrated. The residue was purified by flash column chromatography (silica gel, PE/EtOAc=4:1, v/v) to afford the product (D) as a yellow oil (29.73 g, 91% yield).

$^1$H NMR (400 MHz, DMSO-d$_6$) δ 7.01 (d, J=2.0 Hz, 1H), 6.97 (d, J=2.0 Hz, 1H), 5.10 (br s, 2H), 3.82 (s, 3H), 3.53 (s, 3H), 3.22 (s, 3H).

Step 4: Preparation of 1-(2-amino-5-bromo-3-methoxyphenyl)ethanone (E)

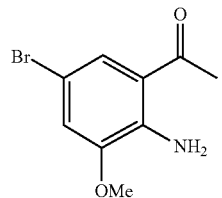

E

To a solution of compound (D) (29.73 g, 103 mmol) in anhydrous THF (300 mL) at −20° C. under argon atmosphere was added methylmagnesium bromide (1M in THF, 206 mL, 206 mmol) dropwise over 30 minutes. The resulting reaction mixture was stirred at −20° C. for 30 minutes, and then quenched with saturated aqueous NH$_4$Cl solution. The mixture was diluted with water (1 L) and extracted with EtOAc (300 mL×3). The combined organic layers were washed with water (300 mL×2) and brine (300 mL), dried over anhydrous Na$_2$SO$_4$, filtered and concentrated. The residue was purified by flash column chromatography (silica gel, PE/EtOAc=15:1, v/v) to afford the product (E) as a yellow oil (6.5 g, 26% yield).

$^1$H NMR (400 MHz, DMSO-d$_6$) δ 7.50 (d, J=2.0 Hz, 1H), 7.08 (d, J=2.0 Hz, 1H), 7.04 (s, 2H), 3.84 (s, 3H), 2.51 (s, 3H).

Step 5: Preparation of 6-bromo-8-methoxy-4-methylquinazolin-2-amine (F)

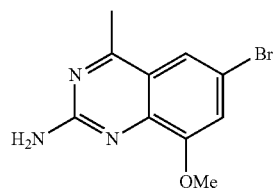

F

A mixture of compound (E) (7.41 g, 30.36 mmol), and concentrated HCl (10 mL) in 50% cyanamide in water (74 mL) was stirred at 120° C. for 15 min. The reaction mixture was cooled to r.t. and diluted with water (300 mL). The resulting solid was collected by filtration, washed with water (100 mL) and ethanol (30 mL), dried to afford the product (F) as a pale yellow solid (8.00 g, 98% yield).

$^1$H NMR (400 MHz, DMSO-d$_6$) δ 7.67 (d, J=2.0 Hz, 1H), 7.20 (d, J=2.0 Hz, 1H), 6.90 (br s, 2H), 3.88 (s, 3H), 2.67 (s, 3H).

Step 6: Preparation of 6-bromo-2-(2,5-dimethyl-1H-pyrrol-1-yl)-8-methoxy-4-methylquinazoline (G)

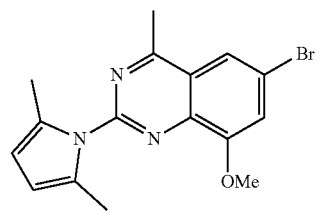

G

A mixture of compound (F) (8.00 g, 29.84 mmol), 2,5-hexanedione (13.61 g, 119.36 mmol) and p-toluenesulfonic acid monohydrate (0.568 g, 2.98 mmol) in NMP (80 mL) and toluene (80 mL) was refluxed to separate water at 160° C. for 6 h. The reaction mixture was cooled to r.t., evaporated under reduced pressure to remove toluene, diluted with water (400 mL) and extracted with EtOAc (100 mL×3). The combined organic layers were washed with water (100 mL×3) and brine (100 mL), dried over anhydrous Na$_2$SO$_4$, filtered and concentrated. The residue was purified by column chromatography (silica gel, PE/EtOAc=30:1, v/v) to afford the product (G) as a yellow solid (8.95 g, 87% yield).

$^1$H NMR (400 MHz, DMSO-d$_6$) δ 8.04 (d, J=1.8 Hz, 1H), 7.57 (d, J=1.8 Hz, 1H), 5.84 (s, 2H), 4.01 (s, 3H), 2.92 (s, 3H), 2.30 (s, 6H).

Step 7: Preparation of 6-bromo-2-(2,5-dimethyl-1H-pyrrol-1-yl)-4-methylquinazolin-8-ol (H)

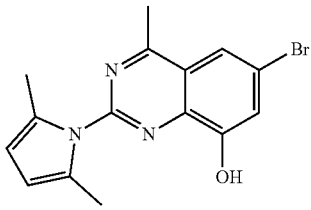

To a solution of compound (G) (3.27 g, 9.56 mmol) in DCE (300 mL) was added AlCl$_3$ (3.83 g, 28.68 mmol). The resulting reaction mixture was stirred at 80° C. for 1.5 h. The reaction mixture was cooled to r.t., diluted with water (300 mL) and extracted with DCM (300 mL×2). The combined organic layers were washed with water (200 mL) and brine (100 mL), dried over anhydrous Na$_2$SO$_4$, filtered and concentrated. The residue was purified by flash column chromatography (silica gel, PE/EtOAc=50:1, v/v) to afford the product (H) as a yellow solid (2.41 g, 77% yield).

$^1$H NMR (400 MHz, DMSO-d$_6$) δ 10.64 (s, 1H), 7.93 (d, J=2.0 Hz, 1H), 7.44 (d, J=2.0 Hz, 1H), 5.84 (s, 2H), 2.91 (s, 3H), 2.29 (s, 6H).

Preparation of General Intermediate (M)

Step 1: Preparation of 6-bromo-8-methoxy-4-methylquinazoline (L)

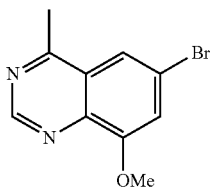

A mixture of compound (E) (3.328 g, 13.63 mmol) and ammonium formate (3.271 g, 54.52 mmol) in formamide (34 mL) was refluxed at 150° C. for 7 h. The reaction mixture was cooled to r.t., diluted with water (150 mL) and extracted with EtOAc (100 mL×3). The combined organic layers were washed with water (100 mL×2) and brine (100 mL), dried over anhydrous Na$_2$SO$_4$, filtered and concentrated. The residue was purified with flash column chromatography (silica gel, PE/EtOAc=10:1, and then 4:1, v/v) to afford the product (L) as a yellow solid (2.492 g, 72.2% yield).

$^1$H NMR (400 MHz, DMSO-d$_6$) δ 9.09 (s, 1H), 8.00 (d, J=1.9 Hz, 1H), 7.54 (d, J=1.9 Hz, 1H), 4.00 (s, 3H), 2.87 (s, 3H).

Step 6: Preparation of 6-bromo-4-methylquinazolin-8-ol (M)

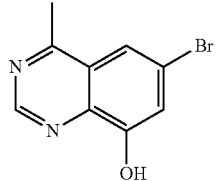

To a solution of compound (L) (4.36 g, 17.23 mmol) in DCE (390 mL) was added AlCl$_3$ (6.90 g, 51.69 mmol). The resulting reaction mixture was stirred at 80° C. for 1.5 h. The reaction mixture was cooled to r.t., diluted with water (400 mL) and extracted with DCM (300 mL×2). The combined organic layers were washed with water (200 mL) and brine (100 mL), dried over anhydrous Na$_2$SO$_4$, filtered and concentrated. The residue was purified with flash column chromatography (silica gel, DCM/MeOH=100:1, v/v) to afford the product (M) as a yellow solid (3.02 g, 73.3% yield).

$^1$H NMR (400 MHz, DMSO-d$_6$) δ 10.83 (s, 1H), 9.10 (s, 1H), 7.87 (d, J=2.0 Hz, 1H), 7.41 (d, J=2.0 Hz, 11H), 2.86 (s, 3H).

Example 1: N-(5-(2-amino-4-methyl-8-((tetrahydro-2H-pyran-4-yl)oxy)quinazolin-6-yl)-2-methoxypyridin-3-yl)-2,4-difluorobenzenesulfonamide (1)

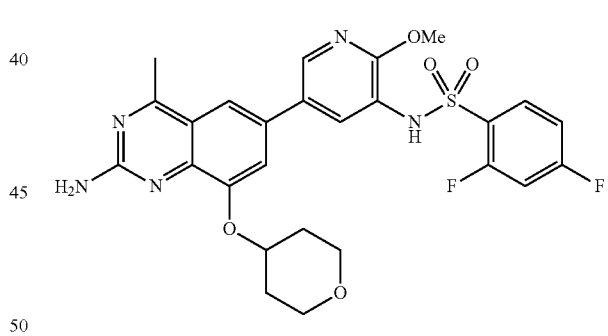

Step 1: Preparation of 6-bromo-2-(2,5-dimethyl-1H-pyrrol-1-yl)-4-methyl-8-((tetrahydro-2H-pyran-4-yl)oxy)quinazoline (I-1)

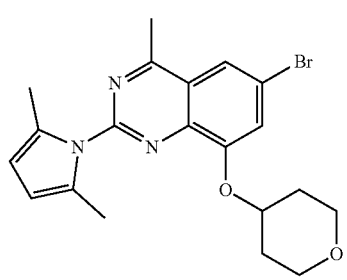

To a stirred solution of compound (H) (3.322 g, 10 mmol), triphenylphosphine (3.148 g, 12 mmol) and tetrahydro-2H-pyran-4-yl (1.226 g, 12 mmol) in anhydrous THF (50 mL) was added diethyl azodicarboxylate (2.09 g, 12 mmol) at r.t. under Ar atmosphere. The resulting reaction mixture was stirred at r.t. overnight. Silica gel (10 g) was added, and the resulting mixture was evaporated to dry under reduced pressure. The residue was purified by flash column chromatography (silica gel, PE/EtOAc=10:1, v/v) to afford the product (I-1) as a yellow oil (2.097 g, 50% yield).

$^1$H NMR (400 MHz, DMSO-d$_6$) δ 8.04 (d, J=1.9 Hz, 1H), 7.70 (d, J=1.8 Hz, 1H), 5.86 (s, 2H), 5.01-4.91 (m, 1H), 3.94-3.80 (m, 2H), 3.56 (ddd, J=11.2, 8.0, 3.2 Hz, 2H), 2.92 (s, 3H), 2.36 (s, 3H), 2.09-1.94 (m, 2H), 1.77-1.65 (m, 2H).

Step 2: Preparation of 6-bromo-4-methyl-8-((tetrahydro-2H-pyran-4-yl)oxy)quinazolin-2-amine (J-1)

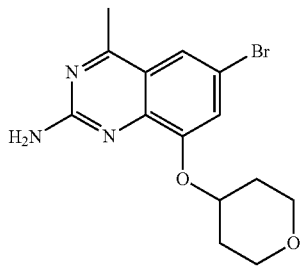

J-1

A mixture of compound (I-1) (2.082 g, 5.0 mmol) and hydroxylamine hydrochloride (1.734 g, 25 mmol) in ethanol (40 mL) and water (4 mL) was refluxed overnight. The resulting mixture was evaporated to dry under reduced pressure, diluted with water (100 mL), neutralized with saturated aqueous NaHCO$_3$ solution, and extracted with DCM (50 mL×3). The combined organic layers were washed with water (50 mL) and brine (50 mL), dried over anhydrous Na$_2$SO$_4$, filtered, and concentrated. The residue was purified by column chromatography (silica gel, DCM/MeOH=50:1, v/v) to afford the product (J-1) as a yellow oil (0.667 g, 39% yield).

$^1$H NMR (400 MHz, DMSO-d$_6$) δ 7.68 (d, J=2.0 Hz, 1H), 7.36 (d, J=2.0 Hz, 1H), 6.85 (s, 2H), 4.82-4.73 (m, 1H), 3.94-3.87 (m, 2H), 3.53-3.45 (m, 2H), 2.65 (s, 3H), 2.05-1.96 (m, 2H), 1.68-1.58 (m, 2H).

MS (ESI+) m/z 337.8, 339.8 [M+H]$^+$.

Step 3: Preparation of N-(5-(2-amino-4-methyl-8-((tetrahydro-2H-pyran-4-yl)oxy)quinazolin-6-yl)-2-methoxypyridin-3-yl)-2,4-difluorobenzenesulfonamide (1)

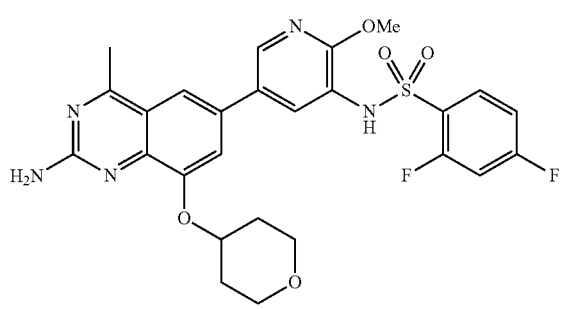

1

A mixture of compound (J-1) (538 mg, 1.59 mmol), N-(2-methoxy-5-(4,4,5,5-tetramethyl-1,3,2-dioxaborolan-2-yl)pyridin-3-yl)-2,4-difluorobenzenesulfonamide (814 mg, 1.91 mmol) and 2M aqueous K$_2$CO$_3$ solution (2.40 mL, 4.8 mmol) in dioxane (15 mL) was degassed and then PdCl$_2$(dppf) (58 mg, 0.08 mmol) was added. The resulting reaction mixture was degassed and back-filled with argon (three cycles), and then stirred at 100° C. under Ar atmosphere for 5 h. The reaction mixture was cooled to r.t., diluted with EtOAc (50 mL) and water (50 mL), acidified with 2M HCl solution until the pH value was 5-6. The two layers were separated and the aqueous layer was extracted with EtOAc (30 mL×2). The combined organic layers were washed with water (50 mL) and brine (50 mL), dried over anhydrous Na$_2$SO$_4$, filtered and concentrated. The residue was purified by flash column chromatography (silica gel, DCM/MeOH=50:1, v/v) to afford the product (1) as a yellow foamed solid (400 mg, 45% yield).

$^1$H NMR (400 MHz, DMSO-d$_6$) δ 10.29 (s, 1H), 8.44 (d, J=2.2 Hz, 1H), 7.96 (d, J=2.2 Hz, 1H), 7.76 (dt, J=8.4, 2.4 Hz, 1H), 7.66 (d, J=1.2 Hz, 1H), 7.64-7.54 (m, 1H), 7.46 (d, J=1.2 Hz, 1H), 7.23 (dt, J=8.6, 2.0 Hz, 1H), 6.79 (s, 2H), 4.97-4.82 (m, 1H), 3.98-3.89 (m, 2H), 3.64 (s, 3H), 3.56-3.45 (m, 2H), 2.75 (s, 3H), 2.10-1.99 (m, 2H), 1.75-1.58 (m, 2H).

MS (ESI+) m/z 558.2 [M+H]$^+$.

Example 2: N-(5-(2-amino-4-methyl-8-((tetrahydro-2H-pyran-4-yl)oxy)quinazolin-6-yl)-2-methoxypyridin-3-yl)-2-chloro-4-fluorobenzenesulfonamide (2)

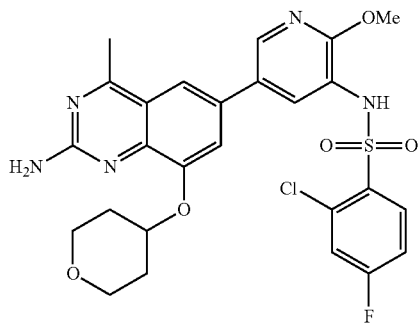

2

Compound (2) was prepared from compound (J-1) and N-(2-methoxy-5-(4,4,5,5-tetramethyl-1,3,2-dioxaborolan-2-yl)pyridin-3-yl)-2-chloro-4-fluorobenzenesulfonamide, according to the method of step 3 in Example 1.

$^1$H NMR (400 MHz, DMSO-d$_6$) δ 10.17 (s, 1H), 8.42 (d, J=2.3 Hz, 1H), 7.94 (dd, J=8.8, 6.0 Hz, 1H), 7.90 (d, J=2.4 Hz, 1H), 7.76 (dd, J=8.8, 2.4 Hz, 1H), 7.62 (d, J=1.6 Hz, 1H), 7.43 (d, J=1.4 Hz, 1H), 7.40-7.33 (m, 1H), 6.79 (s, 2H), 4.94-4.81 (m, 1H), 3.98-3.89 (m, 2H), 3.66 (s, 3H), 3.57-3.45 (m, 2H), 2.75 (s, 3H), 2.10-1.99 (m, 2H), 1.74-1.58 (m, 2H).

MS (ESI+) m/z 574.1 [M+H]$^+$.

Example 3: N-(5-(2-amino-4-methyl-8-((tetrahydro-2H-pyran-4-yl)oxy)quinazolin-6-yl)-2-methoxypyridin-3-yl)-4-fluorobenzenesulfonamide (3)

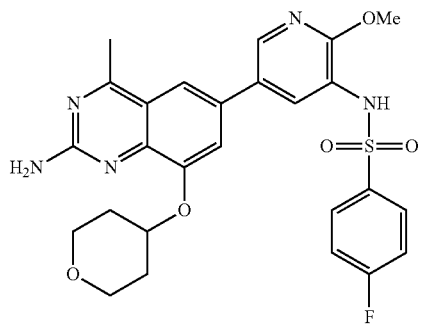

Compound (3) was prepared from compound (J-1) and N-(2-methoxy-5-(4,4,5,5-tetramethyl-1,3,2-dioxaborolan-2-yl)pyridin-3-yl)-4-fluorobenzenesulfonamide, according to the method of step 3 in Example 1.

¹H NMR (400 MHz, DMSO-d₆) δ 10.04 (s, 1H), 8.39 (d, J=2.4 Hz, 1H), 7.88 (d, J=2.4 Hz, 1H), 7.86-7.79 (m, 2H), 7.61 (d, J=1.8 Hz, 1H), 7.47-7.39 (m, 3H), 6.79 (s, 2H), 4.95-4.82 (m, 1H), 3.98-3.89 (m, 2H), 3.65 (s, 3H), 3.56-3.42 (m, 2H), 2.75 (s, 3H), 2.11-1.98 (m, 2H), 1.74-1.59 (m, 2H).

MS (ESI+) m/z 540.2 [M+H]⁺.

Example 4: N-(5-(2-amino-4-methyl-8-((tetrahydro-2H-pyran-4-yl)oxy)quinazolin-6-yl)-2-methoxypyridin-3-yl)-5-chlorothiophene-2-sulfonamide (4)

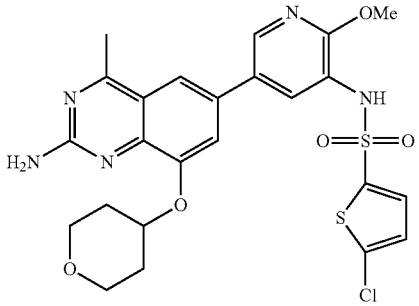

Compound (4) was prepared from compound (J-1) and N-(2-methoxy-5-(4,4,5,5-tetramethyl-1,3,2-dioxaborolan-2-yl)pyridin-3-yl)-5-chlorothiophene-2-sulfonamide, according to the method of step 3 in Example 1.

¹H NMR (400 MHz, DMSO-d₆) δ 10.34 (s, 1H), 8.46 (d, J=2.4 Hz, 1H), 7.95 (d, J=2.4 Hz, 1H), 7.67 (d, J=1.6 Hz, 1H), 7.47 (d, J=1.6 Hz, 1H), 7.39 (d, J=4.0 Hz, 1H), 7.24 (d, J=4.0 Hz, 1H), 6.80 (s, 2H), 4.95-4.84 (m, 1H), 4.00-3.86 (m, 2H), 3.74 (s, 3H), 3.58-3.45 (m, 2H), 2.76 (s, 3H), 2.11-2.00 (m, 2H), 1.77-1.60 (m, 2H).

MS (ESI+) m/z 562.1 [M+H]⁺.

Example 5: N-(5-(2-amino-4-methyl-8-((tetrahydro-2H-pyran-4-yl)oxy)quinazolin-6-yl)-2-methoxypyridin-3-yl)methanesulfonamide (5)

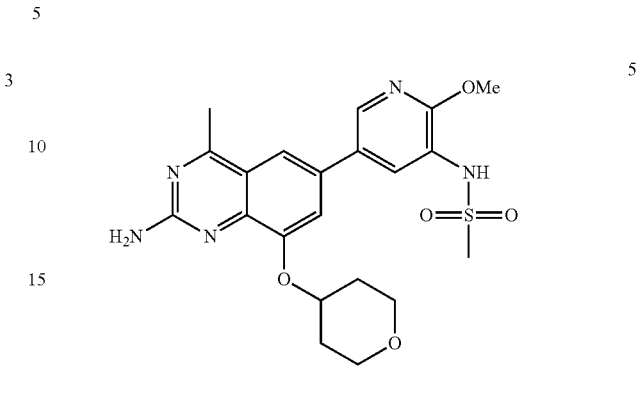

Compound (5) was prepared from compound (J-1) and N-(2-methoxy-5-(4,4,5,5-tetramethyl-1,3,2-dioxaborolan-2-yl)pyridin-3-yl)methanesulfonamide, according to the method of step 3 in Example 1.

¹H NMR (400 MHz, DMSO-d₆) δ 9.34 (s, 1H), 8.43 (d, J=2.3 Hz, 1H), 7.95 (d, J=2.3 Hz, 1H), 7.70 (d, J=1.6 Hz, 1H), 7.47 (d, J=1.6 Hz, 1H), 6.77 (s, 2H), 4.97-4.81 (m, 1H), 3.98 (s, 3H), 3.96-3.88 (m, 2H), 3.55-3.44 (m, 2H), 3.08 (s, 3H), 2.75 (s, 3H), 2.10-2.00 (m, 2H), 1.76-1.57 (m, 2H).

MS (ESI+) m/z 460.2 [M+H]⁺.

Example 6: N-(5-(2-amino-4-methyl-8-((tetrahydro-2H-pyran-4-yl)oxy)quinazolin-6-yl)-2-methoxypyridin-3-yl)cyclopropanesulfonamide (6)

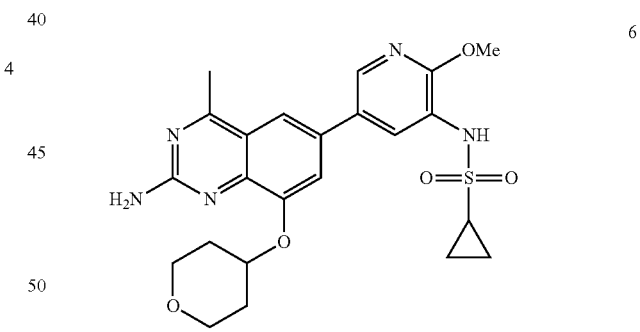

Compound (6) was prepared from compound (J-1) and N-(2-methoxy-5-(4,4,5,5-tetramethyl-1,3,2-dioxaborolan-2-yl)pyridin-3-yl)cyclopropanesulfonamide, according to the method of step 3 in Example 1.

¹H NMR (400 MHz, DMSO-d₆) δ 9.37 (s, 1H), 8.43 (d, J=2.3 Hz, 1H), 7.97 (d, J=2.3 Hz, 1H), 7.69 (d, J=1.8 Hz, 1H), 7.47 (d, J=1.8 Hz, 1H), 6.78 (s, 2H), 4.97-4.80 (m, 1H), 3.98 (s, 3H), 3.96-3.88 (m, 2H), 3.57-3.44 (m, 2H), 2.83-2.70 (m, 4H), 2.12-1.98 (m, 2H), 1.74-1.61 (m, 2H), 1.01-0.89 (m, 4H).

MS (ESI+) m/z 486.2 [M+H]⁺.

Example 7: N-(5-(2-amino-4-methyl-8-((tetrahydro-2H-pyran-4-yl)oxy)quinazolin-6-yl)-2-methylpyridin-3-yl)-2,4-difluorobenzenesulfonamide (7)

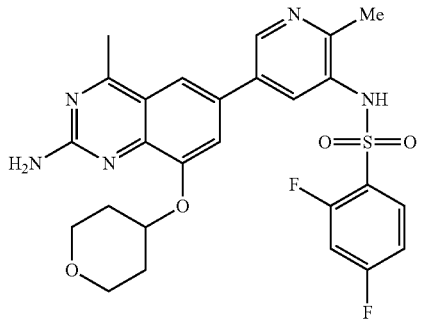

A mixture of compound (J-1) (75 mg, 0.22 mmol), anhydrous potassium acetate (65 mg, 0.66 mmol) and bis(pinacolato)diboron (64 mg, 0.25 mmol) in dioxane (8 mL) was degassed and then PdCl$_2$(dppf) (16 mg, 0.022 mmol) was added. The resulting reaction mixture was degassed and back-filled with argon (three cycles), and then stirred at 100° C. under Ar atmosphere for 4 h. After cooling to r.t., N-(5-bromo-2-methylpyridin-3-yl)-2,4-difluorobenzenesulfonamide (91 mg, 0.25 mmol) and 2M aqueous potassium carbonate solution (0.44 mL, 0.88 mmol) were added to the reaction mixture. The resulting mixture was degassed, and then PdCl$_2$(dppf) (16 mg, 0.022 mmol) was added. The resulting reaction mixture was degassed and backfilled with argon (three cycles), and then stirred at 100° C. under Ar atmosphere for 5 h. The reaction mixture was cooled to r.t., diluted with EtOAc (30 mL) and water (30 mL), acidified with hydrochloric acid until the pH value was 5-6. The two layers were separated and the aqueous layer was extracted with EtOAc (30 mL×2). The combined organic layers were washed with water (50 mL) and brine (50 mL), dried over anhydrous Na$_2$SO$_4$, filtered, and concentrated. The residue was purified by preparative thin layer chromatography (silica gel, DCM/MeOH/ammonium hydroxide=15:1:0.1, v/v) to afford the product (7) as a yellow foamed solid (35 mg, 29% yield).

$^1$H NMR (400 MHz, DMSO-d$_6$) δ 10.45 (s, 1H), 8.73 (s, 1H), 7.80 (dt, J=8.4, 6.4 Hz, 1H), 7.72-7.54 (m, 3H), 7.40 (s, 1H), 7.27 (dt, J=8.4, 2.0 Hz, 1H), 6.84 (s, 2H), 4.91-4.80 (m, 1H), 3.98-3.88 (m, 2H), 3.58-3.43 (m, 2H), 2.73 (s, 3H), 2.33 (s, 3H), 2.08-1.98 (m, 2H), 1.77-1.58 (m, 2H).

MS (ESI+) m/z 542.2 [M+H]$^+$.

Example 8: N-(5-(2-amino-4-methyl-8-((tetrahydro-2H-pyran-4-yl)oxy)quinazolin-6-yl)-2-chloropyridin-3-yl)-4-fluorobenzenesulfonamide (8)

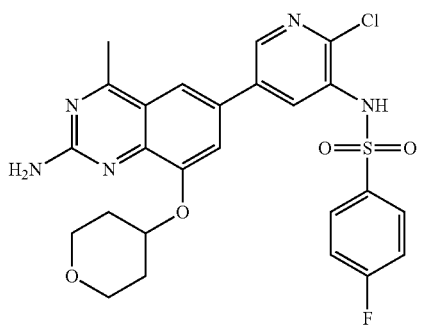

A mixture of compound (J-1) (75 mg, 0.22 mmol), anhydrous potassium acetate (65 mg, 0.66 mmol), and bis(pinacolato)diboron (64 mg, 0.25 mmol) in dioxane (8 mL) was degassed, and then PdCl$_2$(dppf) (16 mg, 0.022 mmol) was added. The resulting reaction mixture was degassed and backfilled with argon (three cycles) and then stirred at 100° C. under Ar atmosphere for 4 h. After cooling to r.t., N-(5-bromo-2-chloropyridin-3-yl)-4-fluorobenzenesulfonamide (91 mg, 0.25 mmol) and 2 M aqueous potassium carbonate solution (0.44 mL, 0.88 mmol) were added to the resulting mixture. The resulting reaction mixture was degassed, and then PdCl$_2$(dppf) (16 mg, 0.022 mmol) was added. The resulting mixture was degassed and backfilled with argon (three cycles) and then stirred at 100° C. under Ar atmosphere for 5 h. The reaction mixture was cooled to r.t., diluted with water (30 mL) and EtOAc (30 mL), acidified with hydrochloric acid until the pH value was 5-6. The two layers were separated, and the aqueous layer was extracted with EtOAc (30 mL×2). The combined organic layers were washed with water (50 mL) and brine (50 mL), dried over anhydrous Na$_2$SO$_4$, filtered, and concentrated. The residue was purified by preparative thin layer chromatography (silica gel, DCM/MeOH/ammonium hydroxide=15:1:0.1, v/v) to afford the product (8) as a yellow foamed solid (30 mg, 25% yield).

$^1$H NMR (400 MHz, DMSO-d$_6$) δ 10.53 (s, 1H), 8.67 (d, J=1.7 Hz, 1H), 7.99 (d, J=2.3 Hz, 11H), 7.87-7.77 (m, 2H), 7.71 (d, J=1.7 Hz, 1H), 7.51-7.40 (m, 3H), 6.90 (s, 2H), 4.95-4.82 (m, 1H), 3.98-3.88 (m, 2H), 3.57-3.44 (m, 2H), 2.76 (s, 3H), 2.12-1.95 (m, 2H), 1.75-1.59 (m, 2H).

MS (ESI+) m/z 544.1 [M+H]$^+$.

Example 9: (R)—N-(5-(2-amino-4-methyl-8-((tetrahydrofuran-3-yl)oxy)quinazolin-6-yl)-2-methoxypyridin-3-yl)-2,4-difluorobenzenesulfonamide (9)

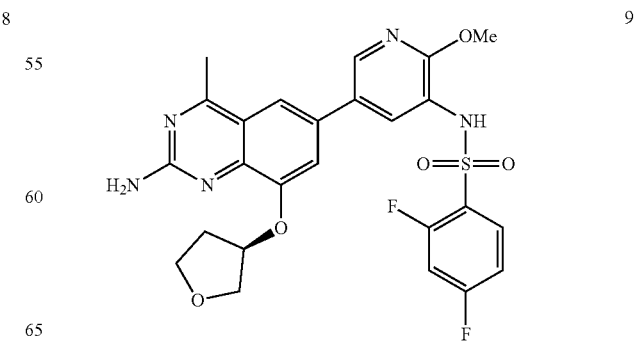

Step 1: Preparation of (R)-6-bromo-2-(2,5-dimethyl-1H-pyrrol-1-yl)-4-methyl-8-((tetrahydrofuran-3-yl)oxy)quinazoline (I-9)

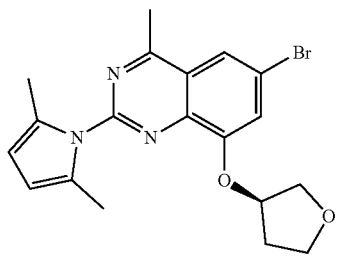
I-9

According to the method of step 1 in Example 1, compound (I-9) was prepared from compound (H) and (S)-tetrahydrofuran-3-ol.

$^1$H NMR (400 MHz, CDCl$_3$) δ 7.82 (d, J=1.6 Hz, 11H), 7.22 (d, J=1.6 Hz, 11H), 5.91 (s, 2H), 5.22-5.14 (m, 1H), 4.18-3.94 (m, 4H), 2.91 (s, 3H), 2.45 (s, 6H), 2.33-2.26 (m, 2H).

Step 2: Preparation of (R)-6-bromo-4-methyl-8-((tetrahydrofuran-3-yl)oxy)quinazolin-2-amine (J-9)

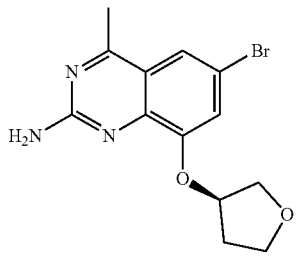
J-9

According to the method of step 2 in Example 1, compound (J-9) was prepared from compound (I-9).

$^1$H NMR (400 MHz, DMSO-d$_6$) δ 7.69 (d, J=2.0 Hz, 1H), 7.21 (d, J=2.0 Hz, 1H), 6.89 (s, 2H), 5.25-5.18 (m, 1H), 3.97-3.83 (m, 3H), 3.80-3.72 (m, 1H), 2.66 (s, 3H), 2.33-2.21 (m, 1H), 2.05-1.93 (m, 1H).

Step 3: Preparation of (R)—N-(5-(2-amino-4-methyl-8-((tetrahydrofuran-3-yl)oxy)quinazolin-6-yl)-2-methoxypyridin-3-yl)-2,4-difluorobenzenesulfonamide (9)

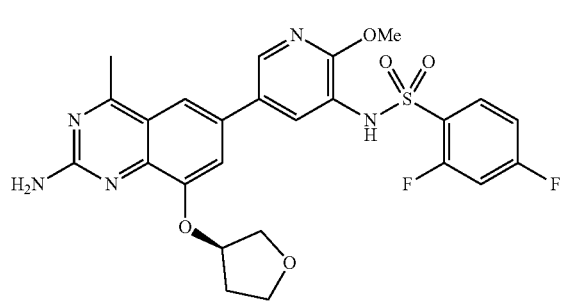
9

Compound (9) was prepared from compound (J-9) and N-(2-methoxy-5-(4,4,5,5-tetramethyl-1,3,2-dioxaborolan-2-yl)pyridin-3-yl)-2,4-difluorobenzenesulfonamide, according to the method of step 3 in Example 1.

$^1$H NMR (400 MHz, DMSO-d$_6$) δ 10.28 (s, 1H), 8.44 (d, J=2.3 Hz, 1H), 7.97 (d, J=2.3 Hz, 1H), 7.82-7.72 (m, 1H), 7.67 (d, J=1.5 Hz, 1H), 7.64-7.53 (m, 1H), 7.32 (d, J=1.5 Hz, 1H), 7.22 (dt, J=8.4, 2.0 Hz, 1H), 6.83 (s, 2H), 5.43-5.29 (m, 1H), 4.02-3.85 (m, 3H), 3.83-3.74 (m, 1H), 3.65 (s, 3H), 2.75 (s, 3H), 2.35-2.22 (m, 1H), 2.08-2.01 (m, 1H).

MS (ESI+) m/z 544.1 [M+H]$^+$.

Example 10: (R)—N-(5-(2-amino-4-methyl-8-((tetrahydrofuran-3-yl)oxy)quinazolin-6-yl)-2-methoxypyridin-3-yl)methanesulfonamide (10)

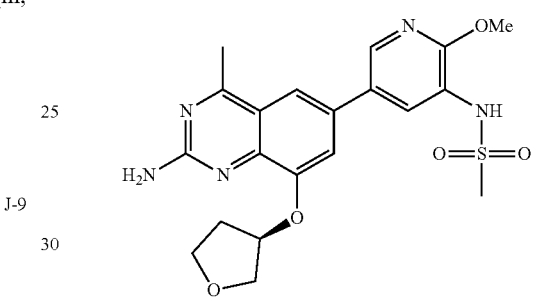
10

Compound (10) was prepared from compound (J-9) and N-(2-methoxy-5-(4,4,5,5-tetramethyl-1,3,2-dioxaborolan-2-yl)pyridin-3-yl)methanesulfonamide, according to the method of step 3 in Example 1.

$^1$H NMR (400 MHz, DMSO-d$_6$) δ 9.35 (s, 1H), 8.44 (d, J=2.3 Hz, 1H), 7.97 (d, J=2.3 Hz, 1H), 7.71 (d, J=1.6 Hz, 1H), 7.34 (d, J=1.6 Hz, 1H), 6.83 (s, 2H), 5.39-5.33 (m, 1H), 3.98 (s, 3H), 3.97-3.87 (m, 3H), 3.82-3.74 (m, 1H), 3.09 (s, 3H), 2.75 (s, 3H), 2.34-2.22 (m, 11H), 2.12-2.00 (m, 1H).

MS (ESI+) m/z 446.1 [M+H]$^+$.

Example 11: (S)—N-(5-(2-amino-4-methyl-8-((tetrahydrofuran-3-yl)oxy)quinazolin-6-yl)-2-methoxypyridin-3-yl)-2,4-difluorobenzenesulfonamide (11)

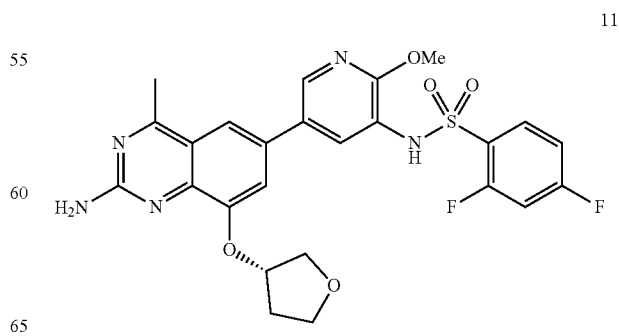
11

Step 1: Preparation of (S)-6-bromo-2-(2,5-dimethyl-1H-pyrrol-1-yl)-4-methyl-8-((tetrahydrofuran-3-yl)oxy)quinazoline (I-11)

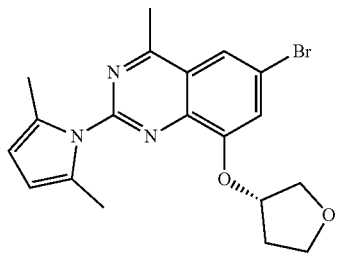

I-11

According to the method of step 1 in Example 1, compound (I-11) was prepared from compound (H) and (R)-tetrahydrofuran-3-ol.

$^1$H NMR (400 MHz, DMSO-d$_6$) δ 8.05 (d, J=1.8 Hz, 1H), 7.58 (d, J=1.8 Hz, 1H), 5.85 (s, 2H), 5.38-5.31 (m, 1H), 4.06-3.75 (m, 4H), 2.92 (s, 3H), 2.34 (s, 6H), 2.32-2.24 (m, 1H), 2.13-2.02 (m, 1H).

Step 2: Preparation of (S)-6-bromo-4-methyl-8-((tetrahydrofuran-3-yl)oxy)quinazolin-2-amine (J-11)

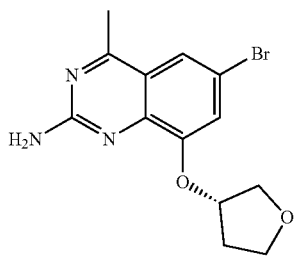

J-11

According to the method of step 2 in Example 1, Compound (J-11) was prepared from compound (I-11).

$^1$H NMR (400 MHz, DMSO-d$_6$) δ 7.69 (d, J=2.0 Hz, 1H), 7.21 (d, J=2.0 Hz, 1H), 6.90 (s, 2H), 5.25-5.18 (m, 1H), 3.97-3.82 (m, 3H), 3.80-3.72 (m, 1H), 2.66 (s, 3H), 2.33-2.21 (m, 1H), 2.05-1.95 (m, 1H). Step 3: Preparation of (S)—N-(5-(2-amino-4-methyl-8-((tetrahydrofuran-3-yl)oxy)quinazolin-6-yl)-2-methoxypyridin-3-yl)-2,4-difluorobenzenesulfonamide (11)

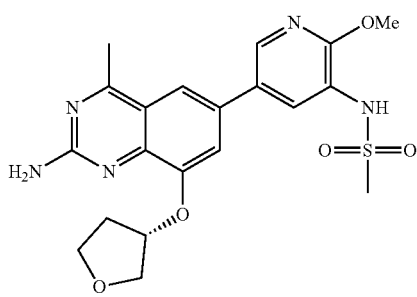

11

Compound (11) was prepared from compound (J-11) and N-(2-methoxy-5-(4,4,5,5-tetramethyl-1,3,2-dioxaborolan-2-yl)pyridin-3-yl)2,4-difluorobenzenesulfonamide, according to the method of step 3 in Example 1.

$^1$H NMR (400 MHz, DMSO-d$_6$) δ 10.28 (s, 1H), 8.44 (d, J=2.3 Hz, 1H), 7.97 (d, J=2.3 Hz, 1H), 7.76 (dt, J=8.6, 6.4 Hz, 1H), 7.67 (d, J=1.6 Hz, 1H), 7.64-7.53 (m, 1H), 7.32 (d, J=1.6 Hz, 1H), 7.22 (dt, J=8.6, 2.3 Hz, 1H), 6.84 (s, 2H), 5.43-5.29 (m, 1H), 4.00-3.85 (m, 3H), 3.83-3.73 (m, 1H), 3.65 (s, 3H), 2.75 (s, 3H), 2.35-2.22 (m, 1H), 2.12-2.01 (m, 1H).

MS (ESI+) m/z 544.1 [M+H]$^+$.

Example 12: (S)—N-(5-(2-amino-4-methyl-8-((tetrahydrofuran-3-yl)oxy)quinazolin-6-yl)-2-methoxypyridin-3-yl)methanesulfonamide (12)

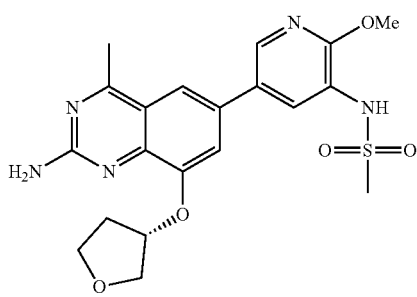

12

Compound (12) was prepared from compound (J-11) and N-(2-methoxy-5-(4,4,5,5-tetramethyl-1,3,2-dioxaborolan-2-yl)pyridin-3-yl)methanesulfonamide, according to the method of step 3 in Example 1.

$^1$H NMR (400 MHz, DMSO-d$_6$) δ 9.35 (s, 1H), 8.44 (d, J=2.3 Hz, 1H), 7.97 (d, J=2.3 Hz, 1H), 7.71 (d, J=1.8 Hz, 1H), 7.34 (d, J=1.8 Hz, 1H), 6.83 (s, 2H), 5.39-5.33 (m, 1H), 3.98 (s, 3H), 3.96-3.86 (m, 3H), 3.83-3.74 (m, 1H), 3.09 (s, 3H), 2.75 (s, 3H), 2.35-2.23 (m, 1H), 2.12-2.02 (m, 1H).

MS (ESI+) m/z 446.1 [M+H]$^+$.

Example 13: N-(5-(2-amino-4-methyl-8-((tetrahydro-2H-pyran-4-yl)methoxy)quinazolin-6-yl)-2-methoxypyridin-3-yl)-2,4-difluorobenzenesulfonamide (13)

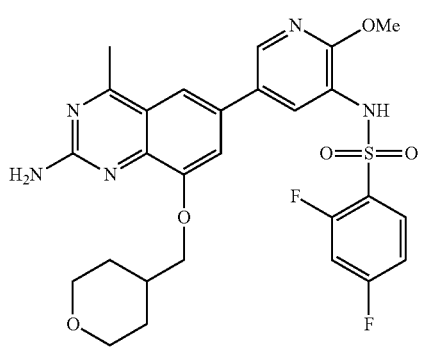

13

Step 1: Preparation of 6-bromo-2-(2,5-dimethyl-1H-pyrrol-1-yl)-4-methyl-8-((tetrahydro-2H-pyran-4-yl)methoxy)quinazoline (I-13)

Step 3: Preparation of N-(5-(2-amino-4-methyl-8-((tetrahydro-2H-pyran-4-yl)methoxy)quinazolin-6-yl)-2-methoxypyridin-3-yl)-2,4-difluorobenzenesulfonamide (13)

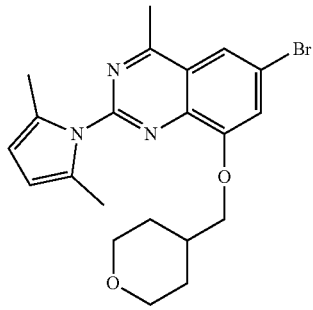

I-13

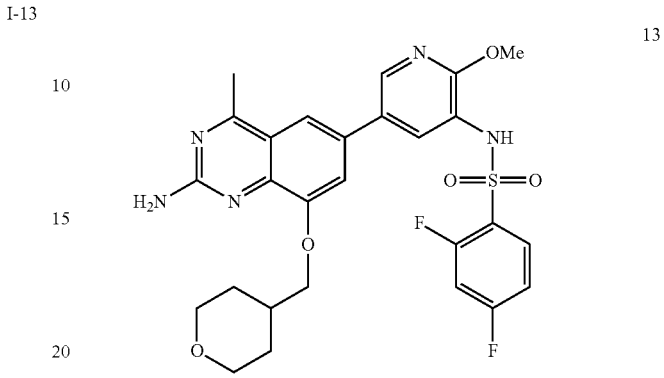

13

According to the method of step 1 in Example 1, compound (I-13) was prepared from compound (H) and (tetrahydro-2H-pyran-4-yl)methanol.

$^1$H NMR (400 MHz, DMSO-d$_6$) δ 8.02 (d, J=1.9 Hz, 1H), 7.55 (d, J=1.9 Hz, 1H), 5.85 (s, 2H), 4.07 (d, J=6.2 Hz, 2H), 3.94-3.86 (m, 2H), 3.36 (dt, J=11.6, 2.0 Hz, 2H), 2.91 (s, 3H), 2.35 (s, 6H), 2.19-2.03 (m, 1H), 1.78-1.69 (m, 2H), 1.52-1.37 (m, 2H).

Compound (13) was prepared from compound (J-13) and N-(2-methoxy-5-(4,4,5,5-tetramethyl-1,3,2-dioxaborolan-2-yl)pyridin-3-yl)-2,4-difluorobenzenesulfonamide, according to the method of step 3 in Example 1.

$^1$H NMR (400 MHz, DMSO-d$_6$) δ 10.28 (s, 1H), 8.45 (d, J=2.1 Hz, 1H), 7.97 (d, J=2.2 Hz, 1H), 7.76 (dt, J=8.6, 6.4 Hz, 1H), 7.64 (s, 1H), 7.63-7.55 (m, 1H), 7.34 (s, 1H), 7.22 (dt, J=8.6, 2.4 Hz, 1H), 6.79 (s, 2H), 4.05 (d, J=6.6 Hz, 2H), 3.90 (dd, J=11.0, 3.0 Hz, 2H), 3.64 (s, 3H), 3.37 (t, J=11.0 Hz, 2H), 2.75 (s, 3H), 2.20-2.05 (m, 1H), 1.84-1.74 (m, 2H), 1.38 (qd, J=12.2, 4.2 Hz, 2H).

MS (ESI+) m/z 572.2 [M+H]$^+$.

Step 2: Preparation of 6-bromo-4-methyl-8-((tetrahydro-2H-pyran-4-yl)methoxy)quinazolin-2-amine (J-13)

Example 14: N-(5-(2-amino-4-methyl-8-((tetrahydro-2H-pyran-4-yl)methoxy)quinazolin-6-yl)-2-methoxypyridin-3-yl)methanesulfonamide (14)

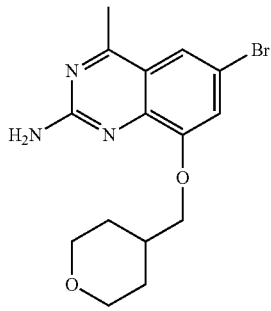

J-13

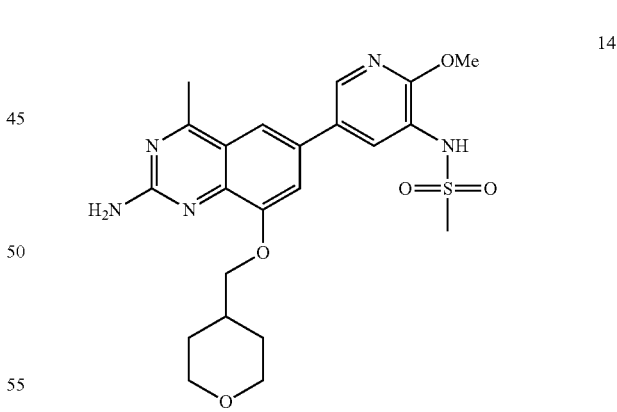

14

According to the method of step 2 in Example 1, compound (J-13) was prepared from compound (I-13).

$^1$H NMR (400 MHz, DMSO-d$_6$) δ 7.65 (d, J=2.0 Hz, 1H), 7.22 (d, J=2.0 Hz, 1H), 6.83 (s, 2H), 3.95 (d, J=6.7 Hz, 2H), 3.92-3.84 (m, 2H), 3.40-3.32 (m, 2H), 2.65 (s, 3H), 2.14-1.99 (m, 1H), 1.78-1.69 (m, 2H), 1.43-1.28 (m, 2H).

Compound (14) was prepared from compound (J-13) and N-(2-methoxy-5-(4,4,5,5-tetramethyl-1,3,2-dioxaborolan-2-yl)pyridin-3-yl)methanesulfonamide, according to the method of step 3 in Example 1.

$^1$H NMR (400 MHz, DMSO-d$_6$) δ 9.35 (s, 1H), 8.44 (d, J=2.2 Hz, 1H), 7.97 (d, J=2.2 Hz, 1H), 7.67 (d, J=1.2 Hz, 1H), 7.36 (d, J=1.2 Hz, 1H), 6.77 (s, 2H), 4.06 (d, J=6.6 Hz, 2H), 3.98 (s, 3H), 3.90 (dd, J=11.2, 3.0 Hz, 2H), 3.36 (t, J=10.9 Hz, 2H), 3.08 (s, 3H), 2.75 (s, 3H), 2.20-2.04 (m, 1H), 1.77 (d, J=12.4 Hz, 2H), 1.38 (qd, J=12.4, 4.4 Hz, 2H).

MS (ESI+) m/z 474.2 [M+H]⁺.

Example 15: N-(5-(2-amino-4-methyl-8-((1-methylpiperidin-4-yl)oxy)quinazolin-6-yl)-2-methoxypyridin-3-yl)-2,4-difluorobenzenesulfonamide (15)

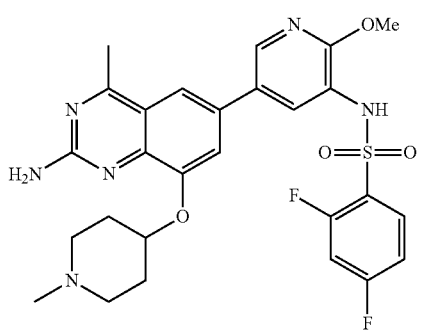

Step 1: Preparation of 6-bromo-2-(2,5-dimethyl-1H-pyrrol-1-yl)-4-methyl-8-((1-methylpiperidin-4-yl)oxy)quinazoline (I-15)

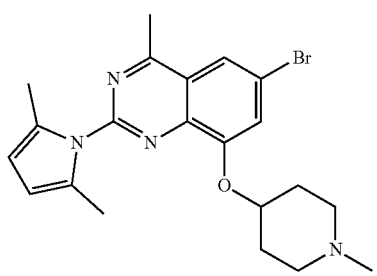

I-15

According to the method of step 1 in Example 1, compound (I-15) was prepared from compound (H) and 1-methylpiperidin-4-ol.

¹H NMR (400 MHz, CDCl₃) δ 8.02 (d, J=2.0 Hz, 1H), 7.64 (d, J=2.0 Hz, 1H), 5.86 (s, 2H), 4.88-4.73 (m, 1H), 2.91 (s, 3H), 2.64-2.54 (m, 2H), 2.37 (s, 6H), 2.35-2.25 (m, 2H), 2.18 (s, 3H), 2.04-1.89 (m, 2H), 1.87-1.71 (m, 2H).

Step 2: Preparation of 6-bromo-4-methyl-8-((1-methylpiperidin-4-yl)oxy)quinazolin-2-amine (J-15)

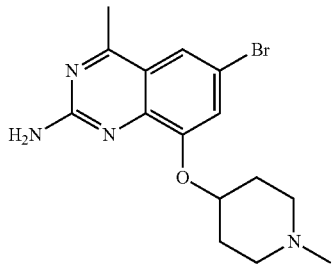

J-15

According to the method of step 2 in Example 1, compound (J-15) was prepared from compound (I-15).

¹H NMR (400 MHz, DMSO-d₆) δ 7.66 (d, J=2.0 Hz, 1H), 7.28 (d, J=2.0 Hz, 1H), 6.83 (s, 2H), 4.64-4.47 (m, 1H), 2.78-2.69 (m, 2H), 2.65 (s, 3H), 2.19 (s, 3H), 2.18-2.10 (m, 2H), 2.04-1.93 (m, 2H), 1.73-1.60 (m, 2H).

Step 3: Preparation of N-(5-(2-amino-4-methyl-8-((1-methylpiperidin-4-yl)oxy)quinazolin-6-yl)-2-methoxypyridin-3-yl)-2,4-difluorobenzenesulfonamide (15)

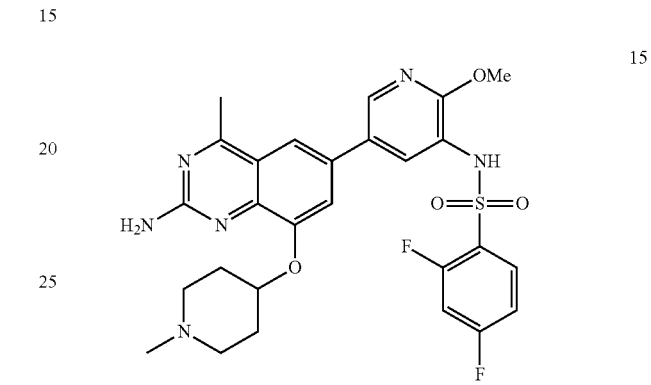

15

Compound (15) was prepared from compound (J-15) and N-(2-methoxy-5-(4,4,5,5-tetramethyl-1,3,2-dioxaborolan-2-yl)pyridin-3-yl)-2,4-difluorobenzenesulfonamide, according to the method of step 3 in Example 1.

¹H NMR (400 MHz, DMSO-d₆) δ 10.56 (br s, 1H), 8.40 (d, J=2.4 Hz, 1H), 7.94 (d, J=2.4 Hz, 1H), 7.76 (dt, J=8.6, 6.4 Hz, 1H), 7.71 (d, J=1.6 Hz, 1H), 7.61-7.51 (m, 2H), 7.22 (dt, J=8.4, 2.1 Hz, 1H), 6.84 (s, 2H), 4.95-4.85 (m, 1H), 3.64 (s, 3H), 3.10-2.95 (m, 2H), 2.76 (s, 3H), 2.69 (s, 3H), 2.25-2.13 (m, 2H), 2.07-1.95 (m, 2H).

MS (ESI+) m/z 571.18994 [M+H]⁺.

Example 16: N-(5-(2-amino-4-methyl-8-(2-morpholinoethoxy)quinazolin-6-yl)-2-methoxypyridin-3-yl)-2,4-difluorobenzenesulfonamide (16)

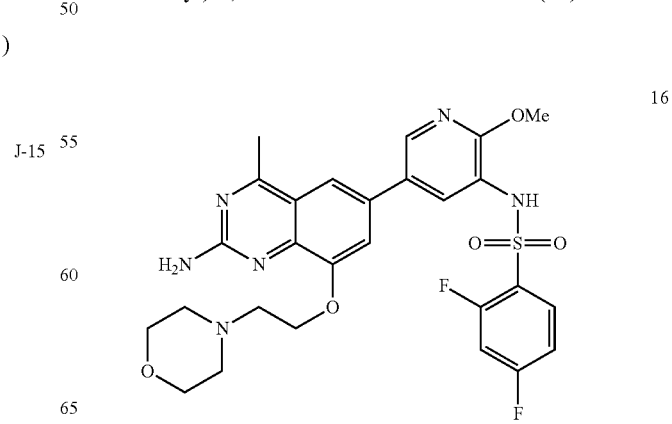

16

Step 1: Preparation of 4-(2-((6-bromo-2-(2,5-dimethyl-1H-pyrrol-1-yl)-4-methylquinazolin-8-yl)oxy)ethyl)morpholine (I-16)

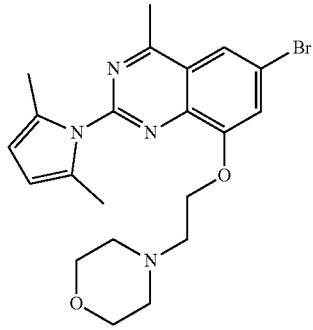

I-16

According to the method of step 1 in Example 1, compound (I-16) was prepared from compound (H) and 2-(morpholinyl)-ethanol.

¹H NMR (400 MHz, CDCl₃) δ 8.02 (d, J=2.0 Hz, 11H), 7.64 (d, J=2.0 Hz, 11H), 5.85 (s, 2H), 4.33 (t, J=5.1 Hz, 2H), 4.04 (q, J=7.0 Hz, 4H), 3.64-3.46 (m, 4H), 2.92 (s, 3H), 2.81 (t, J=5.1 Hz, 2H), 2.53 (s, 6H).

Step 2: Preparation of 6-bromo-4-methyl-8-(2-morpholinoethoxy)quinazolin-2-amine (J-16)

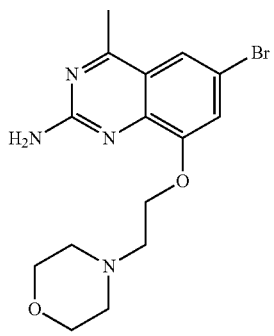

J-16

According to the method of step 2 in Example 1, compound (J-16) was prepared from compound (I-16).

¹H NMR (500 MHz, DMSO-d₆) δ 7.67 (s, 1H), 7.28 (s, 1H), 6.90 (s, 2H), 4.21 (t, J=5.9 Hz, 2H), 3.67-3.50 (m, 4H), 2.74 (t, J=5.8 Hz, 2H), 2.66 (s, 3H), 2.51 (br s, 4H).

Step 3: Preparation of N-(5-(2-amino-4-methyl-8-(2-morpholinoethoxy)quinazolin-6-yl)-2-methoxypyridin-3-yl)-2 4-difluorobenzenesulfonamide (16)

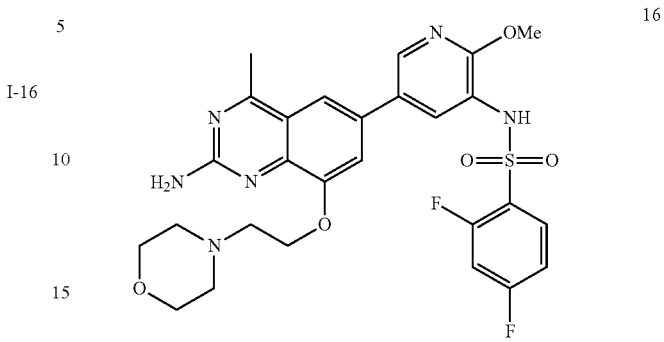

16

Compound (16) was prepared from compound (J-16) and N-(2-methoxy-5-(4,4,5,5-tetramethyl-1,3,2-dioxaborolan-2-yl)pyridin-3-yl)-2,4-difluorobenzenesulfonamide, according to the method of step 3 in Example 1.

¹H NMR (400 MHz, DMSO-d₆) δ 8.44 (d, J=2.2 Hz, 1H), 7.97 (d, J=2.2 Hz, 1H), 7.76 (dt, J=8.6, 6.4 Hz, 1H), 7.65 (d, J=1.6 Hz, 1H), 7.58 (ddd, J=10.4, 9.4, 2.4 Hz, 1H), 7.38 (d, J=1.6 Hz, 1H), 7.26-7.17 (m, 1H), 6.84 (s, 2H), 4.31 (t, J=6.0 Hz, 2H), 3.64 (s, 3H), 3.61 (t, J=4.6 Hz, 4H), 2.81 (t, J=6.0 Hz, 2H), 2.75 (s, 3H), 2.61-2.52 (m, 4H).

MS (ESI+) m/z 587.2 [M+H]⁺.

Example 17: N-(5-(2-amino-8-((4,4-difluorocyclohexyl)oxy)-4-methylquinazolin-6-yl)-2-methoxypyridin-3-yl)-2,4-difluorobenzenesulfonamide (17)

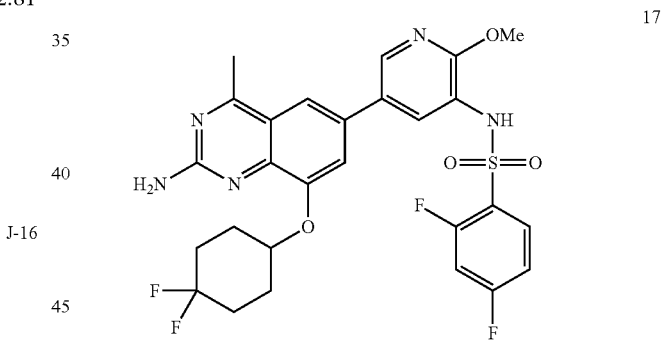

17

Step 1: Preparation of 6-bromo-8-((4,4-difluorocyclohexyl)oxy)-2-(2,5-dimethyl-1H-pyrrol-1-yl)-4-methylquinazoline (I-17)

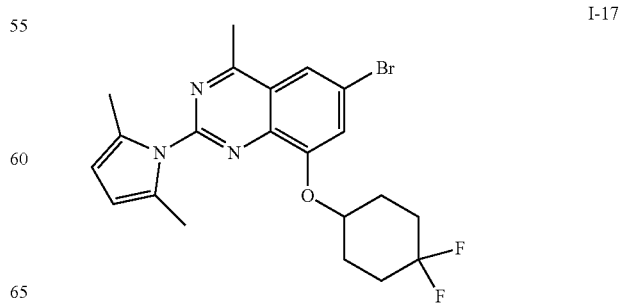

I-17

According to the method of step 1 in Example 1, compound (I-17) was prepared from compound (H) and 4,4-difluorocyclohexanol.

$^1$H NMR (400 MHz, CDCl$_3$) δ 7.82 (d, J=1.8 Hz, 1H), 7.31 (d, J=1.8 Hz, 1H), 5.92 (s, 2H), 4.85-4.77 (m, 1H), 2.91 (s, 3H), 2.45 (s, 6H), 2.28-2.14 (m, 4H), 2.07-1.92 (m, 4H).

Step 2: Preparation of 6-bromo-8-((4,4-difluorocyclohexyl)oxy)-4-methylquinazolin-2-amine (J-17)

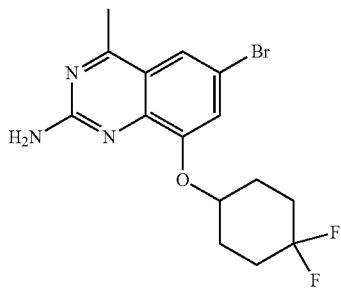

J-17

According to the method of step 2 in Example 1, compound (J-17) was prepared from compound (I-17).

$^1$H NMR (400 MHz, CDCl$_3$) δ 7.65 (d, J=1.6 Hz, 1H), 7.20 (d, J=1.6 Hz, 1H), 5.28 (br s, 2H), 4.71-4.62 (m, 1H), 2.74 (s, 3H), 2.41-2.23 (m, 2H), 2.23-2.10 (m, 2H), 2.07-1.86 (m, 4H).

Step 3: Preparation of N-(5-(2-amino-8-((4,4-difluorocyclohexyl)oxy)-4-methylquinazolin-6-yl)-2-methoxypyridin-3-yl)-2,4-difluorobenzenesulfonamide (17)

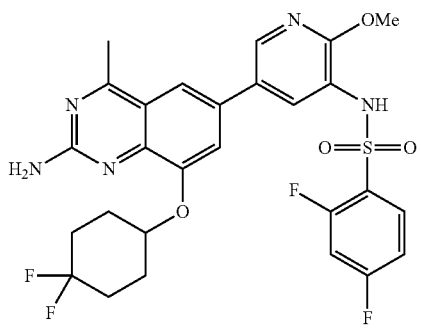

17

Compound (17) was prepared from compound (J-17) and N-(2-methoxy-5-(4,4,5,5-tetramethyl-1,3,2-dioxaborolan-2-yl)pyridin-3-yl)-2,4-difluorobenzenesulfonamide, according to the method of step 3 in Example 1.

$^1$H NMR (400 MHz, DMSO-d$_6$) δ 10.28 (s, 1H), 8.43 (d, J=2.2 Hz, 1H), 7.96 (d, J=2.2 Hz, 1H), 7.76 (dt, J=8.4, 6.6 Hz, 1H), 7.69 (d, J=1.4 Hz, 1H), 7.63-7.54 (m, 1H), 7.50 (d, J=1.4 Hz, 1H), 7.22 (dt, J=8.4, 2.0 Hz, 1H), 6.76 (s, 2H), 4.97-4.88 (m, 1H), 3.64 (s, 3H), 2.76 (s, 3H), 2.28-2.11 (m, 2H), 2.08-1.81 (m, 6H).

MS (ESI+) m/z 592.2 [M+H]$^+$.

Example 18: N-(5-(2-amino-8-((4-methoxycyclohexyl)oxy)-4-methylquinazolin-6-yl)-2-methoxypyridin-3-yl)-2,4-difluorobenzenesulfonamide (18)

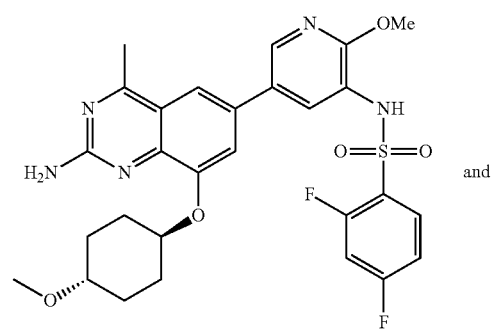

and

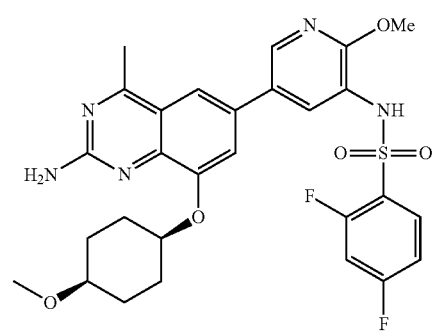

Step 1: Preparation of 6-bromo-2-(2,5-dimethyl-1H-pyrrol-1-yl)-8-((4-methoxycyclohexyl)oxy)-4-methylquinazoline (I-18)

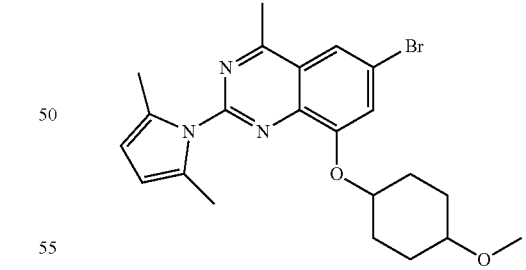

I-18

According to the method of step 1 in Example 1, compound (I-18) was prepared from compound (H) and 4-methoxycyclohexyl-1-ol.

$^1$H NMR (400 MHz, CDCl$_3$) δ 8.01 (d, J=1.9 Hz, 1H), 8.00 (d, J=1.9 Hz, 1H), 7.64 (d, J=1.9 Hz, 1H), 7.62 (d, J=1.8 Hz, 1H), 5.85 (s, 2H), 4.86-4.74 (m, 2H), 3.36-3.26 (m, 2H), 3.25 (s, 3H), 3.24 (s, 3H), 2.91 (s, 6H), 2.36 (s, 6H), 2.35 (s, 6H), 2.08-1.84 (m, 6H), 1.76-1.68 (m, 6H), 1.65-1.54 (m, 2H), 1.53-1.42 (m, 2H).

Step 2: Preparation of 6-bromo-8-((4-methoxycyclohexyl)oxy)-4-methylquinazolin-2-amine (J-18)

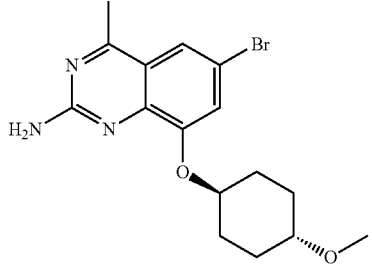

and

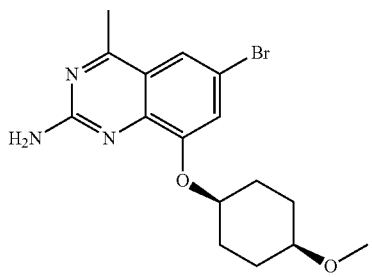

According to the method of step 2 in Example 1, compound (J-18) was prepared from compound (I-18), obtaining two new spots with similar polarity.

The spot of lower polarity:

$^1$H NMR (400 MHz, DMSO-d$_6$) δ 7.65 (d, J=1.8 Hz, 1H), 7.29 (d, J=1.8 Hz, 1H), 6.82 (s, 2H), 4.62-4.52 (m, 1H), 3.29-3.20 (m, 4H), 2.65 (s, 3H), 2.08-1.95 (m, 4H), 1.57-1.30 (m, 4H).

MS (ESI+) m/z 366.1 [M+H]).

The spot of higher polarity:

$^1$H NMR (400 MHz, DMSO-d$_6$) δ 7.65 (d, J=2.0 Hz, 1H), 7.27 (d, J=2.0 Hz, 1H), 6.80 (s, 2H), 4.71-4.54 (m, 1H), 3.36-3.32 (m, 1H), 3.24 (s, 3H), 2.65 (s, 3H), 1.86-1.54 (m, 8H).

MS (ESI+) m/z 366.1 [M+H]$^+$.

Step 3: N-(5-(2-amino-8-((4-methoxycyclohexyl)oxy)-4-methylquinazolin-6-yl)-2-methoxypyridin-3-yl)-2,4-difluorobenzenesulfonamide (18)

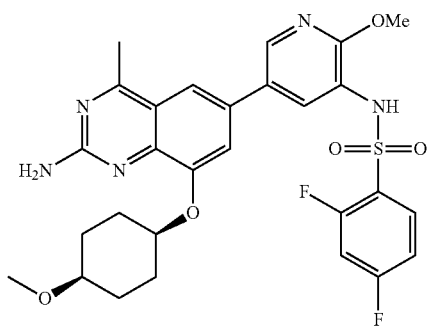

and

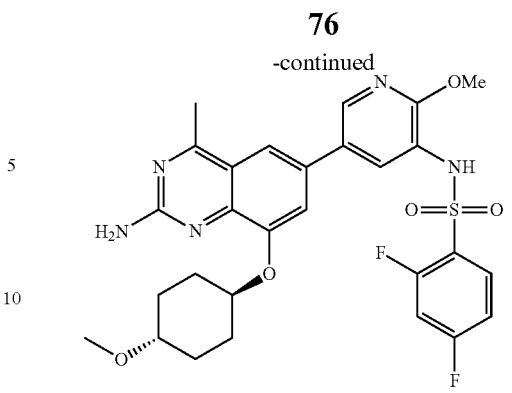

Compound 18-1: prepared from the spot of lower polarity in step 2, according to the method of step 3 in Example 1.

$^1$H NMR (400 MHz, DMSO-d$_6$) δ 10.28 (s, 1H), 8.43 (d, J=2.2 Hz, 1H), 7.95 (d, J=2.2 Hz, 1H), 7.75 (dt, J=8.6, 6.4 Hz, 1H), 7.64 (s, 1H), 7.62-7.55 (m, 1H), 7.41 (s, 1H), 7.22 (dt, J=8.4, 2.4 Hz, 1H), 6.77 (s, 2H), 4.76-4.65 (m, 1H), 3.64 (s, 3H), 3.28-3.22 (m, 4H), 2.75 (s, 3H), 2.12-1.30 (m, 4H), 1.60-1.30 (m, 4H).

MS (ESI+) m/z 586.2 [M+H]$^+$.

Compound 18-2: prepared from the spot of higher polarity in step 2, according to the method of step 3 in Example 1.

$^1$H NMR (400 MHz, DMSO-d$_6$) δ 10.28 (s, 1H), 8.42 (d, J=2.2 Hz, 1H), 7.93 (d, J=2.2 Hz, 1H), 7.76 (dt, J=8.4, 6.4 Hz, 1H), 7.64 (s, 1H), 7.63-7.54 (m, 1H), 7.38 (s, 1H), 7.22 (dt, J=8.4, 2.4 Hz, 1H), 6.74 (s, 2H), 4.83-4.67 (m, 1H), 3.65 (s, 3H), 3.38-3.28 (m, 1H), 3.25 (s, 3H), 2.75 (s, 3H), 1.88-1.70 (m, 6H), 1.69-1.55 (m, 2H).

MS (ESI+) m/z 586.2 [M+H]$^+$.

Example 19: N-(5-(2-amino-8-((2,2-dimethyltetrahydro-2H-pyran-4-yl)oxy)-4-methylquinazolin-6-yl)-2-methoxypyridin-3-yl)-2,4-difluorobenzenesulfonamide (19)

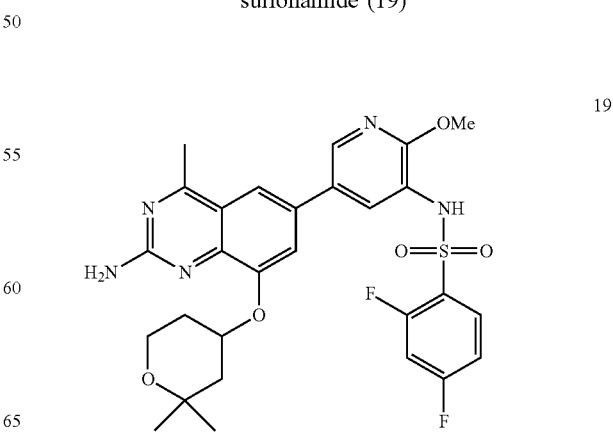

Step 1: Preparation of 6-bromo-2-(2,5-dimethyl-1H-pyrrol-1-yl)-8-((2,2-dimethyltetrahydro-2H-pyran-4-yl)oxy)-4-methylquinazoline (I-19)

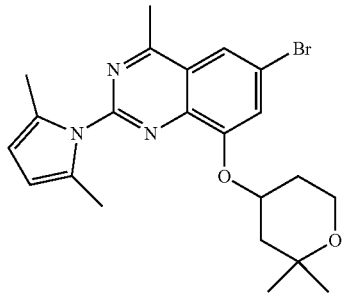

I-19

According to the method of step 1 in Example 1, compound (I-19) was prepared from compound (H) and 2,2-dimethyl-tetrahydro-2H-pyran-4-ol.

$^1$H NMR (400 MHz, CDCl$_3$) δ 7.81 (d, J=1.9 Hz, 11H), 7.29 (d, J=1.9 Hz, 11H), 4.85-4.76 (m, 1H), 4.03-3.95 (m, 1H), 3.80-3.70 (m, 1H), 2.91 (s, 3H), 2.44 (s, 6H), 2.17-2.08 (m, 1H), 2.08-1.99 (m, 1H), 1.92-1.75 (m, 2H), 1.34 (s, 3H), 1.28 (s, 3H).

Step 2: Preparation of 6-bromo-8-((2,2-dimethyltetrahydro-2H-pyran-4-yl)oxy)-4-methylquinazolin-2-amine (J-19)

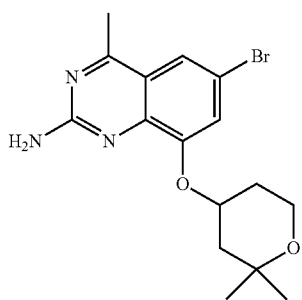

J-19

According to the method of step 2 in Example 1, compound (J-19) was prepared from compound (I-19).

$^1$H NMR (500 MHz, DMSO-d$_6$) δ 7.67 (d, J=1.5 Hz, 1H), 7.36 (d, J=1.5 Hz, 1H), 6.83 (s, 2H), 4.95-4.84 (m, 1H), 3.80-3.61 (m, 2H), 2.66 (s, 3H), 2.06-1.94 (m, 2H), 1.54-1.39 (m, 2H), 1.24 (s, 3H), 1.21 (s, 3H).

Step 3: Preparation of N-(5-(2-amino-8-((2,2-dimethyltetrahydro-2H-pyran-4-yl)oxy)-4-methylquinazolin-6-yl)-2-methoxypyridin-3-yl)-2,4-difluorobenzenesulfonamide (19)

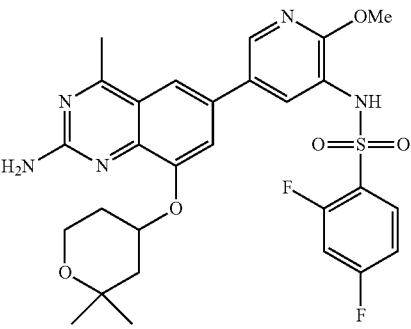

19

Compound (19) was prepared from compound (J-19) and N-(2-methoxy-5-(4,4,5,5-tetramethyl-1,3,2-dioxaborolan-2-yl)pyridin-3-yl)-2,4-difluorobenzenesulfonamide, according to the method of step 3 in Example 1.

$^1$H NMR (400 MHz, DMSO-d$_6$) δ 10.29 (s, 1H), 8.44 (d, J=2.3 Hz, 1H), 7.96 (d, J=2.3 Hz, 1H), 7.76 (dt, J=8.6, 6.4 Hz, 1H), 7.65 (d, J=1.6 Hz, 1H), 7.63-7.54 (m, 1H), 7.44 (d, J=1.6 Hz, 1H), 7.22 (dt, J=8.4, 2.4 Hz, 1H), 6.78 (s, 2H), 5.08-4.93 (m, 1H), 3.82-3.66 (m, 2H), 3.65 (s, 3H), 2.75 (s, 3H), 2.13-1.93 (m, 2H), 1.59-1.41 (m, 2H), 1.25 (s, 3H), 1.22 (s, 3H).

MS (ESI+) m/z 586.2 [M+H]$^+$.

Example 20: N-(5-(2-amino-4-methyl-8-((tetrahydrofuran-2-yl)methoxy)quinazolin-6-yl)-2-methoxypyridin-3-yl)-2,4-difluorobenzenesulfonamide (20)

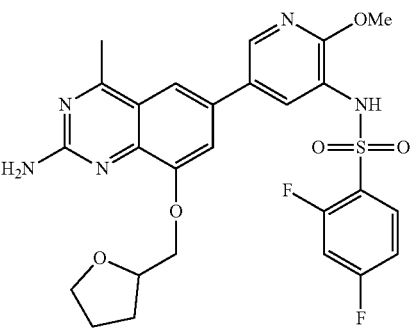

20

Step 1: Preparation of 6-bromo-2-(2,5-dimethyl-1H-pyrrol-1-yl)-4-methyl-8-((tetrahydrofuran-2-yl)methoxy)quinazoline (I-20)

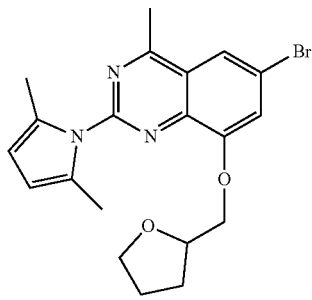

I-20

According to the method of step 1 in Example 1, compound (I-20) was prepared from compound (H) and tetrahydrofurfuryl alcohol.

¹H NMR (400 MHz, DMSO-$d_6$) δ 8.03 (d, J=1.8 Hz, 1H), 7.58 (d, J=1.8 Hz, 1H), 5.85 (s, 2H), 4.32-4.14 (m, 3H), 3.86-3.77 (m, 1H), 3.74-3.66 (m, 1H), 2.92 (s, 3H), 2.34 (s, 6H), 2.10-1.91 (m, 2H), 1.90-1.77 (m, 2H).

Step 2: Preparation of 6-bromo-4-methyl-8-((tetrahydrofuran-2-yl)methoxy)quinazolin-2-amine (J-20)

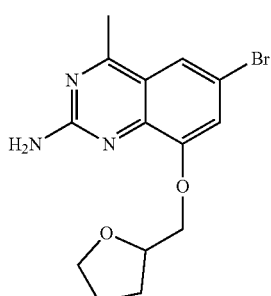

J-20

According to the method of step 2 in Example 1, compound (J-20) was prepared from compound (I-20).

¹H NMR (400 MHz, DMSO-$d_6$) δ 7.66 (d, J=2.0 Hz, 1H), 7.24 (d, J=2.0 Hz, 1H), 6.91 (s, 2H), 4.28-4.18 (m, 1H), 4.11-3.98 (m, 2H), 3.87-3.75 (m, 1H), 3.6673-3.66 (m, 1H), 2.66 (s, 3H), 2.08-1.97 (m, 1H), 1.97-1.77 (m, 2H), 1.74-1.62 (m, 1H).

Step 3: Preparation of N-(5-(2-amino-4-methyl-8-((tetrahydrofuran-2-yl)methoxy)quinazolin-6-yl)-2-methoxypyridin-3-yl)-2,4-difluorobenzenesulfonamide (20)

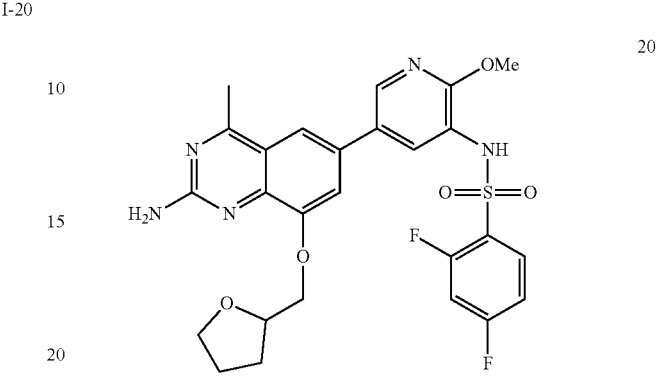

20

According to the method of step 3 in Example 1, Compound (20) was prepared from compound (J-20) and N-(2-methoxy-5-(4,4,5,5-tetramethyl-1,3,2-dioxaborolan-2-yl)pyridin-3-yl)-2,4-difluorobenzenesulfonamide.

¹H NMR (400 MHz, DMSO-$d_6$) δ 10.28 (s, 1H), 8.45 (d, J=2.3 Hz, 1H), 7.97 (d, J=2.3 Hz, 1H), 7.76 (dt, J=8.6, 6.4 Hz, 1H), 7.65 (d, J=1.6 Hz, 1H), 7.63-7.55 (m, 1H), 7.37 (d, J=1.6 Hz, 1H), 7.22 (dt, J=8.4, 2.0 Hz, 11H), 6.85 (s, 2H), 4.32-4.22 (m, 1H), 4.20-4.08 (m, 2H), 3.87-3.79 (m, 1H), 3.71 (dt, J=7.6, 6.4 Hz, 1H), 3.64 (s, 3H), 2.75 (s, 3H), 2.11-2.00 (m, 1H), 2.00-1.80 (m, 2H), 1.78-1.67 (m, 1H).

MS (ESI+) m/z 558.2 [M+H]⁺.

Example 21: N-(5-(2-amino-4-methyl-8-((tetrahydrofuran-3-yl)methoxy)quinazolin-6-yl)-2-methoxypyridin-3-yl)-2,4-difluorobenzenesulfonamide (21)

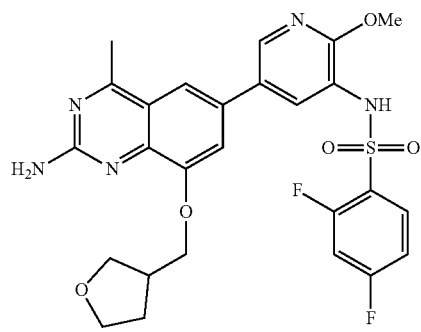

21

Step 1: Preparation of 6-bromo-2-(2,5-dimethyl-1H-pyrrol-1-yl)-4-methyl-8-((tetrahydrofuran-3-yl)methoxy)quinazoline (I-21)

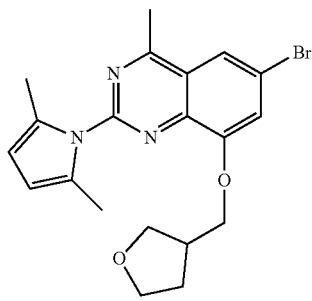

I-21

According to the method of step 1 in Example 1, compound (I-21) was prepared from compound (H) and (tetrahydrofuran-3-yl) methanol.

$^1$H NMR (400 MHz, DMSO-d$_6$) δ 8.03 (d, J=1.6 Hz, 1H), 7.58 (d, J=1.6 Hz, 1H), 5.85 (s, 2H), 4.23-4.08 (m, 2H), 3.88-3.75 (m, 2H), 3.69 (dd, J=14.8, 7.6 Hz, 1H), 3.62 (dd, J=8.6, 5.6 Hz, 1H), 2.92 (s, 3H), 2.84-2.71 (m, 1H), 2.35 (s, 6H), 2.12-2.00 (m, 1H), 1.81-1.70 (m, 1H).

Step 2: Preparation of 6-bromo-4-methyl-8-((tetrahydrofuran-3-yl)methoxy)quinazolin-2-amine (J-21)

J-21

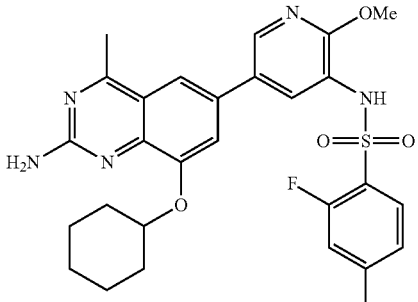

According to the method of step 2 in Example 1, compound (J-21) was prepared from compound (I-21).

$^1$H NMR (400 MHz, DMSO-d$_6$) δ 7.67 (d, J=2.0 Hz, 1H), 7.26 (d, J=2.0 Hz, 1H), 6.86 (s, 2H), 4.08-3.95 (m, 2H), 3.84-3.74 (m, 2H), 3.67 (dt, J=8.0, 6.6 Hz, 1H), 3.59 (dd, J=8.6, 5.0 Hz, 1H), 2.78-2.68 (m, 1H), 2.66 (s, 3H), 2.09-1.98 (m, 1H), 1.75-1.65 (m, 1H).

Step 3: Preparation of N-(5-(2-amino-4-methyl-8-((tetrahydrofuran-3-yl)methoxy)quinazolin-6-yl)-2-methoxypyridin-3-yl)-2,4-difluorobenzenesulfonamide (21)

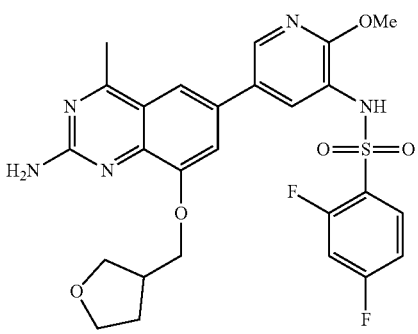

21

According to the method of step 3 in Example 1, Compound (21) was prepared from compound (J-21) and N-(2-methoxy-5-(4,4,5,5-tetramethyl-1,3,2-dioxaborolan-2-yl)pyridin-3-yl)-2,4-difluorobenzenesulfonamide.

$^1$H NMR (400 MHz, DMSO-d$_6$) δ 10.27 (s, 1H), 8.45 (d, J=2.2 Hz, 1H), 7.97 (d, J=2.2 Hz, 1H), 7.75 (dt, J=8.4, 6.4 Hz, 1H), 7.66 (d, J=1.2 Hz, 1H), 7.63-7.54 (m, 1H), 7.38 (d, J=1.2 Hz, 1H), 7.21 (dt, J=8.4, 2.2 Hz, 1H), 6.80 (s, 2H), 4.19-4.03 (m, 2H), 3.85-3.77 (m, 2H), 3.73-3.60 (m, 5H), 2.85-2.70 (m, 4H), 2.12-1.99 (m, 1H), 1.79-1.69 (m, 1H). MS (ESI+) m/z 558.2 [M+H]$^+$.

Example 22: N-(5-(2-amino-8-(cyclohexyloxy)-4-methylquinazolin-6-yl)-2-methoxypyridin-3-yl)-2,4-difluorobenzenesulfonamide (22)

22

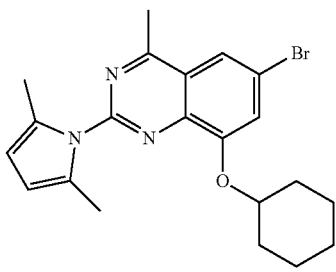

Step 1: Preparation of 6-bromo-8-(cyclohexyloxy)-2-(2,5-dimethyl-1H-pyrrol-1-yl)-4-methylquinazoline (I-22)

I-22

A mixture of compound (H) (1.661 g, 5 mmol), cyclohexyl bromide (8.15 g, 50 mmol), and potassium carbonate (6.91 g, 50 mmol) in acetonitrile (40 mL) in a sealed tube was refluxed overnight. The reaction mixture was cooled to r.t. and then filtered. Silica gel (5 g) was added to the filtrate, and the resulting mixture was evaporated to dry under reduced pressure. The residue was purified by flash column chromatography (silica gel, PE/EtOAc=100:1, v/v) to afford the product (I-22) as a yellow oil (1.7 g, 82% yield).

$^1$H NMR (500 MHz, DMSO-d$_6$) δ 8.00 (d, J=2.0 Hz, 1H), 7.61 (d, J=2.0 Hz, 1H), 5.85 (s, 2H), 4.79-4.72 (m, 1H), 2.91 (s, 3H), 2.35 (s, 6H), 1.95-1.86 (m, 2H), 1.79-1.70 (m, 2H), 1.69-1.57 (m, 2H), 1.56-1.31 (m, 4H).

Step 2: Preparation of 6-bromo-8-(cyclohexyloxy)-4-methylquinazolin-2-amine (J-22)

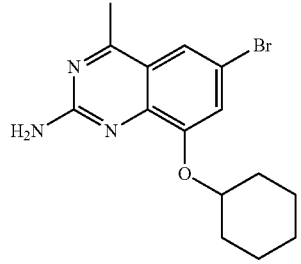

J-22

According to the method of step 2 in Example 1, compound (J-22) was prepared from compound (I-22).

$^1$H NMR (400 MHz, DMSO-d$_6$) δ 7.64 (d, J=2.0 Hz, 1H), 7.25 (d, J=2.0 Hz, 1H), 6.83 (s, 2H), 4.58-4.45 (m, 1H), 2.65 (s, 3H), 2.04-1.95 (m, 2H), 1.82-1.67 (m, 2H), 1.65-1.27 (m, 6H).

Step 3: Preparation of N-(5-(2-amino-8-(cyclohexyloxy)-4-methylquinazolin-6-yl)-2-methoxypyridin-3-yl)-2,4-difluorobenzenesulfonamide (22)

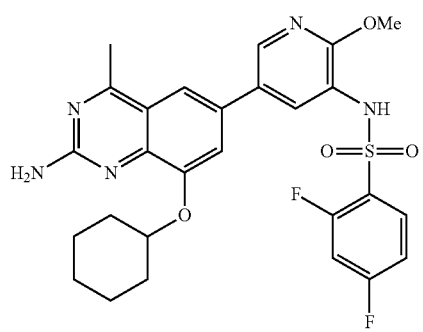

22

According to the method of step 3 in Example 1, Compound (22) was prepared from compound (J-22) and N-(2-methoxy-5-(4,4,5,5-tetramethyl-1,3,2-dioxaborolan-2-yl)pyridin-3-yl)-2,4-difluorobenzenesulfonamide.

$^1$H NMR (400 MHz, DMSO-d$_6$) δ 10.28 (s, 1H), 8.42 (d, J=2.3 Hz, 1H), 7.93 (d, J=2.3 Hz, 1H), 7.76 (dt, J=8.4, 6.4 Hz, 1H), 7.63 (d, J=1.6 Hz, 1H), 7.62-7.56 (m, 1H), 7.36 (d, J=1.4 Hz, 1H), 7.22 (dt, J=8.4, 2.0 Hz, 11H), 6.76 (s, 2H), 4.70-4.60 (m, 1H), 3.65 (s, 3H), 2.74 (s, 3H), 2.09-1.97 (m, 2H), 1.85-1.71 (m, 2H), 1.66-1.30 (m, 6H).

MS (ESI+) m/z 556.2 [M+H]$^+$.

Example 23: N-(5-(2-amino-8-(cyclopentyloxy)-4-methylquinazolin-6-yl)-2-methoxypyridin-3-yl)-2,4-difluorobenzenesulfonamide (23)

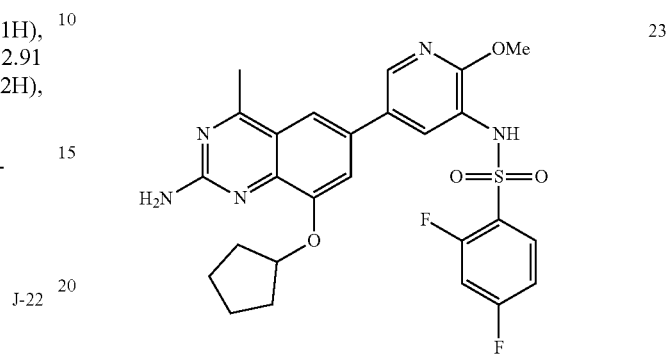

23

Step 1: Preparation of 6-bromo-8-(cyclopentyloxy)-2-(2,5-dimethyl-1H-pyrrol-1-yl)-4-methylquinazoline (I-23)

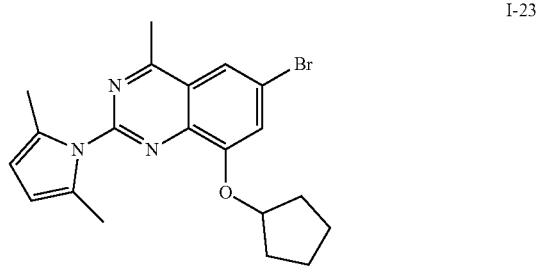 [SMILES: Cc1nc(-n2c(C)ccc2C)nc2c(OC3CCCC3)cc(Br)cc12]

I-23

According to the method of step 1 in Example 22, compound (I-23) was prepared from compound (H) and cyclopentyl bromide.

$^1$H NMR (500 MHz, DMSO-d$_6$) δ 8.00 (d, J=1.5 Hz, 1H), 7.53 (d, J=1.5 Hz, 1H), 5.85 (s, 2H), 5.18-5.09 (m, 1H), 2.91 (s, 3H), 2.34 (s, 6H), 2.03-1.92 (m, 2H), 1.89-1.80 (m, 2H), 1.80-1.70 (m, 2H), 1.69-1.58 (m, 2H).

Step 2: Preparation of 6-bromo-8-(cyclopentyloxy)-4-methylquinazolin-2-amine (J-23)

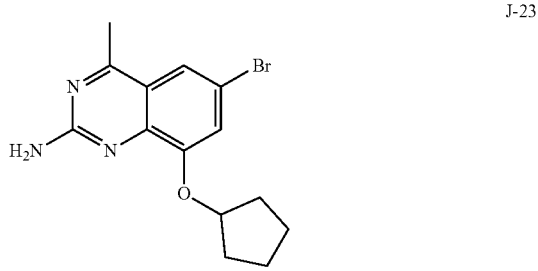 [SMILES: Cc1nc(N)nc2c(OC3CCCC3)cc(Br)cc12]

J-23

According to the method of step 2 in Example 1, compound (J-23) was prepared from compound (I-23).

¹H NMR (400 MHz, DMSO-d₆) δ 7.64 (d, J=2.0 Hz, 1H), 7.16 (d, J=2.0 Hz, 1H), 6.83 (s, 2H), 5.00-4.94 (m, 1H), 2.65 (s, 3H), 2.04-1.91 (m, 2H), 1.80-1.68 (m, 4H), 1.66-1.53 (m, 2H).

Step 3: Preparation of N-(5-(2-amino-8-(cyclopentyloxy)-4-methylquinazolin-6-yl)-2-methoxypyridin-3-yl)-2,4-difluorobenzenesulfonamide (23)

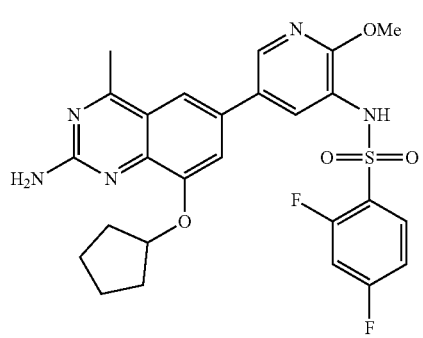

According to the method of step 3 in Example 1, Compound (23) was prepared from compound (J-23) and N-(2-methoxy-5-(4,4,5,5-tetramethyl-1,3,2-dioxaborolan-2-yl)pyridin-3-yl)-2,4-difluorobenzenesulfonamide, ¹H NMR (400 MHz, DMSO-d₆) δ 10.30 (s, 1H), 8.43 (d, J=2.4 Hz, 1H), 7.93 (d, J=2.4 Hz, 1H), 7.77 (dt, J=8.4, 6.4 Hz, 1H), 7.63 (d, J=1.8 Hz, 1H), 7.63-7.56 (m, 1H), 7.27 (d, J=1.6 Hz, 1H), 7.22 (dt, J=8.4, 2.2 Hz, 1H), 6.79 (s, 2H), 5.14-5.08 (m, 1H), 3.66 (s, 3H), 2.75 (s, 3H), 2.10-1.93 (m, 2H), 1.88-1.69 (m, 4H), 1.69-1.51 (m, 2H).

MS (ESI+) m/z 542.2 [M+H]⁺.

Example 24: N-(5-(2-amino-8-cyclobutoxy-4-methylquinazolin-6-yl)-2-methoxypyridin-3-yl)-2,4-difluorobenzenesulfonamide (24)

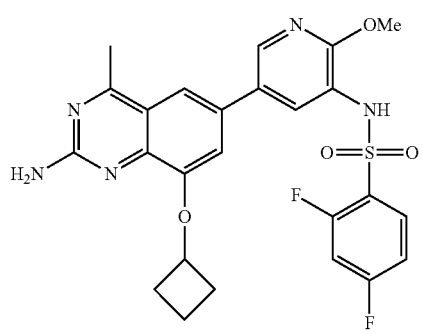

Step 1: Preparation of 6-bromo-8-cyclobutoxy-2-(2,5-dimethyl-1H-pyrrol-1-yl)-4-methylquinazoline (I-24)

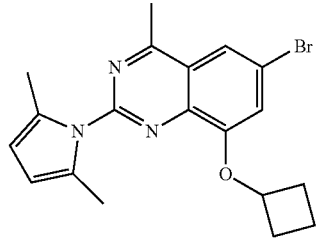

According to the method of step 1 in Example 22, compound (I-24) was prepared from compound (H) and cyclobutyl bromide.

¹H NMR (400 MHz, DMSO-d₆) δ 8.02 (d, J=1.9 Hz, 1H), 7.35 (d, J=1.9 Hz, 1H), 5.85 (s, 2H), 4.98 (p, J=7.0 Hz, 1H), 2.91 (s, 3H), 2.60-2.51 (m, 2H), 2.33 (s, 6H), 2.19-2.05 (m, 2H), 1.92-1.77 (m, 11H), 1.77-1.64 (m, 1H).

Step 2: Preparation of 6-bromo-8-cyclobutoxy-4-methylquinazolin-2-amine (J-24)

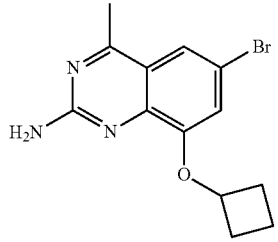

According to the method of step 2 in Example 1, compound (J-24) was prepared from compound (I-24).

¹H NMR (400 MHz, DMSO-d₆) δ 7.65 (d, J=2.0 Hz, 1H), 7.00 (d, J=2.0 Hz, 1H), 6.89 (s, 2H), 4.81 (p, J=7.0 Hz, 1H), 2.65 (s, 3H), 2.49-2.42 (m, 2H), 2.16-2.00 (m, 2H), 1.89-1.57 (m, 2H).

Step 3: Preparation of N-(5-(2-amino-8-cyclobutoxy-4-methylquinazolin-6-yl)-2-methoxypyridin-3-yl)-2,4-difluorobenzenesulfonamide (24)

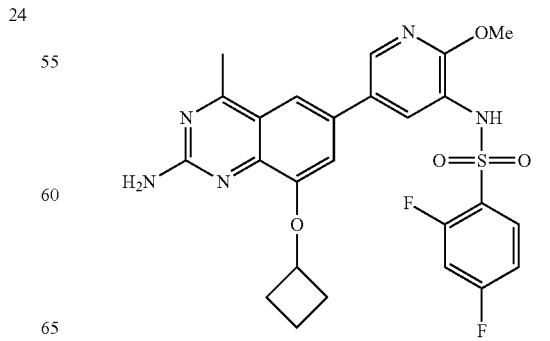

According to the method of step 3 in Example 1, Compound (24) was prepared from compound (J-24) and N-(2-methoxy-5-(4,4,5,5-tetramethyl-1,3,2-dioxaborolan-2-yl)pyridin-3-yl)-2,4-difluorobenzenesulfonamide, $^1$H NMR (400 MHz, DMSO-d$_6$) δ 10.30 (s, 1H), 8.42 (d, J=2.3 Hz, 1H), 7.92 (d, J=2.3 Hz, 1H), 7.77 (dt, J=8.6, 6.4 Hz, 11H), 7.64 (d, J=1.6 Hz, 11H), 7.63-7.55 (m, 1H), 7.23 (dt, J=8.6, 2.4 Hz, 1H), 7.12 (d, J=1.6 Hz, 1H), 6.84 (s, 2H), 4.94 (p, J=7.2 Hz, 1H), 3.66 (s, 3H), 2.75 (s, 3H), 2.55-2.46 (m, 2H), 2.19-2.06 (m, 2H), 1.89-1.62 (m, 2H).

MS (ESI+) m/z 528.1 [M+H]$^+$.

Example 25: Preparation of N-(5-(2-amino-8-(2-methoxyethoxy)-4-methylquinazolin-6-yl)-2-methoxypyridin-3-yl)-2,4-difluorobenzenesulfonamide (25)

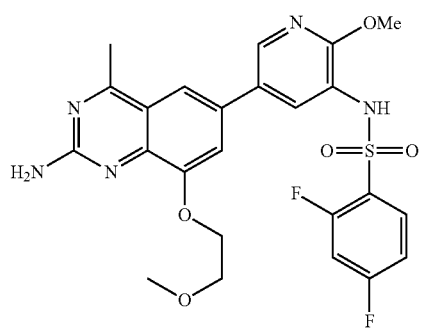

Step 1: Preparation of 6-bromo-2-(2,5-dimethyl-1H-pyrrol-1-yl)-8-(2-methoxyethoxy)-4-methylquinazoline (I-25)

I-25

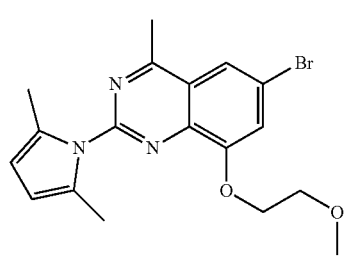

According to the method of step 1 in Example 22, compound (I-25) was prepared from compound (H) and 2-chloroethyl methyl ether.

$^1$H NMR (400 MHz, DMSO-d$_6$) δ 7.80 (d, J=1.9 Hz, 1H), 7.31 (d, J=1.9 Hz, 1H), 5.90 (s, 2H), 4.33 (t J=4.8 Hz, 2H), 3.90 (t, J=4.8 Hz, 3H), 3.48 (s, 3H), 2.91 (s, 3H), 2.43 (s, 6H).

Step 2: Preparation of 6-bromo-8-(2-methoxyethoxy)-4-methylquinazolin-2-amine (J-25)

J-25

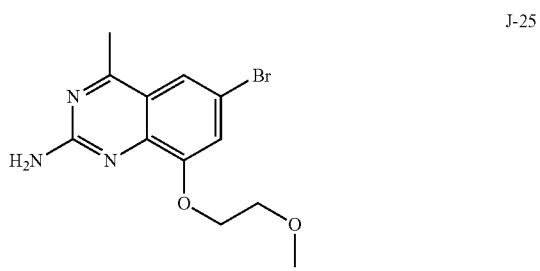 [SMILES: COCCOc1cc(Br)cc2c(C)nc(N)nc12]

According to the method of step 2 in Example 1, compound (J-25) was prepared from compound (I-25).

$^1$H NMR (400 MHz, DMSO-d$_6$) δ 7.67 (d, J=1.8 Hz, 1H), 7.23 (d, J=1.8 Hz, 1H), 6.90 (s, 2H), 4.21 (t, J=4.4 Hz, 2H), 3.90 (t, J=4.4 Hz, 3H), 3.32 (s, 3H), 2.66 (s, 3H).

Step 3: Preparation of N-(5-(2-amino-8-(2-methoxyethoxy)-4-methylquinazolin-6-yl)-2-methoxypyridin-3-yl)-2,4-difluorobenzenesulfonamide (25)

25

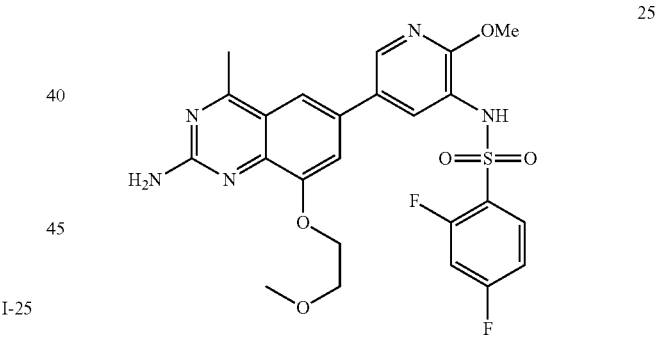

According to the method of step 3 in Example 1, Compound (25) was prepared from compound (J-25) and N-(2-methoxy-5-(4,4,5,5-tetramethyl-1,3,2-dioxaborolan-2-yl)pyridin-3-yl)-2,4-difluorobenzenesulfonamide, $^1$H NMR (400 MHz, DMSO-d$_6$) δ 10.32 (br s, 1H), 8.43 (s, 11H), 7.95 (s, 1H), 7.76 (dt, J=8.5, 6.6 Hz, 1H), 7.64 (d, J=1.4 Hz, 1H), 7.63-7.55 (m, 1H), 7.34 (d, J=1.4 Hz, 1H), 7.22 (dt, J=8.4, 2.4 Hz, 1H), 6.87 (s, 2H), 4.35-4.28 (m, 2H), 3.79-3.73 (m, 2H), 3.64 (s, 3H), 3.35 (s, 3H), 2.75 (s, 3H).

MS (ESI+) m/z 532.1 [M+H]$^+$.

Example 26: N-(5-(2-amino-8-isopropoxy-4-methylquinazolin-6-yl)-2-methoxypyridin-3-yl)-2,4-difluorobenzenesulfonamide (26)

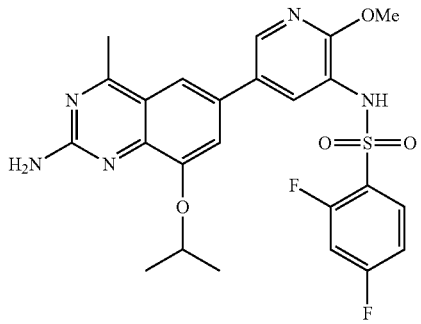

26

Step 1: Preparation of 6-bromo-2-(2,5-dimethyl-1H-pyrrol-1-yl)-8-(2-methoxyethoxy)-4-methylquinazoline (I-26)

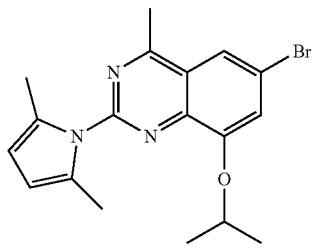

I-26

According to the method of step 1 in Example 22, compound (1-26) was prepared from compound (H) and isopropyl bromide.

1H NMR (400 MHz, DMSO-d$_6$) δ 8.02 (d, J=1.8 Hz, 1H), 7.59 (d, J=1.8 Hz, 1H), 5.85 (s, 2H), 4.98-4.88 (m, 1H), 2.92 (s, 3H), 2.34 (s, 6H), 1.36 (d, J=6.0 Hz, 6H).

Step 2: Preparation of 6-bromo-8-isopropoxy-4-methylquinazolin-2-amine (J-26)

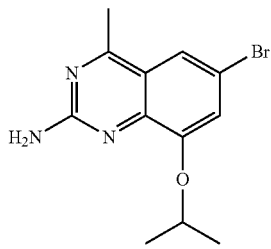

J-26

According to the method of step 2 in Example 22, compound (J-26) was prepared from compound (I-26).

$^1$H NMR (400 MHz, DMSO-d$_6$) δ 7.64 (d, J=2.0 Hz, 1H), 7.22 (d, J=2.0 Hz, 1H), 6.84 (s, 2H), 4.86-4.75 (m, 1H), 2.65 (s, 3H), 1.31 (d, J=6.0 Hz, 6H).

Step 3: Preparation of N-(5-(2-amino-8-isopropoxy-4-methylquinazolin-6-yl)-2-methoxypyridin-3-yl)-2,4-difluorobenzenesulfonamide (26)

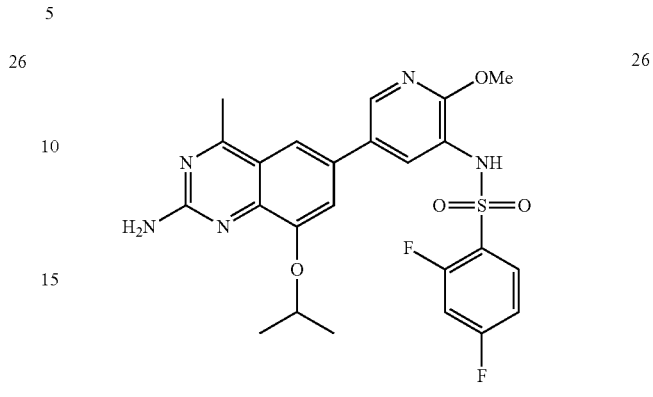

26

According to the method of step 3 in Example 1, Compound (26) was prepared from compound (J-26) and N-(2-methoxy-5-(4,4,5,5-tetramethyl-1,3,2-dioxaborolan-2-yl)pyridin-3-yl)-2,4-difluorobenzenesulfonamide, $^1$H NMR (400 MHz, DMSO-d$_6$) δ 10.30 (s, 1H), 8.44 (d, J=2.3 Hz, 1H), 7.94 (d, J=2.3 Hz, 1H), 7.76 (dt, J=8.6, 6.4 Hz, 1H), 7.64 (d, J=1.6 Hz, 1H), 7.63-7.56 (m, 1H), 7.33 (s, 1H), 7.22 (dt, J=8.4, 2.0 Hz, 1H), 6.83 (s, 2H), 5.00-4.89 (m, 1H), 3.64 (s, 3H), 2.75 (s, 3H), 1.34 (d, J=6.0 Hz, 6H).

MS (ESI+) m/z 516.1 [M+H]$^+$.

Example 27: N-(5-(2-amino-8-(cyclopropylmethoxy)-4-methylquinazolin-6-yl)-2-methoxypyridin-3-yl)-2,4-difluorobenzenesulfonamide (27)

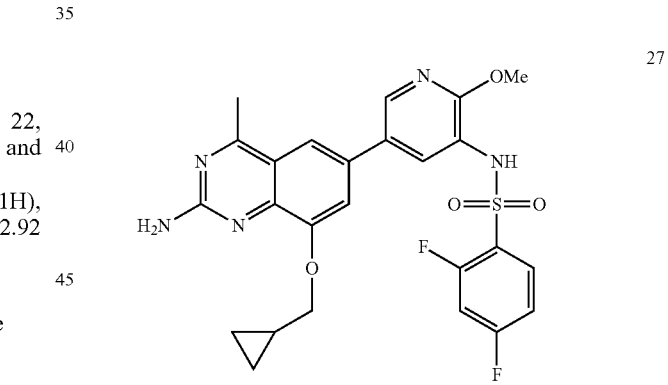

27

Step 1: Preparation of 6-bromo-8-(cyclopropylmethoxy)-2-(2,5-dimethyl-1H-pyrrol-1-yl)-4-methylquinazoline (I-27)

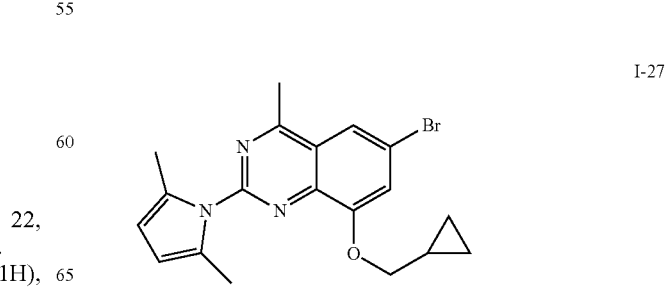

I-27

According to the method of step 1 in Example 22, compound (I-27) was prepared from compound (H) and cyclopropylmethylbromide.

$^1$H NMR (400 MHz, DMSO-d$_6$) δ 7.64 (d, J=1.8 Hz, 1H), 7.14 (d, J=1.8 Hz, 1H), 6.91 (s, 2H), 3.90 (d, J=7.2 Hz, 2H), 2.65 (s, 3H), 1.33-1.23 (m, 1H), 0.65-0.55 (m, 2H), 0.35 (q, J=4.8 Hz, 2H).

Step 2: Preparation of 6-bromo-8-(cyclopropylmethoxy)-4-methylquinazolin-2-amine (J-27)

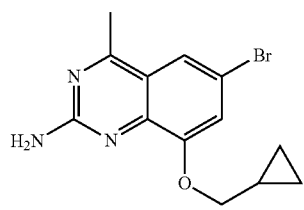

J-27

According to the method of step 2 in Example 22, compound (J-27) was prepared from compound (I-27).

$^1$H NMR (400 MHz, DMSO-d$_6$) δ 7.64 (d, J=1.8 Hz, 1H), 7.14 (d, J=1.8 Hz, 1H), 6.91 (s, 2H), 3.90 (d, J=7.2 Hz, 2H), 2.65 (s, 3H), 1.33-1.23 (m, 1H), 0.65-0.55 (m, 2H), 0.35 (q, J=4.8 Hz, 2H).

Step 3: Preparation of N-(5-(2-amino-8-(cyclopropylmethoxy)-4-methylquinazolin-6-yl)-2-methoxypyridin-3-yl)-2,4-difluorobenzenesulfonamide (27)

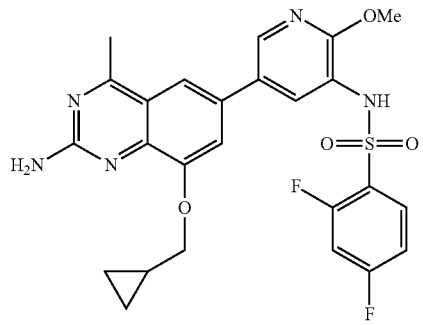

27

Compound (27) was prepared from compound (J-27) and N-(2-methoxy-5-(4,4,5,5-tetramethyl-1,3,2-dioxaborolan-2-yl)pyridin-3-yl)-2,4-difluorobenzenesulfonamide, according to the method of step 3 in Example 1.

$^1$H NMR (400 MHz, DMSO-d$_6$) δ 10.27 (s, 1H), 8.43 (d, J=2.2 Hz, 1H), 7.94 (d, J=2.2 Hz, 1H), 7.75 (dt, J=8.6, 6.4 Hz, 1H), 7.63 (d, J=1.6 Hz, 1H), 7.62-7.55 (m, 1H), 7.27 (d, J=1.6 Hz, 1H), 7.24-7.18 (m, 11H), 6.85 (br s, 2H), 4.00 (d, J=7.0 Hz, 2H), 3.63 (s, 3H), 2.75 (s, 3H), 1.37-1.27 (m, 1H), 0.67-0.57 (m, 2H), 0.40-0.33 (m, 2H).

MS (ESI+) m/z 528.1 [M+H]$^+$.

Example 28: Preparation of N-(5-(2-amino-8-methoxy-4-methylquinazolin-6-yl)-2-methoxypyridin-3-yl)-2,4-difluorobenzenesulfonamide (28)

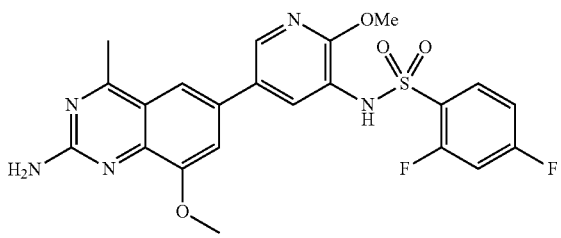

28

Compound (28) was prepared from compound (F) and N-(2-methoxy-5-(4,4,5,5-tetramethyl-1,3,2-dioxaborolan-2-yl)pyridin-3-yl)-2,4-difluorobenzenesulfonamide, according to the method of step 3 in Example 1.

$^1$H NMR (400 MHz, DMSO-d$_6$) δ 10.28 (s, 1H), 8.46 (d, J=2.4 Hz, 1H), 7.97 (d, J=2.4 Hz, 1H), 7.76 (dt, J=8.6, 6.4 Hz, 1H), 7.65 (d, J=1.7 Hz, 1H), 7.63-7.55 (m, 1H), 7.31 (d, J=1.7 Hz, 1H), 7.26-7.18 (m, 1H), 6.83 (s, 2H), 3.95 (s, 3H), 3.64 (s, 3H), 2.76 (s, 3H).

MS (ESI+) m/z 488.1 [M+H]$^+$.

Example 29: N-(2-methoxy-5-(4-methyl-2-(methylamino)-8-((tetrahydro-2H-pyran-4-yl)oxy)quinazolin-6-yl)pyridin-3-yl)-2,4-difluorobenzenesulfonamide (29)

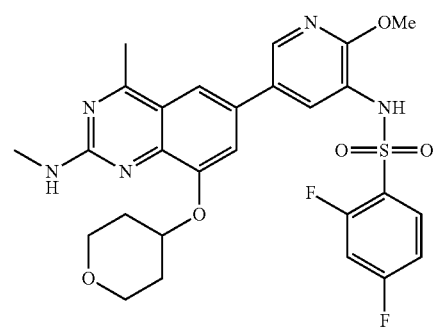

29

Step 1: Preparation of 6-bromo-N,4-dimethyl-8-((tetrahydro-2H-pyran-4-yl)oxy)quinazolin-2-amine (K-1)

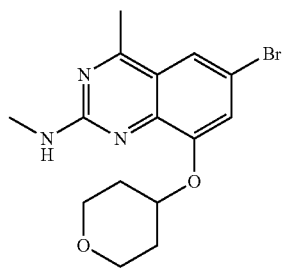

K-1

To a solution of compound (J-1) (517 mg) in DMF (50 mL) at 0° C. was added NaH (60% dispersion in mineral oil, 153 mg, 3.82 mmol). The resulting reaction mixture was stirred at 0° C. for 30 min, and then methyl iodide (217 mg, 1.53 mmol) was added. The resulting reaction mixture was stirred at r.t. for 3 h. The mixture was diluted with water (250 mL), neutralized with 2 M HCl, and extracted with EtOAc (50 mL×3). The combined organic layers were washed with water (50 mL×2) and brine (50 mL), dried over anhydrous Na$_2$SO$_4$, filtered, and concentrated. The residue was purified by flash column chromatography (silica gel, DCM/EtOAc=4:1, v/v) to afford the product (K-1) as a yellow solid (113 mg, 21%).

$^1$H NMR (400 MHz, DMSO-d$_6$) δ 7.74 (d, J=1.8 Hz, 1H), 7.39 (d, J=1.8 Hz, 1H), 7.34 (q, J=4.8 Hz, 1H), 4.94-4.76 (m, 1H), 3.99-3.82 (m, 2H), 3.53-3.43 (m, 2H), 2.88 (d, J=4.8 Hz, 3H), 2.66 (s, 3H), 2.06-1.88 (m, 2H), 1.77-1.57 (m, 2H).

Step 2: N-(2-methoxy-5-(4-methyl-2-(methyl-amino)-8-((tetrahydro-2H-pyran-4-yl)oxy)quinazo-lin-6-yl)pyridin-3-yl)-2,4-difluorobenzenesulfona-mide (29)

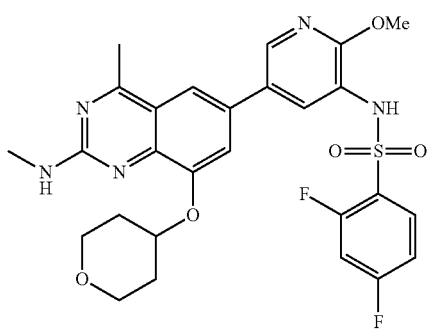

29

A mixture of compound (K-1) (35 mg, 0.1 mmol), N-(2-methoxy-5-(4,4,5,5-tetramethyl-1,3,2-dioxaborolan-2-yl)pyridin-3-yl)-2,4-difluorobenzenesulfonamide (51 mg, 0.12 mmol) and 2M aqueous potassium carbonate solution (0.15 mL, 0.63 mmol) in dioxane (7 mL) was degassed and then PdCl$_2$(dppf) (8 mg, 0.01 mmol) was added. The resulting reaction mixture was degassed and back-filled with argon (three cycles), and then stirred at 100° C. under Ar atmosphere for 5 h. The reaction mixture was cooled to r.t., diluted with EtOAc (30 mL) and water (30 mL), acidified with hydrochloric acid until the pH value was 5-6. The two phases were separated and the aqueous layer was extracted with EtOAc (30 mL×2). The combined organic layers were washed with water (50 mL) and brine (50 mL), dried over anhydrous Na$_2$SO$_4$, filtered and concentrated. The residue was purified by column chromatography (silica gel, DCM/MeOH=20:1, v/v) to afford the product (29) as a yellow solid (40 mg, 70% yield).

$^1$H NMR (400 MHz, DMSO-d$_6$) δ 10.28 (s, 1H), 8.42 (d, J=2.0 Hz, 1H), 7.93 (d, J=2.0 Hz, 1H), 7.83-7.66 (m, 2H), 7.63-7.53 (m, 1H), 7.50 (s, 1H), 7.28 (q, J=4.0 Hz, 1H), 7.21 (dt, J=8.4, 2.0 Hz, 1H), 4.97-4.88 (m 1H), 4.01-3.88 (m, 2H), 3.64 (s, 3H), 3.53-3.44 (m, 2H), 2.91 (d, J=4.4 Hz, 3H), 2.76 (s, 3H), 2.08-1.90 (m, 2H), 1.81-1.63 (m, 2H).

MS (ESI+) m/z 572.2 [M+H]$^+$.

Example 30: N-(5-(2-(ethylamino)-4-methyl-8-((tetrahydro-2H-pyran-4-yl)oxy)quinazolin-6-yl)-2-methoxypyridin-3-yl)-2,4-difluorobenzenesulfona-mide (30)

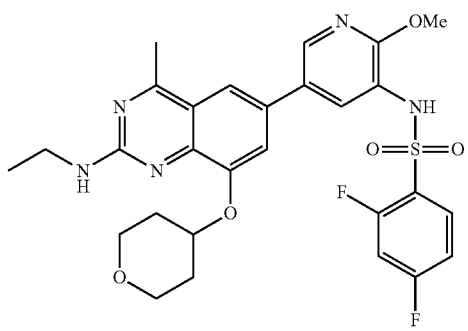

30

Step 1: Preparation of 6-bromo-N-ethyl-4-methyl-8-((tetrahydro-2H-pyran-4-yl)oxy)quinazolin-2-amine (K-2)

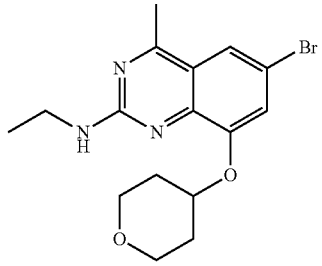

K-2

According to the method of step 1 in Example 29, compound (K-2) was prepared from compound (J-1) and iodoethane.

$^1$H NMR (400 MHz, DMSO-d$_6$) δ 7.73 (d, J=1.6 Hz, 1H), 7.41 (br s, 1H), 7.38 (d, J=1.6 Hz, 1H), 4.90-4.78 (m, 1H), 3.98-3.82 (m, 2H), 3.52-3.43 (m, 2H), 3.43-3.33 (m, 2H), 2.66 (s, 3H), 2.02-1.90 (m, 2H), 1.73-1.61 (m, 2H), 1.17 (t, J=7.2 Hz, 3H).

Step 2: Preparation of N-(5-(2-(ethylamino)-4-methyl-8-((tetrahydro-2H-pyran-4-yl)oxy)quinazo-lin-6-yl)-2-methoxypyridin-3-yl)-2,4-difluorobenze-nesulfonamide (30)

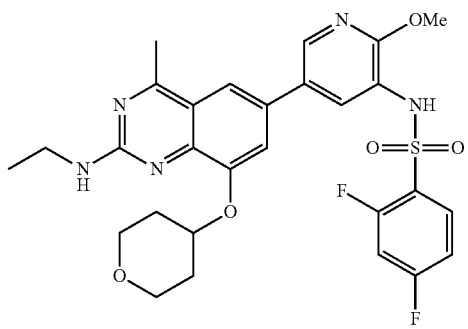

30

Compound (30) was prepared from compound (K-2) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 29.

¹H NMR (400 MHz, DMSO-d₆) δ 10.28 (s, 1H), 8.42 (d, J=2.1 Hz, 1H), 7.93 (d, J=2.3 Hz, 1H), 7.80-7.69 (m, 2H), 7.59 (ddd, J=10.4, 9.6, 2.4 Hz, 1H), 7.49 (d, J=1.2 Hz, 1H), 7.35 (t, J=5.0 Hz, 1H), 7.26-7.16 (m, 1H), 4.95-4.87 (m, 1H), 3.98-3.89 (m, 2H), 3.64 (s, 3H), 3.52-3.36 (m, 4H), 2.75 (s, 3H), 2.05-1.92 (m, 2H), 1.80-1.63 (m, 2H), 1.19 (t, J=7.1 Hz, 3H).

MS (ESI+) m/z 586.2 [M+H]⁺.

Example 31: N-(5-(2-((cyclopropylmethyl)amino)-4-methyl-8-((tetrahydro-2H-pyran-4-yl)oxy)quinazolin-6-yl)-2-methoxypyridin-3-yl)-2,4-difluorobenzenesulfonamide (31)

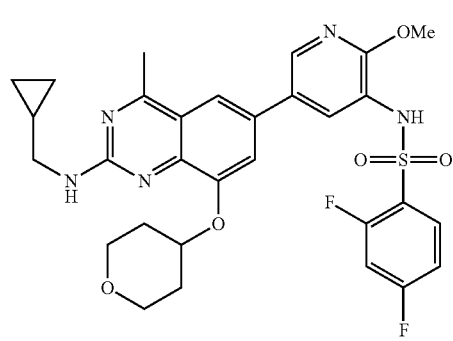

31

Step 1: Preparation of 6-bromo-N-(cyclopropylmethyl)-4-methyl-8-((tetrahydro-2H-pyran-4-yl)oxy)quinazolin-2-amine (K-3)

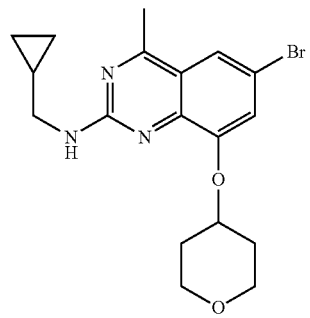

K-3

According to the method of step 1 in Example 29, compound (K-3) was prepared from compound (J-1) and cyclopropylmethyl bromide.

¹H NMR (400 MHz, DMSO-d₆) δ 7.73 (s, 1H), 7.51 (br s, 1H), 7.37 (d, J=1.7 Hz, 1H), 4.88-4.78 (m, 1H), 3.95-3.83 (m, 2H), 3.55-3.39 (m, 2H), 3.24 (t, J=6.3 Hz, 2H), 2.66 (s, 3H), 2.03-1.91 (m, 2H), 1.74-1.59 (m, 2H), 1.15-1.06 (m, 1H), 0.45-0.35 (m, 2H), 0.27 (q, J=4.4 Hz, 2H).

Step 2: Preparation of N-(5-(2-((cyclopropylmethyl)amino)-4-methyl-8-((tetrahydro-2H-pyran-4-yl)oxy)quinazolin-6-yl)-2-methoxypyridin-3-yl)-2,4-difluorobenzenesulfonamide (31)

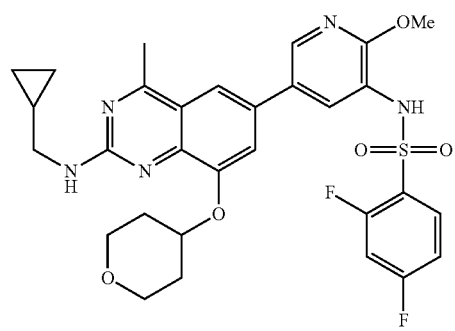

31

Compound (31) was prepared from compound (K-3) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 29.

¹H NMR (400 MHz, DMSO-d₆) δ 10.28 (s, 1H), 8.43 (d, J=2.4 Hz, 1H), 7.94 (d, J=2.4 Hz, 1H), 7.80-7.70 (m, 2H), 7.63-7.55 (m, 1H), 7.48 (d, J=1.2 Hz, 1H), 7.45 (br s, 1H), 7.22 (dt, J=8.4, 2.0 Hz, 1H), 4.96-4.86 (m, 1H), 4.00-3.89 (m, 2H), 3.64 (s, 3H), 3.54-3.42 (m, 2H), 3.28 (t, J=6.4 Hz, 2H), 2.76 (s, 3H), 2.06-1.94 (m, 2H), 1.80-1.63 (m, 2H), 1.21-1.05 (m, 1H), 0.50-0.38 (m, 2H), 0.29 (q, J=4.8 Hz, 2H).

MS (ESI+) m/z 612.2 [M+H]⁺.

Example 32: (R)—N-(2-methoxy-5-(4-methyl-2-(methylamino)-8-((tetrahydrofuran-3-yl)oxy)quinazolin-6-yl)pyridin-3-yl)-2,4-difluorobenzenesulfonamide (32)

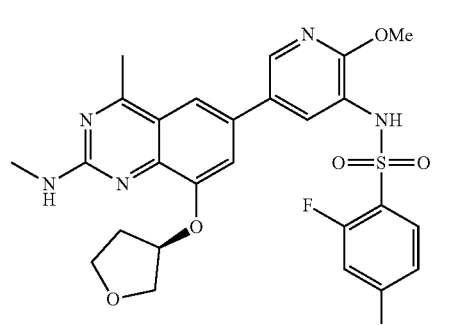

32

Step 1: Preparation of (R)-6-bromo-N,4-dimethyl-8-((tetrahydrofuran-3-yl)oxy)quinazolin-2-amine (K-4)

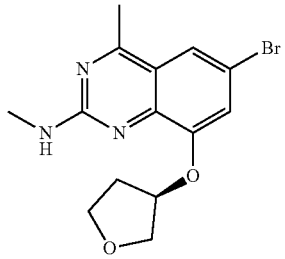

According to the method of step 1 in Example 29, compound (K-4) was prepared from compound (J-9).

¹H NMR (400 MHz, DMSO-d₆) δ 7.72 (d, J=2.0 Hz, 1H), 7.34 (q, J=4.8 Hz, 1H), 7.25 (s, 1H), 5.32-5.22 (m, 1H), 3.96-3.86 (m, 3H), 3.81-3.73 (m, 1H), 2.87 (d, J=4.8 Hz, 3H), 2.66 (s, 3H), 2.28-2.15 (m, 1H), 2.11-1.98 (m, 1H).

Step 2: (R)—N-(2-methoxy-5-(4-methyl-2-(methylamino)-8-((tetrahydrofuran-3-yl)oxy)quinazolin-6-yl)pyridin-3-yl)-2,4-difluorobenzenesulfonamide (32)

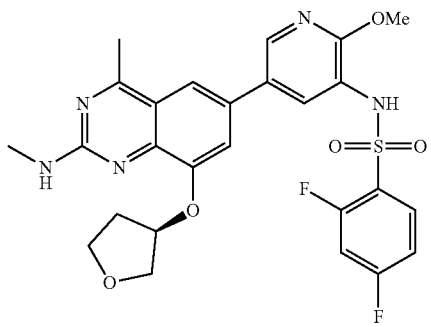

Compound (32) was prepared from compound (K-4) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 29.

¹H NMR (400 MHz, DMSO-d₆) δ 10.28 (s, 11H), 8.44 (d, J=2.2 Hz, 1H), 7.96 (d, J=2.2 Hz, 1H), 7.80-7.70 (m, 2H), 7.63-7.54 (m, 1H), 7.38 (s, 1H), 7.29 (q, J=4.8 Hz, 1H), 7.25-7.17 (m, 1H), 5.43-5.36 (m, 1H), 4.00-3.89 (m, 3H), 3.83-3.76 (m, 1H), 3.64 (s, 3H), 2.91 (d, J=4.8 Hz, 3H), 2.76 (s, 3H), 2.28-2.15 (m, 1H), 2.15-2.02 (m, 1H).

MS (ESI+) m/z 558.2 [M+H]⁺.

Example 33: (R)—N-(2-methoxy-5-(4-methyl-2-(methylamino)-8-((tetrahydrofuran-3-yl)oxy)quinazolin-6-yl)pyridin-3-yl)-2-chloro-4-fluorobenzenesulfonamide (33)

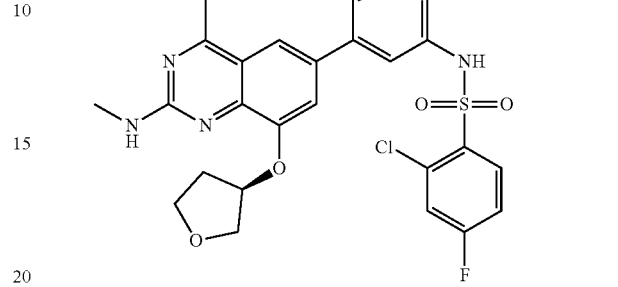

Compound (33) was prepared from compound (K-4) and N-(2-methoxy-5-(4,4,5,5-tetramethyl-1,3,2-dioxaborolan-2-yl)pyridin-3-yl)-2-chloro-4-fluorobenzenesulfonamide, according to the method of step 2 in Example 29.

¹H NMR (400 MHz, DMSO-d₆) δ 10.17 (s, 1H), 8.42 (d, J=2.4 Hz, 1H), 7.94 (dd, J=8.8, 6.0 Hz, 1H), 7.90 (d, J=2.4 Hz, 1H), 7.76 (dd, J=8.8, 2.6 Hz, 1H), 7.69 (d, J=1.6 Hz, 1H), 7.40-7.32 (m, 2H), 7.29 (q, J=4.8 Hz, 1H), 5.42-5.35 (m, 1H), 4.00-3.89 (m, 3H), 3.79 (dt, J=8.0, 4.4 Hz, 1H), 3.66 (s, 3H), 2.90 (d, J=4.8 Hz, 3H), 2.75 (s, 3H), 2.28-2.15 (m, 1H), 2.14-2.04 (m, 1H).

MS (ESI+) m/z 574.1 [M+H]⁺.

Example 34: (R)—N-(2-methoxy-5-(4-methyl-2-(methylamino)-8-((tetrahydrofuran-3-yl)oxy)quinazolin-6-yl)pyridin-3-yl)-5-chlorothiophene-2-sulfonamide (34)

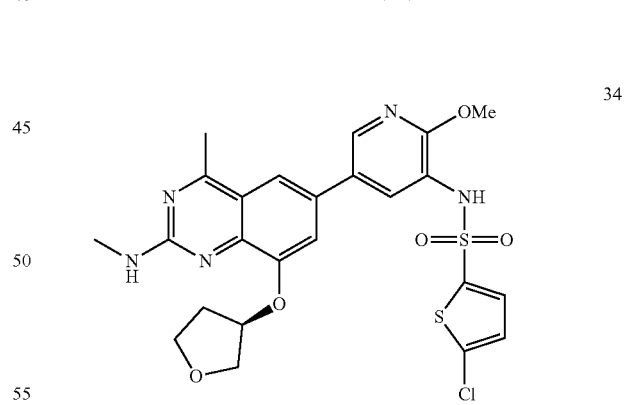

Compound (34) was prepared from compound (K-4) and N-(2-methoxy-5-(4,4,5,5-tetramethyl-1,3,2-dioxaborolan-2-yl)pyridin-3-yl)-5-chlorothiophene-2-sulfonamide, according to the method of step 2 in Example 29.

¹H NMR (400 MHz, DMSO-d₆) δ 10.33 (s, 1H), 8.48 (d, J=2.4 Hz, 1H), 7.96 (d, J=2.4 Hz, 1H), 7.73 (d, J=1.6 Hz, 1H), 7.42-7.38 (m, 2H), 7.29 (t, J=4.8 Hz, 1H), 7.25 (d, J=4.4 Hz, 1H), 5.43-5.36 (m, 1H), 4.00-3.90 (m, 3H), 3.80 (dt, J=8.0, 4.4 Hz, 1H), 3.75 (s, 3H), 2.91 (d, J=4.8 Hz, 3H), 2.77 (s, 3H), 2.30-2.16 (m, 1H), 2.15-2.05 (m, 1H).

Example 35: (S)—N-(2-methoxy-5-(4-methyl-2-(methylamino)-8-((tetrahydrofuran-3-yl)oxy)quinazolin-6-yl)pyridin-3-yl)-2,4-difluorobenzenesulfonamide (35)

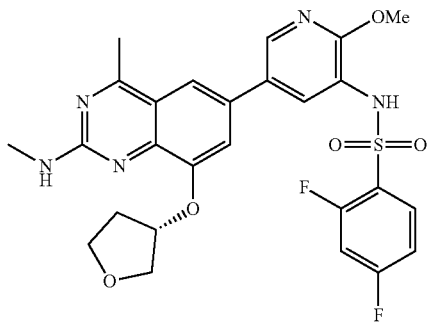

35

Step 1: Preparation of (S)-6-bromo-N,4-dimethyl-8-((tetrahydrofuran-3-yl)oxy)quinazolin-2-amine (K-7)

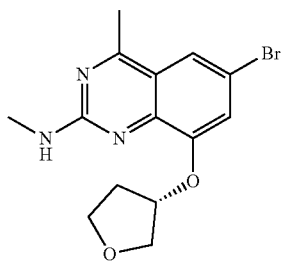

K-7

According to the method of step 1 in Example 29, compound (K-7) was prepared from compound (J-11).

$^1$H NMR (400 MHz, DMSO-d$_6$) δ 7.72 (d, J=2.0 Hz, 1H), 7.34 (q, J=4.8 Hz, 1H), 7.25 (s, 1H), 5.32-5.22 (m, 1H), 3.96-3.86 (m, 3H), 3.77 (dt, J=8.2, 4.6 Hz, 1H), 2.87 (d, J=4.8 Hz, 3H), 2.66 (s, 3H), 2.27-2.17 (m, 1H), 2.09-1.99 (m, 1H).

Step 2: Preparation of(S)—N-(2-methoxy-5-(4-methyl-2-(methylamino)-8-((tetrahydrofuran-3-yl)oxy)quinazolin-6-yl)pyridin-3-yl)-2,4-difluoro-benzenesulfonamide (35)

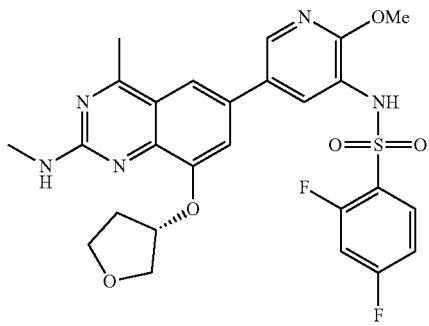

35

According to the method of step 2 in Example 29, compound (35) was prepared from compound (K-7).

$^1$H NMR (400 MHz, DMSO-d$_6$) δ 10.28 (s, 1H), 8.44 (d, J=2.4 Hz, 1H), 7.97 (d, J=2.4 Hz, 1H), 7.80-7.70 (m, 2H), 7.59 (ddd, J=10.4, 9.2, 2.4 Hz, 1H), 7.38 (s, 1H), 7.29 (q, J=4.8 Hz, 11H), 7.22 (dt, J=8.4, 2.4 Hz, 1H), 5.43-5.36 (m, 1H), 4.03-3.87 (m, 3H), 3.79 (dt, J=8.2, 4.6 Hz, 1H), 3.64 (s, 3H), 2.91 (d, J=4.8 Hz, 3H), 2.76 (s, 3H), 2.28-2.16 (m, 11H), 2.15-2.04 (m, 11H).

MS (ESI+) m/z 558.2 [M+H]$^+$.

Example 36: N-(2-methoxy-5-(4-methyl-2-(methylamino)-8-((tetrahydro-2H-pyran-4-yl)methoxy)quinazolin-6-yl)pyridin-3-yl)-2,4-difluoro-benzenesulfonamide (36)

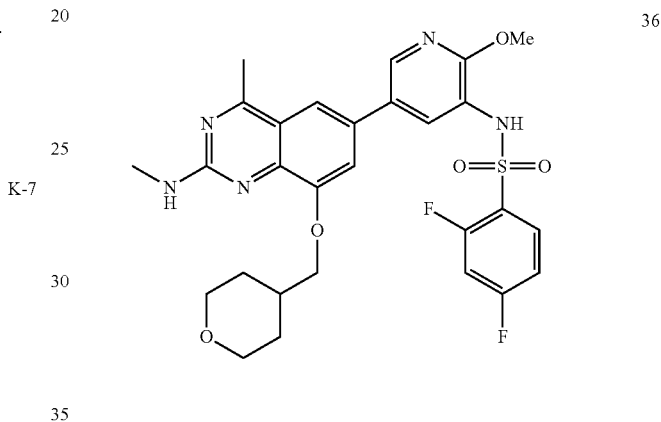

36

Step 1: Preparation of 6-bromo-N,4-dimethyl-8-((tetrahydro-2H-pyran-4-yl)methoxy)quinazolin-2-amine (K-8)

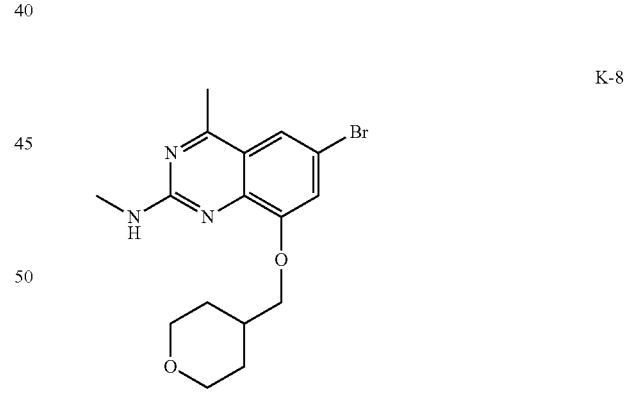

K-8

According to the method of step 1 in Example 29, compound (K-8) was prepared from compound (J-13).

$^1$H NMR (400 MHz, DMSO-d$_6$) δ 7.66 (d, J=2.0 Hz, 1H), 7.28 (q, J=4.8 Hz, 1H), 7.24 (d, J=1.4 Hz, 1H), 3.98 (d, J=6.8 Hz, 2H), 3.94-3.84 (m, 2H), 3.35 (dt, J=11.6, 2.0 Hz, 2H), 2.87 (d, J=4.8 Hz, 3H), 2.66 (s, 3H), 2.16-2.02 (m, 1H), 1.80-1.71 (m, 2H), 1.39 (qd, J=12.4, 4.4 Hz, 2H).

Step 2: Preparation of N-(2-methoxy-5-(4-methyl-2-(methylamino)-8-((tetrahydro-2H-pyran-4-yl)methoxy)quinazolin-6-yl)pyridin-3-yl)-2,4-difluorobenzenesulfonamide (36)

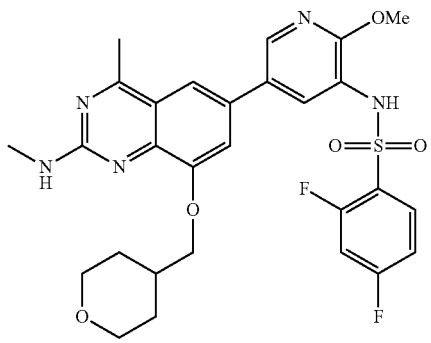

36

Compound (36) was prepared from compound (K-8) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 29.

$^1$H NMR (400 MHz, DMSO-d$_6$) δ 10.27 (s, 1H), 8.44 (d, J=2.0 Hz, 1H), 7.95 (d, J=2.0 Hz, 1H), 7.76 (dt, J=8.6, 6.3 Hz, 1H), 7.65 (d, J=1.6 Hz, 1H), 7.63-7.54 (m, 1H), 7.37 (s, 1H), 7.28-7.17 (m, 2H), 4.08 (d, J=6.4 Hz, 2H), 3.95-3.87 (m, 2H), 3.64 (s, 3H), 3.37 (dt, J=11.6, 2.0 Hz, 2H), 2.90 (d, J=4.8 Hz, 3H), 2.75 (s, 3H), 2.19-2.05 (m, 1H), 1.85-1.74 (m, 2H), 1.49-1.35 (m, 2H).

MS (ESI+) m/z 586.2 [M+H]$^+$.

Example 37: N-(5-(8-((2,2-dimethyltetrahydro-2H-pyran-4-yl)oxy)-4-methyl-2-(methylamino)quinazolin-6-yl)-2-methoxypyridin-3-yl)-2,4-difluorobenzenesulfonamide (37)

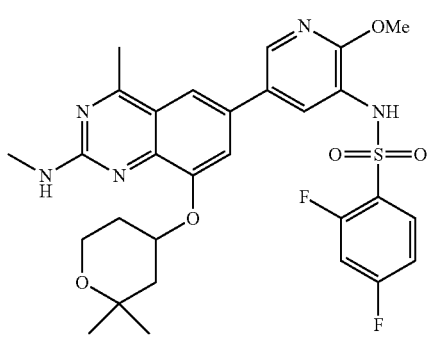

37

Step 1: Preparation of 6-bromo-8-((2,2-dimethyltetrahydro-2H-pyran-4-yl)oxy)-N,4-dimethylquinazolin-2-amine (K-9)

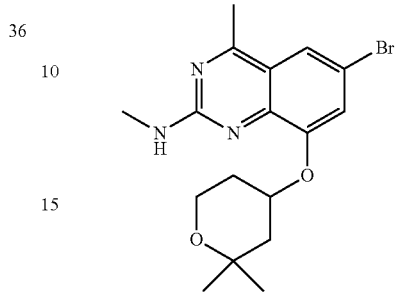

K-9

According to the method of step 1 in Example 29, compound (K-9) was prepared from compound (J-19).

$^1$H NMR (400 MHz, DMSO-d$_6$) δ 7.72 (d, J=2.0 Hz, 1H), 7.35 (d, J=2.0 Hz, 1H), 7.32 (q, J=4.8 Hz, 1H), 5.04-4.92 (m, 1H), 3.78 (dt, J=12.0, 4.4 Hz, 1H), 3.58 (t, J=10.0 Hz, 1H), 2.87 (d, J=4.8 Hz, 3H), 2.66 (s, 3H), 2.01-1.83 (m, 2H), 1.67-1.43 (m, 2H), 1.29 (s, 3H), 1.17 (s, 3H).

Step 2: Preparation of N-(5-(8-((2,2-dimethyltetrahydro-2H-pyran-4-yl)oxy)-4-methyl-2-(methylamino)quinazolin-6-yl)-2-methoxypyridin-3-yl)-2,4-difluorobenzenesulfonamide (37)

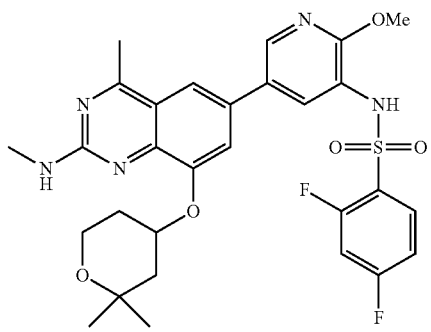

37

Compound (37) was prepared from compound (K-9) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 29.

$^1$H NMR (400 MHz, DMSO-d$_6$) δ 10.28 (s, 1H), 8.43 (d, J=2.4 Hz, 1H), 7.94 (d, J=2.4 Hz, 1H), 7.79-7.71 (m, 2H), 7.59 (ddd, J=10.4, 9.2, 2.4 Hz, 1H), 7.46 (d, J=1.8 Hz, 1H), 7.27 (q, J=4.8 Hz, 1H), 7.25-7.18 (m, 1H), 5.16-4.97 (m, 1H), 3.85-3.76 (m, 1H), 3.64 (s, 3H), 3.62-3.53 (m, 1H), 2.90 (d, J=4.8 Hz, 3H), 2.76 (s, 3H), 2.04-1.91 (m, 2H), 1.66-1.50 (m, 2H), 1.29 (s, 3H), 1.18 (s, 3H).

MS (ESI+) m/z 600.2 [M+H]$^+$.

Example 38: N-(2-methoxy-5-(4-methyl-2-(methylamino)-8-((tetrahydrofuran-3-yl)methoxy)quinazolin-6-yl)pyridin-3-yl)-2,4-difluorobenzenesulfonamide (38)

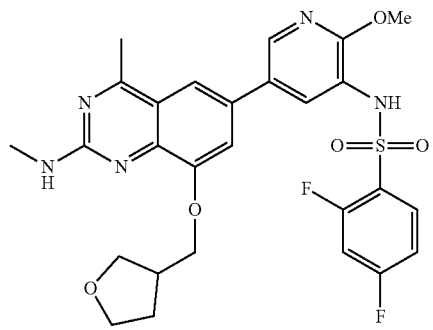

Step 1: Preparation of 6-bromo-N,4-dimethyl-8-((tetrahydrofuran-3-yl)methoxy)quinazolin-2-amine (K-10)

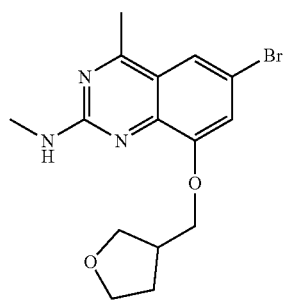

According to the method of step 1 in Example 29, compound (K-10) was prepared from compound (J-21).

¹H NMR (400 MHz, DMSO-d₆) δ 7.68 (d, J=2.0 Hz, 1H), 7.30 (d, J=4.8 Hz, 1H), 7.28 (d, J=1.7 Hz, 1H), 4.18-4.07 (m, 1H), 4.07-3.96 (m, 11H), 3.87-3.76 (m, 2H), 3.74-3.58 (m, 2H), 2.87 (d, J=4.8 Hz, 3H), 2.78-2.68 (m, 1H), 2.66 (s, 3H), 2.10-1.96 (m, 1H), 1.82-1.68 (m, 1H).

Step 2: Preparation of N-(2-methoxy-5-(4-methyl-2-(methylamino)-8-((tetrahydrofuran-3-yl)methoxy)quinazolin-6-yl)pyridin-3-yl)-2,4-difluorobenzenesulfonamide (38)

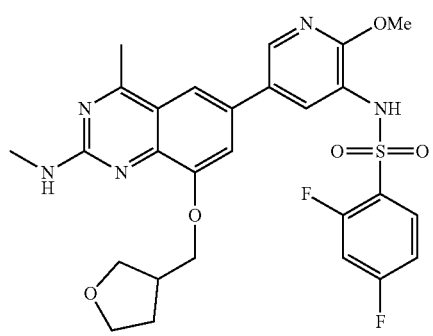

According to the method of step 2 in Example 29, Compound (38) was prepared from compound (K-10).

¹H NMR (400 MHz, DMSO-d₆) δ 10.27 (s, 1H), 8.44 (d, J=2.1 Hz, 1H), 7.96 (d, J=2.2 Hz, 1H), 7.75 (dt, J=8.6, 6.4 Hz, 1H), 7.68 (d, J=1.6 Hz, 1H), 7.63-7.53 (m, 1H), 7.41 (s, 1H), 7.28-7.16 (m, 2H), 4.26-4.16 (m, 1H), 4.11 (dd, J=9.2, 8.0 Hz, 1H), 3.89-3.79 (m, 2H), 3.70 (dt, J=8.0, 6.4 Hz, 2H), 3.63 (s, 3H), 2.90 (d, J=4.8 Hz, 3H), 2.82-2.70 (m, 4H), 2.12-2.00 (m, 1H), 1.85-1.72 (m, 1H).

MS (ESI+) m/z 572.2 [M+H]⁺.

Example 39: N-(5-(8-(cyclohexyloxy)-4-methyl-2-(methylamino)quinazolin-6-yl)-2-methoxypyridin-3-yl)-2,4-difluorobenzenesulfonamide (39)

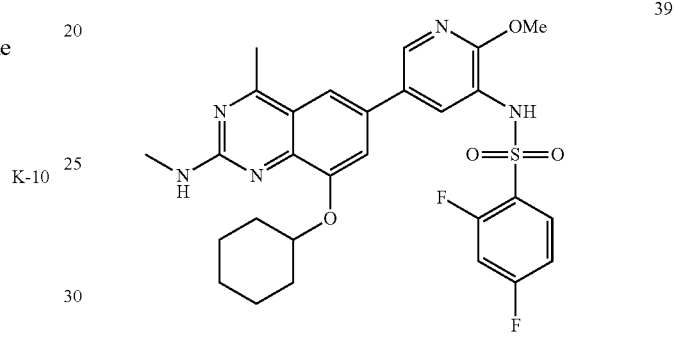

Step 1: Preparation of 6-bromo-8-(cyclohexyloxy)-N,4-dimethylquinazolin-2-amine (K-11)

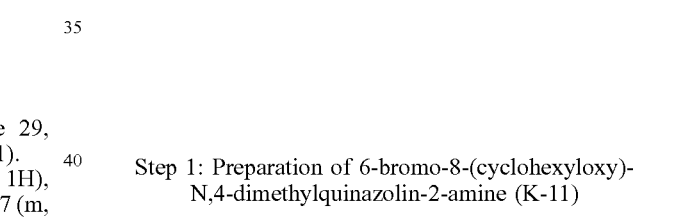

According to the method of step 1 in Example 29, compound (K-11) was prepared from compound (J-22).

¹H NMR (400 MHz, DMSO-d₆) δ 7.70 (d, J=2.0 Hz, 1H), 7.34-7.25 (m, 2H), 4.69-4.54 (m, 1H), 2.87 (d, J=4.8 Hz, 3H), 2.66 (s, 3H), 1.98-1.86 (m, 2H), 1.82-1.71 (m, 2H), 1.61-1.45 (m, 3H), 1.41-1.27 (m, 3H).

Step 2: Preparation of N-(5-(8-(cyclohexyloxy)-4-methyl-2-(methylamino)quinazolin-6-yl)-2-methoxypyridin-3-yl)-2,4-difluorobenzenesulfonamide (39)

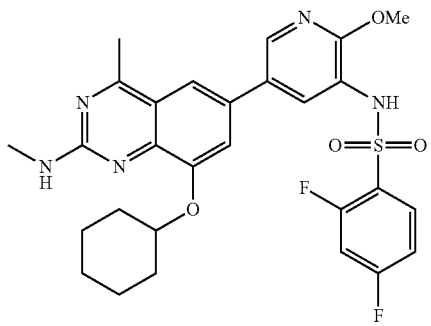

Compound (39) was prepared from compound (K-11) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 29.

$^1$H NMR (400 MHz, DMSO-d$_6$) δ 10.28 (s, 1H), 8.42 (d, J=2.4 Hz, 1H), 7.92 (d, J=2.4 Hz, 1H), 7.76 (dt, J=8.6, 6.4 Hz, 1H), 7.70 (d, J=1.2 Hz, 1H), 7.59 (ddd, J=10.4, 9.2, 2.4 Hz, 1H), 7.41 (d, J=1.2 Hz, 1H), 7.28-7.18 (m, 2H), 4.76-4.66 (m, 1H), 3.65 (s, 3H), 2.91 (d, J=4.8 Hz, 3H), 2.75 (s, 3H), 2.04-1.91 (m, 2H), 1.88-1.73 (m, 2H), 1.67-1.47 (m, 3H), 1.39-1.27 (m, 3H).
MS (ESI+) m/z 570.2 [M+H]$^+$.

Example 40: N-(5-(8-(cyclopentyloxy)-4-methyl-2-(methylamino)quinazolin-6-yl)-2-methoxypyridin-3-yl)-2,4-difluorobenzenesulfonamide (40)

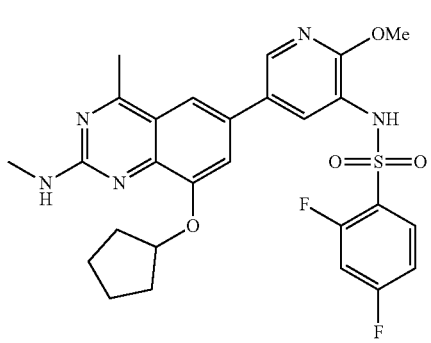

Step 1: Preparation of 6-bromo-8-(cyclopentyloxy)-N,4-dimethylquinazolin-2-amine (K-12)

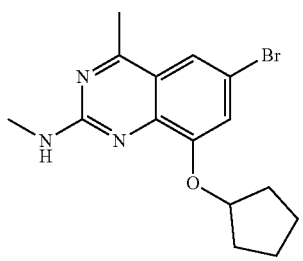

According to the method of step 1 in Example 29, compound (K-12) was prepared from compound (J-23).

$^1$H NMR (400 MHz, DMSO-d$_6$) δ 7.66 (d, J=2.0 Hz, 1H), 7.27 (q, J=4.8 Hz, 1H), 7.20 (s, 1H), 5.11-4.98 (m, 1H), 2.87 (d, J=4.8 Hz, 3H), 2.66 (s, 3H), 1.98-1.85 (m, 2H), 1.84-1.68 (m, 4H), 1.68-1.53 (m, 2H).

Step 2: Preparation of N-(5-(8-(cyclopentyloxy)-4-methyl-2-(methylamino)quinazolin-6-yl)-2-methoxypyridin-3-yl)-2,4-difluorobenzenesulfonamide (40)

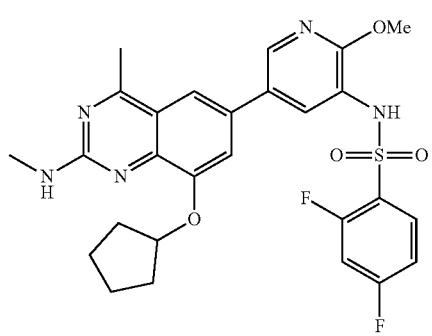

According to the method of step 2 in Example 29, compound (40) was prepared from compound (K-12).

$^1$H NMR (400 MHz, DMSO-d$_6$) δ 10.28 (s, 1H), 8.43 (d, J=2.4 Hz, 1H), 7.92 (d, J=2.4 Hz, 1H), 7.76 (dt, J=8.6, 6.4 Hz, 1H), 7.67 (d, J=1.6 Hz, 1H), 7.64-7.55 (m, 1H), 7.32 (s, 1H), 7.27-7.17 (m, 2H), 5.20-5.13 (m, 1H), 3.65 (s, 3H), 2.90 (d, J=4.8 Hz, 3H), 2.75 (s, 3H), 1.99-1.87 (m, 2H), 1.87-1.75 (m, 4H), 1.69-1.55 (m, 2H).
MS (ESI+) m/z 556.2 [M+H]$^+$.

Example 41: N-(5-(8-cyclobutoxy-4-methyl-2-(methylamino)quinazolin-6-yl)-2-methoxypyridin-3-yl)-2,4-difluorobenzenesulfonamide (41)

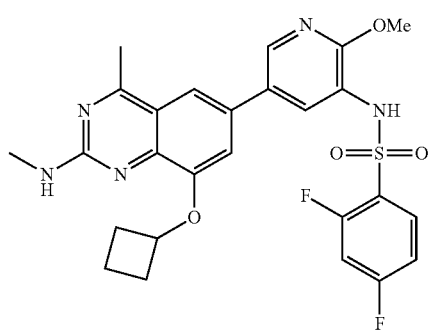

Step 1: 6-bromo-8-cyclobutoxy-N,4-dimethylquinazolin-2-amine (K-13)

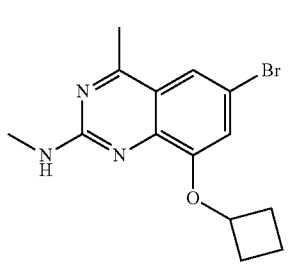

According to the method of step 1 in Example 29, compound (K-13) was prepared from compound (J-24).

¹H NMR (400 MHz, DMSO-d$_6$) δ 7.65 (d, J=2.0 Hz, 1H), 7.30 (br s, 1H), 7.01 (d, J=1.6 Hz, 1H), 4.84 (p, J=7.2 Hz, 1H), 2.88 (d, J=4.8 Hz, 3H), 2.65 (s, 3H), 2.49-2.42 (m, 2H), 2.19-2.03 (m, 2H), 1.89-1.75 (m, 1H), 1.74-1.58 (m, 1H).

Step 2: N-(5-(8-cyclobutoxy-4-methyl-2-(methylamino)quinazolin-6-yl)-2-methoxypyridin-3-yl)-2,4-difluorobenzenesulfonamide (41)

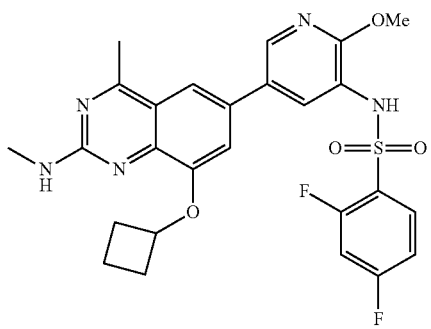

Compound (41) was prepared from compound (K-13) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 29.

¹H NMR (400 MHz, DMSO-d$_6$) δ 10.29 (s, 1H), 8.41 (d, J=2.4 Hz, 1H), 7.91 (d, J=2.4 Hz, 1H), 7.77 (dt, J=8.6, 6.4 Hz, 1H), 7.59 (ddd, J=10.4, 9.2, 2.4 Hz, 1H), 7.31-7.17 (m, 2H), 7.14 (d, J=1.2 Hz, 1H), 5.05-4.88 (m, 1H), 3.66 (s, 3H), 2.91 (d, J=4.8 Hz, 3H), 2.75 (s, 3H), 2.55-2.45 (m, 2H), 2.22-2.09 (m, 2H), 1.90-1.78 (m, 1H), 1.76-1.61 (m, 1H).

MS (ESI+) m/z:542.2 [M+H]⁺.

Example 42: N-(6-(5-(2,4-difluorophenylsulfonamido)-6-methoxypyridin-3-yl)-4-methyl-8-((tetrahydro-2H-pyran-4-yl)oxy)quinazolin-2-yl)acetamide (42)

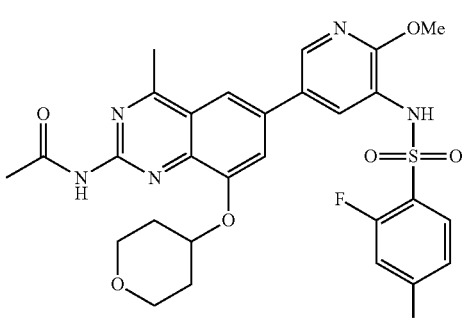

Step 1: Preparation of N-(6-bromo-4-methyl-8-((tetrahydro-2H-pyran-4-yl)oxy)quinazolin-2-yl)acetamide (K-14)

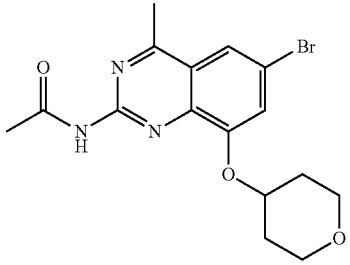

To a mixture of compound (j-1) (338 mg, 1 mmol) and pyridine (396 mg, 5 mmol) in DMF (10 mL) was added acetyl chloride (234 mg, 3 mmol) at r.t. The resulting reaction mixture was stirred at r.t. for 4 h. The reaction mixture was diluted with water (50 mL), acidified with 2M aqueous HCl solution until the pH value was 5, and then extracted with EtOAc (30 mL×3). The combined organic layers were washed with water (30 mL×2) and brine (30 mL), dried over anhydrous Na$_2$SO$_4$, filtered, and concentrated. The residue was purified by flash column chromatography (silica gel, DCM/MeOH=70:1, v/v) to afford the product (K-14) as a yellow solid (290 mg, 76%).

¹H NMR (400 MHz, DMSO-d$_6$) δ 10.57 (s, 1H), 7.94 (d, J=2.0 Hz, 1H), 7.61 (d, J=2.0 Hz, 1H), 5.07-4.94 (m, 1H), 3.93-3.85 (m, 2H), 3.55-3.47 (m, 2H), 2.81 (s, 3H), 2.34 (s, 3H), 2.09-1.93 (m, 2H), 1.74-1.58 (m, 2H).

Step 2: Preparation of N-(6-(5-(2,4-difluorophenylsulfonamido)-6-methoxypyridin-3-yl)-4-methyl-8-((tetrahydro-2H-pyran-4-yl)oxy)quinazolin-2-yl)acetamide (42)

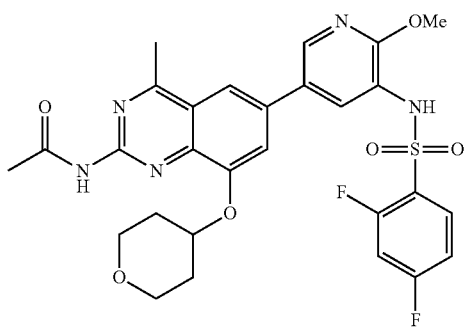

42

Compound (42) was prepared from compound (K-14) and N-(2-methoxy-5-(4,4,5,5-tetramethyl-1,3,2-dioxaborolan-2-yl)pyridin-3-yl)-2,4-difluorobenzenesulfonamide, according to the method of step 3 in Example 1.

$^1$H NMR (400 MHz, DMSO-d$_6$) δ 10.55 (s, 1H), 10.32 (s, 1H), 8.52 (d, J=2.0 Hz, 1H), 8.06 (d, J=2.0 Hz, 1H), 7.91 (d, J=1.0 Hz, 1H), 7.76 (dt, J=8.6, 6.8 Hz, 1H), 7.69 (d, J=1.0 Hz, 1H), 7.64-7.55 (m, 1H), 7.22 (dt, J=8.8, 2.4 Hz, 1H), 5.16-5.07 (m, 1H), 3.96-3.89 (m, 2H), 3.65 (s, 3H), 3.58-3.45 (m, 2H), 2.91 (s, 3H), 2.36 (s, 3H), 2.09-1.99 (m, 2H), 1.79-1.63 (m, 2H).

MS (ESI+) m/z: 600.2 [M+H]$^+$.

Example 43: N-(6-(6-methoxy-5-(methylsulfonamido)pyridin-3-yl)-4-methyl-8-((tetrahydro-2H-pyran-4-yl)oxy)quinazolin-2-yl)acetamide (43)

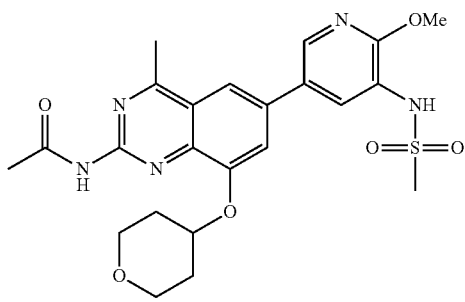

43

Compound (43) was prepared from compound (K-14) and N-(2-methoxy-5-(4,4,5,5-tetramethyl-1,3,2-dioxaborolan-2-yl)pyridin-3-yl)methanesulfonamide, according to the method of step 3 in Example 1.

$^1$H NMR (400 MHz, DMSO-d$_6$) δ 10.55 (s, 1H), 9.39 (s, 1H), 8.51 (d, J=2.3 Hz, 1H), 8.04 (d, J=2.3 Hz, 1H), 7.93 (d, J=1.7 Hz, 1H), 7.70 (d, J=1.7 Hz, 1H), 5.16-5.08 (m, 1H), 3.99 (s, 3H), 3.97-3.87 (m, 2H), 3.55-3.47 (m, 2H), 3.10 (s, 3H), 2.91 (s, 3H), 2.36 (s, 3H), 2.11-1.98 (m, 2H), 1.78-1.64 (m, 2H).

MS (ESI+) m/z 502.2 [M+H]$^+$.

Example 44: N-(2-methoxy-5-(4-methyl-8-((tetrahydro-2H-pyran-4-yl)oxy)quinazolin-6-yl)pyridin-3-yl)-2,4-difluorobenzenesulfonamide (44)

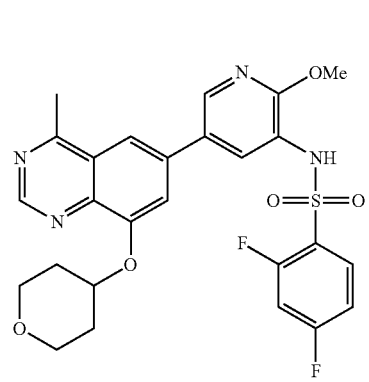

44

Step 1: Preparation of 6-bromo-4-methyl-8-((tetrahydro-2H-pyran-4-yl)oxy)quinazoline (N-1)

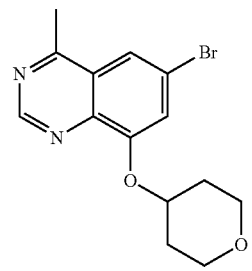

N-1

To a stirred mixture of compound (M) (0.717 g, 3 mmol), triphenylphosphine (0.944 g, 3.6 mmol), and tetrahydro-2H-pyran-4-ol (0.368 g, 3.6 mmol) in anhydrous THF (30 mL) was added DEAD (0.627 g, 3.6 mmol) at r.t. under Ar atmosphere. The resulting reaction mixture was stirred at r.t. overnight. Silica gel (4 g) was added, and the mixture was evaporated to dry under reduced pressure. The residue was purified by flash column chromatography (silica gel, PE/EtOAc=4:1, v/v) to afford the product (N-1) as a yellow solid (0.95 g, 98% yield).

$^1$H NMR (400 MHz, DMSO-d$_6$) δ 9.11 (s, 1H), 8.00 (d, J=2.0 Hz, 1H), 7.71 (d, J=2.0 Hz, 1H), 5.03-4.88 (m, 1H), 3.95-3.87 (m, 2H), 3.58-3.49 (m, 2H), 2.87 (s, 3H), 2.10-2.01 (m, 2H), 1.78-1.61 (m, 2H).

Step 2: Preparation of N-(2-methoxy-5-(4-methyl-8-((tetrahydro-2H-pyran-4-yl)oxy)quinazolin-6-yl)pyridin-3-yl)-2,4-difluorobenzenesulfonamide (44)

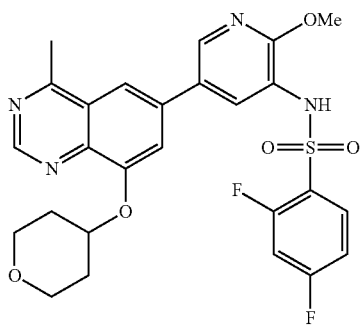

44

A mixture of compound (N-1) (125 mg, 0.39 mmol), N-(2-methoxy-5-(4,4,5,5-tetramethyl-1,3,2-dioxaborolan-2-yl)pyridin-3-yl)-2,4-difluorobenzenesulfonamide (199 mg, 0.47 mmol) and 2M aqueous potassium carbonate solution (0.585 mL, 1.17 mmol) in dioxane (7 mL) was degassed, and then $PdCl_2(dppf)$ (29 mg, 0.04 mmol) was added. The resulting reaction mixture was degassed and back-filled with argon (three cycles), and then stirred at 100° C. under Ar atmosphere for 5 h. The reaction mixture was cooled to r.t., diluted with EtOAc (30 mL) and water (30 mL), acidified with hydrochloric acid until the pH value was 5-6. The two phases were separated and the aqueous layer was extracted with EtOAc (30 mL×2). The combined organic layers were washed with water (50 mL) and brine (50 mL), dried over anhydrous $Na_2SO_4$, filtered and concentrated. The residue was purified by flash column chromatography (silica gel, DCM/MeOH=70:1, and then 50:1, v/v) to afford the product (44) as a yellow foamed solid (178 mg, 85% yield).

$^1$H NMR (400 MHz, DMSO-$d_6$) δ 10.35 (s, 1H), 9.08 (s, 1H), 8.56 (d, J=2.3 Hz, 1H), 8.11 (d, J=2.3 Hz, 1H), 7.94 (d, J=1.6 Hz, 1H), 7.81-7.70 (m, 2H), 7.66-7.54 (m, 11H), 7.22 (dt, J=8.8, 2.4 Hz, 11H), 5.12-4.98 (m, 11H), 3.98-3.90 (m, 2H), 3.66 (s, 3H), 3.61-3.48 (m, 2H), 2.96 (s, 3H), 2.16-2.03 (m, 2H), 1.80-1.65 (m, 2H).

MS (ESI+) m/z 543.1 [M+H]$^+$.

Example 45: N-(2-methoxy-5-(4-methyl-8-((tetrahydro-2H-pyran-4-yl)oxy)quinazolin-6-yl)pyridin-3-yl)-2-chloro-4-fluorobenzenesulfonamide (45)

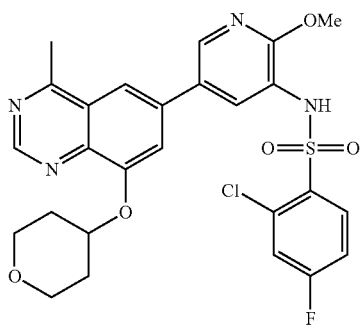

45

Compound (45) was prepared from compound (N-1) and N-(2-methoxy-5-(4,4,5,5-tetramethyl-1,3,2-dioxaborolan-2-yl)pyridin-3-yl)-2-chloro-4-fluorobenzenesulfonamide, according to the method of step 2 in Example 44.

$^1$H NMR (400 MHz, DMSO-$d_6$) δ 10.23 (s, 1H), 9.08 (s, 1H), 8.54 (d, J=2.3 Hz, 11H), 8.05 (d, J=2.2 Hz, 1H), 7.94 (dd, J=8.8, 6.0 Hz, 1H), 7.90 (d, J=1.6 Hz, 11H), 7.77 (dd, J=8.8, 2.4 Hz, 1H), 7.74 (d, J=1.6 Hz, 1H), 7.37 (dt, J=8.4, 2.4 Hz, 11H), 5.11-5.00 (m, 11H), 3.97-3.90 (m, 2H), 3.67 (s, 3H), 3.58-3.50 (m, 2H), 2.95 (s, 3H), 2.15-2.03 (m, 2H), 1.81-1.66 (m, 2H).

MS (ESI+) m/z 559.1 [M+H]$^+$.

Example 46: N-(2-methoxy-5-(4-methyl-8-((tetrahydro-2H-pyran-4-yl)oxy)quinazolin-6-yl)pyridin-3-yl)-5-chlorothiophene-2-sulfonamide (46)

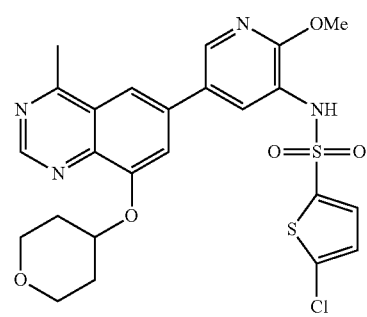

46

Compound (46) was prepared from compound (N-1) and N-(2-methoxy-5-(4,4,5,5-tetramethyl-1,3,2-dioxaborolan-2-yl)pyridin-3-yl)-5-chlorothiophene-2-sulfonamide, according to the method of step 2 in Example 44.

$^1$H NMR (400 MHz, DMSO-$d_6$) δ 10.40 (s, 1H), 9.09 (s, 1H), 8.59 (d, J=2.2 Hz, 1H), 8.10 (d, J=2.2 Hz, 1H), 7.94 (d, J=1.4 Hz, 1H), 7.77 (d, J=1.4 Hz, 1H), 7.40 (d, J=4.0 Hz, 1H), 7.25 (d, J=4.0 Hz, 1H), 5.14-5.00 (m, 1H), 3.98-3.90 (m, 2H), 3.76 (s, 3H), 3.62-3.48 (m, 2H), 2.96 (s, 3H), 2.16-2.03 (m, 2H), 1.82-1.66 (m, 2H).

MS (ESI+) m/z 547.1 [M+H]$^+$.

Example 47: N-(2-methoxy-5-(4-methyl-8-((tetrahydro-2H-pyran-4-yl)oxy)quinazolin-6-yl)pyridin-3-yl)methanesulfonamide (47)

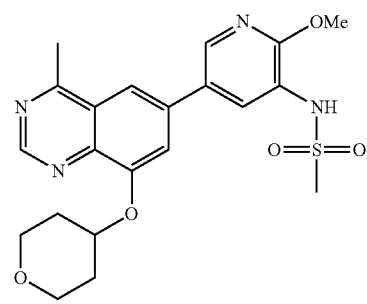

47

Compound (47) was prepared from compound (N-1) and N-(2-methoxy-5-(4,4,5,5-tetramethyl-1,3,2-dioxaborolan-2- yl)pyridin-3-yl)methanesulfonamide, according to the method of step 2 in Example 44.

¹H NMR (400 MHz, DMSO-d₆) δ 9.42 (s, 1H), 9.08 (s, 1H), 8.55 (d, J=2.3 Hz, 1H), 8.08 (d, J=2.3 Hz, 1H), 7.96 (d, J=1.6 Hz, 1H), 7.77 (d, J=1.6 Hz, 1H), 5.13-4.99 (m, 1H), 4.00 (s, 3H), 3.97-3.90 (m, 2H), 3.61-3.47 (m, 2H), 3.10 (s, 3H), 2.96 (s, 3H), 2.14-2.01 (m, 2H), 1.82-1.66 (m, 2H).

MS (ESI+) m/z 445.2 [M+H]⁺.

Example 48: N-(2-methoxy-5-(4-methyl-8-((tetrahydro-2H-pyran-4-yl)oxy)quinazolin-6-yl)pyridin-3-yl)cyclopropanesulfonamide (48)

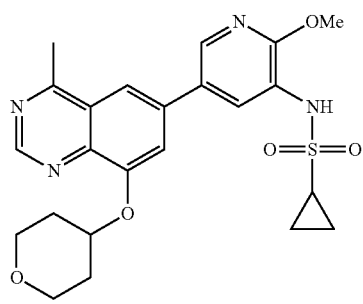

48

Compound (48) was prepared from compound (N-1) and N-(2-methoxy-5-(4,4,5,5-tetramethyl-1,3,2-dioxaborolan-2-yl)pyridin-3-yl)cyclopropanesulfonamide, according to the method of step 2 in Example 44.

¹H NMR (400 MHz, DMSO-d₆) δ 9.48 (s, 1H), 9.08 (s, 1H), 8.56 (d, J=2.4 Hz, 1H), 8.10 (d, J=2.4 Hz, 1H), 7.96 (d, J=1.6 Hz, 1H), 7.78 (d, J=1.6 Hz, 1H), 5.12-5.02 (m, 1H), 4.01 (s, 3H), 3.99-3.90 (m, 2H), 3.60-3.48 (m, 2H), 2.96 (s, 3H), 2.81-2.73 (m, 1H), 2.16-2.03 (m, 2H), 1.81-1.66 (m, 2H), 1.01-0.86 (m, 4H).

MS (ESI+) m/z 471.2 [M+H]⁺.

Example 49: (R)—N-(2-methoxy-5-(4-methyl-8-((tetrahydrofuran-3-yl)oxy)quinazolin-6-yl)pyridin-3-yl)-2,4-difluorobenzenesulfonamide (49)

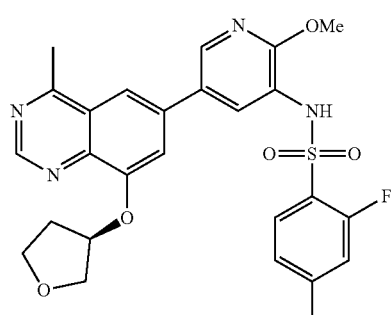

49

Step 1: Preparation of (R)-6-bromo-4-methyl-8-((tetrahydrofuran-3-yl)oxy)quinazoline (N-6)

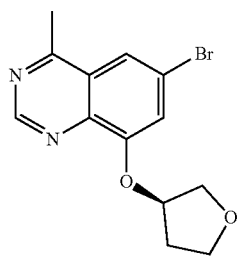

N-6

According to the method of step 1 in Example 44, compound (N-6) was prepared from compound (M) and (S)-tetrahydrofuran-3-ol.

¹H NMR (400 MHz, DMSO-d₆) δ 9.10 (s, 1H), 8.02 (d, J=1.9 Hz, 1H), 7.55 (d, J=1.9 Hz, 1H), 5.37-5.31 (m, 1H), 4.05-3.85 (m, 3H), 3.83-3.76 (m, 1H), 2.87 (s, 3H), 2.39-2.25 (m, 1H), 2.14-2.01 (m, 1H).

Step 2: Preparation of (R)—N-(2-methoxy-5-(4-methyl-8-((tetrahydrofuran-3-yl)oxy)quinazolin-6-yl)pyridin-3-yl)-2,4-difluorobenzenesulfonamide (49)

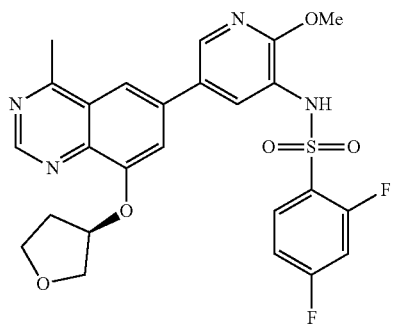

49

Compound (49) was prepared from compound (N-6) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

¹H NMR (400 MHz, DMSO-d₆) δ10.35 (s, 1H), 9.08 (s, 1H), 8.57 (d, J=2.4 Hz, 1H), 8.12 (d, J=2.4 Hz, 11H), 7.95 (d, J=1.6 Hz, 11H), 7.76 (dt, J=8.6, 6.4 Hz, 1H), 7.65-7.54 (m, 2H), 7.22 (dt, J=8.6, 2.4 Hz, 1H), 5.51-5.45 (m, 11H), 4.05-3.90 (m, 3H), 3.86-3.78 (m, 1H), 3.66 (s, 3H), 2.96 (s, 3H), 2.40-2.29 (m, 1H), 2.21-2.08 (m, 1H).

MS (ESI+) m/z 529.1 [M+H]⁺.

Example 50: (R)—N-(2-methoxy-5-(4-methyl-8-((tetrahydrofuran-3-yl)oxy)quinazolin-6-yl)pyridin-3-yl)methanesulfonamide (50)

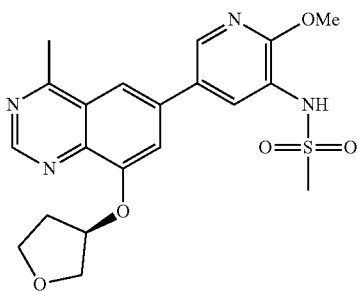

50

Compound (50) was prepared from compound (N-6) and N-(2-methoxy-5-(4,4,5,5-tetramethyl-1,3,2-dioxaborolan-2-yl)pyridin-3-yl)methanesulfonamide, according to the method of step 2 in Example 44.

$^1$H NMR (400 MHz, DMSO-d$_6$) δ 9.42 (s, 11H), 9.08 (s, 1H), 8.55 (d, J=2.4 Hz, 11H), 8.09 (d, J=2.4 Hz, 11H), 7.97 (d, J=1.6 Hz, 11H), 7.63 (d, J=1.6 Hz, 1H), 5.53-5.42 (m, 1H), 4.06-3.90 (m, 6H), 3.86-3.78 (m, 1H), 3.11 (s, 3H), 2.96 (s, 3H), 2.41-2.28 (m, 1H), 2.20-2.09 (m, 1H).

MS (ESI+) m/z 431.1 [M+H]$^+$.

Example 51: (S)—N-(2-methoxy-5-(4-methyl-8-((tetrahydrofuran-3-yl)oxy)quinazolin-6-yl)pyridin-3-yl)-2,4-difluorobenzenesulfonamide (51)

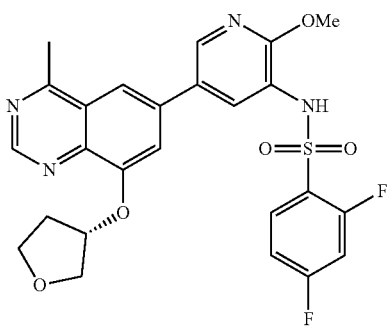

51

Step 1: Preparation of (S)-6-bromo-4-methyl-8-((tetrahydrofuran-3-yl)oxy)quinazoline (N-8)

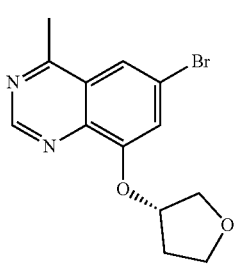

N-8

According to the method of step 1 in Example 44, compound (N-8) was prepared from compound (M) and (R)-tetrahydrofuran-3-ol.

$^1$H NMR (400 MHz, DMSO-d$_6$) δ 9.10 (s, 1H), 8.02 (d, J=1.9 Hz, 1H), 7.55 (d, J=1.9 Hz, 1H), 5.37-5.31 (m, 1H), 4.05-3.85 (m, 3H), 3.83-3.76 (m, 1H), 2.87 (s, 3H), 2.39-2.27 (m, 1H), 2.14-2.01 (m, 1H).

Step 2: Preparation of (S)—N-(2-methoxy-5-(4-methyl-8-((tetrahydrofuran-3-yl)oxy)quinazolin-6-yl)pyridin-3-yl)-2,4-difluorobenzenesulfonamide (51)

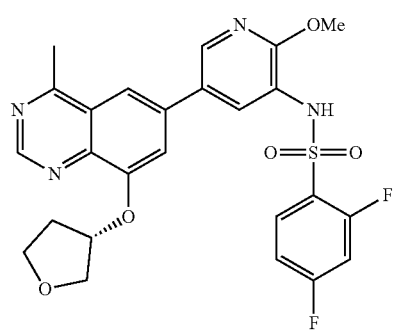

51

Compound (51) was prepared from compound (N-8) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-d$_6$) δ 10.35 (s, 1H), 9.08 (s, 1H), 8.57 (d, J=2.2 Hz, 1H), 8.12 (d, J=2.2 Hz, 1H), 7.95 (d, J=1.2 Hz, 1H), 7.77 (dt, J=8.8, 6.6 Hz, 1H), 7.66-7.55 (m, 2H), 7.22 (dt, J=8.8, 2.4 Hz, 1H), 5.52-5.43 (m, 1H), 4.06-3.89 (m, 3H), 3.86-3.78 (m, 1H), 3.66 (s, 3H), 2.96 (s, 3H), 2.40-2.29 (m, 1H), 2.20-2.08 (m, 1H).

MS (ESI+) m/z 529.1 [M+H]$^+$.

Example 52: (S)—N-(2-methoxy-5-(4-methyl-8-((tetrahydrofuran-3-yl)oxy)quinazolin-6-yl)pyridin-3-yl)methanesulfonamide (52)

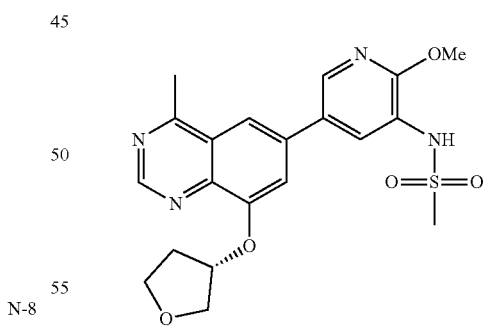

52

Compound (52) was prepared from compound (N-8) and N-(2-methoxy-5-(4,4,5,5-tetramethyl-1,3,2-dioxaborolan-2-yl)pyridin-3-yl)methanesulfonamide, according to the method of step 2 in Example 44.

$^1$H NMR (400 MHz, DMSO-d$_6$) δ 9.42 (s, 1H), 9.08 (s, 1H), 8.55 (d, J=2.3 Hz, 1H), 8.09 (d, J=2.3 Hz, 1H), 7.98 (d, J=1.6 Hz, 1H), 7.63 (d, J=1.6 Hz, 1H), 5.51-5.45 (m, 1H), 4.04-3.9 (m, 6H), 3.88-3.76 (m, 1H), 3.11 (s, 3H), 2.96 (s, 3H), 2.42-2.26 (m, 1H), 2.22-2.06 (m, 1H).

MS (ESI+) m/z 431.1 [M+H]$^+$.

Example 53: N-(2-methoxy-5-(4-methyl-8-((tetrahydro-2H-pyran-4-yl)methoxy)quinazolin-6-yl)pyridin-3-yl)-2,4-difluorobenzenesulfonamide (53)

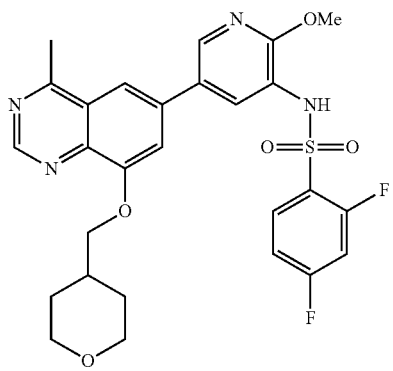

Step 1: Preparation of 6-bromo-4-methyl-8-((tetrahydro-2H-pyran-4-yl)methoxy)quinazoline (N-10)

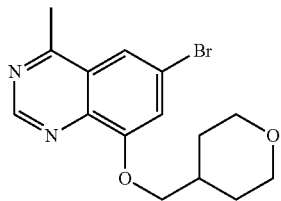

According to the method of step 1 in Example 44, compound (N-10) was prepared from compound (M) and (tetrahydro-2H-pyran-4-yl)methanol.

$^1$H NMR (400 MHz, DMSO-d$_6$) δ 9.11 (s, 1H), 7.99 (d, J=1.9 Hz, 1H), 7.56 (d, J=1.9 Hz, 1H), 4.08 (d, J=6.5 Hz, 2H), 3.94-3.87 (m, 2H), 3.38 (dt, J=11.8, 2.0 Hz, 2H), 2.87 (s, 3H), 2.21-2.08 (m, 1H), 1.80-1.72 (m, 2H), 1.48-1.34 (m, 2H).

Step 2: Preparation of N-(2-methoxy-5-(4-methyl-8-((tetrahydro-2H-pyran-4-yl)methoxy)quinazolin-6-yl)pyridin-3-yl)-2,4-difluorobenzenesulfonamide (53)

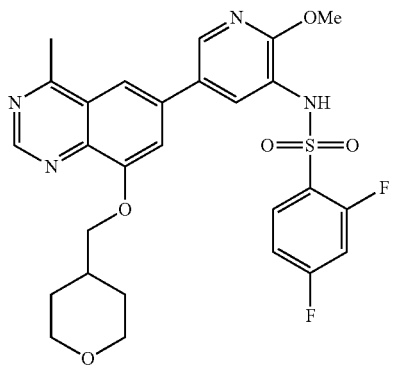

Compound (53) was prepared from compound (N-10) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-d$_6$) δ 10.34 (s, 1H), 9.08 (s, 1H), 8.58 (d, J=2.3 Hz, 1H), 8.12 (d, J=2.3 Hz, 1H), 7.92 (d, J=1.6 Hz, 1H), 7.76 (dt, J=8.6, 6.4 Hz, 1H), 7.63 (d, J=1.6 Hz, 1H), 7.62-7.55 (m, 1H), 7.22 (dt, J=8.4, 2.2 Hz, 1H), 4.17 (d, J=6.5 Hz, 2H), 3.96-3.87 (m, 2H), 3.66 (s, 3H), 3.40 (dt, J=11.4, 1.8 Hz, 2H), 2.96 (s, 3H), 2.26-2.11 (m, 1H), 1.84-1.76 (m, 2H), 1.51-1.38 (m, 2H).

MS (ESI+) m/z 557.2 [M+H]$^+$.

Example 54: N-(2-methoxy-5-(4-methyl-8-((tetrahydro-2H-pyran-4-yl)methoxy)quinazolin-6-yl)pyridin-3-yl)methanesulfonamide (54)

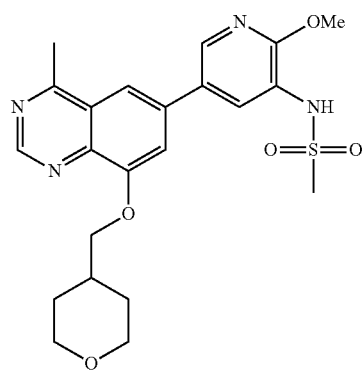

Compound (54) was prepared from compound (N-10) and N-(2-methoxy-5-(4,4,5,5-tetramethyl-1,3,2-dioxaborolan-2-yl)pyridin-3-yl)methanesulfonamide, according to the method of step 2 in Example 44.

$^1$H NMR (400 MHz, DMSO-d$_6$) δ 9.41 (s, 1H), 9.08 (s, 1H), 8.56 (d, J=2.4 Hz, 1H), 8.09 (d, J=2.4 Hz, 1H), 7.94 (d, J=1.6 Hz, 1H), 7.65 (d, J=1.6 Hz, 1H), 4.17 (d, J=6.5 Hz, 2H), 4.01 (s, 3H), 3.96-3.88 (m, 2H), 3.39 (dt, J=11.7, 1.9 Hz, 2H), 3.10 (s, 3H), 2.95 (s, 3H), 2.25-2.11 (m, 1H), 1.84-1.75 (m, 2H), 1.51-1.37 (m, 2H).

MS (ESI+) m/z 459.2 [M+H]$^+$.

Example 55: N-(5-(8-(cyclohexyloxy)-4-methylquinazolin-6-yl)-2-methoxypyridin-3-yl)-2,4-difluorobenzenesulfonamide (55)

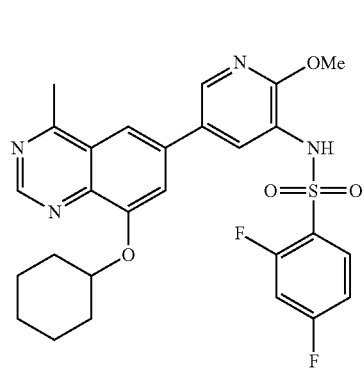

Step 1: Preparation of 6-bromo-8-(cyclohexyloxy)-4-methylquinazoline (N-12)

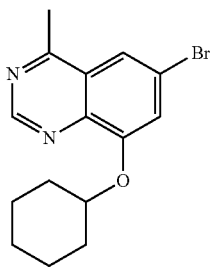

According to the method of step 1 in Example 44, compound (N-12) was prepared from compound (M) and cyclohexanol.

¹H NMR (400 MHz, DMSO-d$_6$) δ 9.09 (s, 1H), 7.97 (d, J=1.9 Hz, 1H), 7.61 (d, J=1.9 Hz, 1H), 4.78-4.65 (m, 1H), 2.86 (s, 3H), 2.05-1.93 (m, 2H), 1.82-1.72 (m, 2H), 1.62-1.49 (m, 3H), 1.49-1.37 (m, 2H), 1.37-1.25 (m, 11H).

Step 2: Preparation of N-(5-(8-(cyclohexyloxy)-4-methylquinazolin-6-yl)-2-methoxypyridin-3-yl)-2,4-difluorobenzenesulfonamide (55)

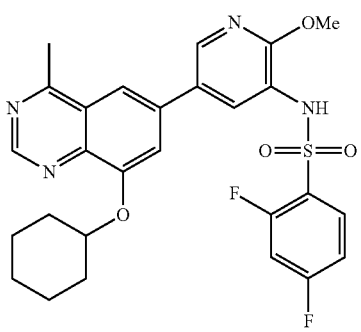

Compound (55) was prepared from compound (N-12) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

¹H NMR (400 MHz, DMSO-d$_6$) δ 10.35 (s, 1H), 9.07 (s, 1H), 8.55 (d, J=2.4 Hz, 1H), 8.09 (d, J=2.4 Hz, 1H), 7.90 (d, J=1.6 Hz, 1H), 7.76 (dt, J=8.6, 6.4 Hz, 1H), 7.67 (d, J=1.6 Hz, 11H), 7.64-7.56 (m, 1H), 7.26-7.19 (m, 1H), 4.90-4.77 (m, 1H), 3.67 (s, 3H), 2.95 (s, 3H), 2.08-1.95 (m, 2H), 1.87-1.73 (m, 2H), 1.65-1.53 (m, 3H), 1.52-1.27 (m, 3H).

MS (ESI+) m/z 541.2 [M+H]⁺.

Example 56: N-(5-(8-(cyclopentyloxy)-4-methylquinazolin-6-yl)-2-methoxypyridin-3-yl)-2,4-difluorobenzenesulfonamide (56)

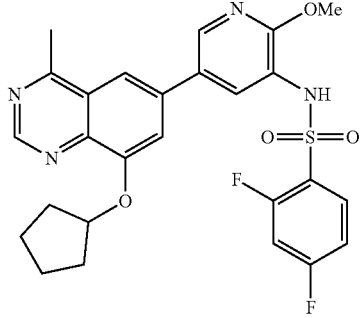

Step 1: Preparation of 6-bromo-8-(cyclopentyloxy)-4-methylquinazoline (N-13)

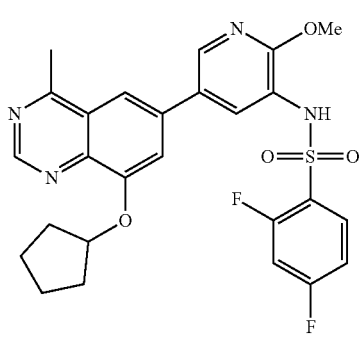

According to the method of step 1 in Example 44, compound (N-13) was prepared from compound (M) and cyclopentanol.

¹H NMR (400 MHz, DMSO-d$_6$) δ 9.09 (s, 1H), 7.96 (d, J=2.0 Hz, 1H), 7.50 (d, J=2.0 Hz, 1H), 5.17-5.06 (m, 1H), 2.86 (s, 3H), 2.09-1.96 (m, 2H), 1.88-1.72 (m, 4H), 1.68-1.57 (m, 2H).

Step 2: Preparation of N-(5-(8-(cyclopentyloxy)-4-methylquinazolin-6-yl)-2-methoxypyridin-3-yl)-2,4-difluorobenzenesulfonamide (56)

Compound (56) was prepared from compound (N-13) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-d$_6$) δ 10.35 (s, 1H), 9.06 (s, 1H), 8.55 (d, J=2.4 Hz, 1H), 8.08 (d, J=2.4 Hz, 1H), 7.90 (d, J=1.6 Hz, 1H), 7.77 (dt, J=8.6, 6.4 Hz, 1H), 7.64-7.57 (m, 1H), 7.57 (d, J=1.6 Hz, 1H), 7.27-7.19 (m, 1H), 5.29-5.21 (m, 1H), 3.67 (s, 3H), 2.95 (s, 3H), 2.12-1.96 (m, 2H), 1.94-1.73 (m, 4H), 1.73-1.57 (m, 2H).

MS (ESI+) m/z 527.2 [M+H]$^+$.

Example 57: N-(5-(8-((4,4-difluorocyclohexyl)oxy)-4-methylquinazolin-6-yl)-2-methoxypyridin-3-yl)-2,4-difluorobenzenesulfonamide (57)

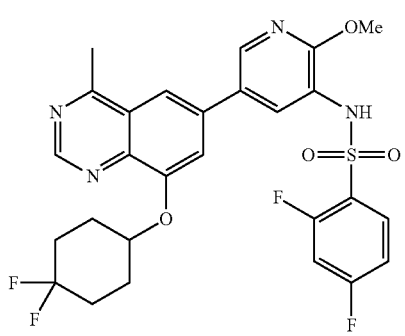

Step 1: Preparation of 6-bromo-8-((4,4-difluorocyclohexyl)oxy)-4-methylquinazoline (N-14)

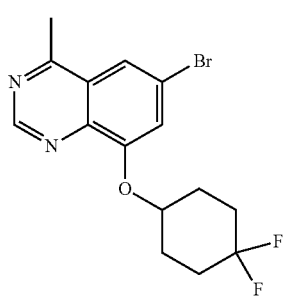

According to the method of step 1 in Example 44, compound (N-14) was prepared from compound (M) and 4,4-difluorocyclohexanol.

$^1$H NMR (400 MHz, DMSO-d$_6$) δ 9.12 (s, 1H), 8.03 (d, J=1.9 Hz, 1H), 7.75 (d, J=1.9 Hz, 1H), 5.02-4.94 (m, 1H), 2.87 (s, 3H), 2.25-1.85 (m, 8H).

Step 2: Preparation of N-(5-(8-((4,4-difluorocyclohexyl)oxy)-4-methylquinazolin-6-yl)-2-methoxypyridin-3-yl)-2,4-difluorobenzenesulfonamide (57)

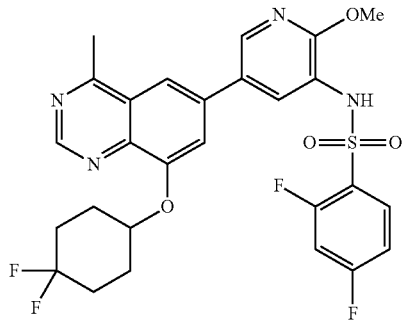

Compound (57) was prepared from compound (N-14) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-d$_6$) δ 10.35 (s, 1H), 9.10 (s, 1H), 8.57 (d, J=2.4 Hz, 1H), 8.12 (d, J=2.4 Hz, 1H), 7.97 (d, J=1.6 Hz, 1H), 7.82 (d, J=1.6 Hz, 1H), 7.76 (dt, J=8.6, 6.4 Hz, 1H), 7.64-7.55 (m, 1H), 7.22 (dt, J=8.4, 2.2 Hz, 1H), 5.15-5.05 (m, 1H), 3.66 (s, 3H), 2.96 (s, 3H), 2.31-2.11 (m, 2H), 2.10-1.93 (m, 6H).

MS (ESI+) m/z 577.2 [M+H]$^+$.

Example 58: N-(5-(8-((2,2-dimethyltetrahydro-2H-pyran-4-yl)oxy)-4-methylquinazolin-6-yl)-2-methoxypyridin-3-yl)-2,4-difluorobenzenesulfonamide (58)

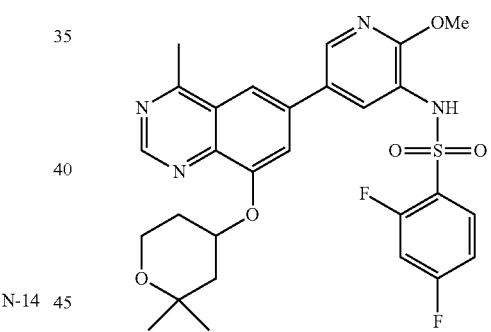

Step 1: Preparation of 6-bromo-8-((2,2-dimethyltetrahydro-2H-pyran-4-yl)oxy)-4-methylquinazoline (N-15)

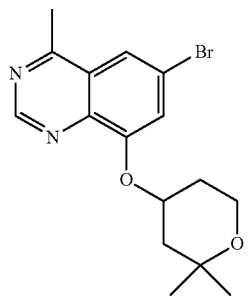

According to the method of step 1 in Example 44, compound (N-15) was prepared from compound (M) and 2,2-dimethyltetrahydro-2H-pyran-4-ol.

$^1$H NMR (400 MHz, DMSO-d$_6$) δ 9.09 (s, 1H), 7.99 (d, J=1.8 Hz, 1H), 7.72 (d, J=1.8 Hz, 1H), 5.12-4.97 (m, 1H), 3.84-3.62 (m, 2H), 2.86 (s, 3H), 2.14-1.94 (m, 2H), 1.64-1.45 (m, 2H), 1.25 (s, 3H), 1.24 (s, 3H).

Step 2: Preparation of N-(5-(8-((2,2-dimethyltetra-hydro-2H-pyran-4-yl)oxy)-4-methylquinazolin-6-yl)-2-methoxypyridin-3-yl)-2,4-difluorobenzene-sulfonamide (58)

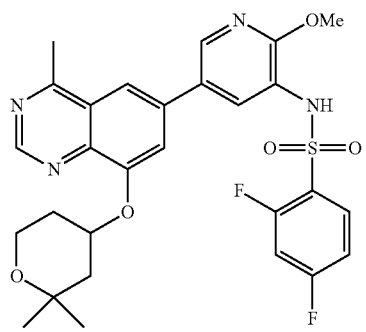

58

Compound (58) was prepared from compound (N-15) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-d$_6$) δ 10.35 (s, 1H), 9.07 (s, 1H), 8.57 (d, J=2.4 Hz, 1H), 8.12 (d, J=2.4 Hz, 1H), 7.93 (d, J=1.6 Hz, 1H), 7.81-7.71 (m, 2H), 7.64-7.56 (m, 1H), 7.26-7.19 (m, 1H), 5.24-5.09 (m, 1H), 3.86-3.77 (m, 1H), 3.75-3.67 (m, 1H), 3.66 (s, 3H), 2.96 (s, 3H), 2.14-2.01 (m, 2H), 1.65-1.52 (m, 2H), 1.26 (s, 3H), 1.25 (s, 3H).

MS (ESI+) m/z 571.2 [M+H]$^+$.

Example 59: N-(2-methoxy-5-(4-methyl-8-((3-methyloxetan-3-yl)methoxy)quinazolin-6-yl)pyridin-3-yl)-2,4-difluoro-benzenesulfonamide (59)

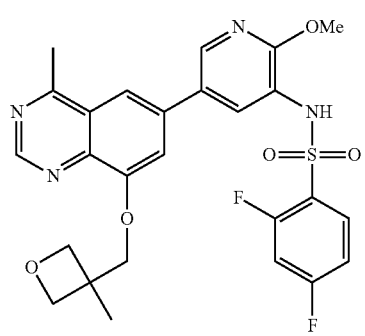

59

Step 1: Preparation of 6-bromo-4-methyl-8-((3-methyloxetan-3-yl)methoxy)quinazoline (N-16)

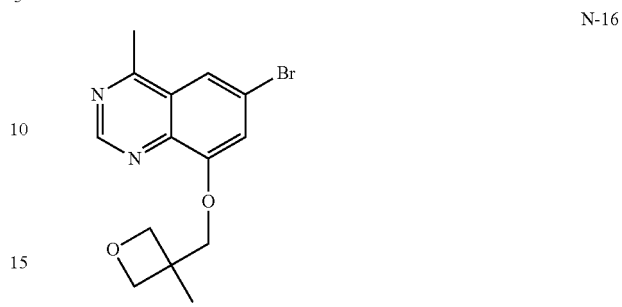

N-16

According to the method of step 1 in Example 44, compound (N-16) was prepared from compound (M) and (3-methyloxetan-3-yl)methanol.

$^1$H NMR (400 MHz, DMSO-d$_6$) δ 9.13 (s, 1H), 8.02 (d, J=1.9 Hz, 1H), 7.64 (d, J=1.9 Hz, 1H), 4.57 (d, J=5.8 Hz, 2H), 4.37 (d, J=5.8 Hz, 2H), 4.32 (s, 2H), 2.88 (s, 3H), 1.45 (s, 3H).

Step 2: Preparation of N-(2-methoxy-5-(4-methyl-8-((3-methyloxetan-3-yl)methoxy)quinazolin-6-yl)pyridin-3-yl)-2,4-difluoro-benzenesulfonamide (59)

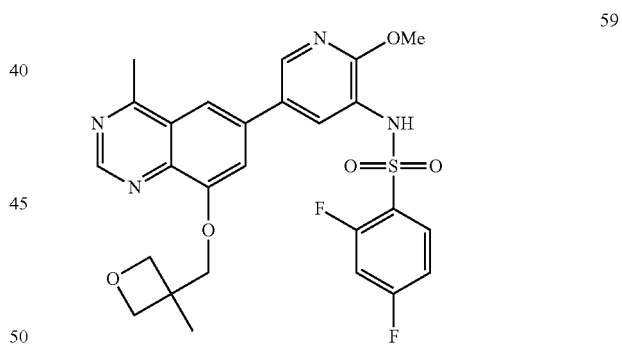

59

Compound (59) was prepared from compound (N-16) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-d$_6$) δ 10.34 (s, 1H), 9.10 (s, 1H), 8.59 (d, J=2.4 Hz, 1H), 8.14 (d, J=2.4 Hz, 1H), 7.96 (d, J=1.6 Hz, 1H), 7.80-7.74 (m, 1H), 7.73 (d, J=1.6 Hz, 1H), 7.64-7.56 (m, 1H), 7.22 (dt, J=8.4, 2.4 Hz, 1H), 4.61 (d, J=5.8 Hz, 2H), 4.41 (s, 2H), 4.40 (d, J=5.8 Hz, 2H), 3.65 (s, 3H), 2.97 (s, 3H), 1.49 (s, 3H).

MS (ESI+) m/z 543.1 [M+H]$^+$.

Example 60: N-(2-methoxy-5-(4-methyl-8-((tetrahydrofuran-2-yl)methoxy)quinazolin-6-yl)pyridin-3-yl)-2,4-difluorobenzenesulfonamide (60)

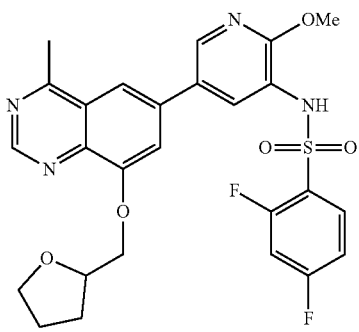

Step 1: Preparation of 6-bromo-4-methyl-8-((tetrahydrofuran-2-yl)methoxy)quinazoline (N-17)

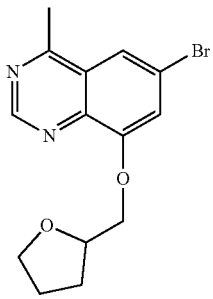

According to the method of step 1 in Example 44, compound (N-17) was prepared from compound (M) and tetrahydrofurfuryl alcohol.

$^1$H NMR (400 MHz, DMSO-$d_6$) δ 9.11 (s, 1H), 7.99 (d, J=1.8 Hz, 1H), 7.57 (d, J=1.8 Hz, 1H), 4.34-4.25 (m, 1H), 4.24-4.12 (m, 2H), 3.83 (dd, J=14.2, 7.2 Hz, 1H), 3.71 (dd, J=14.2, 7.2 Hz, 1H), 2.87 (s, 3H), 2.11-1.92 (m, 2H), 1.90-1.70 (m, 2H).

Step 2: Preparation of N-(2-methoxy-5-(4-methyl-8-((tetrahydrofuran-2-yl)methoxy)quinazolin-6-yl)pyridin-3-yl)-2,4-difluoro-benzenesulfonamide (60)

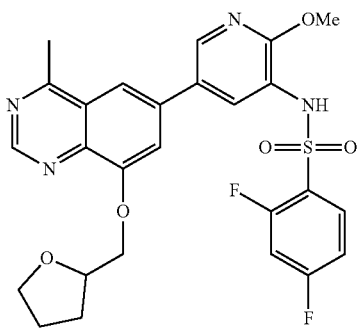

Compound (60) was prepared from compound (N-17) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-$d_6$) δ 10.34 (s, 1H), 9.08 (s, 1H), 8.58 (d, J=2.2 Hz, 1H), 8.13 (d, J=2.2 Hz, 1H), 7.93 (d, J=1.2 Hz, 1H), 7.76 (dt, J=8.4, 6.4 Hz, 1H), 7.65 (d, J=1.2 Hz, 1H), 7.64-7.55 (m, 1H), 7.21 (dt, J=8.6, 2.2 Hz, 1H), 4.39-4.21 (m, 3H), 3.86 (dd, J=14.2, 7.0 Hz, 1H), 3.73 (dd, J=14.2, 7.0 Hz, 1H), 3.65 (s, 3H), 2.96 (s, 3H), 2.14-1.93 (m, 2H), 1.93-1.73 (m, 2H).

MS (ESI+) m/z 543.1 [M+H]$^+$.

Example 61: N-(2-methoxy-5-(4-methyl-8-((tetrahydrofuran-3-yl)methoxy)quinazolin-6-yl)pyridin-3-yl)-2,4-difluorobenzenesulfonamide (61)

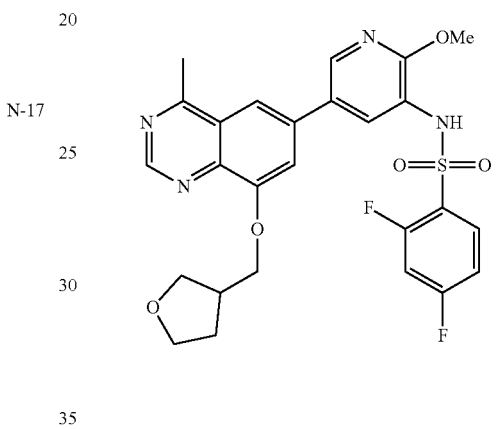

Step 1: Preparation of 6-bromo-4-methyl-8-((tetrahydrofuran-3-yl)methoxy)quinazoline (N-18)

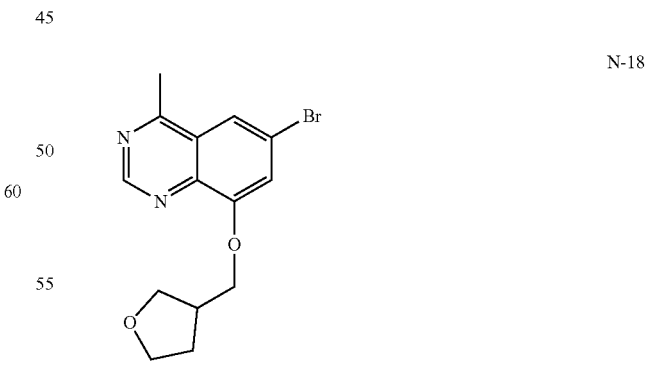

According to the method of step 1 in Example 44, compound (N-18) was prepared from compound (M) and (tetrahydrofuran-3-yl)methanol.

$^1$H NMR (400 MHz, DMSO-$d_6$) δ 9.12 (s, 1H), 8.00 (d, J=1.8 Hz, 1H), 7.59 (d, J=1.8 Hz, 1H), 4.21-4.08 (m, 2H), 3.91-3.75 (m, 2H), 3.74-3.59 (m, 2H), 2.87 (s, 3H), 2.84-2.75 (m, 1H), 2.11-2.02 (m, 1H), 1.80-1.69 (m, 1H).

Step 2: Preparation of N-(2-methoxy-5-(4-methyl-8-((tetrahydrofuran-3-yl)methoxy)quinazolin-6-yl)pyridin-3-yl)-2,4-difluoro-benzenesulfonamide (61)

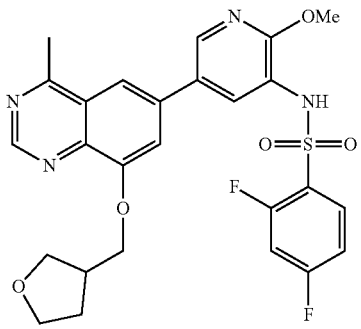

61

Compound (61) was prepared from compound (N-18) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-d$_6$) δ 10.34 (s, 1H), 9.09 (s, 1H), 8.58 (d, J=2.2 Hz, 1H), 8.13 (d, J=2.2 Hz, 1H), 7.94 (d, J=1.0 Hz, 1H), 7.76 (dd, J=8.6, 6.6 Hz, 1H), 7.67 (d, J=1.0 Hz, 1H), 7.65-7.53 (m, 11H), 7.22 (dt, J=8.6, 2.4 Hz, 1H), 4.35-4.16 (m, 2H), 3.93-3.78 (m, 2H), 3.75-3.60 (m, 5H), 2.96 (s, 3H), 2.92-2.76 (m, 1H), 2.16-2.05 (m, 1H), 1.83-1.73 (m, 1H).

MS (ESI+) m/z 543.1 [M+H]$^+$.

Example 62: N-(2-methoxy-5-(4-methyl-8-((1-methylpiperidin-4-yl)oxy)quinazolin-6-yl)pyridin-3-yl)-2,4-difluoro-benzenesulfonamide (62)

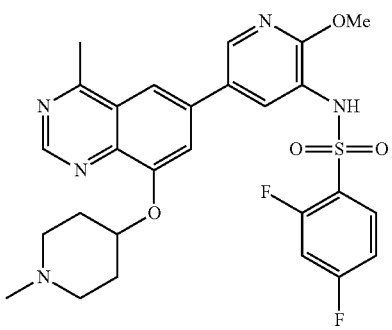

62

Step 1: Preparation of 6-bromo-4-methyl-8-((1-methylpiperidin-4-yl)oxy)quinazoline (N-19)

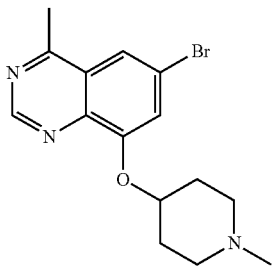

N-19

According to the method of step 1 in Example 44, compound (N-19) was prepared from compound (M) and 1-methylpiperidin-4-ol.

$^1$H NMR (400 MHz, DMSO-d$_6$) δ 9.10 (s, 1H), 7.99 (d, J=1.9 Hz, 1H), 7.64 (d, J=1.9 Hz, 1H), 4.80-4.66 (m, 1H), 2.88-2.85 (m, 3H), 2.74-2.63 (m, 2H), 2.30-2.14 (m, 6H), 2.07-1.95 (m, 2H), 1.82-1.69 (m, 2H).

Step 2: Preparation of N-(2-methoxy-5-(4-methyl-8-((1-methylpiperidin-4-yl)oxy)quinazolin-6-yl)pyridin-3-yl)-2,4-difluorobenzenesulfonamide (62)

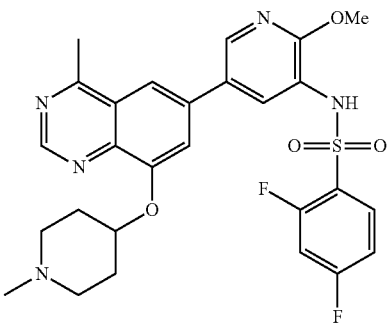

62

Compound (62) was prepared from compound (N-19) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-d$_6$) δ 9.07 (s, 1H), 8.35 (d, J=2.2 Hz, 1H), 7.93 (d, J=2.2 Hz, 1H), 7.86 (d, J=1.6 Hz, 1H), 7.79 (dt, J=8.6, 6.6 Hz, 1H), 7.66 (d, J=1.6 Hz, 1H), 7.54-7.44 (m, 1H), 7.18 (dt, J=8.4, 2.4 Hz, 1H), 4.95-4.82 (m, 1H), 3.70 (s, 3H), 2.94 (s, 3H), 2.93-2.86 (m, 2H), 2.51 (s, 1H), 2.39 (s, 3H), 2.15-2.04 (m, 2H), 1.92-1.80 (m, 2H).

MS (ESI+) m/z 556.2 [M+H]$^+$.

Example 63: N-(2-methoxy-5-(4-methyl-8-(2-(pyrrolidin-1-yl)ethoxy)quinazolin-6-yl)pyridin-3-yl)-2,4-difluorobenzenesulfonamide (63)

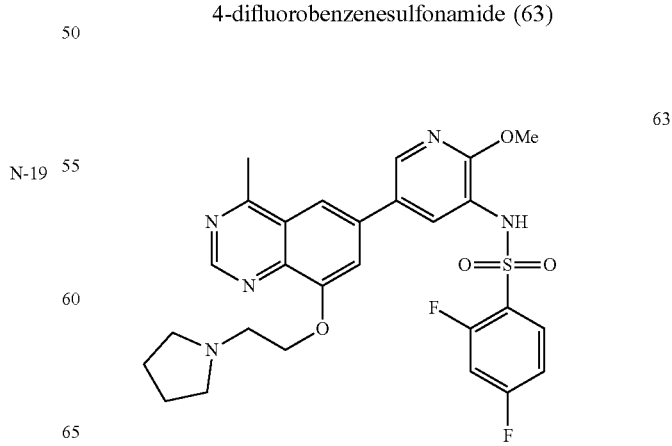

63

Step 1: Preparation of 6-bromo-4-methyl-8-(2-(pyrrolidin-1-yl)ethoxy)quinazoline (N-20)

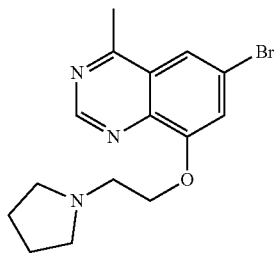

N-20

Example 64: N-(5-(8-(2-(1H-pyrazol-1-yl)ethoxy)-4-methylquinazolin-6-yl)-2-methoxypyridin-3-yl)-2,4-difluorobenzenesulfonamide (64)

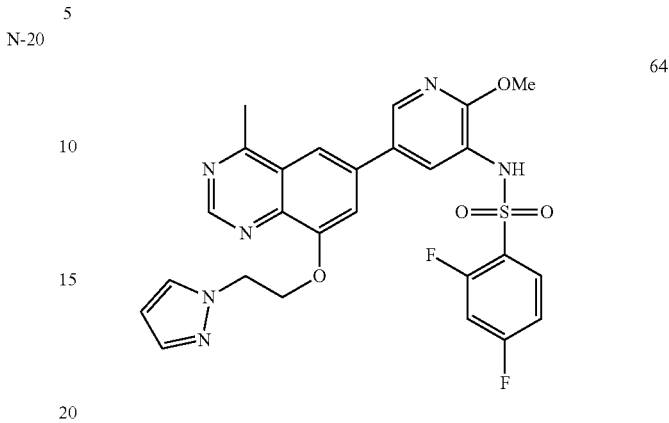

64

According to the method of step 1 in Example 44, compound (N-20) was prepared from compound (M) and 2-(pyrrolidin-1-yl)ethan-1-ol.

$^1$H NMR (400 MHz, DMSO-d$_6$) δ 9.10 (s, 1H), 7.99 (d, J=1.9 Hz, 1H), 7.58 (d, J=1.9 Hz, 1H), 4.30 (t, J=5.8 Hz, 2H), 2.93 (t, J=5.8 Hz, 2H), 2.87 (s, 3H), 2.64-2.55 (m, 4H), 1.76-1.62 (m, 4H).

Step 2: Preparation of N-(2-methoxy-5-(4-methyl-8-(2-(pyrrolidin-1-yl)ethoxy)quinazolin-6-yl)pyridin-3-yl)-2,4-difluorobenzenesulfonamide (63)

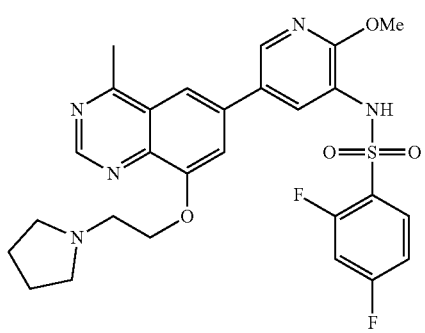

63

Step 1: Preparation of 8-(2-(1H-pyrazol-1-yl)ethoxy)-6-bromo-4-methylquinazoline (N-21)

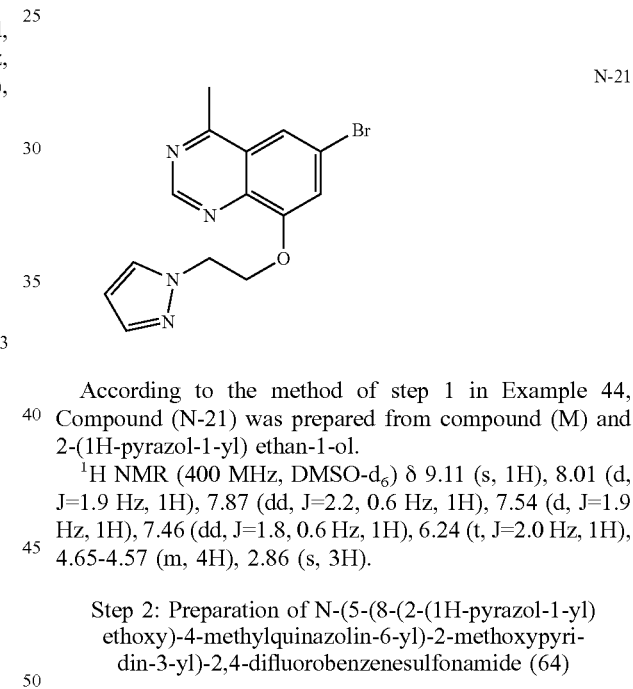

N-21

According to the method of step 1 in Example 44, Compound (N-21) was prepared from compound (M) and 2-(1H-pyrazol-1-yl) ethan-1-ol.

$^1$H NMR (400 MHz, DMSO-d$_6$) δ 9.11 (s, 1H), 8.01 (d, J=1.9 Hz, 1H), 7.87 (dd, J=2.2, 0.6 Hz, 1H), 7.54 (d, J=1.9 Hz, 1H), 7.46 (dd, J=1.8, 0.6 Hz, 1H), 6.24 (t, J=2.0 Hz, 1H), 4.65-4.57 (m, 4H), 2.86 (s, 3H).

Step 2: Preparation of N-(5-(8-(2-(1H-pyrazol-1-yl)ethoxy)-4-methylquinazolin-6-yl)-2-methoxypyridin-3-yl)-2,4-difluorobenzenesulfonamide (64)

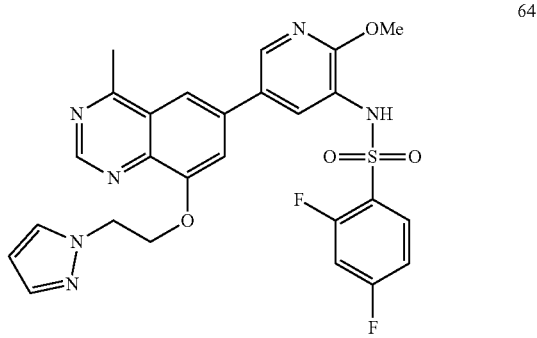 [SMILES: COc1ncc(-c2cc(OCCn3cccn3)c3ncnc(C)c3c2)cc1NS(=O)(=O)c1ccc(F)cc1F]

64

Compound (63) was prepared from compound (N-20) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-d$_6$) δ 9.08 (s, 1H), 8.37 (d, J=2.2 Hz, 1H), 7.96 (d, J=2.2 Hz, 1H), 7.86 (d, J=1.4 Hz, 1H), 7.80 (dt, J=8.6, 6.6 Hz, 1H), 7.61 (d, J=1.4 Hz, 1H), 7.53-7.45 (m, 11H), 7.19 (dt, J=8.4, 2.4 Hz, 1H), 4.45 (t, J=5.5 Hz, 2H), 3.69 (s, 3H), 3.18 (t, J=5.5 Hz, 2H), 2.95 (s, 3H), 2.91-2.81 (m, 4H), 1.83-1.75 (m, 4H).

MS (ESI+) m/z 556.2 [M+H]$^+$.

Compound (64) was prepared from compound (N-21) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-d$_6$) δ 10.33 (s, 1H), 9.09 (s, 1H), 8.56 (d, J=2.3 Hz, 1H), 8.12 (d, J=2.3 Hz, 1H), 7.95 (d, J=1.6 Hz, 1H), 7.92 (dd, J=2.2, 0.6 Hz, 1H), 7.76 (dt, J=8.4, 6.4 Hz, 1H), 7.62 (d, J=1.6 Hz, 1H), 7.61-7.56 (m, 1H), 7.46 (dd, J=1.8, 0.6 Hz, 1H), 7.22 (dt, J=8.4, 2.0 Hz, 1H), 6.27-6.23 (m, 1H), 4.76-4.60 (m, 4H), 3.65 (s, 3H), 2.95 (s, 3H).

MS (ESI+) m/z 553.1 [M+H]$^+$.

Example 65: N-(2-methoxy-5-(4-methyl-8-(2-morpholinoethoxy)quinazolin-6-yl)pyridin-3-yl)-2,4-difluorobenzenesulfonamide (65)

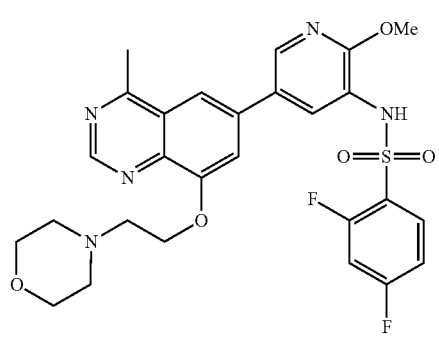

Step 1: Preparation of 4-(2-((6-bromo-4-methylquinazolin-8-yl)oxy)ethyl)morpholine (N-22)

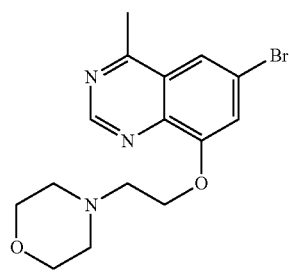

According to the method of step 1 in Example 44, compound (N-22) was prepared from compound (M) and 2-morpholinoethan-1-ol.

$^1$H NMR (400 MHz, DMSO-d$_6$) δ 9.10 (s, 1H), 7.99 (d, J=1.9 Hz, 1H), 7.61 (d, J=1.9 Hz, 1H), 4.33 (t, J=5.7 Hz, 2H), 3.63-3.53 (m, 4H), 2.87 (s, 3H), 2.82 (t, J=5.7 Hz, 2H), 2.59-2.51 (m, 4H).

Step 2: Preparation of N-(2-methoxy-5-(4-methyl-8-(2-morpholinoethoxy)quinazolin-6-yl)pyridin-3-yl)-2,4-difluoro-benzenesulfonamide (65)

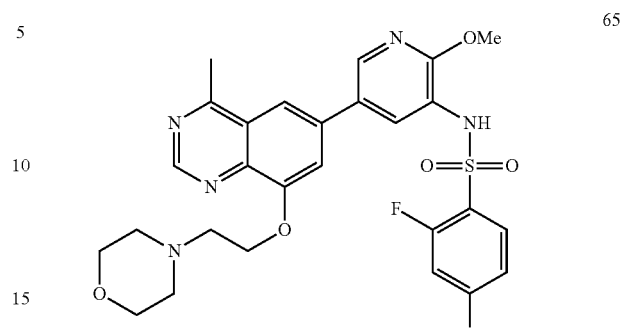

Compound (65) was prepared from compound (N-22) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-d$_6$) δ 10.33 (s, 1H), 9.08 (s, 1H), 8.57 (d, J=2.4 Hz, 1H), 8.12 (d, J=2.4 Hz, 1H), 7.93 (d, J=1.6 Hz, 1H), 7.76 (dt, J=8.6, 6.4 Hz, 1H), 7.67 (d, J=1.6 Hz, 1H), 7.59 (ddd, J=10.6, 9.2, 2.4 Hz, 1H), 7.27-7.18 (m, 1H), 4.43 (t, J=5.6 Hz, 2H), 3.66 (s, 3H), 3.64-3.57 (m, 4H), 2.96 (s, 3H), 2.89 (t, J=5.6 Hz, 2H), 2.65-2.56 (m, 4H).

MS (ESI+) m/z 571.2 [M+H]$^+$.

Example 66: N-(2-methoxy-5-(4-methyl-8-((1-methylpiperidin-4-yl)methoxy)quinazolin-6-yl)pyridin-3-yl)-2,4-difluoro-benzenesulfonamide (66)

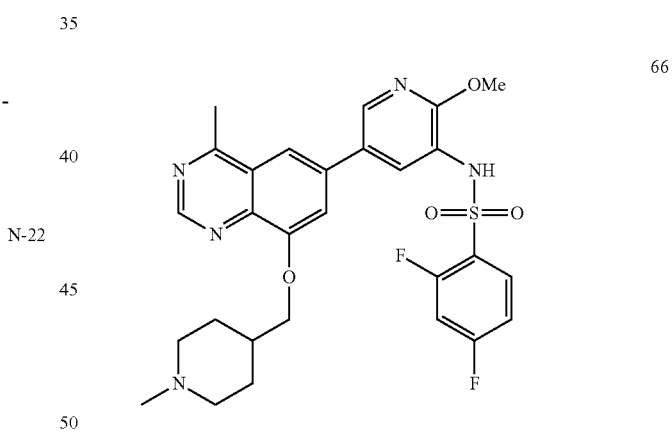

Step 1: Preparation of 6-bromo-4-methyl-8-((1-methylpiperidin-4-yl)methoxy)quinazoline (N-23)

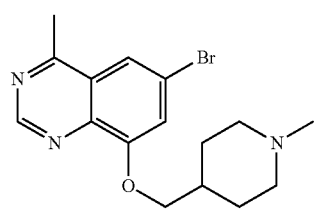

According to the method of step 1 in Example 44, compound (N-23) was prepared from compound (M) and (1-methylpiperidin-4-yl)methanol.

¹H NMR (400 MHz, DMSO-d₆) δ 9.11 (s, 1H), 7.98 (d, J=1.8 Hz, 1H), 7.54 (d, J=1.8 Hz, 1H), 4.06 (d, J=6.0 Hz, 2H), 2.86 (s, 3H), 2.84-2.76 (m, 1H), 2.17 (s, 3H), 1.95-1.75 (m, 5H), 1.44-1.31 (m, 2H).

Step 2: Preparation of N-(2-methoxy-5-(4-methyl-8-((1-methylpiperidin-4-yl)methoxy)quinazolin-6-yl)pyridin-3-yl)-2,4-difluorobenzenesulfonamide (66)

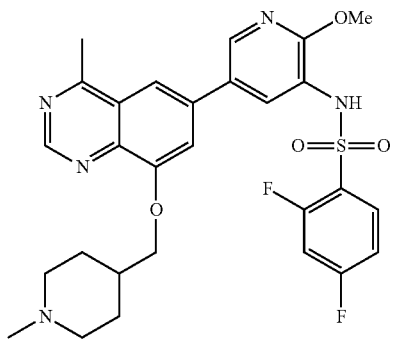

66

Compound (66) was prepared from compound (N-23) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

¹H NMR (400 MHz, DMSO-d₆) δ 9.06 (s, 1H), 8.25 (d, J=1.6 Hz, 1H), 7.86-7.80 (m, 2H), 7.78 (d, J=1.4 Hz, 1H), 7.51 (d, J=1.4 Hz, 1H), 7.43 (dt, J=9.8, 2.4 Hz, 1H), 7.16 (dt, J=8.4, 2.4 Hz, 1H), 4.15 (d, J=6.0 Hz, 2H), 3.72 (s, 3H), 3.16-3.07 (m, 2H), 2.93 (s, 3H), 2.48-2.34 (m, 5H), 2.08-1.87 (m, 3H), 1.61-1.41 (m, 2H).

MS (ESI+) m/z 570.2 [M+H]⁺.

Example 67: N-(5-(8-(2-(dimethylamino)ethoxy)-4-methylquinazolin-6-yl)-2-methoxypyridin-3-yl)-2,4-difluorobenzenesulfonamide (67)

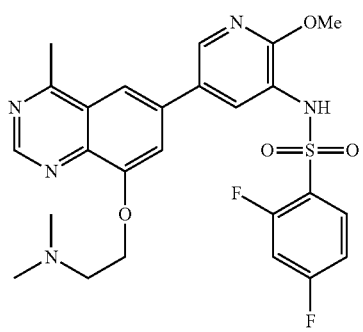

67

Step 1: Preparation of 2-((6-bromo-4-methylquinazolin-8-yl)oxy)-N,N-dimethylethanol-1-amine (N-24)

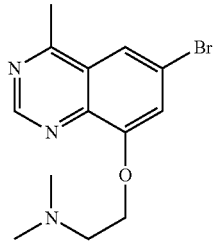

N-24

According to the method of step 1 in Example 44, compound (N-24) was prepared from compound (M) and 2-(dimethylamino) ethan-1-ol.

¹H NMR (400 MHz, DMSO-d₆) δ 9.11 (s, 1H), 8.03 (d, J=1.9 Hz, 1H), 7.63 (d, J=1.9 Hz, 1H), 4.40 (t, J=5.2 Hz, 2H), 3.03 (t, J=5.2 Hz, 2H), 2.88 (s, 3H), 2.48 (s, 6H).

Step 2: Preparation of N-(5-(8-(2-(dimethylamino)ethoxy)-4-methylquinazolin-6-yl)-2-methoxypyridin-3-yl)-2,4-difluorobenzenesulfonamide (67)

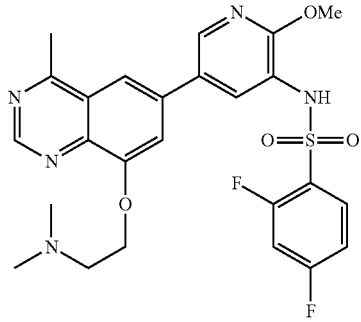

67

Compound (67) was prepared from compound (N-24) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

¹H NMR (400 MHz, DMSO-d₆) δ 9.08 (s, 1H), 8.44 (d, J=2.3 Hz, 1H), 8.01 (d, J=2.3 Hz, 1H), 7.89 (d, J=1.6 Hz, 1H), 7.79 (dt, J=8.6, 6.4 Hz, 1H), 7.64 (d, J=1.6 Hz, 1H), 7.56-7.48 (m, 1H), 7.24-7.16 (m, 1H), 4.43 (t, J=5.6 Hz, 2H), 3.68 (s, 3H), 2.98 (t, J=5.6 Hz, 2H), 2.95 (s, 3H), 2.44 (s, 6H).

MS (ESI+) m/z 530.2 [M+H]⁺.

Example 68: N-(5-(8-(cyclopropylmethoxy)-4-methylquinazolin-6-yl)-2-methoxypyridin-3-yl)-2,4-difluorobenzenesulfonamide (68)

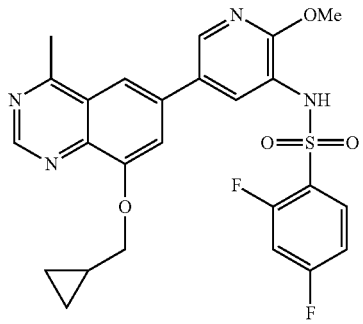

68

Step 1: Preparation of 6-bromo-8-(cyclopropylmethoxy)-4-methylquinazoline (N-25)

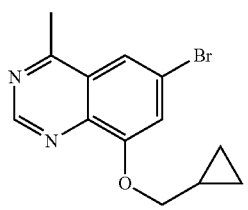

N-25

A mixture of compound (M) (0.120 g, 0.5 mmol), cyclopropylmethyl bromide (0.675 g, mmol), and potassium carbonate (0.691 g, 5 mmol) in acetonitrile (8 mL) in a sealed tube was stirred at 85° C. overnight. The reaction mixture was cooled to r.t. and filtered. Silica gel (1 g) was added to the filtrate, and the resulting mixture was evaporated to dry under reduced pressure. The residue was purified by flash column chromatography (silica gel, PE/EtOAc=150:1, v/v) to afford the product (N-25) as a yellow oil (0.142 g, 97% yield).

$^1$H NMR (400 MHz, DMSO-$d_6$) δ 9.11 (s, 1H), 7.97 (d, J=2.0 Hz, 1H), 7.49 (d, J=2.0 Hz, 1H), 4.05 (d, J=7.1 Hz, 2H), 2.87 (s, 3H), 1.41-1.29 (m, 1H), 0.68-0.57 (m, 2H), 0.43-0.36 (m, 2H).

Step 2: Preparation of N-(5-(8-(cyclopropylmethoxy)-4-methylquinazolin-6-yl)-2-methoxypyridin-3-yl)-2,4-difluorobenzenesulfonamide (68)

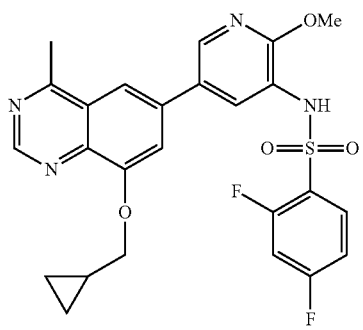

68

Compound (68) was prepared from compound (N-25) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-$d_6$) δ 10.33 (s, 1H), 9.08 (s, 1H), 8.55 (d, J=2.2 Hz, 1H), 8.09 (d, J=2.2 Hz, 1H), 7.91 (d, J=1.4 Hz, 1H), 7.76 (dt, J=8.6, 6.4 Hz, 1H), 7.63-7.57 (m, 11H), 7.57 (d, J=1.4 Hz, 11H), 7.21 (dt, J=8.4, 2.4 Hz, 11H), 4.15 (d, J=7.0 Hz, 2H), 3.65 (s, 3H), 2.96 (s, 3H), 1.47-1.32 (m, 1H), 0.71-0.60 (m, 2H), 0.46-0.37 (m, 2H).

MS (ESI+) m/z 513.1 [M+H]$^+$.

Example 69: N-(5-(8-isopropoxy-4-methylquinazolin-6-yl)-2-methoxypyridin-3-yl)-2,4-difluorobenzenesulfonamide (69)

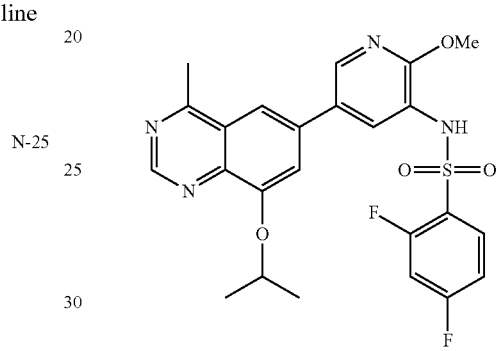

69

Step 1: Preparation of 6-bromo-8-isopropoxy-4-methylquinazoline (N-26)

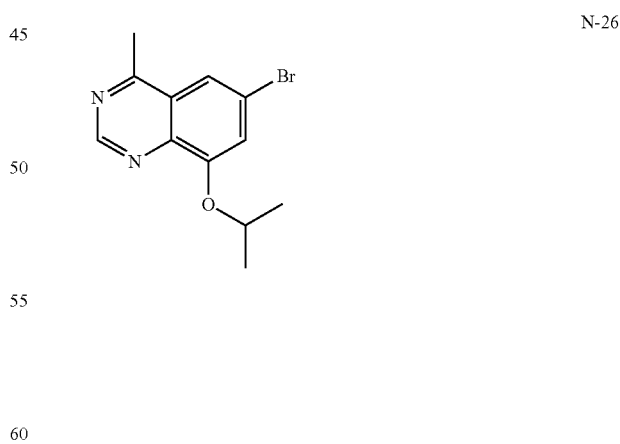

N-26

According to the method of step 1 in Example 68, compound (N-26) was prepared from compound (M) and isopropyl bromide.

$^1$H NMR (400 MHz, DMSO-$d_6$) δ 9.08 (s, 1H), 7.97 (d, J=2.0 Hz, 1H), 7.57 (d, J=2.0 Hz, 1H), 5.00-4.89 (m, 1H), 2.86 (s, 3H), 1.37 (d, J=6.0 Hz, 6H).

Step 2: Preparation of N-(5-(8-isopropoxy-4-methylquinazolin-6-yl)-2-methoxypyridin-3-yl)-2,4-difluorobenzenesulfonamide (69)

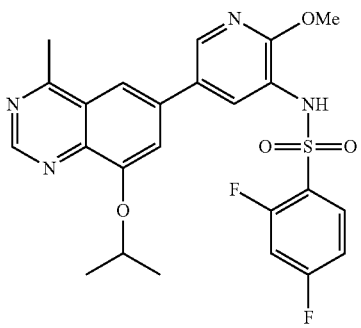

Compound (69) was prepared from compound (N-26) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-d$_6$) δ 10.34 (s, 1H), 9.06 (s, 1H), 8.55 (d, J=2.3 Hz, 1H), 8.08 (d, J=2.3 Hz, 1H), 7.91 (d, J=1.6 Hz, 1H), 7.77 (dt, J=8.6, 6.4 Hz, 1H), 7.63 (d, J=1.6 Hz, 1H), 7.62-7.55 (m, 1H), 7.22 (dt, J=8.4, 2.2 Hz, 1H), 5.13-5.02 (m, 1H), 3.67 (s, 3H), 2.95 (s, 3H), 1.40 (d, J=6.0 Hz, 6H).

MS (ESI+) m/z 501.1 [M+H]$^+$.

Example 70: N-(5-(8-cyclobutoxy-4-methylquinazolin-6-yl)-2-methoxypyridin-3-yl)-2,4-difluorobenzenesulfonamide (70)

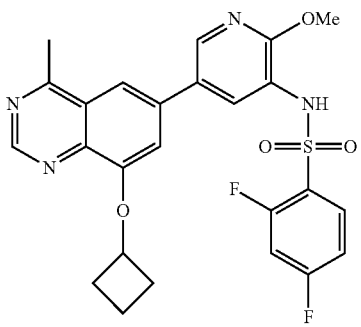

Step 1: Preparation of 6-bromo-8-cyclobutoxy-4-methylquinazoline (N-27)

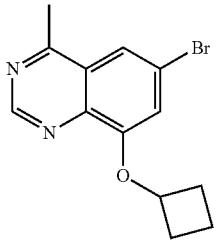

According to the method of step 1 in Example 68, compound (N-27) was prepared from compound (M) and cyclobutyl bromide.

$^1$H NMR (400 MHz, DMSO-d$_6$) δ 9.10 (s, 1H), 7.99 (d, J=1.9 Hz, 1H), 7.33 (d, J=1.9 Hz, 1H), 4.97 (p, J=7.2 Hz, 1H), 2.86 (s, 3H), 2.59-2.52 (m, 2H), 2.23-2.08 (m, 2H), 1.91-1.80 (m, 1H), 1.79-1.61 (m, 1H).

Step 2: Preparation of N-(5-(8-cyclobutoxy-4-methylquinazolin-6-yl)-2-methoxypyridin-3-yl)-2,4-difluorobenzenesulfonamide (70)

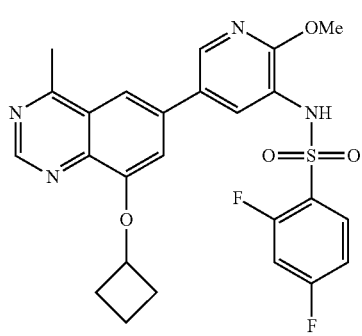

Compound (70) was prepared from compound (N-27) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-d$_6$) δ 10.36 (s, 1H), 9.07 (s, 1H), 8.54 (d, J=2.2 Hz, 1H), 8.07 (d, J=2.2 Hz, 1H), 7.92 (s, 1H), 7.76 (dt, J=8.4, 6.4 Hz, 1H), 7.64-7.56 (m, 1H), 7.40 (s, 1H), 7.23 (dt, J=8.4, 2.4 Hz, 1H), 5.16-5.02 (m, 1H), 3.68 (s, 3H), 2.95 (s, 3H), 2.62-2.52 (m, 2H), 2.29-2.10 (m, 2H), 1.94-1.81 (m, 1H), 1.80-1.65 (m, 1H).

MS (ESI+) m/z 513.1 [M+H]$^+$.

Example 71: N-(5-(8-(difluoromethoxy)-4-methylquinazolin-6-yl)-2-methoxypyridin-3-yl)-2,4-difluorobenzenesulfonamide (71)

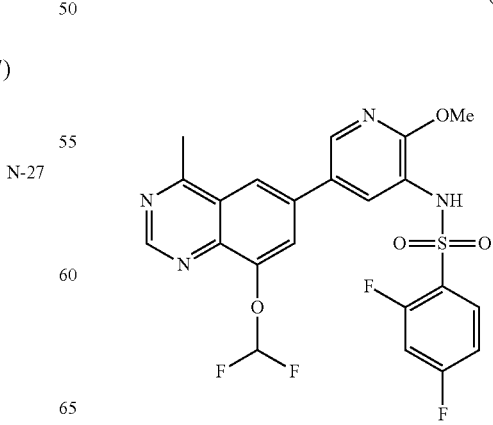

Step 1: Preparation of 6-bromo-8-(difluoromethoxy)-4-methylquinazoline (N-28)

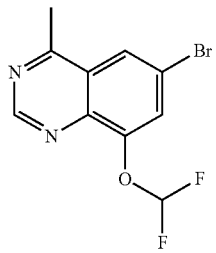

N-28

A mixture of compound (M) (0.120 g, 0.5 mmol), methyl chlorodifluoroacetate (0.217 g, 1.5 mmol), and sodium carbonate (0.159 g, 1.5 mmol) in dimethylformamide (3 mL) in a sealed tube was stirred at 70° C. for 8 h. The resulting mixture was cooled to r.t., diluted with water (30 mL), and extracted with EtOAc (30 mL×3). The combined organic layers were washed with water (30 mL) and brine (30 mL), dried over anhydrous $Na_2SO_4$, filtered and concentrated. The residue was purified by preparative thin layer chromatography (silica gel, DCM/MeOH=40:1, v/v) to afford the product (N-28) as a yellow oil (0.080 g, 55% yield).

$^1$H NMR (400 MHz, DMSO-$d_6$) δ 9.21 (s, 1H), 8.43 (d, J=2.0 Hz, 1H), 7.98 (d, J=2.0 Hz, 1H), 7.53 (t, J=73.8 Hz, 1H), 2.94 (s, 3H).

Step 2: Preparation of N-(5-(8-(difluoromethoxy)-4-methylquinazolin-6-yl)-2-methoxypyridin-3-yl)-2,4-difluorobenzenesulfonamide (71)

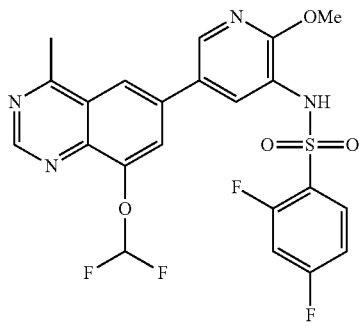

71

Compound (71) was prepared from compound (N-28) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-$d_6$) δ 10.37 (s, 1H), 9.18 (s, 1H), 8.59 (d, J=2.4 Hz, 1H), 8.35 (d, J=1.8 Hz, 1H), 8.16 (d, J=2.4 Hz, 1H), 8.06 (d, J=1.8 Hz, 1H), 7.76 (dt, J=8.6, 6.4 Hz, 1H), 7.64-7.55 (m, 1H), 7.56 (t, J=74.0 Hz, 1H), 7.21 (dt, J=8.4, 2.0 Hz, 1H), 3.66 (s, 3H), 3.03 (s, 3H).

Example 72: N-(2-methoxy-5-(8-methoxy-4-methylquinazolin-6-yl)pyridin-3-yl)-2,4-difluorobenzenesulfonamide (72)

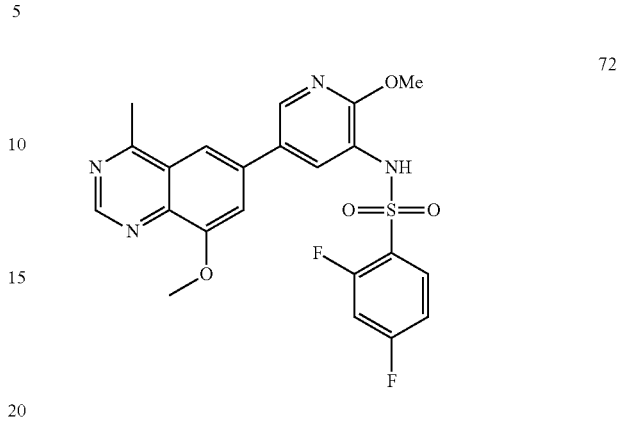

72

Compound (72) was prepared from compound (L) and N-(2-methoxy-5-(4,4,5,5-tetramethyl-1,3,2-dioxaborolan-2-yl)pyridin-3-yl)-2,4-difluorobenzenesulfonamide, according to the method of step 2 in Example 44.

$^1$H NMR (400 MHz, DMSO-$d_6$) δ 10.35 (s, 1H), 9.06 (s, 1H), 8.58 (d, J=2.2 Hz, 1H), 8.13 (d, J=2.2 Hz, 1H), 7.93 (d, J=1.6 Hz, 1H), 7.77 (dt, J=8.4, 6.4 Hz, 1H), 7.65-7.54 (m, 2H), 7.23 (dt, J=8.6, 2.4 Hz, 1H), 4.08 (s, 3H), 3.67 (s, 3H), 2.96 (s, 3H).

MS (ESI+) m/z 473.1 [M+H]$^+$.

Example 73: N-(2-chloro-5-(4-methyl-8-((tetrahydro-2H-pyran-4-yl)oxy)quinazolin-6-yl)pyridin-3-yl)-4-fluorobenzenesulfonamide (73)

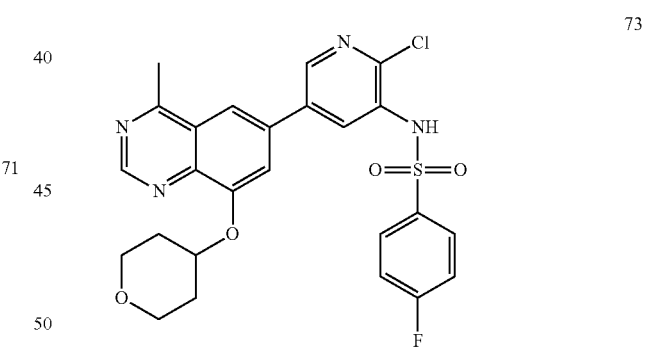

73

A mixture of compound (N-1) (71 mg, 0.22 mmol), anhydrous potassium acetate (65 mg, 0.66 mmol) and bis(pinacolato)diboron (64 mg, 0.25 mmol) in dioxane (8 mL) was degassed and then PdCl$_2$(dppf) (16 mg, 0.022 mmol) was added. The resulting reaction mixture was degassed and back-filled with argon (three cycles), and then stirred at 100 □C under Ar atmosphere for 4 h. After cooling to r.t., N-(5-bromo-2-methylpyridin-3-yl)-2,4-difluorobenzenesulfonamide (91 mg, 0.25 mmol) and 2M aqueous potassium carbonate solution (0.44 mL, 0.88 mmol) were added to the resulting mixture. The resulting mixture was degassed, and then PdCl$_2$ (dppf) (16 mg, 0.022 mmol) was added. The resulting reaction mixture was degassed and backfilled with argon (three cycles) and then stirred at 100° C. under Ar atmosphere for 5 h. The reaction mixture was cooled to r.t., diluted with EtOAc (30 mL) and water (30 mL), acidified with hydrochloric acid until the pH value was 5-6. The two phases were separated and the aqueous layer was extracted with EtOAc (30 mL×2). The combined organic layers were washed with water (50 mL) and brine (50 mL), dried over $Na_2SO_4$, filtered, and concentrated. The residue was purified by preparative thin layer chromatography (silica gel, DCM/MeOH=15:1, v/v) to afford the compound (73) as a yellow foamed solid (42 mg, 35% yield).

$^1$H NMR (400 MHz, DMSO-$d_6$) δ 10.57 (s, 1H), 9.12 (s, 1H), 8.79 (d, J=2.2 Hz, 1H), 8.16 (d, J=2.2 Hz, 1H), 8.00 (d, J=1.6 Hz, 1H), 7.87-7.80 (m, 2H), 7.78 (d, J=1.6 Hz, 1H), 7.50-7.39 (m, 2H), 5.12-5.00 (m, 1H), 3.98-3.90 (m, 2H), 3.60-3.50 (m, 2H), 2.97 (s, 3H), 2.15-2.02 (m, 2H), 1.82-1.65 (m, 2H).

MS (ESI+) m/z 529.1 [M+H]$^+$.

Example 74: N-(2-methyl-5-(4-methyl-8-((tetrahydro-2H-pyran-4-yl)oxy)quinazolin-6-yl)pyridin-3-yl)-2,4-difluorobenzenesulfonamide (74)

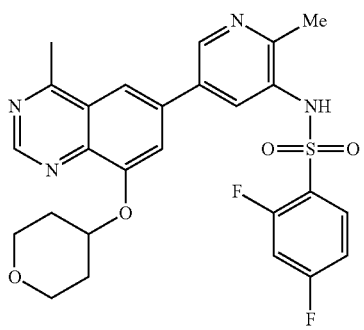

A mixture of compound (N-1) (71 mg, 0.22 mmol), anhydrous potassium acetate (65 mg, 0.66 mmol) and bis(pinacolato)diboron (64 mg, 0.25 mmol) in dioxane (8 mL) was degassed and then PdCl$_2$(dppf) (16 mg, 0.022 mmol) was added. The resulting reaction mixture was degassed and back-filled with argon (three cycles), and then stirred at 100 °C under Ar atmosphere for 4 h. After cooling to r.t., N-(5-bromo-2-methylpyridin-3-yl)-2,4-difluorobenzenesulfonamide (91 mg, 0.25 mmol) and 2M aqueous potassium carbonate solution (0.44 mL, 0.88 mmol) were added to the resulting mixture. The resulting mixture was degassed, and then PdCl$_2$ (dppf) (16 mg, 0.022 mmol) was added. The resulting reaction mixture was degassed and backfilled with argon (three cycles) and then stirred at 100° C. under Ar atmosphere for 5 h. The reaction mixture was cooled to r.t., diluted with EtOAc (30 mL) and water (30 mL), acidified with hydrochloric acid until the pH value was 5-6. The two phases were separated and the aqueous layer was extracted with EtOAc (30 mL×2). The combined organic layers were washed with water (50 mL) and brine (50 mL), dried over anhydrous $Na_2SO_4$, filtered, and concentrated. The residue was purified by preparative thin layer chromatography (silica gel, DCM/MeOH=15:1, v/v) to afford the product (74) as a yellow foamed solid (46 mg, 40% yield).

$^1$H NMR (400 MHz, DMSO-$d_6$) δ 10.53 (s, 1H), 9.10 (s, 1H), 8.84 (s, 1H), 7.88 (d, J=1.6 Hz, 1H), 7.85 (d, J=2.0 Hz, 1H), 7.80 (dt, J=8.6, 6.4 Hz, 1H), 7.71 (d, J=1.6 Hz, 1H), 7.67-7.59 (m, 1H), 7.30-7.24 (m, 1H), 5.08-4.99 (m, 1H), 3.97-3.90 (m, 2H), 3.58-3.50 (m, 2H), 2.94 (s, 3H), 2.34 (s, 3H), 2.16-2.01 (m, 2H), 1.82-1.64 (m, 2H).

MS (ESI+) m/z 527.2 [M+H]$^+$.

Evaluation of Pharmacological Activity

Experimental Example 1: Biochemical Evaluation of Activity of PI3Kα

The potency of compounds in the present intention against PI3Kα was assessed by in vitro kinase assay. The kinase activity of PI3Kα was determined by detecting the level of ADP produced in the kinase reaction with luciferase-based luminescence detection.

The Kinase-Glo™ Kinase Assay Kit was purchased from Promega. All assays were performed at room temperature using white OptiPlate™-384 well plate. The PI3Kα kinase was purchased from Invitrogen. The substrate was PIP2 from Invitrogen. The kinase buffer contained 50 mM Hepes (pH 7.5), 3 mM MgCl$_2$, 100 mM NaCl, 1 mM EGTA, 0.03% CHAPS and 2 mM DTT. The PI3Kα kinase solution was prepared by diluting PI3Kα kinase to 6.6 nM in kinase buffer. The substrate solution contained 100 μM PIP2 and 50 μM ATP. The test compound was diluted to 10 mM in 100% DMSO and serially diluted three times into ten different concentrations in 100% DMSO. The compound diluted in 100% DMSO was diluted 25-fold in 1×kinase buffer. 2.5 μL of the diluted compound solution and 2.5 μL PI3Kα kinase solution were added to each well of a 384-well plate. The reaction was initiated by addition of 5 μL substrate solution to each well. The final reaction volume was 10 μL, the ATP concentration was 25 μM, the PIP2 concentration was 50 μM, and the PI3Kα kinase concentration was 1.65 nM. The plate was then covered and the reaction was allowed to proceed for one hour at room temperature, followed by the addition of 10 μL Kinase-Glo™ reagent to each well to stop the reaction. The plate was incubated for fifteen minutes and the luminescence was read on an EnVision 2014 multilabel microplate detector plate reader.

The percentage of inhibition was calculated as follows:

$$\text{Inhibition \%} = 100 - (\text{max} - \text{sample RLU})/(\text{max} - \text{min}) * 100$$

wherein sample RLU was the luminescence reading for a given compound concentration, min was the reading of DMSO control, and max was the reading of the enzyme-free control. The IC$_{50}$ value was calculated with the XLfit program in Excel. The results were shown in Table 1.

TABLE 1

| The inhibitory activity of PI3Kα | |
|---|---|
| Example | PI3Kα IC$_{50}$ (nM) |
| 1 | 0.80 |
| 2 | 0.72 |
| 3 | 1.1 |
| 4 | 0.74 |
| 5 | 2.7 |
| 6 | 2.3 |
| 7 | 1.1 |
| 8 | 1.0 |
| 9 | 0.86 |
| 10 | 3.8 |
| 11 | 0.94 |
| 12 | 4.5 |
| 13 | 0.84 |
| 14 | 3.3 |
| 15 | 5.5 |
| 16 | 4.1 |
| 17 | 2.3 |
| 18-1 | 1.1 |
| 18-2 | 0.8 |

TABLE 1-continued

The inhibitory activity of PI3Kα

| Example | PI3Kα IC$_{50}$ (nM) |
|---|---|
| 19 | 1.0 |
| 20 | 1.3 |
| 21 | 1.0 |
| 22 | 0.6 |
| 23 | 1.1 |
| 24 | 0.8 |
| 25 | 1.6 |
| 26 | 0.79 |
| 27 | 1.7 |
| 28 | 1.2 |
| 29 | 1.1 |
| 30 | 1.3 |
| 31 | 3.8 |
| 32 | 0.82 |
| 33 | 1.7 |
| 34 | 1.6 |
| 35 | 1.8 |
| 36 | 2.2 |
| 37 | 2.3 |
| 38 | 2.3 |
| 39 | 15 |
| 40 | 8.5 |
| 41 | 5.0 |
| 42 | 1.1 |
| 43 | 10 |
| 44 | 0.65 |
| 45 | 0.92 |
| 46 | 0.70 |
| 47 | 1.4 |
| 48 | 2.1 |
| 49 | 0.76 |
| 50 | 2.2 |
| 51 | 0.72 |
| 52 | 2.1 |
| 53 | 0.73 |
| 54 | 1.6 |
| 55 | 1.7 |
| 56 | 0.92 |
| 57 | 1.7 |
| 58 | 1.0 |
| 59 | 0.74 |
| 60 | 1.3 |
| 61 | 1.0 |
| 62 | 2.5 |
| 63 | 10 |
| 64 | 1.5 |
| 65 | 2.7 |
| 66 | 1.7 |
| 67 | 6.1 |
| 68 | 1.6 |
| 69 | 2.2 |
| 70 | 0.90 |
| 71 | 1.9 |
| 72 | 0.70 |
| 73 | 1.3 |
| 74 | 1.1 |

Experimental Example 2: Measurement of Tumor Cell Viability by MTT Assay

The human lung cancer cell NCI-H460 in logarithmic growth phase was digested with 0.25% trypsin-EDTA, and prepared into a single-cell suspension which was then added in a 96-well plate at 1200 cells/well with 100 μL per well. After 24 hours, 100 μL of fresh medium containing different concentrations of test compounds and the corresponding solvent control was added into each well to a final concentration of DMSO less than 0.2%. Six to nine concentration groups were set for each test compound, and three parallel wells were set for each group. The plate was incubated at 5% CO$_2$, 37° C. for 96 hours. 20 μL of freshly prepared PBS solution containing 5 mg/mL MTT was added to each well. The supernatant was discarded after incubation for another 4 hours. 150 μL DMSO was added to each well to dissolve the MTT formazan precipitate. After being mixed by a micro-oscillator, the optical density (OD) was measured at the wavelength of 570 nm, and the tumor cells treated with DMSO were used as a control group. The inhibitory rate of the test compound on tumor cell growth was calculated as follows, and the IC$_{50}$ value was calculated with SPSS 16.0:

Inhibitory rate (%)=(OD$_{control}$−OD$_{compound}$)/OD$_{controix}$×100%

Wherein OD$_{control}$ was the average OD value of the control group, and OD$_{compound}$ was the average OD value of the test compound group at a given concentration.

The results were shown in Table 2.

TABLE 2

Antiproliferative activity against human lung cancer cell NCI-H460

| Example | H460 IC$_{50}$ (μM) |
|---|---|
| 1 | 0.029 |
| 2 | 0.017 |
| 3 | 0.096 |
| 4 | 0.025 |
| 5 | 0.86 |
| 6 | 0.93 |
| 7 | 2.1 |
| 8 | 1.2 |
| 9 | 0.093 |
| 10 | 2.2 |
| 11 | 0.094 |
| 12 | 2.3 |
| 13 | 0.021 |
| 14 | 2.0 |
| 15 | 0.66 |
| 16 | 1.1 |
| 17 | 0.083 |
| 18-1 | 0.030 |
| 18-2 | 0.057 |
| 19 | 0.041 |
| 20 | 0.24 |
| 21 | 0.063 |
| 22 | 0.096 |
| 23 | 0.094 |
| 24 | 0.063 |
| 25 | 0.20 |
| 26 | 0.14 |
| 27 | 0.20 |
| 28 | 0.28 |
| 29 | 0.059 |
| 30 | 0.24 |
| 31 | 0.41 |
| 32 | 0.10 |
| 33 | 0.10 |
| 34 | 0.11 |
| 35 | 0.10 |
| 36 | 0.40 |
| 37 | 0.25 |
| 38 | 0.31 |
| 39 | 1.7 |
| 40 | 2.0 |
| 41 | 1.4 |
| 42 | 0.53 |
| 43 | 4.0 |
| 44 | 0.029 |
| 45 | 0.045 |
| 46 | 0.029 |
| 47 | 0.57 |
| 48 | 0.28 |
| 49 | 0.034 |
| 50 | 0.79 |
| 51 | 0.032 |
| 52 | 0.67 |
| 53 | 0.038 |
| 54 | 0.40 |
| 55 | 0.097 |

TABLE 2-continued

Antiproliferative activity against human lung cancer cell NCI-H460

| Example | H460 IC$_{50}$ (μM) |
|---|---|
| 56 | 0.073 |
| 57 | 0.45 |
| 58 | 0.056 |
| 59 | 0.017 |
| 60 | 0.24 |
| 61 | 0.045 |
| 62 | 0.26 |
| 63 | 2.1 |
| 64 | 0.39 |
| 65 | 0.63 |
| 66 | 0.23 |
| 67 | 3.5 |
| 68 | 0.34 |
| 69 | 0.050 |
| 70 | 0.022 |
| 71 | 1.0 |
| 72 | 0.50 |
| 73 | 0.74 |
| 74 | 0.87 |

Experimental Example 3: Study on the Xenograft Efficacy in Nude Mice

Figure 2:
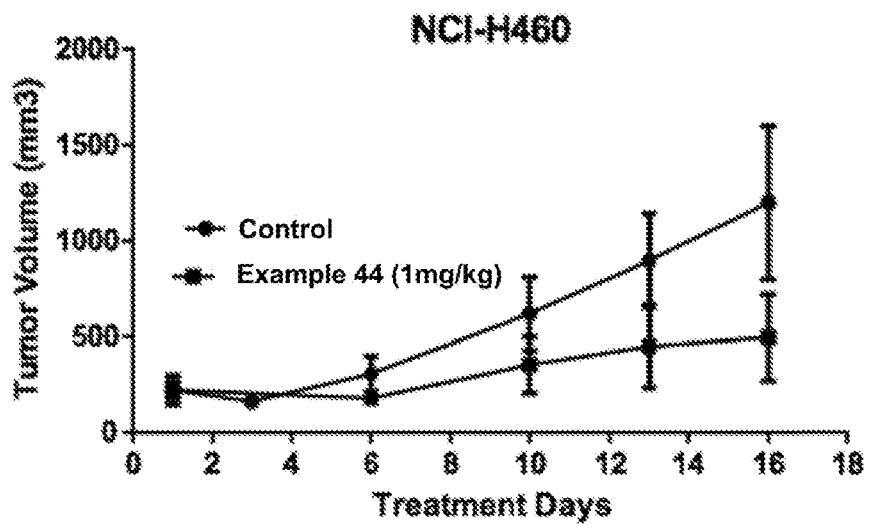
FIG. 2 is a tumor growth curve, which shows growth inhibitory effect of Example 44 on human lung cancer NCI-H460 subcutaneous xenograft tumor in nude mice.

Human lung cancer NCI-H460 cells were collected under aseptic conditions, and the cell density was adjusted to 1×10$^6$ cells/mL with sterile saline, 0.2 mL of which was implanted into the back of the nude mice. When the tumor grew to a diameter of about 1 cm, it was removed under septic condition and cut into pieces of 1 mm×1 mm which was implanted into the back of the nude mice. When the tumor grew to 100-300 mm$^3$ after 6 days, the animals were randomly divided into groups and administration was started (marked as Day 1). The test compound was administered orally every day. Body weight was measured twice a week and the length and width of the tumor were measured with a vernier caliper. After 16 days of dosing, the nude mice were sacrificed by cervical dislocation and the tumor issues were exfoliated, weighed and photographed. Finally, the tumor inhibitory rate was calculated. The antitumor efficacy was evaluated by the tumor inhibitory rate. The results were shown in Table 3, Table 4, FIG. 1 and FIG. 2.

The tumor volume was calculated as follows:

$$\text{Tumor volume} = (a \times b^2)/2,$$

where a and b represented the length and width of the tumor.

The percentage of tumor growth inhibition was calculated as follows:

$$\text{Tumor growth inhibition (\%)} = (1 - T/C) \times 100,$$

where T was the final volume of the tumor in the test compound group and C was the final volume of the tumor in the solvent control group.

TABLE 3

Growth inhibition of Example 9 on human lung cancer NCI-H460 in subcutaneous xenografts in nude mice

| Cell line | Tumor type | Initial tumor volume (mm$^3$) | Dose (mg/kg/day) | Growth inhibition (%) |
|---|---|---|---|---|
| NCI-H460 | Lung cancer | 220.8 | 0 | |
| | | 287.2 | 5 | 39.2 |
| | | 171.5 | 10 | 56.3 |
| | | 266.2 | 20 | 77.0 |

TABLE 4

Growth inhibition of Example 44 on human lung cancer NCI-H460 in subcutaneous xenografts in nude mice

| Cell line | Tumor type | Initial tumor volume (mm$^3$) | Dose (mg/kg/day) | Growth inhibition (%) |
|---|---|---|---|---|
| NC1-H460 | Lung cancer | 220.8 | 0 | |
| | | 222.2 | 1 | 60.3 |

Figure 3:
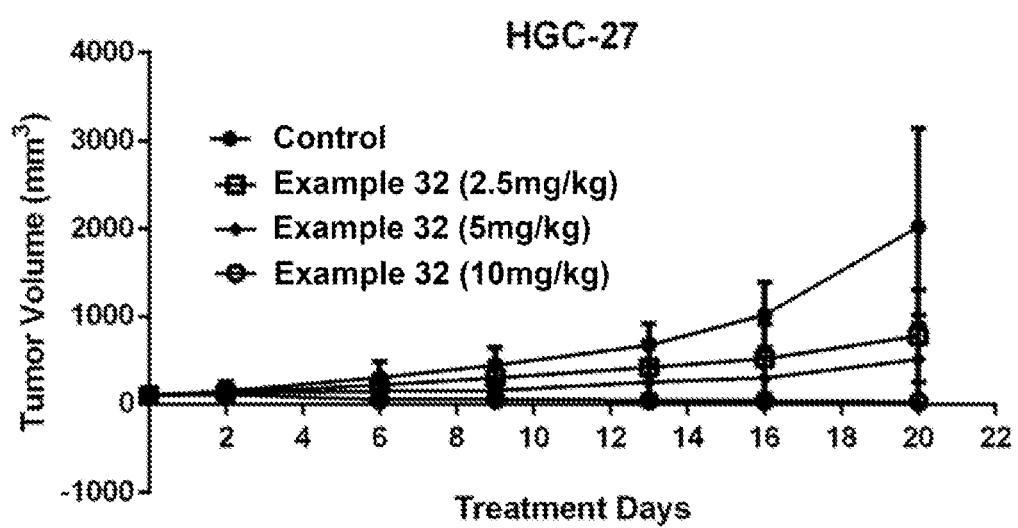
FIG. 3 is a tumor growth curve, which shows growth inhibitory effect of Example 32 on human gastric cancer HGC-27 subcutaneous xenograft tumor in nude mice.

Human gastric cancer HGC-27 cells were collected under aseptic conditions, and the cell density was adjusted to 1×10$^6$ cells/mL with sterile saline, 0.2 mL of which was implanted into the back of the nude mice. When the tumor grew to a diameter of about 1 cm, it was removed under septic condition and cut into pieces of 1 mm×1 mm which was implanted into the back of the nude mice. When the tumor grew to 100-300 mm$^3$ after 6 days, the animals were randomly divided into groups and administration was started (marked as Day 0). The test compound was administered orally every day. Body weight was measured twice a week and the length and width of the tumor were measured with a vernier caliper. After 20 days of dosing, the nude mice were sacrificed by cervical dislocation and the tumor issues were exfoliated, weighed and photographed. Finally, the tumor inhibitory rate was calculated. The antitumor efficacy was evaluated by the tumor inhibitory rate. The results were shown in Table 5 and FIG. 3.

The tumor volume was calculated as follows:

$$\text{Tumor volume} = (a \times b^2)/2,$$

where a and b represented the length and width of the tumor.

The percentage of tumor growth inhibition was calculated as follows:

$$\text{Tumor growth inhibition (\%)} = (1 - T/C) \times 100,$$

where T was the final volume of the tumor in the test compound group and C was the final volume of the tumor in the solvent control group.

The percentage of tumor regression was calculated by 100×(final tumor volume−initial tumor volume)/initial tumor volume.

TABLE 5

Growth inhibition of Example 32 on human gastric cancer HGC-27 in subcutaneous xenografts in nude mice

| Cell line | Tumor type | Initial tumor volume (mm$^3$) | Dose (mg/kg/day) | Growth inhibition (%) | Regression (%) |
|---|---|---|---|---|---|
| HGC-27 | Gastric cancer | 107.0 | 0 | | |
| | | 99.3 | 2.5 | 62.3 | |
| | | 104.6 | 5 | 76.9 | |
| | | 103.3 | 10 | | 70.5 |

Summary of Pharmacological Activities:

All examples showed strong inhibitory activity against PI3Kα with IC$_{50}$ values of less than 11 nM. All examples showed strong anti-proliferative activities against human lung cancer cell NCI-H460 with IC$_{50}$ values of less than 5 μM. Among them, Examples 9 and 44 had significant inhibitory effects against the growth of human lung cancer cell NCI-H460 in subcutaneous xenografts in nude mice, and Example 32 showed a significant inhibitory effect on the growth of human gastric cancer cell HGC-27 in subcutaneous xenografts in nude mice.

The invention claimed is:

1. A compound represented by Formula (IV), or a stereoisomer, a geometric isomer, a tautomer or a pharmaceutically acceptable salt thereof:

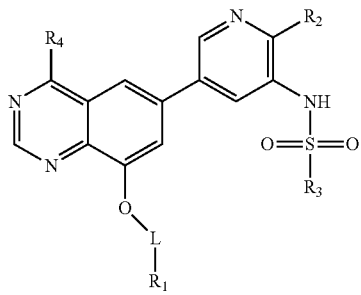

(IV)

wherein, $R_4$ is $C_{1-3}$ alkyl;

L is selected from a single bond or $C_{1-3}$ alkylene, wherein said $C_{1-3}$ alkylene is optionally substituted with one or more Ra;

Ra is selected from hydrogen, halogen or $C_{1-3}$ alkyl;

$R_1$ is selected from hydrogen, $C_{1-3}$ alkyl, $C_{1-3}$ alkoxy, 3- to 7-membered cycloalkyl, 3- to 7-membered heterocycloalkyl or 5- to 6-membered heteroaryl, when $R_1$ is not hydrogen, it is optionally substituted with m $R_6$;

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino;

$R_2$ is selected from $C_{1-3}$ alkoxy, halogen or $C_{1-3}$ alkyl; and $R_3$ is selected from $C_{1-3}$ alkyl, 3- to 7-membered cycloalkyl, 6- to 10-membered aryl or 5- to 6-membered heteroaryl, wherein said 6- to 10-membered aryl and 5- to 6-membered heteroaryl are optionally substituted with one or more groups independently selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy.

2. The compound according to claim 1, or the stereoisomer, the geometric isomer, the tautomer or the pharmaceutically acceptable salt thereof, characterized in that, $R_1$ is selected from cyclopropyl, cyclobutyl, cyclopentyl, cyclohexyl; $R_1$ is optionally substituted with m $R_6$;

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino.

3. The compound according to claim 1, or the stereoisomer, the geometric isomer, the tautomer or the pharmaceutically acceptable salt thereof, characterized in that, $R_1$ is 3- to 7-membered heterocycloalkyl containing oxygen, and $R_1$ is optionally substituted with m R;

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino.

4. The compound according to claim 3, or the stereoisomer, the geometric isomer, the tautomer or the pharmaceutically acceptable salt thereof, characterized in that, said $R_1$ is selected from:

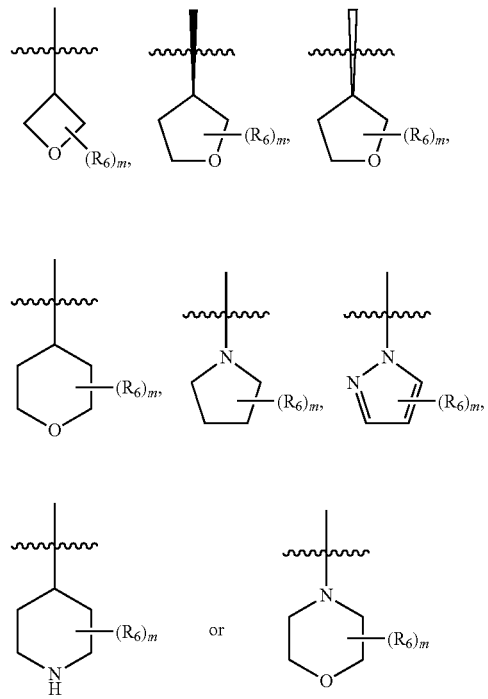

m is 0, 1, 2, 3 or 4;

each $R_6$ is independently selected from halogen, cyano, hydroxyl, trifluoromethyl, $C_{1-3}$ alkyl, $C_{1-3}$ alkoxy, $C_{1-3}$ hydroxyalkyl, $C_{1-3}$ alkylamino or di($C_{1-3}$ alkyl)amino.

5. The compound according to claim 1, or the stereoisomer, the geometric isomer, the tautomer or the pharmaceutically acceptable salt thereof, characterized in that, each $R_6$ is independently selected from F or methyl.

6. The compound according to claim 1, or the stereoisomer, the geometric isomer, the tautomer or the pharmaceutically acceptable salt thereof, wherein, L is selected from a single bond or —$CH_2$—.

7. The compound according to claim 1, or the stereoisomer, the geometric isomer, the tautomer or the pharmaceutically acceptable salt thereof, wherein, $R_2$ is selected from methoxy, chloro or methyl.

8. The compound according to claim 1, or the stereoisomer, the geometric isomer, the tautomer or the pharmaceutically acceptable salt thereof, wherein, $R_3$ is selected from $C_{1-3}$ alkyl, 3- to 7-membered cycloalkyl, phenyl or thienyl, wherein said phenyl or thienyl are optionally substituted with one or more groups independently selected from hydrogen, halogen, $C_{1-3}$ alkyl, amino, $C_{1-3}$ alkylamino, di($C_{1-3}$ alkyl)amino, trifluoromethyl, difluoromethyl, cyano or $C_{1-3}$ alkoxy.

9. The compound according to claim 8, or the stereoisomer, the geometric isomer, the tautomer or the pharmaceutically acceptable salt thereof, wherein, $R_3$ is selected from phenyl or thienyl, said phenyl and thienyl are optionally substituted with one or more groups independently selected from fluoro or chloro.

10. The compound according to claim 1, or the stereoisomer, the geometric isomer, the tautomer or the pharmaceutically acceptable salt thereof, wherein, said compound is selected from the group consisting of:

149
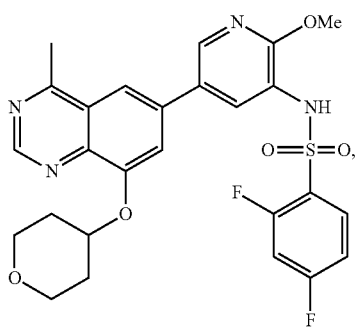
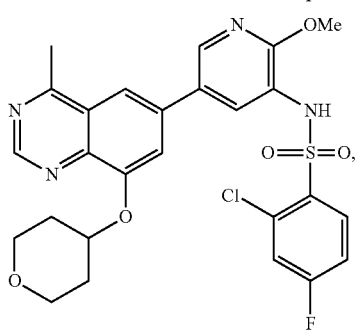
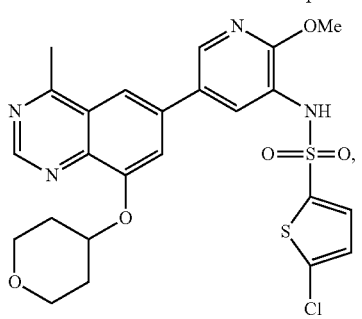
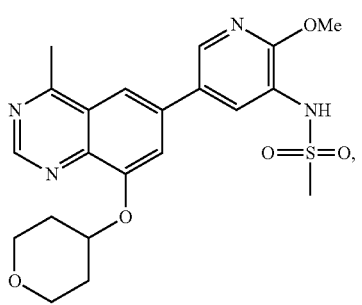
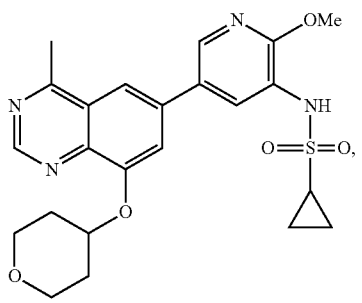
150
-continued
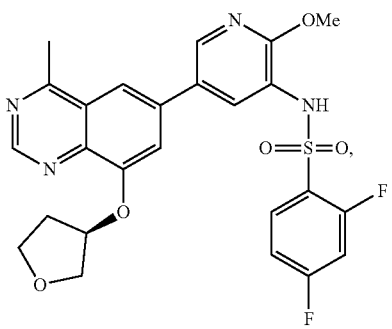
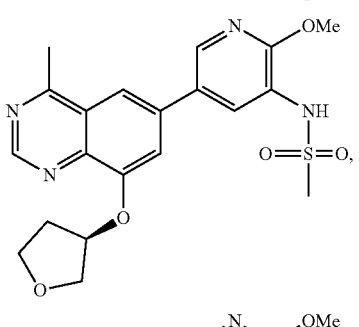
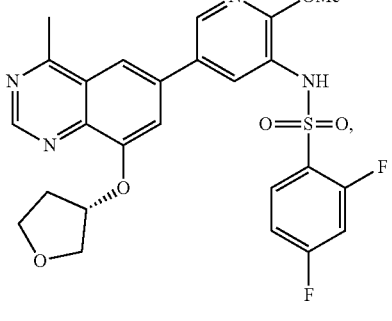
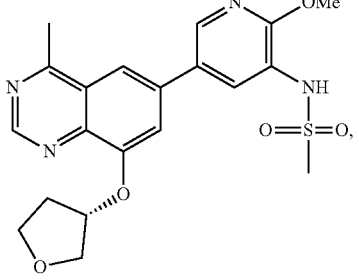
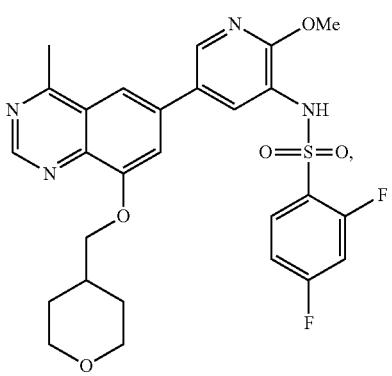

-continued
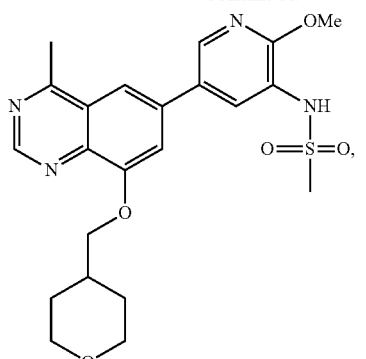
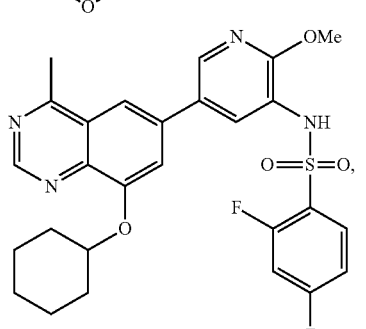
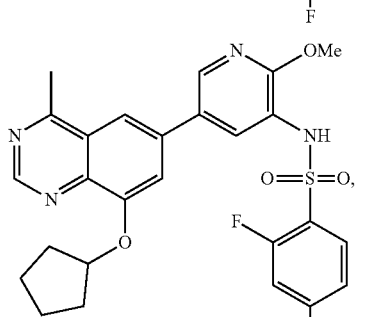
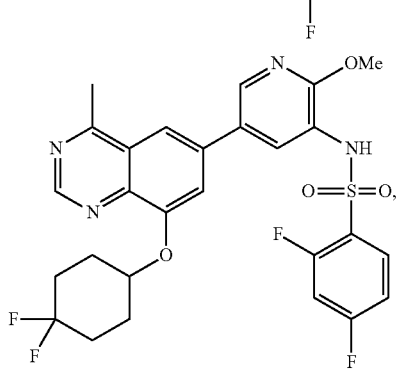
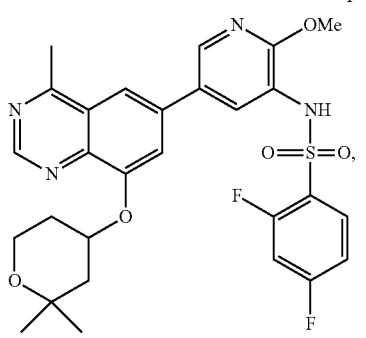
-continued
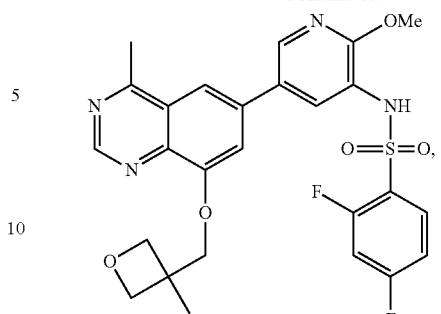
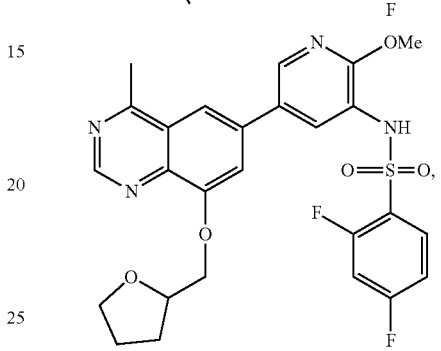
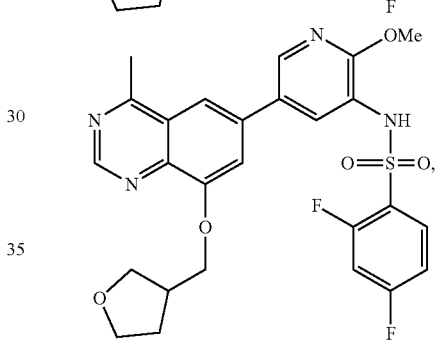
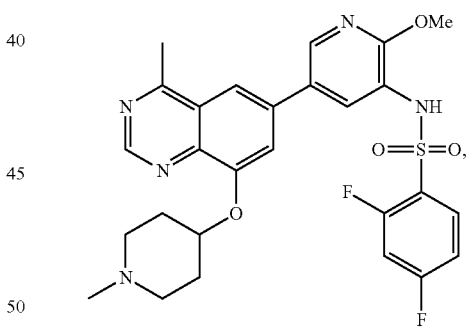
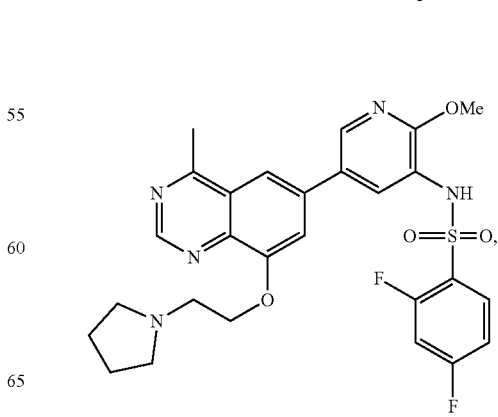

153
-continued
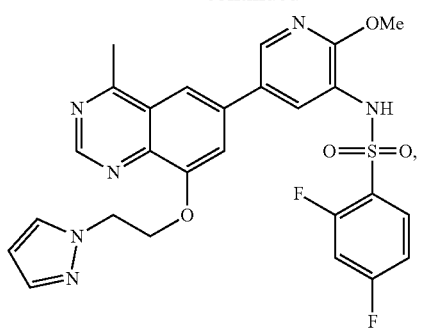
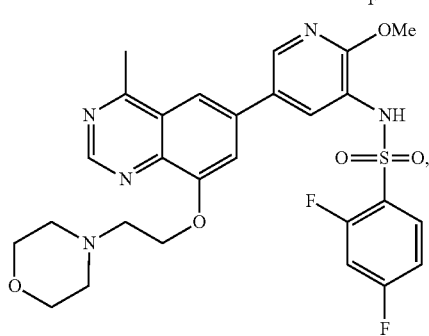
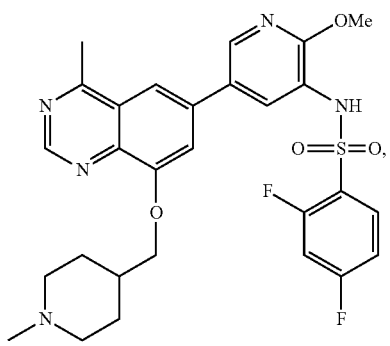
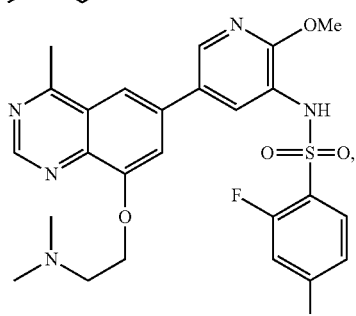
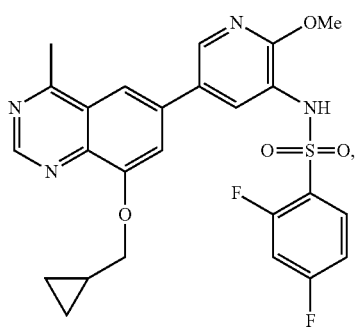
154
-continued
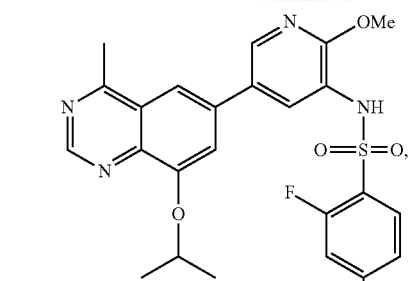
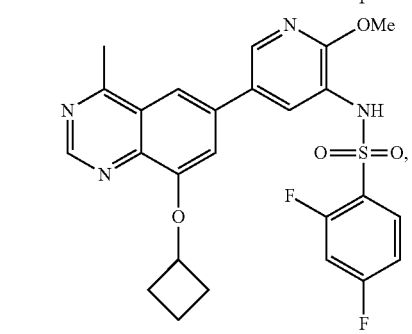
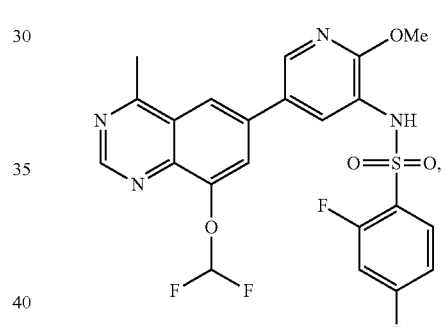
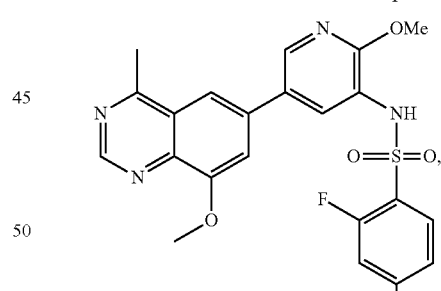
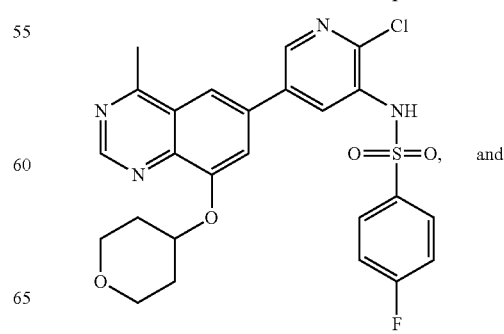
and -continued

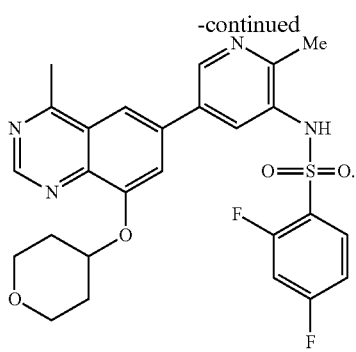

11. A pharmaceutical composition comprising at least one compound according to claim 1, or a stereoisomer, a geometric isomer, a tautomer or a pharmaceutically acceptable salt thereof, and optionally a pharmaceutically acceptable carrier and/or excipient.

12. A method for treating a PI3K-mediated disease, in a subject in need of such treatment, the method comprising administering to the subject an effective amount of the compound of claim 1, or a stereoisomer, a geometric isomer, a tautomer or a pharmaceutically acceptable salt thereof.

13. The method according to claim 12, wherein, said PI3K-mediated disease includes cancer, immune diseases, cardiovascular diseases, viral infections, inflammation, metabolism/endocrine function disorders or neurological diseases.

* * * * *